US012617769B2

(12) United States Patent
Gu et al.

(10) Patent No.: US 12,617,769 B2
(45) Date of Patent: May 5, 2026

(54) CHEMICAL COMPOUND AS THYROID HORMONE BETA RECEPTOR AGONIST AND USE THEREOF

(71) Applicant: SUNSHINE LAKE PHARMA CO., LTD., Dongguan (CN)

(72) Inventors: Zheng Gu, Dongguan (CN); Jianhao Li, Dongguan (CN); Xinshan Deng, Dongguan (CN); Zheng Li, Dongguan (CN); Daoqian Chen, Dongguan (CN); Jianchao Deng, Dongguan (CN); Aizhen Lv, Dongguan (CN); Jianyu Liu, Dongguan (CN)

(73) Assignee: SUNSHINE LAKE PHARMA CO., LTD., Dongguan (CN)

( * ) Notice: Subject to any disclaimer, the term of this patent is extended or adjusted under 35 U.S.C. 154(b) by 994 days.

(21) Appl. No.: 17/763,578

(22) PCT Filed: Sep. 23, 2020

(86) PCT No.: PCT/CN2020/117131

§ 371 (c)(1),
(2) Date: Mar. 24, 2022

(87) PCT Pub. No.: WO2021/057791

PCT Pub. Date: Apr. 1, 2021

(65) Prior Publication Data

US 2022/0411400 A1 Dec. 29, 2022

(30) Foreign Application Priority Data

Sep. 24, 2019 (CN) ........................ 201910901997.0
Mar. 11, 2020 (CN) ........................ 202010164947.1
Mar. 27, 2020 (CN) ........................ 202010231242.7

(51) Int. Cl.

| | |
|---|---|
| ***C07D 403/14*** | (2006.01) |
| ***A61P 5/14*** | (2006.01) |
| ***A61P 5/16*** | (2006.01) |
| ***C07D 401/10*** | (2006.01) |
| ***C07D 401/12*** | (2006.01) |
| ***C07D 401/14*** | (2006.01) |
| ***C07D 403/10*** | (2006.01) |
| ***C07D 403/12*** | (2006.01) |
| ***C07D 405/14*** | (2006.01) |
| ***C07D 413/14*** | (2006.01) |
| ***C07D 417/14*** | (2006.01) |

(52) U.S. Cl.

CPC .............. *C07D 401/10* (2013.01); *A61P 5/14* (2018.01); *C07D 401/14* (2013.01); *C07D 403/10* (2013.01); *C07D 403/14* (2013.01); *C07D 405/14* (2013.01); *C07D 413/14* (2013.01); *C07D 417/14* (2013.01)

(58) Field of Classification Search

CPC .. C07D 401/10; C07D 401/14; C07D 403/10; C07D 403/14; C07D 405/14; C07D 413/14; C07D 417/14; A61P 5/14

See application file for complete search history.

(56) References Cited

U.S. PATENT DOCUMENTS

| | | | | |
|---|---|---|---|---|
| 6,787,652 | B1 | 9/2004 | Dow et al. | |
| 6,930,107 | B2 | 8/2005 | Dow et al. | |
| 7,452,882 | B2 * | 11/2008 | Haynes | A61P 35/00 544/239 |
| 7,807,674 | B2 | 10/2010 | Haynes et al. | |
| 8,076,334 | B2 | 12/2011 | Haynes et al. | |
| 2020/0347035 | A1 | 11/2020 | Wang et al. | |
| 2021/0115022 | A1 | 4/2021 | Jin et al. | |

FOREIGN PATENT DOCUMENTS

WO WO-2020169069 A1 * 8/2020 ................ A61P 9/10

OTHER PUBLICATIONS

Chagas, C. M., Moss, S. & Alisaraie, L. Int. J. Pharma. 2018, 549, 133-149 (Year: 2018).*
Kishimoto, T. et al. Int. J. Mol. Sci. 2020, 21(1), 34 (Year: 2020).*
Najjar, A. & Karaman, R. Expert Opinion on Drug Discovery, 2018, 14(3), 199-220 (Year: 2018).*
Dec. 21, 2020 International Search Report issued in International Patent Application No. PCT/CN2020/117131.
Dec. 21, 2020 Written Opinion issued in International Patent Application No. PCT/CN2020/117131.

* cited by examiner

*Primary Examiner* — Clinton A Brooks
*Assistant Examiner* — Kendall Nicole Heitmeier
(74) *Attorney, Agent, or Firm* — Oliff PLC

(57) ABSTRACT

Provided is a chemical compound as a thyroid hormone Beta receptor agonist and a use thereof, further comprising a pharmaceutical composition containing the chemical compound. The chemical compound or pharmaceutical composition can be used in the preparation of drugs for preventing, treating or mitigation of diseases mediated by agonistic thyroid hormone β receptor, particularly for the preparation of drugs for treating non-alcoholic fatty liver diseases.

9 Claims, No Drawings

CHEMICAL COMPOUND AS THYROID HORMONE BETA RECEPTOR AGONIST AND USE THEREOF

CROSS-REFERENCE TO RELATED APPLICATION

This application claims the priorities and benefits of Chinese Patent Application No.s 201910901997.0, 202010164947.1 and 202010231242.7, filed with the State Intellectual Property Office of China on Sep. 24, 2019, Mar. 11, 2020, and Mar. 27, 2020 respectively, which are incorporated herein by reference in their entirety.

FIELD

The present invention belongs to the field of medicine, and specifically relates to a compound as a thyroid hormone Beta receptor agonist and use thereof, and further relates to a pharmaceutical composition comprising the compound. The invention further relates to the use of the compound and the pharmaceutical composition in the manufacture of a medicament for preventing, treating or alleviating diseases mediated by activated thyroid hormone β receptors, especially in the manufacture of a medicament for treating non-alcoholic fatty liver disease.

BACKGROUND

Thyroid hormone (TH) plays an extremely important role in growth, differentiation, development and maintenance of metabolic balance. Thyroid hormone is synthesized by the thyroid gland and is secreted into the circulatory system in two main forms, triiodothyronine (T3) and tetraiodothyronine (T4). Although T4 is the main form secreted by the thyroid, T3 is a physiologically more active form. T4 is converted to T3 by tissue-specific deiodinase, which is present in all tissues, but mainly in the liver and kidney.

The physiological function of TH is mainly carried out through thyroid hormone receptor (TR). TR belongs to the nuclear receptor superfamily and is a transcription factor induced by ligand T3. It is at the core of mediating the role of ligand T3. TR is mainly located in the nucleus and forms a heterodimer with the retinoid X receptor (RXR) and other nuclear receptors and binds to the thyroid hormone response element (TRE) of the target gene promoter region, thereby regulating gene transcription. There are two subtypes of TR: TRα and TRβ. TRα can be divided into TRα1 and TRα2, and TRβ can be divided into TRβ1 and TRβ2. Among them, only TRα1, TRβ1 and TRβ2 can bind to ligand T3. TRα mainly regulates heart rate, TRβ plays a key role in controlling liver cholesterol metabolism and inhibiting the release of thyroid stimulating hormone (TSH), which may be related to the high expression of TRβ in the liver and pituitary gland.

If side effects can be minimized or eliminated, then thyroid hormone has certain therapeutic benefits (Paul M. Yen et. al. Physiological Reviews, Vol. 81(3): pp. 1097-1126 (2001); Paul Webb et. al. Expert Opin. Investig. Drugs, Vol. 13(5): pp. 489-500 (2004)). For example, thyroid hormones can increase metabolic rate, oxygen consumption and calorie production, thereby reducing body weight. Reducing body weight will improve the co-morbidity associated with obesity and have a beneficial effect on obese patients, and may also have a beneficial effect on glycemic control in obese patients with type 2 diabetes.

Thyroid hormone can also reduce serum low density lipoprotein (LDL) (Eugene Morkin et. al. Journal of Molecular and Cellular Cardiology, Vol. 37: pp. 1137-1146 (2004)). It has been found that hyperthyroidism is associated with low total serum cholesterol, which is attributed to the fact that thyroid hormone increases liver LDL receptor expression and stimulates the metabolism of cholesterol to bile acids (J J. Abrams et. al. J. Lipid Res., Vol. 22: pp. 323-38 (1981)). Hypothyroidism is related to hypercholesterolemia, and there have been reports that thyroid hormone replacement therapy reduces total cholesterol (M. Aviram et. al. Clin. Biochem., Vol. 15: pp. 62-66 (1982); J J. Abrams et. al. J. Lipid Res., Vol. 22: pp. 323-38 (1981)). In animal models, thyroid hormone has been shown to have the beneficial effect of increasing HDL cholesterol and increasing the conversion rate of LDL to HDL by increasing the expression of apo A-1 (one of HDL's major apolipoproteins) (Gene C. Ness et. al. Biochemical Pharmacology, Vol. 56: pp. 121-129 (1998); G J. Grover et. al. Endocrinology, Vol. 145: pp. 1656-1661 (2004); G J. Grover et. al. Proc. Natl. Acad. Sci. USA, Vol. 100: pp. 10067-10072 (2003)). The incidence of atherosclerotic vascular disease is directly related to LDL cholesterol levels. Through the regulation of LDL and HDL, thyroid hormones may also reduce the risk of atherosclerosis and other cardiovascular diseases. In addition, there is evidence that thyroid hormone can reduce lipoprotein (a), which is a risk factor for atherosclerosis, and increased in patients with atherosclerosis (Paul Webb et. al. Expert Opin. Investig. Drugs, Vol. 13(5): pp. 489-500 (2004); de Bruin et. al. J. Clin. Endo. Metab., Vol. 76: pp. 121-126 (1993)).

In addition, non-alcoholic fatty liver disease (NAFLD) is also closely related to thyroid hormones. On the one hand, NAFLD have an effect on the conversion and inactivation of thyroid hormones in the patients, which can lead to a decrease in serum thyroid hormone levels; on the other hand, the decrease in thyroid hormone levels further causes disorders of lipid metabolism and glucose metabolism, and participates in the occurrence of NAFLD. Studies have shown that a diet deficient in choline-methionine induces the formation of fatty liver in rats, and reversal of fatty liver can be observed after feeding T3 (Perra A, et al. Faseb, 2008, 22 (8): 2981).

However, endogenous thyroid hormones are non-selective and have side effects such as hyperthyroidism, especially cardiovascular toxicity-related side effects. Therefore, the development of thyroid hormone analogs (such as thyroid hormone β receptor agonists) that avoid the adverse effects of hyperthyroidism while maintaining the beneficial effects of thyroid hormone will open new ways to treat patients with the following diseases: such as obesity, hyperlipidemia, hypercholesterolemia, diabetes, hepatic steatosis, non-alcoholic fatty liver disease, atherosclerosis, cardiovascular disease, hypothyroidism, thyroid cancer, thyroid disease, and related conditions and diseases.

SUMMARY OF THE INVENTION

The present invention provides a class of compounds with good agonistic activity on thyroid hormone β receptors. Such compounds and compositions thereof can be used in the manufacture of a medicament for preventing, treating or alleviating non-alcoholic fatty liver disease, atherosclerosis, coronary heart disease, hypertension, hypercholesterolemia, hyperlipidemia, hypertriglyceridemia, dyslipidemia, obesity, diabetes, metabolic disorders, type 1A glycogen storage disease, hypothyroidism or thyroid cancer in a subject.

In one aspect, the invention relates to a compound having Formula (I) or a stereoisomer, a geometric isomer, a tautomer, an N-oxide, a solvate, a metabolite, a pharmaceutically acceptable salt or a prodrug thereof, (I)

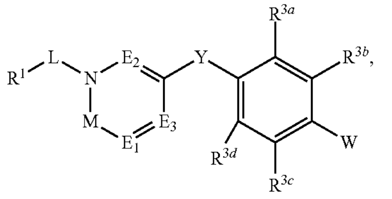

wherein,

Y is —O—, —S—, —$NR^c$—, —$CR^aR^b$—, —S(═O)$_2$—, —S(═O)— or —C(═O)—;

L is absent, —O—, —S—, $NR^c$—, —$CR^dR^e$—, —S(═O)$_2$—, —S(═O)— or —C(═O)—; each of $R^a$, $R^b$, $R^c$, $R^d$ and $R^e$ is independently H, deuterium, F, Cl, Br, I, —CN, —$NO_2$, —COOH, —OH, —$NH_2$, —SH, $C_{1-6}$ alkyl, $C_{1-6}$ alkoxy, $C_{1-6}$ haloalkyl or $C_{1-6}$ haloalkoxy;

each of $R^{3a}$, $R^{3b}$, $R^{3c}$ and $R^{3d}$ is independently H, deuterium, F, Cl, Br, I, —CN, —$NO_2$, —COOH, —OH, —$NH_2$, —SH, $C_{1-6}$ alkyl, $C_{1-6}$ alkoxy, $C_{1-6}$ alkylthio, $C_{1-6}$ alkylamino, $C_{1-6}$ haloalkyl, $C_{1-6}$ haloalkoxy, hydroxy $C_{1-6}$ alkyl, amino $C_{1-6}$ alkyl or cyano $C_{1-6}$ alkyl;

M is —C(═O)—, —C(═S)—, —S(═O)$_2$— or —S(═O)—; $E_1$ is N, CH or $CR^z$, wherein $R^z$ is deuterium, F, Cl, Br, I, —CN, —$NO_2$, —COOH, —$NH_2$, —SH, $C_{1-6}$ alkyl, $C_{1-6}$ haloalkyl, $C_{1-6}$ haloalkoxy, $C_{1-6}$ alkoxy, $C_{2-6}$ alkenyl, $C_{2-6}$ alkynyl, hydroxy $C_{1-6}$ alkyl, $C_{3-8}$ cycloalkyl, $C_{3-8}$ cycloalkyl $C_{1-6}$ alkyl, 3-8 membered heterocyclyl, (3-8 membered heterocyclyl) $C_{1-6}$ alkyl, $C_{6-10}$ aryl, $C_{6-10}$ aryl $C_{1-6}$ alkyl, 5-10 membered heteroaryl or (5-10 membered heteroaryl) $C_{1-6}$ alkyl;

$E_2$ is $CR^2$;

$E_3$ is N or $CR^3$;

each of $R^2$ and $R^3$ is independently H, deuterium, F, Cl, Br, I, —CN, —$NO_2$, —COOH, —$NH_2$, —SH, $C_{1-6}$ alkyl, $C_{1-6}$ haloalkyl, $C_{1-6}$ haloalkoxy, $C_{1-6}$ alkoxy, $C_{2-6}$ alkenyl, $C_{2-6}$ alkynyl, hydroxy $C_{1-6}$ alkyl, $C_{3-8}$ cycloalkyl, $C_{3-8}$ cycloalkyl $C_{1-6}$ alkyl, 3-8 membered heterocyclyl, (3-8 membered heterocyclyl) $C_{1-6}$ alkyl, $C_{6-10}$ aryl, $C_{6-10}$ aryl $C_{1-6}$ alkyl, 5-10 membered heteroaryl or (5-10 membered heteroaryl) $C_{1-6}$ alkyl;

$R^1$ is H, deuterium, F, Cl, Br, I, —CN, —$NO_2$, —COOH, —C(═O)$NH_2$, —S(═O)$_2NH_2$, —OH, —$NH_2$, —SH, $C_{1-6}$ alkyl, $C_{1-6}$ alkoxy, $C_{1-6}$ haloalkyl, $C_{1-6}$ haloalkoxy, —C(═O)—$C_{1-6}$ alkoxy, —C(═O)—$C_{1-6}$ alkylamino, —C(═O)—$C_{1-6}$ alkyl, —S(═O)$_2$—$C_{1-6}$ alkyl, —S(═O)$_2$—$C_{1-6}$ alkylamino, $C_{2-6}$ alkenyl, $C_{2-6}$ alkynyl, $C_{3-8}$ cycloalkyl, 5-8 membered heterocyclyl, $C_{6-10}$ aryl or 5-8 membered heteroaryl, wherein each of the $C_{1-6}$ alkyl, $C_{1-6}$ alkoxy, $C_{1-6}$ haloalkyl, $C_{1-6}$ haloalkoxy, —C(═O)—$C_{1-6}$ alkoxy, —C(═O)—$C_{1-6}$ alkylamino, —C(═O)—$C_{1-6}$ alkyl, —S(═O)$_2$—$C_{1-6}$ alkyl, —S(═O)$_2$—$C_{1-6}$ alkylamino, $C_{2-6}$ alkenyl, $C_{2-6}$ alkynyl, $C_{3-8}$ cycloalkyl, 5-8 membered heterocyclyl, $C_{6-10}$ aryl and 5-8 membered heteroaryl is independently unsubstituted or substituted with 1, 2 or 3 substituents selected from deuterium, F, Cl, Br, I, —CN, —$NO_2$, —COOH, —C(═O)$NH_2$, —S(═O)$_2NH_2$, —SH, —OH, —$NH_2$, ═O, —C(═O)—$C_{1-6}$ alkyl, —C(═O)—$C_{1-6}$ alkoxy, $C_{1-6}$ alkyl, $C_{1-6}$ alkoxy, $C_{1-6}$ haloalkyl or $C_{1-6}$ haloalkoxy;

W is —$OCH_2COOH$, —NHC(═O)COOH, —$NHCH_2COOH$,

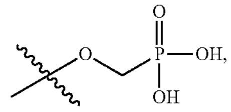

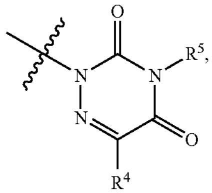

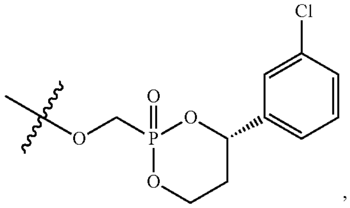

,

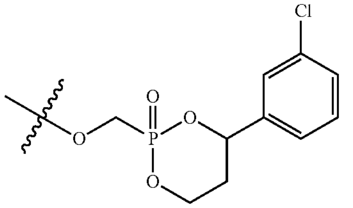

or

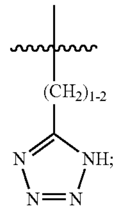

$R^4$ is H, deuterium, F, Cl, Br, I, —CN, —$NO_2$, —COOH, —OH, —$NH_2$, —SH, $C_{1-6}$ alkyl, $C_{2-6}$ alkenyl, $C_{2-6}$ alkynyl, —C(═O)—$C_{1-6}$ alkoxy, —C(═O)—$C_{1-6}$ alkyl, —C(═O)—$C_{1-6}$ alkylamino, —C(═O)$NH_2$, —S(═O)$_2$—$C_{1-6}$ alkyl, —S(═O)$_2$—$C_{1-6}$ alkylamino, $C_{1-6}$ alkylamino, $C_{1-6}$ alkoxy, $C_{1-6}$ haloalkyl, $C_{1-6}$ haloalkoxy, hydroxy $C_{1-6}$ alkyl, amino $C_{1-6}$ alkyl, carboxy $C_{1-6}$ alkyl or cyano $C_{1-6}$ alkyl, wherein each of the $C_{1-6}$ alkyl, $C_{2-6}$ alkenyl, $C_{2-6}$ alkynyl, —C(═O)—$C_{1-6}$ alkoxy, —C(═O)—$C_{1-6}$ alkyl, —C(═O)—$C_{1-6}$ alkylamino, —C(═O)$NH_2$, —S(═O)$_2$—$C_{1-6}$ alkyl, —S(═O)$_2$—$C_{1-6}$ alkylamino, $C_{1-6}$ alkylamino, $C_{1-6}$ alkoxy, $C_{1-6}$ haloalkyl, $C_{1-6}$ haloalkoxy, hydroxy $C_{1-6}$ alkyl, amino $C_{1-6}$ alkyl, carboxy $C_{1-6}$ alkyl and cyano $C_{1-6}$ alkyl is independently unsubstituted or substituted with 1, 2 or 3 substituents selected from deuterium, F, Cl, Br, I, —CN, —$NO_2$, —COOH, —OH, —$NH_2$, —SH, $C_{1-6}$ alkyl, $C_{2-6}$ alkenyl or $C_{2-6}$ alkynyl;

$R^5$ is H, deuterium, $C_{1-6}$ alkyl, $C_{2-6}$ alkenyl, $C_{2-6}$ alkynyl, $C_{3-6}$ cycloalkyl, 5-6 membered heterocyclyl, $C_{6-10}$ aryl or 5-6 membered heteroaryl.

In some embodiments, each of $R^{3a}$, $R^{3b}$, $R^{3c}$, and $R^{3d}$ is independently H, deuterium, F, Cl, Br, I, —CN, —$NO_2$, —COOH, —OH, $NH_2$, —SH, methyl, ethyl, n-propyl, isopropyl, methoxy, ethoxy, methylthio, methylamino, —$CF_3$, —$CHF_2$, —$CH_2F$, —$CH_2CF_3$, trifluoromethoxy, difluoromethoxy, hydroxymethyl, aminomethyl or cyanomethyl.

In some embodiments, each of $R^a$, $R^b$, $R^c$, $R^d$ and $R^e$ is independently H, deuterium, F, Cl, Br, I, —CN, —$NO_2$, —COOH, —OH, $NH_2$, —SH, methyl, ethyl, n-propyl, isopropyl, methoxy, ethoxy, —$CF_3$, —$CHF_2$, —$CH_2F$, —$CH_2CF_3$ or trifluoromethoxy.

In some embodiments, $R^z$ is deuterium, F, Cl, Br, I, —CN, —$NO_2$, —COOH, —$NH_2$, —SH, methyl, ethyl, n-propyl, isopropyl, n-butyl, tert-butyl, trifluoromethyl, difluoromethyl, trifluoromethoxy, difluoromethoxy, methoxy, ethoxy, n-propoxy, isopropoxy, $C_{2-4}$ alkenyl, $C_{2-4}$ alkynyl, hydroxymethyl, hydroxyethyl, hydroxypropyl, $C_{3-6}$ cycloalkyl, $C_{3-6}$ cycloalkyl $C_{1-3}$ alkyl, 5-6 membered heterocyclyl, (5-6 membered heterocyclyl) $C_{1-3}$ alkyl, phenyl, phenylmethyl, phenylethyl, pyridyl, pyrimidinyl, pyridazinyl, pyrrolyl, pyridylmethyl, pyridylethyl or pyrimidinylmethyl;

each of $R^2$ and $R^3$ is independently H, deuterium, F, Cl, Br, I, —CN, —$NO_2$, —COOH, —$NH_2$, —SH, methyl, ethyl, n-propyl, isopropyl, n-butyl, tert-butyl, trifluoromethyl, difluoromethyl, trifluoromethoxy, difluoromethoxy, methoxy, ethoxy, n-propoxy, isopropoxy, $C_{2-4}$ alkenyl, $C_{2-4}$ alkynyl, hydroxymethyl, hydroxyethyl, hydroxypropyl, $C_{3-6}$ cycloalkyl, $C_{3-6}$ cycloalkyl $C_{1-3}$ alkyl, 5-6 membered heterocyclyl, (5-6 membered heterocyclyl) $C_{1-3}$ alkyl, phenyl, phenylmethyl, phenylethyl, pyridyl, pyrimidinyl, pyridazinyl, pyrrolyl, pyridylmethyl, pyridylethyl or pyrimidinylmethyl.

In some embodiments, $R^1$ is H, deuterium, F, Cl, Br, I, —CN, —$NO_2$, —COOH, —C(═O)$NH_2$, —S(═O)$_2$$NH_2$, —OH, —$NH_2$, —SH, $C_{1-4}$ alkyl, $C_{1-4}$ alkoxy, $C_{1-4}$ haloalkyl, $C_{1-4}$ haloalkoxy, —C(═O)—$C_{1-4}$ alkoxy, —C(═O)—$C_{1-4}$ alkylamino, —C(═O)—$C_{1-4}$ alkyl, —S(═O)$_2$—$C_{1-4}$ alkyl, —S(═O)$_2$—$C_{1-4}$ alkylamino, $C_{2-4}$ alkenyl, $C_{2-4}$ alkynyl, $C_{3-6}$ cycloalkyl, 5-6 membered heterocyclyl, $C_{6-10}$ aryl or 5-6 membered heterocyclyl, wherein each of the $C_{1-4}$ alkyl, $C_{1-4}$ alkoxy, $C_{1-4}$ haloalkyl, $C_{1-4}$ haloalkoxy, —C(═O)—$C_{1-4}$ alkoxy, —C(═O)—$C_{1-4}$ alkylamino, —C(═O)—$C_{1-4}$ alkyl, —S(═O)$_2$—$C_{1-4}$ alkyl, —S(═O)$_2$ —$C_{1-4}$ alkylamino, $C_{2-4}$ alkenyl, $C_{2-4}$ alkynyl, $C_{3-6}$ cycloalkyl, 5-6 membered heterocyclyl, $C_{6-10}$ aryl and 5-6 membered heterocyclyl is independently unsubstituted or substituted with 1, 2 or 3 substituents selected from Deuterium, F, Cl, Br, I, —CN, —$NO_2$, —COOH, —C(═O)$NH_2$, —S(═O)$_2$$NH_2$, —SH, —OH, —$NH_2$, ═O, —C(═O)—$C_{1-4}$ alkyl, —C(═O)—$C_{1-4}$ alkoxy, $C_{1-4}$ alkyl, $C_{1-4}$ alkoxy, $C_{1-4}$ haloalkyl or $C_{1-4}$ haloalkoxy.

In some embodiments, $R^1$ is H, deuterium, F, Cl, Br, I, —CN, —$NO_2$, —COOH, —C(═O)$NH_2$, —S(═O)$_2$$NH_2$, —OH, —$NH_2$, —SH, methyl, ethyl, n-propyl, isopropyl, n-butyl, isobutyl, sec-butyl, tert-butyl, methoxy, ethoxy, n-propoxy, isopropoxy, —$CF_3$, —$CHF_2$, —$CH_2F$, —$CH_2CF_3$, trifluoromethoxy, difluoromethoxy, —C(═O)—$OCH_3$, —C(═O)—$OCH_2CH_3$, —C(═O)—$OCH(CH_3)_2$, —C(═O)—$OCH_2CH_2CH_3$, —C(═O)—O$(CH_2)_3CH_3$, —C(═O)—$OCH_2CH(CH_3)_2$, —C(═O)—$NHCH_3$, —C(═O)—$N(CH_3)_2$, —C(═O)—$CH_3$, —C(═O)—$CH_2CH_3$, —S(═O)$_2$—$CH_3$, —S(═O)$_2$—$CH_2CH_3$, —S(═O)$_2$—$CH_2CH_2CH_3$, —S(═O)$_2$—$NHCH_3$, —S(═O)$_2$—$N(CH_3)_2$, —CH═$CH_2$, —$CH_2$CH═$CH_2$, —CH═$CHCH_3$, —C≡CH, cyclopropyl, cyclobutyl, cyclopentyl, cyclohexyl, pyrrolidinyl, pyrazolidinyl, imidazolidinyl, piperidinyl, morpholinyl, thiomorpholinyl, piperazinyl, tetrahydropyrrolyl, tetrahydrofuranyl, tetrahydropyranyl, tetrahydrothienyl, tetrahydropyridinyl, tetrahydropyrimidinyl, tetrahydropyrazinyl, tetrahydropyridazinyl, dihydropyrrolyl, dihydrofuranyl, dihydropyranyl, dihydrothienyl, dihydropyridyl, dihydropyrimidinyl, dihydropyrazinyl, dihydropyridazinyl, phenyl, naphthyl, furyl, thienyl, imidazolyl, pyrazolyl, pyrimidinyl, pyridyl, pyrrolyl, pyrazinyl, pyridazinyl, thiazolyl, tetrazolyl, triazolyl, isoxazolyl, isothiazolyl, oxadiazolyl or oxazolyl, wherein each of the methyl, ethyl, n-propyl, isopropyl, n-butyl, isobutyl, sec-butyl, tert-butyl, methoxy, ethoxy, n-propoxy, isopropoxy, —$CHF_2$, —$CH_2F$, —$CH_2CF_3$, difluoromethoxy, —C(═O)—$OCH_3$, —C(═O)—$OCH_2CH_3$, —C(═O)—$OCH(CH_3)_2$, —C(═O)—$OCH_2CH_2CH_3$, —C(═O)—O$(CH_2)_3CH_3$, —C(═O)—$OCH_2CH(CH_3)_2$, —C(═O)—$NHCH_3$, —C(═O)—$N(CH_3)_2$, —C(═O)—$CH_3$, —C(═O)—$CH_2CH_3$, —S(═O)$_2$—$CH_3$, —S(═O)$_2$—$CH_2CH_3$, —S(═O)$_2$—$CH_2CH_2CH_3$, —S(═O)$_2$—$NHCH_3$, —S(═O)$_2$—$N(CH_3)_2$, —CH═$CH_2$, —$CH_2$CH═$CH_2$, —CH═$CHCH_3$, —C≡CH, cyclopropyl, cyclobutyl, cyclopentyl, cyclohexyl, pyrrolidinyl, pyrazolidinyl, imidazolidinyl, piperidinyl, morpholinyl, thiomorpholinyl, piperazinyl, tetrahydropyrrolyl, tetrahydrofuranyl, tetrahydropyranyl, tetrahydrothienyl, tetrahydropyridinyl, tetrahydropyrimidinyl, tetrahydropyrazinyl, tetrahydropyridazinyl, dihydropyrrolyl, dihydrofuranyl, dihydropyranyl, dihydrothienyl, dihydropyridyl, dihydropyrimidinyl, dihydropyrazinyl, dihydropyridazinyl, phenyl, naphthyl, furyl, thienyl, imidazolyl, pyrazolyl, pyrimidinyl, pyridyl, pyrrolyl, pyrazinyl, pyridazinyl, thiazolyl, tetrazolyl, triazolyl, isoxazolyl, isothiazolyl, oxadiazolyl and oxazolyl is independently unsubstituted or substituted with 1, 2 or 3 substituents selected from deuterium, F, Cl, Br, I, —CN, —$NO_2$, —COOH, —C(═O)$NH_2$, —S(═O)$_2$$NH_2$, —SH, —OH, —$NH_2$, ═O, —C(═O)—$CH_3$, —C(═O)—$CH_2CH_3$, —C(═O)—$OCH_3$, —C(═O)—$OCH_2CH_3$, —C(═O)—$OCH(CH_3)_2$, —C(═O)—$OCH_2CH_2CH_3$, —C(═O)—O$(CH_2)_3CH_3$, —C(═O)—$OCH_2CH(CH_3)_2$, —C(═O)—$CH_3$, —C(═O)—$CH_2CH_3$, methyl, ethyl, n-propyl, isopropyl, methoxy, ethoxy, n-propoxy, isopropoxy, —$CF_3$, —$CHF_2$, —$CH_2CF_3$, trifluoromethoxy or difluoromethoxy.

In some embodiments, $R^4$ is H, deuterium, F, Cl, Br, I, —CN, —$NO_2$, —COOH, —OH, —$NH_2$, —SH, methyl, ethyl, n-propyl, isopropyl, —CH═$CH_2$, —$CH_2$CH═$CH_2$, —CH═$CHCH_3$, —C≡CH, —C(═O)—$OCH_3$, —C(═O)—$OCH_2CH_3$, —C(═O)—$OCH(CH_3)_2$, —C(═O)—$OCH_2CH_2CH_3$, —C(═O)—O$(CH_2)_3CH_3$, —C(═O)—$OCH_2CH(CH_3)_2$, —C(═O)—$CH_3$, —C(═O)—$CH_2CH_3$, —C(═O)—$NHCH_3$, —C(═O)—N$(CH_3)_2$, —C(═O)$NH_2$, —S(═O)$_2$—$CH_3$, —S(═O)$_2$—$CH_2CH_3$, —S(═O)$_2$—$NHCH_3$, methylamino, ethylamino, methoxy, ethoxy, —$CF_3$, —$CHF_2$, —$CH_2F$, —$CH_2CF_3$, —$CH_2CHF_2$, trifluoromethoxy, difluoromethoxy, hydroxymethyl, aminomethyl, carboxymethyl or cyanomethyl, wherein each of the methyl, ethyl, n-propyl, isopropyl, —CH═$CH_2$, —$CH_2$CH═$CH_2$, —CH═$CHCH_3$, —C≡CH, —C(═O)—$OCH_3$, —C(═O)—$OCH_2CH_3$, —C(═O)—$OCH(CH_3)_2$, —C(═O)—$OCH_2CH_2CH_3$, —C(═O)—O$(CH_2)_3CH_3$, —C(═O)—$OCH_2CH(CH_3)_2$, —C(═O)—$CH_3$, —C(═O)—$CH_2CH_3$, —C(═O)—$NHCH_3$, —C(═O)—$N(CH_3)_2$, —C(═O)$NH_2$, S(═O)$_2$—$CH_3$, —S(═O)$_2$—$CH_2CH_3$, —S(═O)$_2$—$NHCH_3$, methylamino, ethylamino, methoxy, ethoxy, —$CHF_2$, —$CH_2F$, —$CH_2CF_3$, —$CH_2CHF_2$, difluoromethoxy, hydroxymethyl, aminomethyl, carboxymethyl and cyanomethyl is independently unsubstituted or substituted with 1, 2 or 3 substituents selected from deuterium, F, Cl, Br, I, —CN, —$NO_2$, —COOH, —OH, —$NH_2$, —SH, $C_{1-6}$ alkyl, $C_{2-6}$ alkenyl or $C_{2-6}$ alkynyl.

In some embodiments, $R^5$ is H, deuterium, methyl, ethyl, n-propyl, isopropyl, tert-butyl, —CH═$CH_2$, —$CH_2$CH═$CH_2$, —CH═$CHCH_3$, —C≡CH, cyclopropyl, cyclobutyl, cyclopentyl, cyclohexyl, 5-6 membered heterocyclyl, phenyl, naphthyl or 5-6 membered heteroaryl.

In another aspect, the invention relates to a pharmaceutical composition comprising the compound of the invention, optionally further comprising any one of a pharmaceutically acceptable carrier, excipient, adjuvant, vehicle or a combination thereof.

In another aspect, the present invention relates to use of the compound or the pharmaceutical composition of the present invention in the manufacture of a medicament for agonizing thyroid hormone receptors; or for preventing, treating or alleviating diseases mediated by agonistic thyroid hormone receptors in a subject.

In some embodiments, the thyroid hormone receptor of the present invention is a thyroid hormone β receptor.

In some embodiments, the disease mediated by agonistic thyroid hormone receptors of the present invention is non-alcoholic fatty liver disease, atherosclerosis, coronary heart disease, hypertension, hypercholesterolemia, hyperlipidemia, hypertriglyceridemia, dyslipidemia, obesity, diabetes, metabolic disorders, type 1A glycogen storage disease, hypothyroidism or thyroid cancer.

In some embodiments, the non-alcoholic fatty liver disease of the present invention is non-alcoholic simple fatty liver, non-alcoholic steatohepatitis, cryptogenic cirrhosis or primary liver cancer.

In some embodiments, the metabolic disorders of the present invention are lipid metabolism disorders or glucose metabolism disorders.

The foregoing merely summarizes certain aspects disclosed herein and is not intended to be limiting in nature. These aspects and other aspects and embodiments are described more fully below.

EXAMPLES

The present invention provides a class of compounds with good agonistic activity on thyroid hormone 3 receptor, a preparation method, a pharmaceutical composition containing the compound and use thereof. Skilled in the art can learn from this article to properly improve the process parameters to implement the preparation method. Of particular note is that all similar substitutions and modifications to the skilled person is obvious, and they are deemed to be included in the present invention.

DEFINITIONS AND GENERAL TERMINOLOGY

Reference will now be made in detail to certain embodiments of the invention, examples of which are illustrated in the accompanying structures and formulas. The invention is intended to cover all alternatives, modifications, and equivalents which may be included within the scope of the present invention. One skilled in the art will recognize many methods and materials similar or equivalent to those described herein, which could be used in the practice of the present invention. The present invention is by no means limited to the methods and materials described herein. In the event that one or more of the incorporated literature, patents, and similar materials differs from or contradicts this application, including but not limited to defined terms, term usage, described techniques, or the like, this application controls.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

Unless defined otherwise, all technical and scientific terms used herein have the same meaning as is commonly understood by one skilled in the art to which this invention belongs. All patents and publications referred to herein are incorporated by reference in their entirety.

As used herein, the following definitions shall apply unless otherwise indicated. For purposes of this invention, the chemical elements are identified in accordance with the Periodic Table of the Elements, CAS version, and the Handbook of Chemistry and Physics, 75th Ed. 1994. Additionally, general principles of organic chemistry are described in "Organic Chemistry", Thomas Sorrell, University Science Books, Sausalito: 1999, and Smith et al., "March's Advanced Organic Chemistry", John Wiley & Sons, New York: 2007, the entire contents of which are hereby incorporated by reference.

The grammatical articles "a", "an" and "the", as used herein, are intended to include "at least one" or "one or more" unless otherwise indicated herein or clearly contradicted by the context. Thus, the articles used herein refer to one or more than one (i.e. at least one) articles of the grammatical objects. By way of example, "a component" means one or more components, and thus, possibly, more than one component is contemplated and may be employed or used in an implementation of the described embodiments.

Unless otherwise stated, the terms used in the specification and claims of the present invention have the following definitions.

The term "comprise" is an open expression, it means comprising the contents disclosed herein, but don't exclude other contents.

As described herein, compounds disclosed herein may optionally be substituted with one or more substituents, such as are illustrated generally below, or as exemplified by particular classes, subclasses, and species of the invention. It will be appreciated that the phrase "optionally substituted" is used interchangeably with the phrase "substituted or unsubstituted". The terms "optionally" or "optional" mean that the subsequently described event or condition can but does not necessarily occur, and the description includes the case where the event or condition occurs, and the case where the event or condition does not occur. In general, unless otherwise indicated, an optionally substituted group may have a substituent at each substitutable position of the group. When more than one position in a given structure can be substituted with more than one substituent selected from a specified group, the substituent may be either the same or different at each position. The substituents described herein may be, but are not limited to, H, deuterium, F, Cl, Br, I, $-CN$, $-NO_2$, $-COOH$, $-C(=O)NH_2$, $-S(=O)_2NH_2$, $-OH$, $=O$, $-NH_2$, $-SH$, $-OCH_2COOH$, $-NHC(=O)COOH$, $-NHCH_2COOH$,

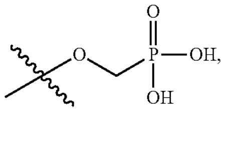
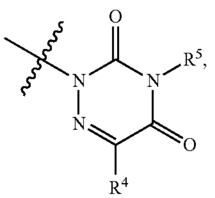
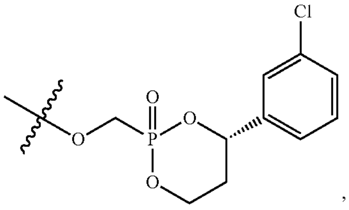
,

-continued

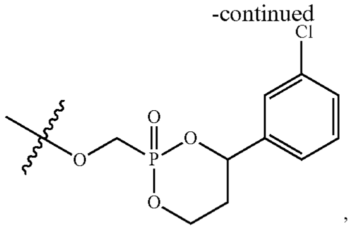

,

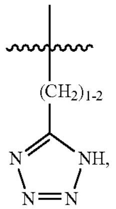

—C(═O)-alkoxy, —C(═O)-alkyl, —C(═O)-alkylamino, —S(═O)$_2$-alkyl, —S(═O)$_2$—$C_{1-6}$ alkylamino, alkyl, alkoxy, alkylthio, alkylamino, haloalkyl, haloalkoxy, hydroxyalkyl, aminoalkyl, cyanoalkyl, carboxyalkyl, alkenyl, alkynyl, cycloalkyl, carbocyclyl, heterocyclyl, aryl, heteroaryl, etc., wherein the $R^4$ and $R^5$ have the definitions described herein.

Furthermore, what need to be explained is that the phrases "each . . . is independently" and "each of . . . and . . . is independently", unless otherwise stated, should be broadly understood, which can mean that the specific options expressed by the same symbol are independent of each other in different groups; or the specific options expressed by the same symbol are independent of each other in same groups.

At each part of the present specification, substitutes of compounds disclosed herein are disclosed in groups or in ranges. It is specifically intended that the invention includes each and every individual subcombination of the members of such groups and ranges. For example, the term "$C_{1-6}$ alkyl" particularly refers to independently disclosed $C_1$ alkyl (methyl), $C_2$ alkyl (ethyl), $C_3$ alkyl, $C_4$ alkyl, $C_5$ alkyl, and $C_6$ alkyl; "$C_{3-8}$ cycloalkyl" especially refers to independently disclosed $C_3$ cycloalkyl, $C_4$ cycloalkyl, $C_5$ cycloalkyl, $C_6$ cycloalkyl, $C_7$ cycloalkyl and $C_8$ cycloalkyl; "5-8 membered heteroaryl" refers to a heteroaryl consisting of 5 ring atoms, a heteroaryl consisting of 6 ring atoms, a heteroaryl consisting of 7 ring atoms and a heteroaryl consisting of 8 ring atoms.

At various places in the present specification, linking substituents are described. Where the structure clearly requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "alkyl" or "alkyl group" refers to a saturated linear or branched-chain monovalent hydrocarbon group of 1-20 carbon atoms, wherein the alkyl group is optionally substituted with one or more substituents described herein. In some embodiments, the alkyl group contains 1-10 carbon atoms, i.e., $C_{1-10}$ alkyl. In some embodiments, the alkyl group contains 1-8 carbon atoms, i.e., $C_{1-8}$ alkyl. In other embodiments, the alkyl group contains 1-6 carbon atoms, i.e., $C_{1-6}$ alkyl. In other embodiments, the alkyl group contains 1-4 carbon atoms, i.e., $C_{1-4}$ alkyl. In still other embodiment, the alkyl group contains 1-3 carbon atoms, i.e., $C_{1-3}$ alkyl. In yet other embodiment, the alkyl group contains 1-2 carbon atoms, i.e., $C_{1-2}$ alkyl.

Some non-limiting examples of the alkyl group include, methyl (Me, —$CH_3$), ethyl (Et, —$CH_2CH_3$), n-propyl (n-Pr, —$CH_2CH_2CH_3$), isopropyl (i-Pr, —$CH(CH_3)_2$), n-butyl (n-Bu, —$CH_2CH_2CH_2CH_3$), isobutyl (i-Bu, —$CH_2CH(CH_3)_2$), sec-butyl (s-Bu, —$CH(CH_3)CH_2CH_3$), tert-butyl (t-Bu, —$C(CH_3)_3$), n-pentyl (—$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), n-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$)), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, n-heptyl and n-octyl, etc.

The term "alkenyl" refers to linear or branched-chain monovalent hydrocarbon radical of 2 to 12 carbon atoms with at least one site of unsaturation, i.e., a carbon-carbon, $sp^2$ double bond, wherein the alkenyl radical may be optionally substituted with one or more substituents described herein, and includes radicals having "cis" and "trans" orientations, or alternatively, "E" and "Z" orientations. In some embodiments, the alkenyl contains 2 to 8 carbon atoms, i.e. $C_{2-8}$ alkenyl. In other embodiments, the alkenyl contains 2 to 6 carbon atoms, i.e., $C_{2-6}$ alkenyl. In still other embodiments, the alkenyl contains 2 to 4 carbon atoms, i.e., $C_{2-4}$ alkenyl.

Some non-limiting examples of the alkenyl group include vinyl (—CH═$CH_2$), allyl (—$CH_2$CH═$CH_2$), propenyl (—CH═$CHCH_3$), butenyl (—CH═$CHCH_2CH_3$, —$CH_2$CH═$CHCH_3$, —$CH_2CH_2$CH═$CH_2$, —CH═$C(CH_3)_2$, —CH═$C(CH_3)_2$, —$CH_2C(CH_3)$═$CH_2$), pentenyl (—$CH_2CH_2CH_2$CH═$CH_2$, —$CH_2CH_2$CH═$CHCH_3$, —$CH_2CH_2$CH═$CHCH_3$, —$CH_2$CH═$CHCH_2CH_3$, —CH═$CHCH_2CH_2CH_3$, —$CH_2CH_2C(CH_3)$═$CH_2$, —$CH_2$CH═$C(CH_3)_2$, —CH═$CHCH(CH_3)_2$, —$C(CH_2CH_3)$═$CHCH_3$, —$CH(CH_2CH_3)$CH═$CH_2$), and so on.

The term "alkynyl" refers to a linear or branched monovalent hydrocarbon radical of 2 to 12 carbon atoms with at least one site of unsaturation, i.e., a carbon-carbon, sp triple bond, wherein the alkynyl radical may be optionally substituted with one or more substituents described herein. In some embodiments, the alkynyl contains 2 to 8 carbon atoms, i.e., $C_{2-8}$ alkynyl. In other embodiments, the alkynyl contains 2 to 6 carbon atoms, i.e., $C_{2-6}$ alkynyl. In still other embodiments, the alkynyl contains 2 to 4 carbon atoms, i.e., $C_{2-4}$ alkynyl. Some non-limiting examples of the alkynyl group include ethynyl (—C≡CH), 1-propynyl (—C≡CH—$CH_3$), propargyl (—$CH_2$C≡CH), 1-butynyl, 2-butynyl, 1-pentynyl, 2-pentynyl, 3-methyl-1-butynyl, 1-hexynyl, 1-heptynyl and 1-octynyl, etc.

The term "alkoxy" refers to an alkyl group, as previously defined, attached to parent molecular moiety via an oxygen atom, i.e., —O-alkyl, wherein the alkoxy group may be optionally substituted with one or more substituents described in the present invention. In some embodiments, the alkoxy group contains 1-8 carbon atoms, i.e., $C_{1-6}$ alkoxy. In other embodiments, the alkoxy group contains 1-6 carbon atoms, i.e., $C_{1-6}$ alkoxy. In other embodiments, the alkoxy group contains 1-4 carbon atoms, i.e., $C_{1-4}$ alkoxy. In still other embodiments, the alkoxy group contains 1-3 carbon atoms, i.e., $C_{1-3}$ alkoxy. In yet other embodiments, the alkoxy group contains 1-2 carbon atoms, i.e., $C_{1-2}$ alkoxy.

Some non-limiting examples of the alkoxy group include, but are not limited to, methoxy (MeO, —$OCH_3$), ethoxy (EtO, —$OCH_2CH_3$), n-propyloxy (n-PrO, n-propoxy, —$OCH_2CH_2CH_3$), isopropyloxy (i-PrO, i-propoxy, —OCH $(CH_3)_2$), 1-butoxy (n-BuO, n-butoxy, $—OCH_2CH_2CH_2CH_3$), 2-methyl-1-propoxy (i-BuO, i-butoxy, $—OCH_2CH(CH_3)_2$), 2-butoxy (s-BuO, s-butoxy, $—OCH(CH_3)CH_2CH_3$), 2-methyl-isopropyloxy (t-BuO, t-butoxy, $—OC(CH_3)_3$), 1-pentoxy (n-pentoxy, $—OCH_2CH_2CH_2CH_2CH_3$), 2-pentoxy ($—OCH(CH_3)CH_2CH_2CH_3$), 3-pentoxy ($—OCH(CH_2CH_3)_2$), 2-methyl-2-butoxy ($—OC(CH_3)_2CH_2CH_3$), 3-methyl-2-butoxy ($—OCH(CH_3)CH(CH_3)_2$), 3-methyl-1-butoxy ($—OCH_2CH_2CH(CH_3)_2$), 2-methyl-1-butoxy ($—OCH_2CH(CH_3)CH_2CH_3$), and the like.

The term "alkylamino" embraces "N-alkylamino" and "N,N-dialkylamino", i.e., an amino group is independently substituted with one or two alkyl radicals and wherein the alkyl group is as defined herein. Wherein, the alkyl group may be optionally substituted with one or more substituents disclosed herein. In some embodiments, the alkylamino group is one or two $C_{1-6}$ alkyl groups attached to a nitrogen atom, i.e., $C_{1-6}$ alkylamino. In some embodiments, the alkylamino group is one or two $C_{1-4}$ alkyl groups attached to a nitrogen atom, i.e., $C_{1-4}$ alkylamino. In some embodiments, the alkylamino group is one or two $C_{1-2}$ alkyl groups attached to a nitrogen atom, i.e., $C_{1-2}$ alkylamino. Examples of alkylamino groups include, but are not limited to, methylamino (N-methylamino), ethylamino (N-ethylamino), dimethylamino (N,N-dimethylamino), diethylamino (N,N-diethylamino), n-propylamino (N-n-propylamino), isopropylamino (N-isopropylamino), tert-butylamino (N-tert-butylamino) and so on.

The term "alkylthio" refers to an alkyl group, as previously defined, attached to parent molecular moiety via a sulfur atom, i.e., —S-alkyl, wherein the alkylthio group may be optionally substituted with one or more substituents described in the present invention. In some embodiments, the alkylthio group contains 1-8 carbon atoms, i.e., $C_{1-8}$ alkylthio. In other embodiments, the alkylthio group contains 1-6 carbon atoms, i.e., $C_{1-6}$ alkylthio. In other embodiments, the alkylthio group contains 1-4 carbon atoms, i.e., $C_{1-4}$ alkylthio. In still other embodiments, the alkylthio group contains 1-3 carbon atoms, i.e., $C_{1-3}$ alkylthio. In yet other embodiments, the alkylthio group contains 1-2 carbon atoms, i.e., $C_{1-2}$ alkylthio. Examples of alkylthio group include, but are not limited to, methylthio ($—SCH_3$) and ethylthio ($—SCH_2CH_3$) and so on.

The term "haloalkyl" refers to an alkyl group having one or more halogen substituents, wherein the haloalkyl group may be optionally substituted with one or more substituents disclosed herein. In some embodiments, the haloalkyl group contains 1-10 carbon atoms, i.e., $C_{1-10}$ haloalkyl. In some embodiments, the haloalkyl group contains 1-8 carbon atoms, i.e., $C_{1-8}$ haloalkyl. In other embodiments, the haloalkyl group contains 1-6 carbon atoms, i.e., $C_{1-6}$ haloalkyl. In other embodiments, the haloalkyl group contains 1-4 carbon atoms, i.e., $C_{1-4}$ haloalkyl. In still other embodiment, the haloalkyl group contains 1-3 carbon atoms, i.e., $C_{1-3}$ haloalkyl. In yet other embodiment, the haloalkyl group contains 1-2 carbon atoms, i.e., $C_{1-2}$ haloalkyl. Examples of haloalkyl groups include, but are not limited to, fluoromethyl ($—CH_2F$), difluoromethyl ($—CHF_2$), trifluoromethyl ($—CF_3$), fluoroethyl ($—CHFCH_3$, $—CH_2CH_2F$), difluoroethyl ($—CF_2CH_3$, $—CFHCFH_2$, $—CH_2CHF_2$), perfluoroethyl, fluoropropyl ($—CHFCH_2CH_3$, $—CH_2CHFCH_3$, $—CH_2CH_2CH_2F$), difluoropropyl ($—CF_2CH_2CH_3$, $—CFHCFHCH_3$, $—CH_2CH_2CHF_2$, $—CH_2CF_2CH_3$, $—CH_2CHFCH_2F$), trifluoropropyl ($—CH_2CH_2CF_3$), 1,1-dichloroethyl, 1,2-dichloropropyl, etc.

The term "haloalkoxy" refers to an alkoxy group having one or more halogen substituents, wherein the haloalkoxy group may be optionally substituted with one or more substituents disclosed herein. In some embodiments, the haloalkoxy group contains 1-10 carbon atoms, i.e., $C_{1-10}$ haloalkoxy. In some embodiments, the haloalkoxy group contains 1-8 carbon atoms, i.e., $C_{1-8}$ haloalkoxy. In other embodiments, the haloalkoxy group contains 1-6 carbon atoms, i.e., $C_{1-6}$ haloalkoxy. In other embodiments, the haloalkoxy group contains 1-4 carbon atoms, i.e., $C_{1-4}$ haloalkoxy. In still other embodiment, the haloalkoxy group contains 1-3 carbon atoms, i.e., $C_{1-3}$ haloalkoxy. In yet other embodiment, the haloalkoxy group contains 1-2 carbon atoms, i.e., $C_{1-2}$ haloalkoxy. Some non-limiting examples of the haloalkoxy group include trifluoromethoxy ($—OCF_3$), difluoromethoxy ($—OCHF_2$), etc.

The term "hydroxyalkyl" refers to an alkyl group substituted with one or more hydroxy groups (—OH), wherein the alkyl group are as defined herein, wherein the hydroxyalkyl group may be optionally substituted with one or more substituents disclosed herein. In some embodiments, the hydroxyalkyl group in the present invention refers to $C_{1-6}$ alkyl substituted with one or more hydroxy groups (—OH), i.e., hydroxy $C_{1-6}$ alkyl; in some embodiments, the hydroxyalkyl group refers to $C_{1-4}$ alkyl substituted with one or more hydroxy groups (—OH), i.e., hydroxy $C_{1-4}$ alkyl; in some embodiments, the hydroxyalkyl group refers to $C_{1-2}$ alkyl substituted with one or more hydroxy groups (—OH), i.e., hydroxy $C_{1-2}$ alkyl. Examples of hydroxyalkyl groups include, but are not limited to, hydroxymethyl (e.g., $—CH_2OH$), hydroxyethyl (e.g., 2-hydroxyethyl), hydroxy-n-propyl (e.g., $—CH_2CH_2CH_2OH$), and the like.

The term "aminoalkyl" refers to an alkyl group substituted with one or more amino groups ($—NH_2$), wherein the alkyl group are as defined herein, wherein the aminoalkyl group may be optionally substituted with one or more substituents disclosed herein. In some embodiments, the aminoalkyl group in the present invention refers to $C_{1-6}$ alkyl substituted with one or more amino groups ($—NH_2$), i.e., amino $C_{1-6}$ alkyl; in some embodiments, the aminoalkyl group refers to $C_{1-4}$ alkyl substituted with one or more amino groups ($—NH_2$), i.e., amino $C_{1-4}$ alkyl; in some embodiments, the aminoalkyl group refers to $C_{1-2}$ alkyl substituted with one or more amino groups ($—NH_2$), i.e., amino $C_{1-2}$ alkyl. Examples of aminoalkyl groups include, but are not limited to, aminomethyl ($—CH_2NH_2$), diaminomethyl ($—CH(NH_2)_2$), aminoethyl (e.g., 2-aminoethyl), amino-n-propyl (e.g., $—CH_2CH_2CH_2NH_2$), and so on.

The term "cyanoalkyl" refers to an alkyl group substituted with one or more cyano groups (—CN), wherein the alkyl group are as defined herein, wherein the cyanoalkyl group may be optionally substituted with one or more substituents disclosed herein. In some embodiments, the cyanoalkyl group in the present invention refers to $C_{1-6}$ alkyl substituted with one or more cyano groups (—CN), i.e., cyano $C_{1-6}$ alkyl; in some embodiments, the cyanoalkyl group refers to $C_{1-4}$ alkyl substituted with one or more cyano groups (—CN), i.e., cyano $C_{1-4}$ alkyl; in some embodiments, the cyanoalkyl group refers to $C_{1-2}$ alkyl substituted with one or more cyano groups (—CN), i.e., cyano $C_{1-2}$ alkyl. Examples of cyanoalkyl groups include, but are not limited to, cyanomethyl (e.g., $—CH_2CN$), cyanoethyl (e.g., 2-cyanoethyl), and the like.

The term "carboxyalkyl" refers to an alkyl group substituted with one or more carboxy groups (—COOH), wherein the alkyl group are as defined herein, wherein the carboxyalkyl group may be optionally substituted with one or more substituents disclosed herein. In some embodiments, the carboxyalkyl group in the present invention refers to $C_{1-6}$ alkyl substituted with one or more carboxy groups (—COOH), i.e., carboxy $C_{1-6}$ alkyl; in some embodiments, the carboxyalkyl group refers to $C_{1-4}$ alkyl substituted with one or more carboxy groups (—COOH), i.e., carboxy $C_{1-4}$ alkyl; in some embodiments, the carboxyalkyl group refers to $C_{1-2}$ alkyl substituted with one or more carboxy groups (—COOH), i.e., carboxy $C_{1-2}$ alkyl. Examples of carboxyalkyl groups include, but are not limited to, carboxymethyl, carboxyethyl (e.g., 2-carboxyethyl), and the like.

The term "cycloalkyl" refers to a monovalent or multivalent non-aromatic saturated ring having 3 to 12 ring carbon atoms as a monocyclic, bicyclic, or tricyclic ring system, wherein the cycloalkyl group is optionally substituted with the substituents described in the present invention. In some embodiments, cycloalkyl is a ring system containing 3-10 ring carbon atoms, i.e., $C_{3-10}$ cycloalkyl; in still other embodiments, cycloalkyl is a ring system containing 3-8 ring carbon atoms, i.e., $C_{3-8}$ cycloalkyl; in yet other embodiments, cycloalkyl is a ring system containing 3-6 ring carbon atoms, i.e., $C_{3-6}$ cycloalkyl. Examples of cycloalkyl groups include, but are not limited to, cyclopropyl, cyclobutyl, cyclopentyl, cyclohexyl, cycloheptyl, cyclooctyl, and the like.

The term "carbocycle" or "carbocyclyl" refers to a monovalent or multivalent, nonaromatic, saturated or partially unsaturated ring having 3 to 14 ring carbon atoms as a monocyclic, bicyclic or tricyclic ring system. The terms "carbon ring", "carbocyclyl" or "carbocyclic" can be used interchangeably here. In some embodiments, the ring carbon atom number of the carbocyclyl is 3 to 12, i.e., $C_{3-12}$ carbocyclyl; in other embodiments, the ring carbon atom number of the carbocyclyl is 3 to 10, i.e., $C_{3-10}$ carbocyclyl; in other embodiments, the ring carbon atom number of the carbocyclyl is 3 to 8, i.e., $C_{3-8}$ carbocyclyl; in other embodiments, the ring carbon atom number of the carbocyclyl is 3 to 6, i.e., $C_{3-6}$ carbocyclyl; in other embodiments, the ring carbon atom number of the carbocyclyl is 5 to 6, i.e., $C_{5-6}$ carbocyclyl; in other embodiments, the ring carbon atom number of the carbocyclyl is 5 to 8, i.e., $C_{5-8}$ carbocyclyl. In some embodiments, the ring carbon atom number of the carbocyclyl is 6 to 8, i.e., $C_{6-8}$ carbocyclyl. Some non-limiting examples of the carbocyclyl group include cycloalkyl, cycloalkenyl and cycloalkynyl. Further examples of carbocyclyl group include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, bicyclo[2.2.2]octyl, bicyclo[2.2.1]heptyl, bicyclo[3.3.1]nonyl, bicyclo [3.2.3]nonyl, and the like, The term "heterocyclyl" refers to a saturated or partially unsaturation, nonaromatic ring having 3 to 12 ring atoms as a monocyclic, bicyclic, or tricyclic ring system, in which at least one ring member is selected from heteroatoms such as nitrogen, sulfur, oxygen and phosphorus. Wherein, the heterocyclic group is non-aromatic and does not contain any aromatic ring, and the heterocyclic group ring may be optionally substituted with one or more substituents described in the present invention. The term "heterocyclyl" includes monocyclic, bicyclic or polycyclic fused, spiro or bridged heterocyclic ring systems. Bicyclic heterocyclic groups include bridged bicyclic heterocyclyl, fused bicyclic heterocyclyl and spiro bicyclic heterocyclyl. The terms "heterocyclyl", "heterocyclic group" and "heterocycle" are used interchangeably herein. Unless otherwise specified, the heterocyclyl group may be carbon or nitrogen linked, and a $—CH_2—$ group can be optionally replaced by a —C(═O)— group. In which, the sulfur can be optionally oxygenized to S-oxide, and the nitrogen can be optionally oxygenized to N-oxide, and the phosphorus can be optionally oxygenized to P-oxide. In some embodiments, the heterocyclyl is a ring system composed of 3-10 ring atoms, i.e., 3-10 membered heterocyclyl; in some embodiments, the heterocyclyl is a ring system composed of 5-10 ring atoms, i.e., 5-10 membered heterocyclyl; in some embodiments, the heterocyclyl is a ring system composed of 5-8 ring atoms, i.e., 5-8 membered heterocyclyl; in some embodiments, the heterocyclyl is a ring system composed of 6-8 ring atoms, i.e., 6-8 membered heterocyclyl; in some embodiments, the heterocyclyl is a ring system composed of 5-6 ring atoms, i.e., 5-6 membered heterocyclyl; in other embodiments, the heterocyclyl is a ring system composed of 3-6 ring atoms, i.e., 3-6 membered heterocyclyl; in other embodiments, the heterocyclyl is a ring system composed of 3 ring atoms; in other embodiments, the heterocyclyl is a ring system composed of 4 ring atoms; in other embodiments, the heterocyclyl is a ring system composed of 5 ring atoms; in other embodiments, the heterocyclyl is a ring system composed of 6 ring atoms.

Examples of the heterocyclyl group include, but are not limited to, oxiranyl, azetidinyl, oxetanyl, thietanyl, pyrrolidinyl, 2-pyrrolinyl, 3-pyrrolinyl, pyrazolinyl, pyrazolidinyl, imidazolinyl, imidazolidinyl, tetrahydropyrrolyl, dihydropyrrolyl, tetrahydrofuranyl, dihydrofuranyl, tetrahydropyranyl, dihydropyranyl, tetrahydrothienyl, dihydrothienyl, tetrahydropyridyl, dihydropyridyl (for example, 1,2-dihydropyridyl, 1,4-dihydropyridyl), tetrahydropyrimidinyl, dihydropyrimidinyl, tetrahydropyrazinyl, dihydropyrazinyl, tetrahydropyridazinyl, dihydropyridazinyl, 1,3-dioxopentyl, dithiocyclopentyl, 2H-pyranyl, 4H-pyranyl, tetrahydrothiopyranyl, piperidinyl, morpholinyl, thiomorpholinyl, piperazinyl, dioxanyl, dithianyl, thiazinyl, homopiperazinyl, homopiperidinyl, oxepanyl, thiepanyl, and the like. Some non-limiting examples of heterocyclyl wherein $—CH_2—$ group is replaced by —C(═O)— moiety include 2-oxopyrrolidinyl, oxo-1,3-thiazolidinyl, 2-piperidinonyl and 3,5-dioxopiperidinyl. Some non-limited examples of the heterocyclyl group wherein the ring sulfur atom is oxidized is sulfolanyl and 1,1-dioxo-thiomorpholinyl. Bridged heterocyclyl groups include, but are not limited to, 2-oxabicyclo [2.2.2] octyl, 1-azabicyclo [2.2.2] octyl, 3-azabicyclo [3.2.1] octyl, etc.

The term "m-membered", where m is an integer typically describes the number of ring-forming atoms in a moiety where the number of ring-forming atoms is m. For example, piperidinyl is an example of a 6 membered heterocyclyl group and furanyl is an example of a 5 membered heteroaryl group. As another example, "5-8 membered heteroaryl" refers to a heteroaryl group consisting of 5, 6, 7, or 8 atoms.

The term "aryl" refers to monocyclic, bicyclic and tricyclic aromatic carbocyclic ring systems having 6 to 14 ring atoms, wherein each ring in the system contains 3 to 7 ring atoms. In some embodiments, the aryl group is a carbocyclic ring system having 6-12 ring atoms, i.e., $C_{6-12}$ aryl. In some embodiments, the aryl group is a carbocyclic ring system having 6-10 ring atoms, i.e., $C_{6-10}$ aryl. Wherein the aryl may be optionally substituted with one or more substituents disclosed herein. The term "aryl" may be used interchangeably with the term "aryl ring" or "aromatic ring". Some non-limiting examples of the aryl group include phenyl, indenyl, naphthyl and anthracenyl.

The term "heteroaryl" refers to a monovalent or multivalent monocyclic, bicyclic or tricyclic aromatic systems having 5 to 14 ring atoms, wherein at least one ring member is selected from heteroatom, and each ring in the system contains 5 to 7 ring members and at least one ring in the system is aromatic. Wherein the heteroaryl may be optionally substituted with one or more substituents disclosed herein. Unless otherwise stated, the heteroaryl group may be connected to the rest of the molecule (such as the parent nucleus structure in the general formula) through any reasonable position (which may be C in CH or N in NH). When a —$CH_2$— group is present in the heteroaryl group, the —$CH_2$— group may be optionally replaced by —C(=O)—. The term "heteroaryl" and "heteroaromatic ring" or "heteroaromatic compound" can be used interchangeably herein. In some embodiments, heteroaryl is a heteroaryl group of 5-8 ring atoms comprising 1, 2, 3 or 4 heteroatoms independently selected from O, S, P and N; in other embodiments, heteroaryl is a heteroaryl group of 5-7 ring atoms comprising 1, 2, 3 or 4 heteroatoms independently selected from O, S, P and N; in other embodiments, heteroaryl is a heteroaryl group of 5-6 ring atoms comprising 1, 2, 3 or 4 heteroatoms independently selected from O, S, P and N; in other embodiments, heteroaryl is a heteroaryl group of 5 ring atoms comprising 1, 2, 3 or 4 heteroatoms independently selected from O, S, P and N; in other embodiments, heteroaryl is a heteroaryl group of 6 ring atoms comprising 1, 2, 3 or 4 heteroatoms independently selected from O, S, P and N.

Some non-limiting examples of heteroaryl include the following monocyclic groups: furyl (2-furanyl, 3-furanyl), imidazolyl (N-imidazolyl, 2-imidazolyl, 4-imidazolyl, 5-imidazolyl), isoxazolyl (3-isoxazolyl, 4-isoxazolyl, 5-isoxazolyl), oxazolyl (2-oxazolyl, 4-oxazolyl, 5-oxazolyl), pyrrolyl (N-pyrrolyl, 2-pyrrolyl, 3-pyrrolyl), pyridyl (2-pyridyl, 3-pyridyl, 4-pyridyl), pyrimidinyl (2-pyrimidinyl, 4-pyrimidinyl, 5-pyrimidinyl), pyridazinyl (e.g., 3-pyridazinyl), thiazolyl (2-thiazolyl, 4-thiazolyl, 5-thiazolyl), tetrazolyl (e.g., 5H-tetrazolyl, 2H-tetrazolyl), triazolyl (e.g., 2-triazolyl, 5-triazolyl, 4H-1,2,4-triazolyl, 1H-1,2,4-triazolyl, 1,2,3-triazolyl), thienyl (2-thienyl, 3-thienyl), pyrazolyl (e.g., 2-pyrazolyl and 3-pyrazolyl), isothiazolyl, oxadiazolyl (e.g., 1,2,3-oxadiazolyl, 1,2,5-oxadiazolyl, 1,2,4-oxadiazolyl, 1,3,4-oxadiazolyl), 1,2,3-thiodiazolyl, 1,3,4-thiodiazolyl, 1,2,5-thiodiazolyl, pyrazinyl, 1,3,5-triazinyl, pyridine-2(1H)-keto, pyridine-4(1H)-keto, and the following bi- or tricyclic groups: indolinyl, 1,2,3,4-tetrahydroisoquinolinyl, benzimidazolyl, benzofuryl, benzothiophenyl, indolyl (e.g., 2-indolyl), purinyl, quinolinyl (e.g., 2-quinolinyl, 3-quinolinyl, 4-quinolinyl), isoquinolinyl (e.g., 1-isoquinolinyl, 3-isoquinolinyl or 4-isoquinolinyl), phenoxothiyl, dibenzimidazolyl, dibenzofuranyl, dibenzothienyl.

The terms "cycloalkylalkyl", "heterocyclylalkyl", "arylalkyl" and "heteroarylalkyl" refer to cycloalkyl, heterocyclyl, aryl, and heteroaryl are independently connected with the rest of the molecule through an alkyl group, respectively. The cycloalkyl, heterocyclyl, aryl, heteroaryl and alkyl have the meanings described herein. Such examples include, but are not limited to, cyclopropylmethyl, morpholinylmethyl, piperidinylmethyl, tetrahydrofuranylmethyl, phenylmethyl (i.e., benzyl), phenylethyl, pyridylmethyl, pyridylethyl or pyrimidinylmethyl, and the like.

The term "heteroatom" refers to one or more of oxygen, sulfur, nitrogen, phosphorus and silicon, including any oxidized form of nitrogen, sulfur, or phosphorus; the quaternized form of any basic nitrogen; or a substitutable nitrogen of a heterocyclic ring, for example, N (as in 3,4-dihydro-2H-pyrrolyl), NH (as in pyrrolidinyl) or $NR^T$ (as in N-substituted pyrrolidinyl, $R^T$ is a substituent on N).

The term "halogen" refers to fluoro (F), chloro (Cl), bromo (Br), or iodo (I).

The term "nitro" refers to —$NO_2$.

The term "mercapto" refers to —SH.

The term "hydroxy" refers to —OH.

The term "amino" refers to —$NH_2$.

The term "cyano" refers to —CN.

The term "carboxylic acid" or "carboxy" refers to —C(=O)OH or —COOH.

The term "carbonyl" refers to —(C=O)—.

The term "deuterium" refers to D, i.e., $^2H$.

The term "oxo" refers to =O.

The term "protecting group" or "PG" refers to a substituent that is commonly employed to block or protect a particular functionality while reacting with other functional groups on the compound. For example, an "amino-protecting group" is a substituent attached to an amino group that blocks or protects the amino functionality in the compound. Suitable amino-protecting groups include acetyl, trifluoroacetyl, t-butoxy-carbonyl (BOC, Boc), benzyloxycarbonyl (CBZ, Cbz) and 9-fluorenylmethylenoxy-carbonyl (Fmoc). Similarly, a "hydroxy-protecting group" refers to a substituent of a hydroxy group that blocks or protects the hydroxy functionality. Suitable protecting groups include, but are not limited to, acetyl, benzoyl, benzyl, p-methoxybenzyl, silyl, and the like. A "carboxy-protecting group" refers to a substituent of the carboxy group that blocks or protects the carboxy functionality. Common carboxy-protecting groups include —$CH_2CH_2SO_2Ph$, cyanoethyl, 2-(trimethylsilyl) ethyl, 2-(trimethylsilyl) ethoxy-methyl, 2-(p-toluenesulfonyl) ethyl, 2-(p-nitrophenylsulfonyl)-ethyl, 2-(diphenylphosphino)-ethyl, nitroethyl and the like. For a general description of protecting groups and their use, see T. W. Greene, Protective Groups in Organic Synthesis, John Wiley & Sons, New York, 1991; and P. J. Kocienski, Protecting Groups, Thieme, Stuttgart, 2005.

The term "leaving group" or "LG" refers to an atom or functional group that is detached from a larger molecule in a chemical reaction, and is a term used in nucleophilic substitution reactions and elimination reactions. In a nucleophilic substitution reaction, a reactant attacked by a nucleophilic reagent is called a substrate, and an atom or atomic group that breaks out with a pair of electrons from a substrate molecule is called a leaving group. Common leaving groups are, for example, but not limited to, halogen atoms, ester groups, sulfonate groups, nitro groups, azide groups, or hydroxy groups.

The phrase "pharmaceutically acceptable" refers to that the substance or composition must be chemically and/or toxicologically compatible with the other ingredients comprising a formulation, and/or the mammal being treated therewith. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

The term "carrier" includes any solvents, dispersion media, coating agents, surfactants, antioxidants, preservatives (e.g., antibacterial agents, antifungal agents), isotonic agents, salt, drug stabilizers, binders, excipients, dispersants, lubricants, sweetening agents, flavoring agents, coloring agents, or a combination thereof, all of which are well known to the skilled in the art. (e.g., Remington's Pharmaceutical Sciences, 18th Ed. Mack Printing Company, 1990, pp. 1289-1329, all of which are incorporated herein by reference). Except any conventional carrier is incompatible with the active ingredient, the pharmaceutically acceptable carriers are effectively used in the treatment or pharmaceutical compositions.

The term "pharmaceutical composition" refers to a mixture of one or more of the compounds described herein, or physiologically/pharmaceutically acceptable salts or prodrugs thereof, and other chemical components, such as physiologically/pharmaceutically acceptable carriers, excipients, diluents, binders, fillers, and other additional therapeutic agents, such as anti-diabetic agents, antihyperglycemic agents, antiadipositas agents, antihypertensive agents, antiplatelet agents, antiatherosclerotic agents, lipid-lowering agents, etc. The purpose of the pharmaceutical composition is to facilitate administration of a compound to an organism.

The term "prodrug" refers to a compound that is transformed in vivo into a compound of Formula (I). Such a transformation can be affected, for example, by hydrolysis of the prodrug form in blood or enzymatic transformation to the parent form in blood or tissue. Prodrugs of the compounds disclosed herein may be, for example, esters. Some common esters which have been utilized as prodrugs are phenyl esters, aliphatic ($C_{1-24}$) esters, acyloxymethyl esters, carbonates, carbamates and amino acid esters. For example, a compound disclosed herein that contains a hydroxy group may be acylated at this position in its prodrug form. Other prodrug forms include phosphates, such as, those phosphate compounds derived from the phosphonation of a hydroxy group on the parent compound. A thorough discussion of prodrugs is provided in Higuchi et al., Pro-drugs as Novel Delivery Systems, Vol. 14, A.C.S. Symposium Series; Roche, et al. ed., Bioreversible Carriers in Drug Design, American Pharmaceutical Association and Pergamon Press, 1987; Rautio et al., Prodrugs: Design and Clinical Applications, Nature Reviews Drug Discovery, 2008, 7, 255-270, and Hecker et al., Prodrugs of Phosphates and Phosphonates, J. Med. Chem., 2008, 51, 2328-2345, all of which are incorporated herein by reference in their entireties.

The term "metabolite" refers to a product produced through metabolism in the body of a specified compound or salt thereof. The metabolites of a compound may be identified using routine techniques known in the art and their activities determined using tests such as those described herein. Such products may result for example from oxidation, reduction, hydrolysis, amidation, deamidation, esterification, deesterification, enzyme cleavage, and the like, of the administered compound. Accordingly, the invention includes metabolites of compounds disclosed herein, including metabolites produced by contacting a compound disclosed herein with a mammal for a sufficient time period.

The term "pharmaceutically acceptable salt" refers to organic or inorganic salts of a compound disclosed herein. Pharmaceutically acceptable salts are well known in the art. For example, the pharmaceutically acceptable salts are described in detail in Berge et al., J. Pharmacol Sci, 1977, 66: 1-19, which is incorporated herein by reference in its entirety.

The term "solvate" refers to an association or complex of one or more solvent molecules and a compound disclosed herein. Some non-limiting examples of the solvent that form solvates include water, isopropanol, ethanol, methanol, dimethylsulfoxide (DMSO), ethyl acetate, acetic acid and ethanolamine. The term "hydrate" refers to the complex where the solvent molecule is water.

The term "N-oxide" refers to one or more than one nitrogen atoms oxidised to form an N-oxide, where a compound contains several amine functions. Particular examples of N-oxides are the N-oxides of a tertiary amine or a nitrogen atom of a nitrogen-containing heterocycle. N-oxides can be formed by treatment of the corresponding amine with an oxidizing agent such as hydrogen peroxide or a per-acid (e.g., a peroxycarboxylic acid) (See, Advanced Organic Chemistry, by Jerry March, 4th Edition, Wiley Interscience, pages). More particularly, N-oxides can be made by the procedure of L. W. Deady (Syn. Comm. 1977, 7, 509-514) in which the amine compound is reacted with m-chloroperoxybenzoic acid (MCPBA), for example, in an inert solvent such as dichloromethane.

Any asymmetric atom (e.g., carbon or the like) of the compound(s) disclosed herein can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. If possible, the substituent on the atom having an unsaturated double bond may exist in the form of cis-(Z)- or trans-(E)-.

Therefore, as the invention described, the compound disclosed herein may exist in the form of any possible isomer, rotamer, atropisomer, tautomer, or a mixture thereof, e.g., substantially pure geometric (cis- or trans-) isomer, diastereoisomer, optical isomer (enantiomer), racemate or a mixture thereof.

Any resulting mixtures of stereoisomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by methods known to those skilled in the art, e.g., by separation of the diastereomeric salts thereof. Racemic products can also be resolved by chiral chromatography, e.g., high performance liquid chromatography (HPLC) using a chiral adsorbent. Preferred enantiomers can also be prepared by asymmetric syntheses. See, for example, Jacques, et al., Enantiomers, Racemates and Resolutions (Wiley Interscience, New York, 1981); Principles of Asymmetric Synthesis (2nd Ed. Robert E. Gawley, Jeffrey Aubé, Elsevier, Oxford, U K, 2012); Eliel, E. L. Stereochemistry of Carbon Compounds (McGraw-Hill, N Y, 1962); Wilen, S. H. Tables of Resolving Agents and Optical Resolutions p. 268 (E. L. Eliel, Ed., Univ. of Notre Dame Press, Notre Dame, IN 1972);

The present invention also includes isotopically-labeled compounds of the present invention, which are the same as those described in the present invention except for the fact that one or more atoms are replaced by atoms whose atomic mass or mass number is different from the atomic mass or mass number commonly found in nature. Examples of isotopes that can be incorporated into compounds of the invention include isotopes of hydrogen, carbon, nitrogen, oxygen, phosphorous, sulfur, fluorine, and chlorine, such as $^{2}H$, $^{3}H$, $^{13}C$, $^{14}C$, $^{15}N$, $^{16}O$, $^{17}O$, $^{31}P$, $^{32}P$, $^{36}S$, $^{18}F$ and $^{37}Cl$, respectively.

The compounds disclosed herein containing isotopes described above or other atom isotopes and pharmaceutical salts thereof are included within the scope of the present invention. Certain isotopically-labeled compounds of the present invention, for example those into which radioactive isotopes such as $^{3}H$ or $^{14}C$ are incorporated, are useful in drug and/or substrate tissue distribution assays. Because of easy preparation and detection, isotopes such as tritiated, i.e., $^{3}H$, and carbon-14, i.e., $^{14}C$ are preferred. Further, substitution with heavier isotopes, particularly deuterium (i.e., $^{2}H$ or D) may afford certain therapeutic advantages resulting from greater metabolic stability, for example increased in vivo half-life or reduced dosage requirements. Therefore, the heavier isotopes may be preferred in somewhere.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds disclosed herein may contain asymmetric or chiral centers, and therefore exist in different stereoisomeric forms. It is intended that all stereoisomeric forms of the compounds disclosed herein, including, but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and 1 or (+) and (−) are employed to designate the sign of rotation of plane-polarized light by the compound, with (−) or 1 meaning that the compound is levorotatory. A compound prefixed with (+) or d is dextrorotatory. For a given chemical structure, different optically active compounds are called stereoisomers and are identical except that they are mirror images of one another. A specific stereoisomer is referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process.

Depending on the choice of the starting materials and procedures, the compounds can be present in the form of one of the possible stereoisomers or as mixtures thereof, such as racemates and diastereoisomer mixtures, depending on the number of asymmetric carbon atoms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration.

Unless otherwise specified, the Formula described herein also contains all the isomers thereof (such as, enantiomers, diastereomers, atropisomers and geometric (conformational) isomers; such as all (R)- and (S)-isomers, (Z) and (E) isomers around the double bond, (Z) and (E) conformational isomers. Therefore, single stereochemical isomers as well as enantiomeric, diastereomeric, or geometric mixtures (or conformers) of the present compounds are within the scope disclosed herein.

The term "tautomer" or "tautomeric form" refers to structural isomers of different energies which are interconvertible via a low energy barrier. Where tautomerization is possible (e.g. in solution), a chemical equilibrium of tautomers can be reached. For example, protontautomers (also known as prototropic tautomers) include interconversions via migration of a proton, such as keto-enol and imine-enamine isomerizations. Valence tautomers include interconversions by reorganization of some of the bonding electrons. A specific example of keto-enol tautomerization is the interconversion of pentane-2,4-dione and 4-hydroxypent-3-en-2-one tautomers. Another example of tautomerization is phenol-keto tautomerization. The specific example of phenol-keto tautomerisms is pyridin-4-ol and pyridin-4(1H)-one tautomerism. Unless otherwise stated, all tautomeric forms of the compounds disclosed herein are within the scope of the invention.

The term "geometric isomer" is also known as "cis-trans isomer", which is caused by the double bond (including the double bond of olefin, C═N double bond and N═N double bond) or the single bond of ring carbon atom that cannot rotate freely.

The term "subject" can be used interchangeably with "patient" in the invention. The term "subject" and "patient" refer to animals (e.g., birds such as chicken, quail or turkey, or mammals), specially mammals including non-primates (e.g., cattle, pigs, horses, sheep, rabbits, guinea pigs, rats, dogs, cats and mice) and primates (e.g., monkeys, chimpanzees and humans), more specially humans. In one embodiment, the subject is a non-human animal, such as a domestic animal (e.g., horse, cow, pig, or sheep) or a pet (e.g., dog, cat, guinea pig or rabbit). In some embodiments, "patient" refers to a human.

Additionally, unless otherwise stated, structures depicted herein are also meant to include compounds that differ only in the presence of one or more isotopically enriched atoms.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

DESCRIPTION OF COMPOUNDS OF THE INVENTION

The present invention provides a class of compounds with good agonistic activity on thyroid hormone β receptors. Such compounds can be used in the manufacture of a medicament for treating non-alcoholic fatty liver disease, atherosclerosis, coronary heart disease, hypertension, hypercholesterolemia, hyperlipidemia, hypertriglyceridemia, dyslipidemia, obesity, diabetes, metabolic disorders, type 1A glycogen storage disease, hypothyroidism or thyroid cancer in a subject. The present invention also provides methods of preparing these compounds, pharmaceutical compositions comprising these compounds, and methods of using these compounds and compositions to prepare medicaments for the above-mentioned diseases in mammals, especially humans. Compared with the existing similar compounds, the compounds of the present invention not only have better pharmacological activity and selectivity, but also have better in vivo metabolic kinetic properties and in vivo pharmacodynamic properties. The preparation method of the compound of the present invention is simple and easy, and the technological method is stable, which is suitable for industrial production. Therefore, the compound provided by the present invention has better druggability compared with the existing similar compounds.

Specifically:

In one aspect, the invention relates to a compound having Formula (I) or a stereoisomer, a geometric isomer, a tautomer, an N-oxide, a solvate, a metabolite, a pharmaceutically acceptable salt or a prodrug thereof, (I)

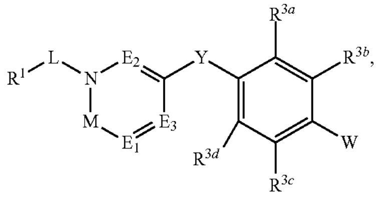

wherein, L, W, Y, M, $E_1$, $E_2$, $E_3$, $R^1$, $R^{3a}$, $R^{3b}$, $R^{3c}$ and $R^{3d}$ have the definitions as described herein.

In some embodiments, Y is —O—, —S—, —$NR^c$—, —$CR^aR^b$—, —S(═O)$_2$—, —S(═O)— or —C(═O)—, wherein the $R^a$, $R^b$ and $R^c$ have the definitions as described herein.

In some embodiments, L is absent, —O—, —S—, —$NR^c$—, —$CR^dR^c$—, —S(═O)$_2$—, —S(═O)— or —C(═O)—, wherein the $R^c$, $R^d$ and $R^e$ have the definitions as described herein.

In some embodiments, each of $R^a$, $R^b$, R, $R^d$ and $R^e$ is independently H, deuterium, F, Cl, Br, I, —CN, —$NO_2$, —COOH, —OH, —$NH_2$, —SH, $C_{1-6}$ alkyl, $C_{1-6}$ alkoxy, $C_{1-6}$ haloalkyl or $C_{1-6}$ haloalkoxy.

In some embodiments, each of $R^{3a}$, $R^{3b}$, $R^{3c}$ and $R^{3d}$ is independently H, deuterium, F, Cl, Br, I, —CN, —$NO_2$, —COOH, —OH, —$NH_2$, —SH, $C_{1-6}$ alkyl, $C_{1-6}$ alkoxy, $C_{1-6}$ alkylthio, $C_{1-6}$ alkylamino, $C_{1-6}$ haloalkyl, $C_{1-6}$ haloalkoxy, hydroxy $C_{1-6}$ alkyl, amino $C_{1-6}$ alkyl or cyano $C_{1-6}$ alkyl.

In some embodiments, M is —C(═O)—, —C(═S)—, —S(═O)$_2$— or —S(═O)—.

In some embodiments, $E_1$ is N, CH or $CR^z$, wherein the $R^z$ has the definition as described herein.

In some embodiments, $E_2$ is N or $CR^2$, wherein the $R^2$ has the definition as described herein. Preferably, $E_2$ is $CR^2$, wherein the $R^2$ has the definition as described herein.

In some embodiments, $E_3$ is N or $CR^3$, wherein the $R^3$ has the definition as described herein.

In some embodiments, $R^z$ is deuterium, F, Cl, Br, I, —CN, —$NO_2$, —COOH, —$NH_2$, —SH, $C_{1-6}$ alkyl, $C_{1-6}$ haloalkyl, $C_{1-6}$ haloalkoxy, $C_{1-6}$ alkoxy, $C_{2-6}$ alkenyl, $C_{2-6}$ alkynyl, hydroxy $C_{1-6}$ alkyl, $C_{3-8}$ cycloalkyl, $C_{3-8}$ cycloalkyl $C_{1-6}$ alkyl, 3-8 membered heterocyclyl, (3-8 membered heterocyclyl) $C_{1-6}$ alkyl, $C_{6-10}$ aryl, $C_{6-10}$ aryl $C_{1-6}$ alkyl, 5-10 membered heteroaryl or (5-10 membered heteroaryl) $C_{1-6}$ alkyl.

In some embodiments, each of $R^2$ and $R^3$ is independently H, deuterium, F, Cl, Br, I, —CN, —$NO_2$, —COOH, —$NH_2$, —SH, $C_{1-6}$ alkyl, $C_{1-6}$ haloalkyl, $C_{1-6}$ haloalkoxy, $C_{1-6}$ alkoxy, $C_{2-6}$ alkenyl, $C_{2-6}$ alkynyl, hydroxy $C_{1-6}$ alkyl, $C_{3-8}$ cycloalkyl, $C_{3-8}$ cycloalkyl $C_{1-6}$ alkyl, 3-8 membered heterocyclyl, (3-8 membered heterocyclyl) $C_{1-6}$ alkyl, $C_{6-10}$ aryl, $C_{6-10}$ aryl $C_{1-6}$ alkyl, 5-10 membered heteroaryl or (5-10 membered heteroaryl) $C_{1-6}$ alkyl.

In some embodiments, $R^1$ is H, deuterium, F, Cl, Br, I, —CN, —$NO_2$, —COOH, —C(═O)$NH_2$, —S(═O)$_2NH_2$, —OH, —$NH_2$, —SH, $C_{1-6}$ alkyl, $C_{1-6}$ alkoxy, $C_{1-6}$ haloalkyl, $C_{1-6}$ haloalkoxy, —C(═O)—$C_{1-6}$ alkoxy, —C(═O)—$C_{1-6}$ alkylamino, —C(═O)—$C_{1-6}$ alkyl, —S(═O)$_2$—$C_{1-6}$ alkyl, —S(═O)$_2$—$C_{1-6}$ alkylamino, $C_{2-6}$ alkenyl, $C_{2-6}$ alkynyl, $C_{3-8}$ cycloalkyl, 5-8 membered heterocyclyl, $C_{6-10}$ aryl or 5-8 membered heteroaryl, wherein each of the $C_{1-6}$ alkyl, $C_{1-6}$ alkoxy, $C_{1-6}$ haloalkyl, $C_{1-6}$ haloalkoxy, —C(═O)—$C_{1-6}$ alkoxy, —C(═O)—$C_{1-6}$ alkylamino, —C(═O)—$C_{1-6}$ alkyl, —S(═O)$_2$—$C_{1-6}$ alkyl, —S(═O)$_2$—$C_{1-6}$ alkylamino, $C_{2-6}$ alkenyl, $C_{2-6}$ alkynyl, $C_{3-8}$ cycloalkyl, 5-8 membered heterocyclyl, $C_{6-10}$ aryl and 5-8 membered heteroaryl is independently unsubstituted or substituted with 1, 2 or 3 substituents selected from deuterium, F, Cl, Br, I, —CN, —$NO_2$, —COOH, —C(═O)$NH_2$, —S(═O)$_2NH_2$, —SH, —OH, —$NH_2$, ═O, —C(═O)—$C_{1-6}$ alkyl, —C(═O)—$C_{1-6}$ alkoxy, $C_{1-6}$ alkyl, $C_{1-6}$ alkoxy, $C_{1-6}$ haloalkyl or $C_{1-6}$ haloalkoxy.

In some embodiments, W is —$OCH_2COOH$, —NHC(═O)COOH, —$NHCH_2COOH$,

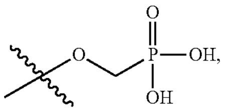

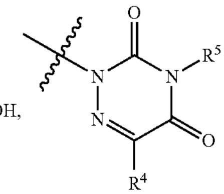

,

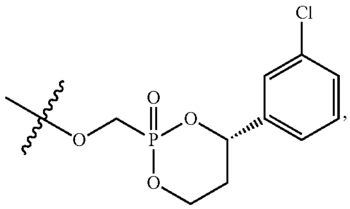

,

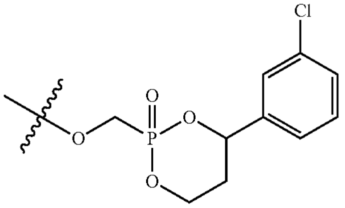

or

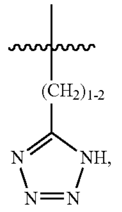

wherein the $R^4$ and $R^5$ have the definitions as described herein.

In some embodiments, $R^4$ is H, deuterium, F, Cl, Br, I, —CN, —$NO_2$, —COOH, —OH, —$NH_2$, —SH, $C_{1-6}$ alkyl, $C_{2-6}$ alkenyl, $C_{2-6}$ alkynyl, —C(═O)—$C_{1-6}$ alkoxy, —C(═O)—$C_{1-6}$ alkyl, —C(═O)—$C_{1-6}$ alkylamino, —C(═O)$NH_2$, —S(═O)$_2$—$C_{1-6}$ alkyl, —S(═O)$_2$—$C_{1-6}$ alkylamino, $C_{1-6}$ alkylamino, $C_{1-6}$ alkoxy, $C_{1-6}$ haloalkyl, $C_{1-6}$ haloalkoxy, hydroxy $C_{1-6}$ alkyl, amino $C_{1-6}$ alkyl, carboxy $C_{1-6}$ alkyl or cyano $C_{1-6}$ alkyl, wherein each of the $C_{1-6}$ alkyl, $C_{2-6}$ alkenyl, $C_{2-6}$ alkynyl, —C(═O)—$C_{1-6}$ alkoxy, —C(═O)—$C_{1-6}$ alkyl, —C(═O)—$C_{1-6}$ alkylamino, —C(═O)$NH_2$, —S(═O)$_2$—$C_{1-6}$ alkyl, —S(═O)$_2$—$C_{1-6}$ alkylamino, $C_{1-6}$ alkylamino, $C_{1-6}$ alkoxy, $C_{1-6}$ haloalkyl, $C_{1-6}$ haloalkoxy, hydroxy $C_{1-6}$ alkyl, amino $C_{1-6}$ alkyl, carboxy $C_{1-6}$ alkyl and cyano $C_{1-6}$ alkyl is independently unsubstituted or substituted with 1, 2 or 3 substituents selected from deuterium, F, Cl, Br, I, —CN, —$NO_2$, —COOH, —OH, —$NH_2$, —SH, $C_{1-6}$ alkyl, $C_{2-6}$ alkenyl or $C_{2-6}$ alkynyl.

In some embodiments, $R^5$ is H, deuterium, $C_{1-6}$ alkyl, $C_{2-6}$ alkenyl, $C_{2-6}$ alkynyl, $C_{3-6}$ cycloalkyl, 5-6 membered heterocyclyl, $C_{6-10}$ aryl or 5-6 membered heteroaryl.

In some embodiments, each of $R^{3a}$, $R^{3b}$, $R^{3c}$ and $R^{3d}$ is independently H, deuterium, F, Cl, Br, I, —CN, —$NO_2$, —COOH, —OH, —$NH_2$, —SH, $C_{1-4}$ alkyl, $C_{1-4}$ alkoxy, $C_{1-4}$ alkylthio, $C_{1-4}$ alkylamino, $C_{1-4}$ haloalkyl, $C_{1-4}$ haloalkoxy, hydroxy $C_{1-4}$ alkyl, amino $C_{1-4}$ alkyl or cyano $C_{1-4}$ alkyl.

In some embodiments, each of $R^{3a}$, $R^{3b}$, $R^{3c}$, and $R^{3d}$ is independently H, deuterium, F, Cl, Br, I, —CN, —$NO_2$, —COOH, —OH, $NH_2$, —SH, methyl, ethyl, n-propyl, isopropyl, methoxy, ethoxy, methylthio, methylamino, —$CF_3$, —$CHF_2$, —$CH_2F$, —$CH_2CF_3$, trifluoromethoxy, difluoromethoxy, hydroxymethyl, aminomethyl or cyanomethyl.

In some embodiments, each of $R^a$, $R^b$, $R^c$, $R^d$ and $R^e$ is independently H, deuterium, F, Cl, Br, I, —CN, —$NO_2$, —COOH, —OH, $NH_2$, —SH, $C_{1-4}$ alkyl, $C_{1-4}$ alkoxy, $C_{1-4}$ haloalkyl or $C_{1-4}$ haloalkoxy.

In some embodiments, each of $R^a$, $R^b$, $R^c$, $R^d$ and $R^e$ is independently H, deuterium, F, Cl, Br, I, —CN, —$NO_2$, —COOH, —OH, $NH_2$, —SH, methyl, ethyl, n-propyl, isopropyl, methoxy, ethoxy, —$CF_3$, —$CHF_2$, —$CH_2F$, —$CH_2CF_3$ or trifluoromethoxy.

In some embodiments, $R^z$ is deuterium, F, Cl, Br, I, —CN, —$NO_2$, —COOH, —$NH_2$, —SH, $C_{1-4}$ alkyl, $C_{1-4}$ haloalkyl, $C_{1-4}$ haloalkoxy, $C_{1-4}$ alkoxy, $C_{2-4}$ alkenyl, $C_{2-4}$ alkynyl, hydroxy $C_{1-4}$ alkyl, $C_{3-6}$ cycloalkyl, $C_{3-6}$ cycloalkyl $C_{1-3}$ alkyl, 3-6 membered heterocyclyl, (3-6 membered heterocyclyl) $C_{1-3}$ alkyl, $C_{6-10}$ aryl, $C_{6-10}$ aryl $C_{1-3}$ alkyl, 5-6 membered heteroaryl or (5-6 membered heteroaryl) $C_{1-3}$ alkyl.

In some embodiments, $R^z$ is deuterium, F, Cl, Br, I, —CN, —$NO_2$, —COOH, —$NH_2$, —SH, methyl, ethyl, n-propyl, isopropyl, n-butyl, tert-butyl, trifluoromethyl, difluoromethyl, trifluoromethoxy, difluoromethoxy, methoxy, ethoxy, n-propoxy, isopropoxy, $C_{2-4}$ alkenyl, $C_{2-4}$ alkynyl, hydroxymethyl, hydroxyethyl, hydroxypropyl, $C_{3-6}$ cycloalkyl, $C_{3-6}$ cycloalkyl $C_{1-3}$ alkyl, 5-6 membered heterocyclyl, (5-6 membered heterocyclyl) $C_{1-3}$ alkyl, phenyl, phenylmethyl, phenylethyl, pyridyl, pyrimidinyl, pyridazinyl, pyrrolyl, pyridylmethyl, pyridylethyl or pyrimidinylmethyl.

In some embodiments, each of $R^2$ and $R^3$ is independently H, deuterium, F, Cl, Br, I, —CN, —$NO_2$, —COOH, —$NH_2$, —SH, $C_{1-4}$ alkyl, $C_{1-4}$ haloalkyl, $C_{1-4}$ haloalkoxy, $C_{1-4}$ alkoxy, $C_{2-4}$ alkenyl, $C_{2-4}$ alkynyl, hydroxy $C_{1-4}$ alkyl, $C_{3-6}$ cycloalkyl, $C_{3-6}$ cycloalkyl $C_{1-3}$ alkyl, 5-6 membered heterocyclyl, (5-6 membered heterocyclyl) $C_{1-3}$ alkyl, $C_{6-10}$ aryl, $C_{6-10}$ aryl $C_{1-3}$ alkyl, 5-6 membered heteroaryl or (5-6 membered heteroaryl) $C_{1-3}$ alkyl.

In some embodiments, each of $R^2$ and $R^3$ is independently H, deuterium, F, Cl, Br, I, —CN, —$NO_2$, —COOH, —$NH_2$, —SH, methyl, ethyl, n-propyl, isopropyl, n-butyl, tert-butyl, trifluoromethyl, difluoromethyl, trifluoromethoxy, difluoromethoxy, methoxy, ethoxy, n-propoxy, isopropoxy, $C_{2-4}$ alkenyl, $C_{2-4}$ alkynyl, hydroxymethyl, hydroxyethyl, hydroxypropyl, $C_{3-6}$ cycloalkyl, $C_{3-6}$ cycloalkyl $C_{1-3}$ alkyl, 5-6 membered heterocyclyl, (5-6 membered heterocyclyl) $C_{1-3}$ alkyl, phenyl, phenylmethyl, phenylethyl, pyridyl, pyrimidinyl, pyridazinyl, pyrrolyl, pyridylmethyl, pyridylethyl or pyrimidinylmethyl.

In some embodiments, $R^1$ is H, deuterium, F, Cl, Br, I, —CN, —$NO_2$, —COOH, —C(═O)$NH_2$, —S(═O)$_2NH_2$, —OH, —$NH_2$, —SH, $C_{1-4}$ alkyl, $C_{1-4}$ alkoxy, $C_{1-4}$ haloalkyl, $C_{1-4}$ haloalkoxy, —C(═O)—$C_{1-4}$ alkoxy, —C(═O)—$C_{1-4}$ alkylamino, —C(═O)—$C_{1-4}$ alkyl, —S(═O)$_2$—$C_{1-4}$ alkyl, —S(═O)$_2$—$C_{1-4}$ alkylamino, $C_{2-4}$ alkenyl, $C_{2-4}$ alkynyl, $C_{3-6}$ cycloalkyl, 5-6 membered heterocyclyl, $C_{6-10}$ aryl or 5-6 membered heterocyclyl, wherein each of the $C_{1-4}$ alkyl, $C_{1-4}$ alkoxy, $C_{1-4}$ haloalkyl, $C_{1-4}$ haloalkoxy, —C(═O)—$C_{1-4}$ alkoxy, —C(═O)—$C_{1-4}$ alkylamino, —C(═O)—$C_{1-4}$ alkyl, —S(═O)$_2$—$C_{1-4}$ alkyl, —S(═O)$_2$—$C_{1-4}$ alkylamino, $C_{2-4}$ alkenyl, $C_{2-4}$ alkynyl, $C_{3-6}$ cycloalkyl, 5-6 membered heterocyclyl, $C_{6-10}$ aryl and 5-6 membered heterocyclyl is independently unsubstituted or substituted with 1, 2 or 3 substituents selected from Deuterium, F, Cl, Br, I, —CN, —$NO_2$, —COOH, —C(═O)$NH_2$, —S(═O)$_2NH_2$, —SH, —OH, —$NH_2$, ═O, —C(═O)—$C_{1-4}$ alkyl, —C(═O)—$C_{1-4}$ alkoxy, $C_{1-4}$ alkyl, $C_{1-4}$ alkoxy, $C_{1-4}$ haloalkyl or $C_{1-4}$ haloalkoxy.

In some embodiments, $R^1$ is H, deuterium, F, Cl, Br, I, —CN, —$NO_2$, —COOH, —C(═O)$NH_2$, —S(═O)$_2NH_2$, —OH, —$NH_2$, —SH, methyl, ethyl, n-propyl, isopropyl, n-butyl, isobutyl, sec-butyl, tert-butyl, methoxy, ethoxy, n-propoxy, isopropoxy, —$CF_3$, —$CHF_2$, —$CH_2F$, —$CH_2CF_3$, trifluoromethoxy, difluoromethoxy, —C(═O)—$OCH_3$, —C(═O)—$OCH_2CH_3$, —C(═O)—$OCH(CH_3)_2$, —C(═O)—$OCH_2CH_2CH_3$, —C(═O)—O$(CH_2)_3CH_3$, —C(═O)—$OCH_2CH(CH_3)_2$, —C(═O)—$NHCH_3$, —C(═O)—$N(CH_3)_2$, —C(═O)—$CH_3$, —C(═O)—$CH_2CH_3$, —S(═O)$_2$—$CH_3$, —S(═O)$_2$—$CH_2CH_3$, —S(═O)$_2$—$CH_2CH_2CH_3$, —S(═O)$_2$—$NHCH_3$, —S(═O)$_2$—$N(CH_3)_2$, —CH═$CH_2$, —$CH_2$CH═$CH_2$, —CH═$CHCH_3$, —C≡CH, cyclopropyl, cyclobutyl, cyclopentyl, cyclohexyl, pyrrolidinyl, pyrazolidinyl, imidazolidinyl, piperidinyl, morpholinyl, thiomorpholinyl, piperazinyl, tetrahydropyrrolyl, tetrahydrofuranyl, tetrahydropyranyl, tetrahydrothienyl, tetrahydropyridinyl, tetrahydropyrimidinyl, tetrahydropyrazinyl, tetrahydropyridazinyl, dihydropyrrolyl, dihydrofuranyl, dihydropyranyl, dihydrothienyl, dihydropyridyl, dihydropyrimidinyl, dihydropyrazinyl, dihydropyridazinyl, phenyl, naphthyl, furyl, thienyl, imidazolyl, pyrazolyl, pyrimidinyl, pyridyl, pyrrolyl, pyrazinyl, pyridazinyl, thiazolyl, tetrazolyl, triazolyl, isoxazolyl, isothiazolyl, oxadiazolyl or oxazolyl, wherein each of the methyl, ethyl, n-propyl, isopropyl, n-butyl, isobutyl, sec-butyl, tert-butyl, methoxy, ethoxy, n-propoxy, isopropoxy, —$CHF_2$, —$CH_2F$, —$CH_2CF_3$, difluoromethoxy, —C(═O)—$OCH_3$, —C(═O)—$OCH_2CH_3$, —C(═O)—$OCH(CH_3)_2$, —C(═O)—$OCH_2CH_2CH_3$, —C(═O)—O$(CH_2)_3CH_3$, —C(═O)—$OCH_2CH(CH_3)_2$, —C(═O)—$NHCH_3$, —C(═O)—$N(CH_3)_2$, —C(═O)—$CH_3$, —C(═O)—$CH_2CH_3$, —S(═O)$_2$—$CH_3$, —S(═O)$_2$—$CH_2CH_3$, —S(═O)$_2$—$CH_2CH_2CH_3$, —S(═O)$_2$—$NHCH_3$, —S(═O)$_2$—$N(CH_3)_2$, —CH═$CH_2$, —$CH_2$CH═$CH_2$, —CH═$CHCH_3$, —C≡CH, cyclopropyl, cyclobutyl, cyclopentyl, cyclohexyl, pyrrolidinyl, pyrazolidinyl, imidazolidinyl, piperidinyl, morpholinyl, thiomorpholinyl, piperazinyl, tetrahydropyrrolyl, tetrahydrofuranyl, tetrahydropyranyl, tetrahydrothienyl, tetrahydropyridinyl, tetrahydropyrimidinyl, tetrahydropyrazinyl, tetrahydropyridazinyl, dihydropyrrolyl, dihydrofuranyl, dihydropyranyl, dihydrothienyl, dihydropyridyl, dihydropyrimidinyl, dihydropyrazinyl, dihydropyridazinyl, phenyl, naphthyl, furyl, thienyl, imidazolyl, pyrazolyl, pyrimidinyl, pyridyl, pyrrolyl, pyrazinyl, pyridazinyl, thiazolyl, tetrazolyl, triazolyl, isoxazolyl, isothiazolyl, oxadiazolyl and oxazolyl is independently unsubstituted or substituted with 1, 2 or 3 substituents selected from deuterium, F, Cl, Br, I, —CN, —$NO_2$, —COOH, —C(═O)$NH_2$, —S(═O)$_2NH_2$, —SH, —OH, —$NH_2$, ═O, —C(═O)—$CH_3$, —C(═O)—$CH_2CH_3$, —C(═O)—

$OCH_3$, —C(═O)—$OCH_2CH_3$, —C(═O)—$OCH(CH_3)_2$, —C(═O)—$OCH_2CH_2CH_3$, —C(═O)—$O(CH_2)_3CH_3$, —C(═O)—$OCH_2CH(CH_3)_2$, —C(═O)—$CH_3$, —C(═O)—$CH_2CH_3$, methyl, ethyl, n-propyl, isopropyl, methoxy, ethoxy, n-propoxy, isopropoxy, —$CF_3$, —$CHF_2$, —$CH_2CF_3$, trifluoromethoxy or difluoromethoxy.

In some embodiments, $R^4$ is H, deuterium, F, Cl, Br, I, —CN, —$NO_2$, —COOH, —OH, —$NH_2$, —SH, $C_{1-4}$ alkyl, $C_{2-4}$ alkenyl, $C_{2-4}$ alkynyl, —C(═O)—$C_{1-4}$ alkoxy, —C(═O)—$C_{1-4}$ alkyl, —C(═O)—$C_{1-4}$ alkylamino, —C(═O)$NH_2$, —S(═O)$_2$—$C_{1-4}$ alkyl, —S(═O)$_2$—$C_{1-4}$ alkylamino, $C_{1-4}$ alkylamino, $C_{1-4}$ alkoxy, $C_{1-4}$ haloalkyl, $C_{1-4}$ haloalkoxy, hydroxy $C_{1-4}$ alkyl, amino $C_{1-4}$ alkyl, carboxy $C_{1-4}$ alkyl or cyano $C_{1-4}$ alkyl, wherein each of the $C_{1-4}$ alkyl, $C_{2-4}$ alkenyl, $C_{2-4}$ alkynyl, —C(═O)—$C_{1-4}$ alkoxy, —C(═O)—$C_{1-4}$ alkyl, —C(═O)—$C_{1-4}$ alkylamino, —C(═O)$NH_2$, —S(═O)$_2$—$C_{1-4}$ alkyl, —S(═O)$_2$—$C_{1-4}$ alkylamino, $C_{1-4}$ alkylamino, $C_{1-4}$ alkoxy, $C_{1-4}$ haloalkyl, $C_{1-4}$ haloalkoxy, hydroxy $C_{1-4}$ alkyl, amino $C_{1-4}$ alkyl, carboxy $C_{1-4}$ alkyl and cyano $C_{1-4}$ alkyl is independently unsubstituted or substituted with 1, 2 or 3 substituents selected from Deuterium, F, Cl, Br, I, —CN, —$NO_2$, —COOH, —OH, —$NH_2$, —SH, $C_{1-6}$ alkyl, $C_{2-6}$ alkenyl or $C_{2-6}$ alkynyl.

In some embodiments, $R^4$ is H, deuterium, F, Cl, Br, I, —CN, —$NO_2$, —COOH, —OH, —$NH_2$, —SH, methyl, ethyl, n-propyl, isopropyl, —CH═$CH_2$, —$CH_2$CH═$CH_2$, —CH═$CHCH_3$, —C≡CH, —C(═O)—$OCH_3$, —C(═O)—$OCH_2CH_3$, —C(═O)—$OCH(CH_3)_2$, —C(═O)—$OCH_2CH_2CH_3$, —C(═O)—$O(CH_2)_3CH_3$, —C(═O)—$OCH_2CH(CH_3)_2$, —C(═O)—$CH_3$, —C(═O)—$CH_2CH_3$, —C(═O)—$NHCH_3$, —C(═O)$NH_2$, —C(═O)—$N(CH_3)_2$, —S(═O)$_2$—$CH_3$, —S(═O)$_2$—$CH_2CH_3$, —S(═O)$_2$—$NHCH_3$, methylamino, ethylamino, methoxy, ethoxy, —$CF_3$, —$CHF_2$, —$CH_2F$, —$CH_2CF_3$, —$CH_2CHF_2$, trifluoromethoxy, difluoromethoxy, hydroxymethyl, aminomethyl, carboxymethyl or cyanomethyl, wherein each of the methyl, ethyl, n-propyl, isopropyl, —CH═$CH_2$, —$CH_2$CH═$CH_2$, —CH═$CHCH_3$, —C≡CH, —C(═O)—$OCH_3$, —C(═O)—$OCH_2CH_3$, —C(═O)—$OCH(CH_3)_2$, —C(═O)—$OCH_2CH_2CH_3$, —C(═O)—O$(CH_2)_3CH_3$, —C(═O)—$OCH_2CH(CH_3)_2$, —C(═O)—$CH_3$, —C(═O)—$CH_2CH_3$, —C(═O)—$NHCH_3$, —C(═O)—$N(CH_3)_2$, —C(═O)$NH_2$, S(═O)$_2$—$CH_3$, —S(═O)$_2$—$CH_2CH_3$, —S(═O)$_2$—$NHCH_3$, methylamino, ethylamino, methoxy, ethoxy, —$CHF_2$, —$CH_2F$, —$CH_2CF_3$, —$CH_2CHF_2$, difluoromethoxy, hydroxymethyl, aminomethyl, carboxymethyl and cyanomethyl is independently unsubstituted or substituted with 1, 2 or 3 substituents selected from deuterium, F, Cl, Br, I, —CN, —$NO_2$, —COOH, —OH, —$NH_2$, —SH, $C_{1-6}$ alkyl, $C_{2-6}$ alkenyl or $C_{2-6}$ alkynyl.

In some embodiments, $R^5$ is H, deuterium, $C_{1-4}$ alkyl, $C_{2-4}$ alkenyl, $C_{2-4}$ alkynyl, $C_{3-6}$ cycloalkyl, 5-6 membered heterocyclyl, $C_{6-10}$ aryl or 5-6 membered heteroaryl.

In some embodiments, $R^5$ is H, deuterium, methyl, ethyl, n-propyl, isopropyl, tert-butyl, —CH═$CH_2$, —$CH_2$CH═$CH_2$, —CH═$CHCH_3$, —C≡CH, cyclopropyl, cyclobutyl, cyclopentyl, cyclohexyl, 5-6 membered heterocyclyl, phenyl, naphthyl or 5-6 membered heteroaryl.

In another aspect, the present invention relates to one of the following structures, or a stereoisomer, a geometric isomer, a tautomer, an N-oxide, a solvate, a metabolite, a pharmaceutically acceptable salt or a prodrug thereof, (1)

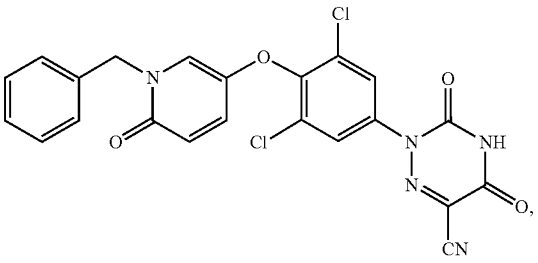

(2)

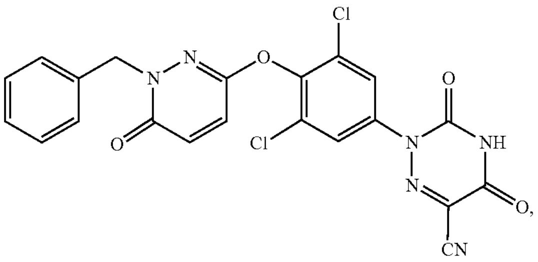

(3)

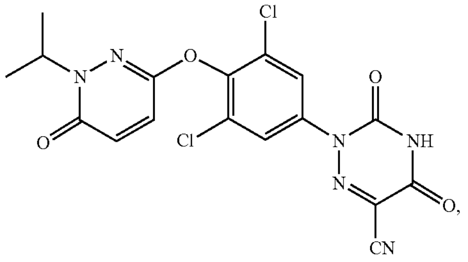

(4)

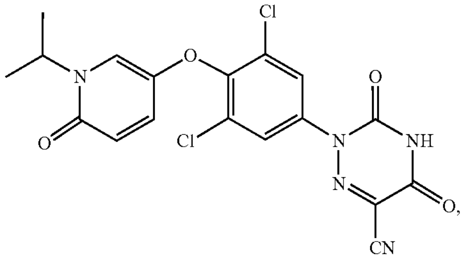

(5)

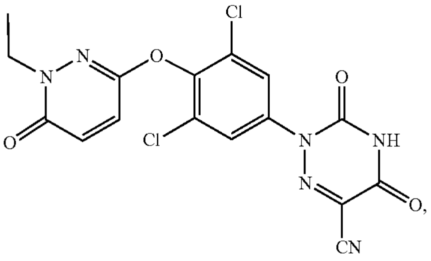

(6)

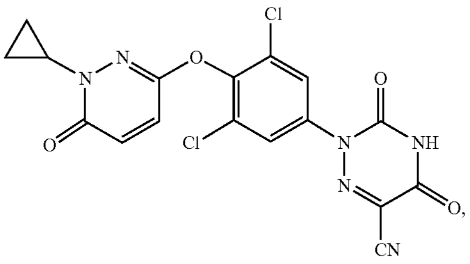

-continued
(7)
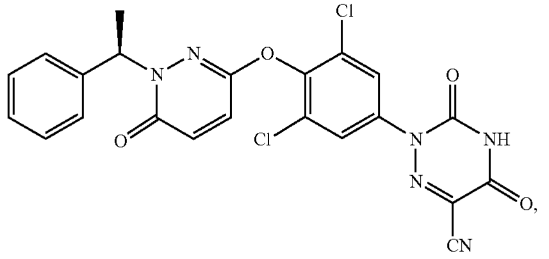
(8)
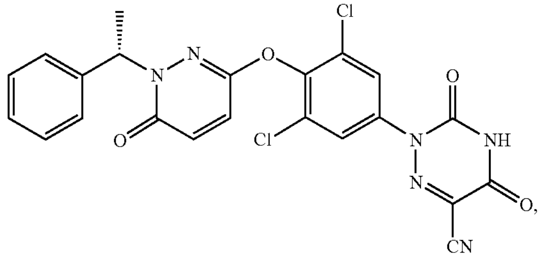
(9)
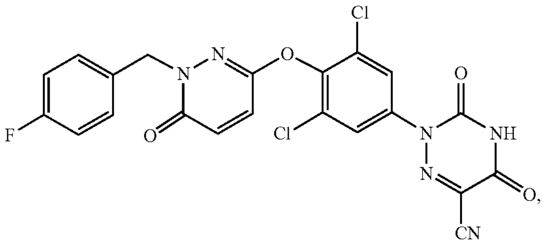
(10)
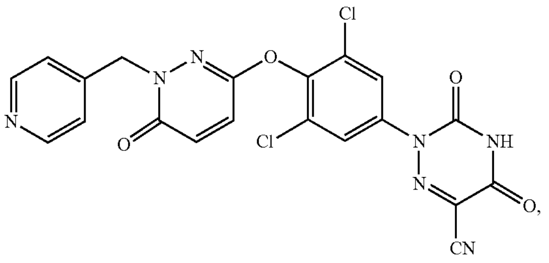
(11)
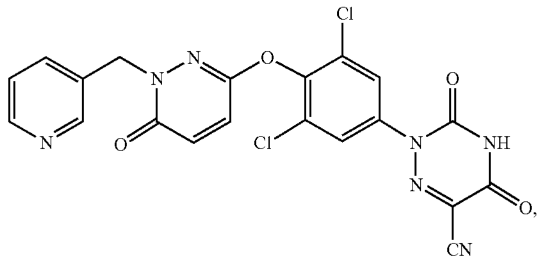
-continued
(12)
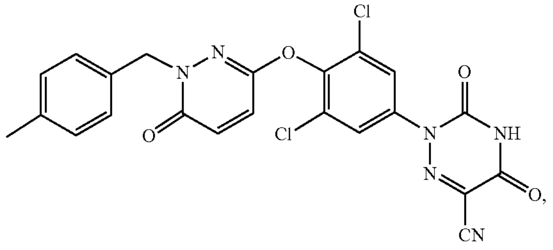
(13)
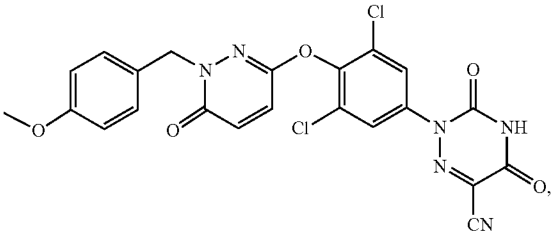
(14)
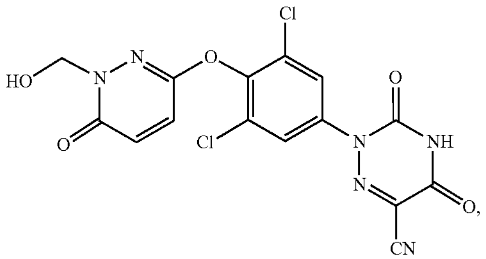
(15)
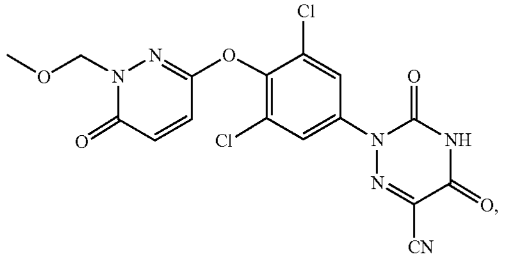
(16)
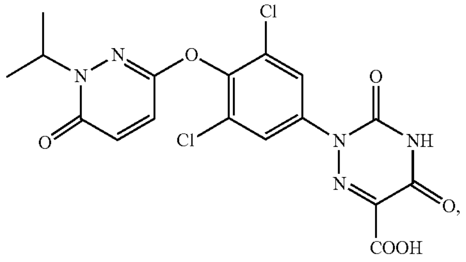
(17)
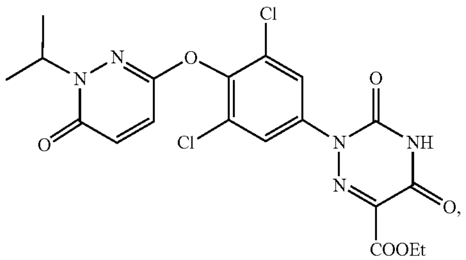

-continued
(18)
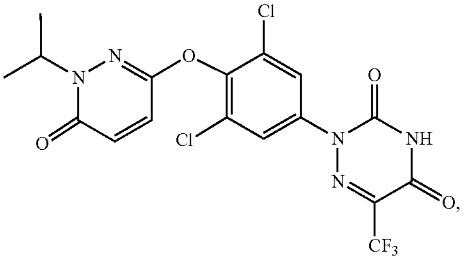
(19)
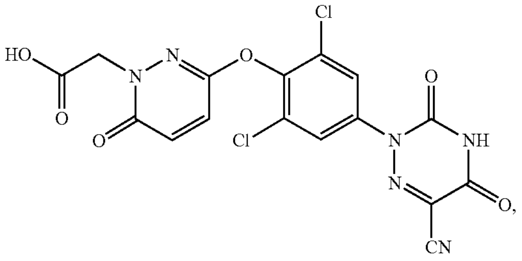
(20)
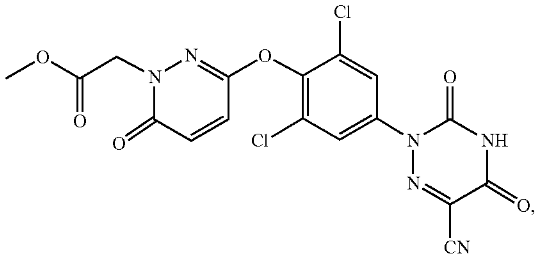
(21)
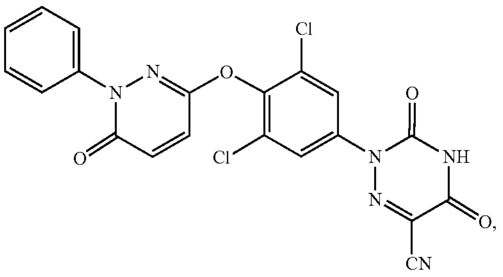
(22)
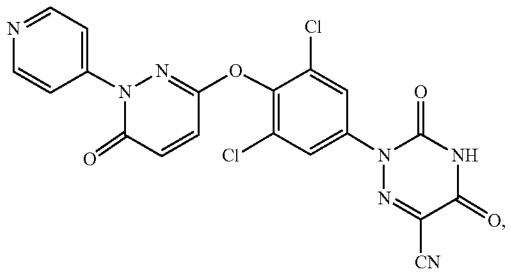
-continued
(23)
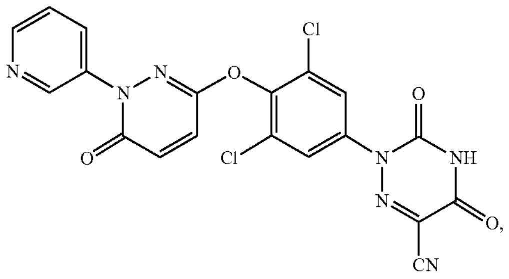
(24)
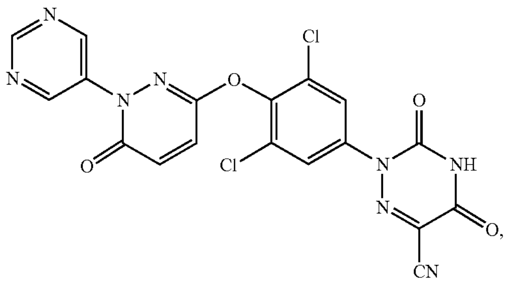
(25)
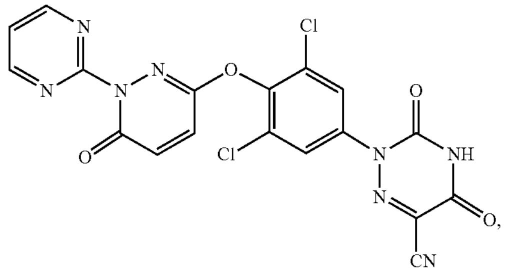
(26)
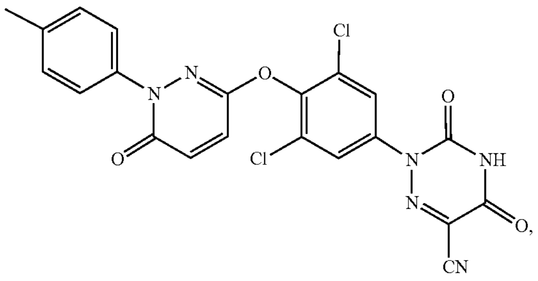
(27)
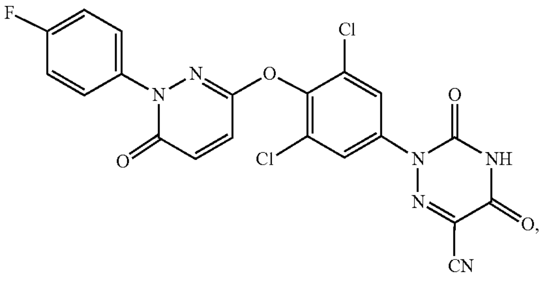

-continued
(28)
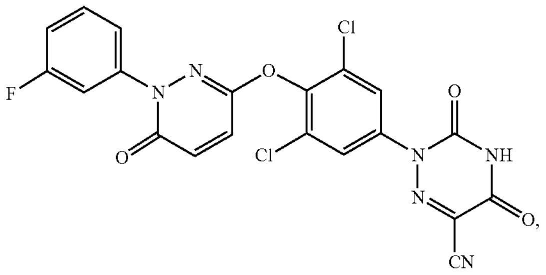
(29)
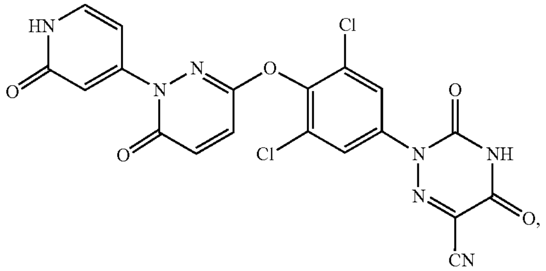
(30)
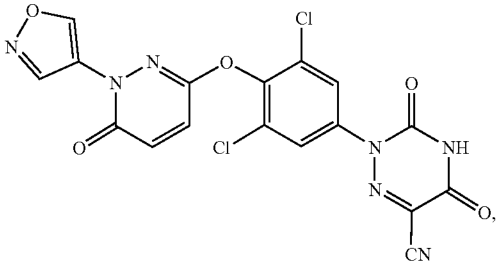
(31)
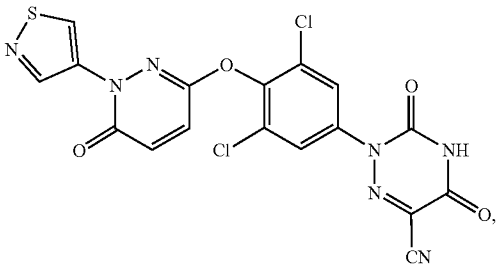
(32)
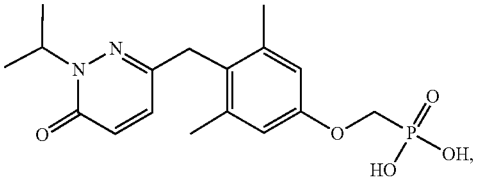
(33)
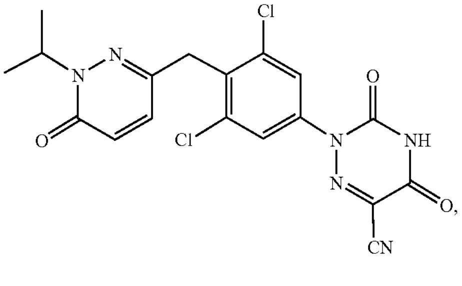
-continued
(34)
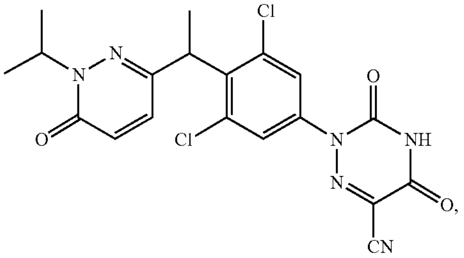
(35)
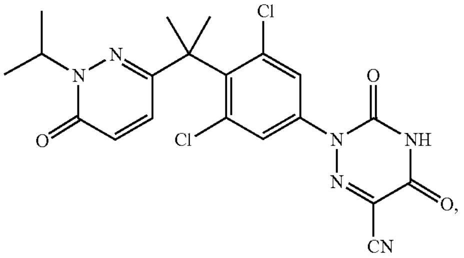
(36)
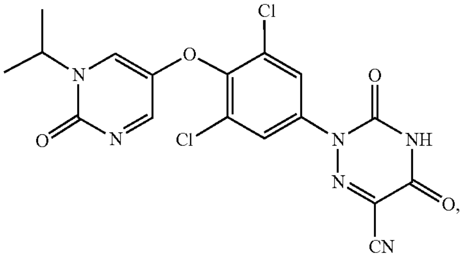
(37)
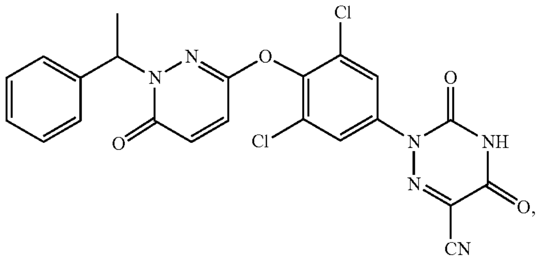
(38)
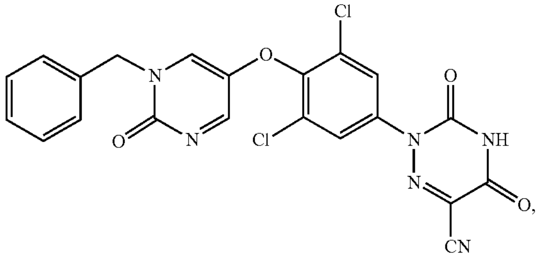
(39)
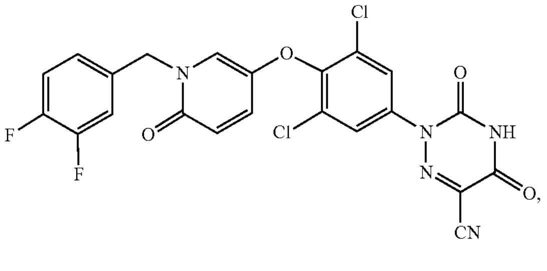

-continued
(40)
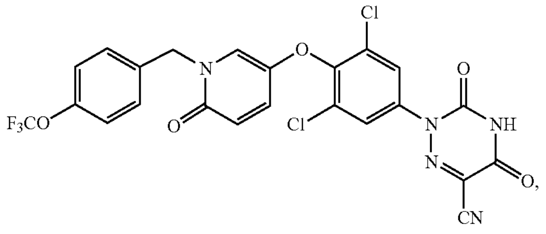
(41)
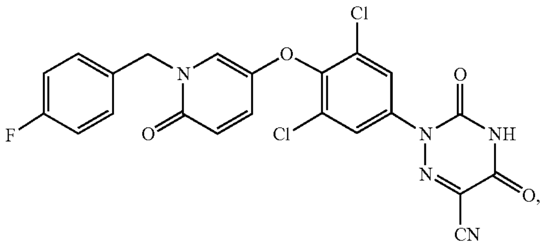
(42)
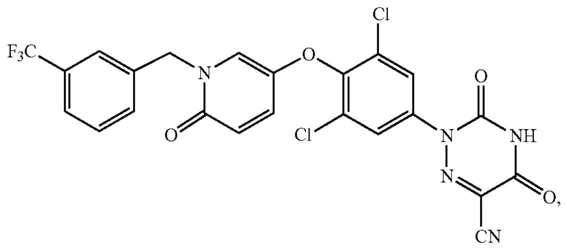
(43)
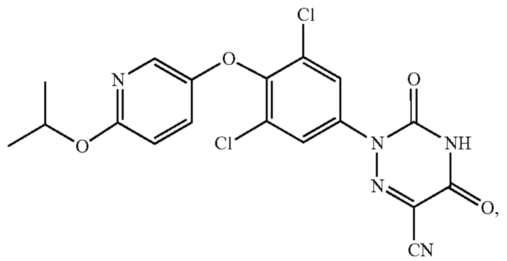
(44)
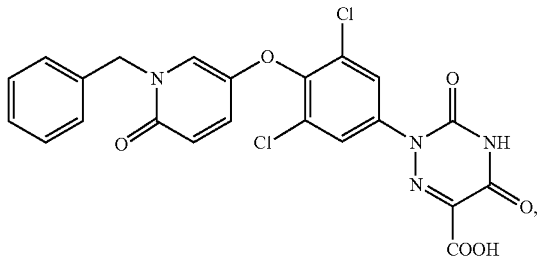
(45)
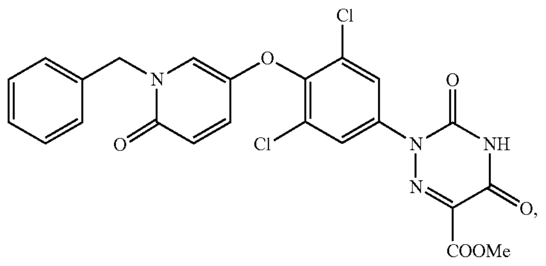
-continued
(46)
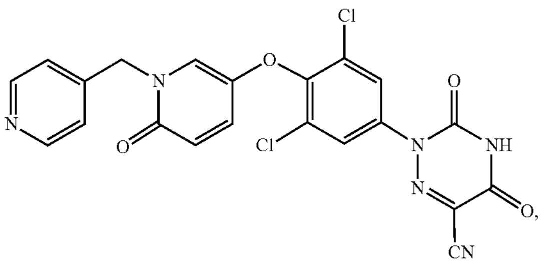
(47)
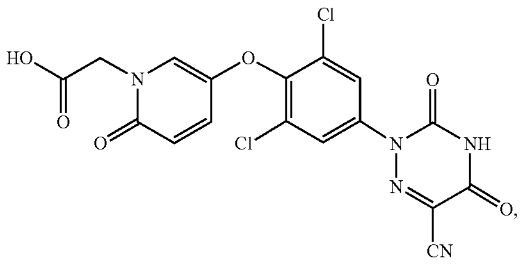
(48)
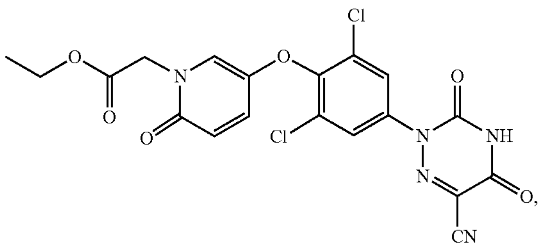
(49)
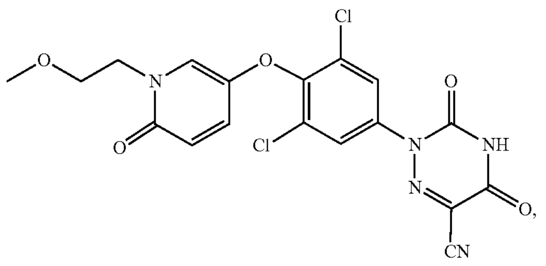
(50)
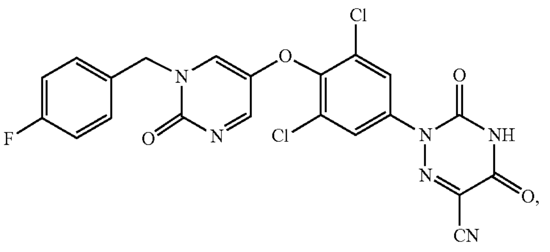

-continued
(51)
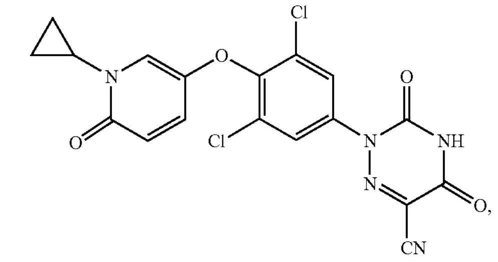
(52)
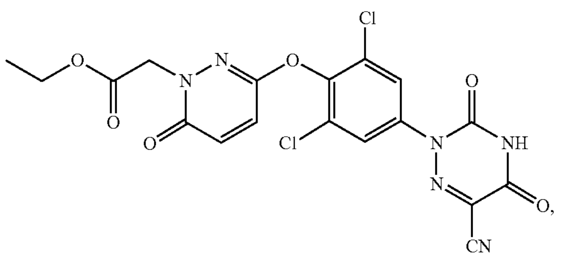
(53)
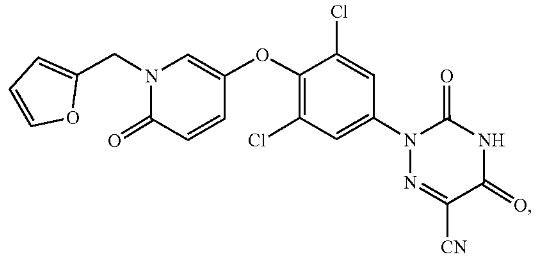
(54)
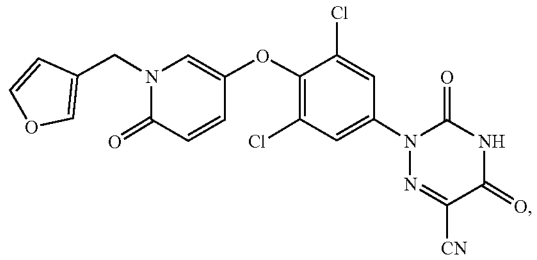
(55)
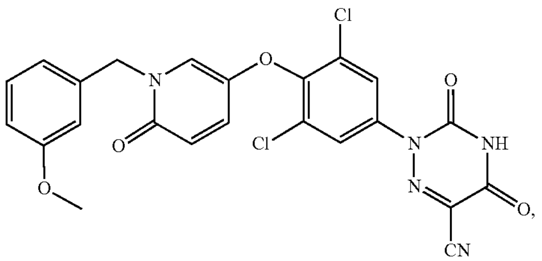
-continued
(56)
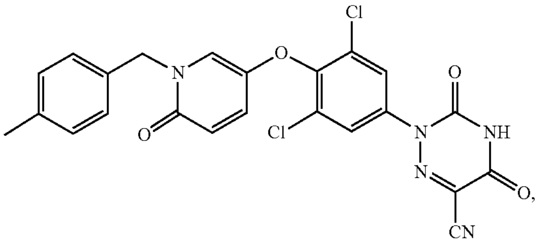
(57)
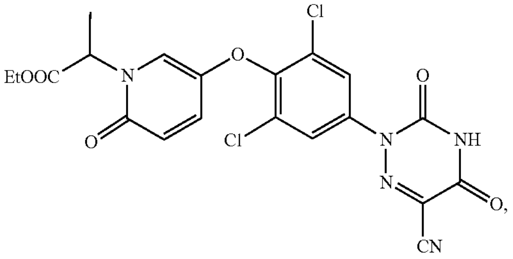
(58)
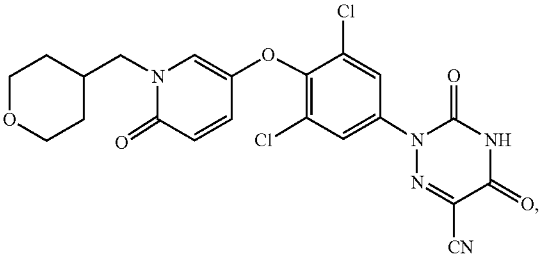
(59)
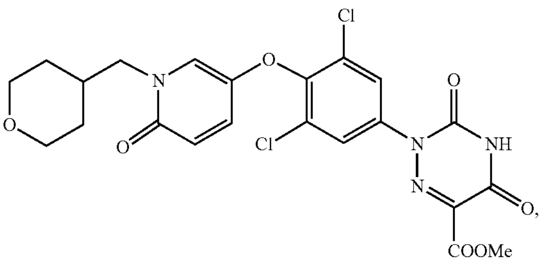
(60)
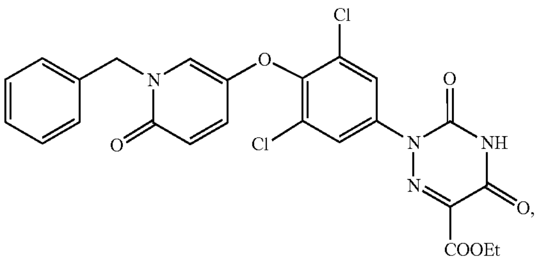

-continued
(61)
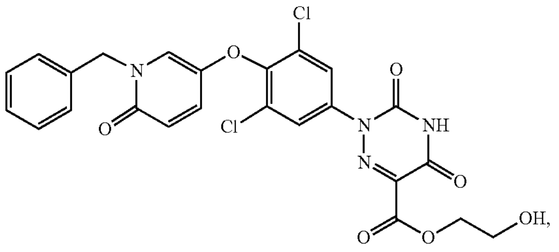
(62)
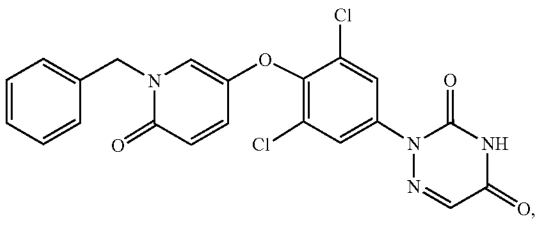
(63)
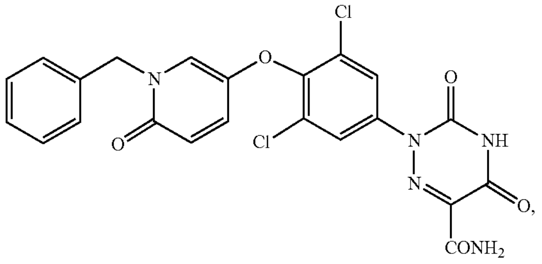
(64)
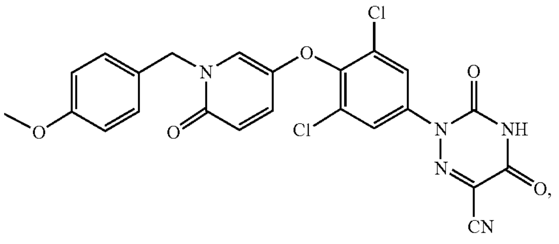
(65)
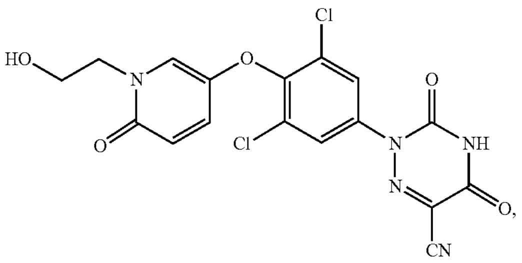
-continued
(66)
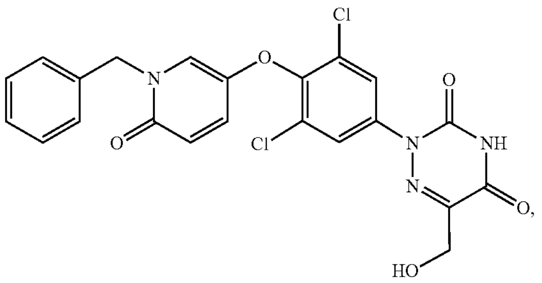
(67)
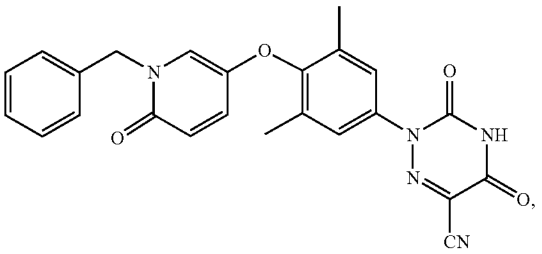
(68)
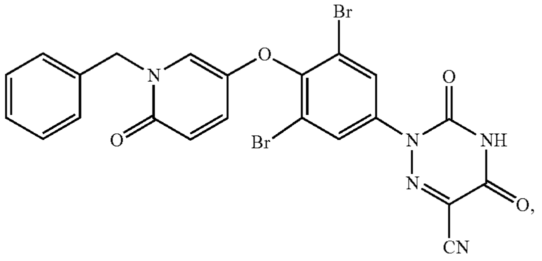
(69)
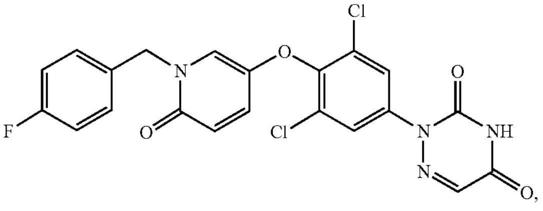
(70)
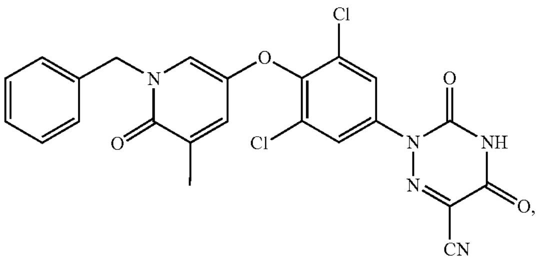

-continued (71)

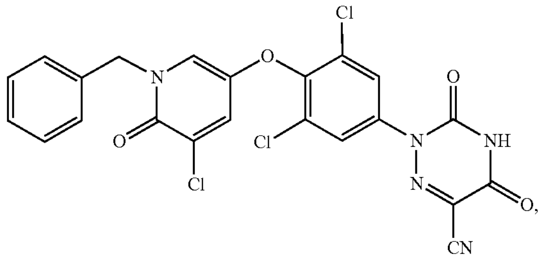

(72)

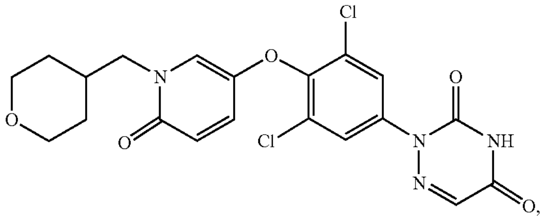

(73)

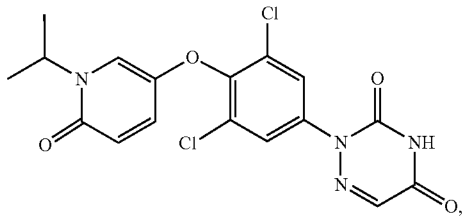

(74)

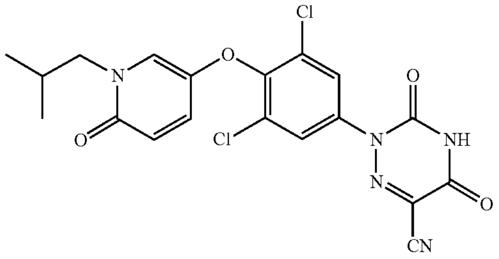

or (75)

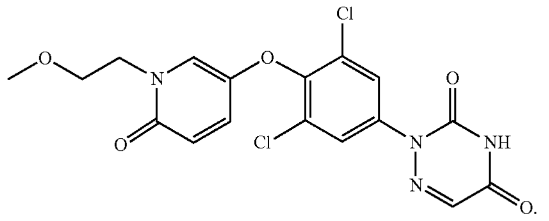

In other aspect, provided herein is a pharmaceutical composition comprising the compound disclosed herein.

In some embodiments, the pharmaceutical composition disclosed herein, optionally, further comprises any one of a pharmaceutically acceptable carrier, excipient, adjuvant, vehicle or a combination thereof.

In another aspect, the present invention relates to use of the compound of the present invention or the pharmaceutical composition of the present invention in the manufacture of a medicament for agonizing thyroid hormone receptors; or for preventing, treating or alleviating diseases mediated by agonistic thyroid hormone in a subject.

In another aspect, provided herein is a method of agonizing thyroid hormone receptors, or preventing, treating or alleviating diseases mediated by thyroid hormone receptors comprising administering to the subject in need a therapeutically effective amount of the compound or the the pharmaceutical composition disclosed herein. Moreover, the compound provided by the present invention or the pharmaceutical composition thereof can be co-administered with other therapies or therapeutic agents. The mode of administration can be simultaneous, sequential or at certain time intervals.

In another aspect, the present invention relates to the compound or the pharmaceutical composition of the present invention for use in agonizing thyroid hormone receptors; or in preventing, treating or alleviating diseases mediated by thyroid hormone receptors.

In some embodiments, the diseases mediated by thyroid receptors of the present invention are diseases mediated by agonistic thyroid receptors.

In some embodiments, the thyroid hormone receptor of the present invention is a thyroid hormone β receptor.

In some embodiments, the disease mediated by thyroid hormone receptors of the present invention is non-alcoholic fatty liver disease, atherosclerosis, coronary heart disease, hypertension, hypercholesterolemia, hyperlipidemia, hypertriglyceridemia, dyslipidemia, obesity, diabetes, metabolic disorders, type 1A glycogen storage disease, hypothyroidism or thyroid cancer.

In some embodiments, the non-alcoholic fatty liver disease of the present invention is non-alcoholic simple fatty liver, non-alcoholic steatohepatitis, cryptogenic cirrhosis or primary liver cancer.

In some embodiments, the metabolic disorders described in the present invention comprise lipid metabolism disorders or glucose metabolism disorders.

The dosage of the compound or pharmaceutical composition required for the implementation of treatment, prevention or delay is usually dependent on the specific compound administered, the patient, the specific disease or condition and its severity, the route and frequency of administration, etc., and needs to be determined by the attending physician based on the specific situation. For example, when the compound or pharmaceutical composition provided by the present invention is administered by an intravenous route, it can be administered once a week or even at longer intervals.

In some embodiments, the salt refers to a pharmaceutically acceptable salt. The phrase "pharmaceutically acceptable" refers to that the substance or composition must be chemically and/or toxicologically compatible with the other ingredients comprising a formulation, and/or the mammal being treated therewith.

The compounds of the present invention also include other salts of such compounds, which are not necessarily pharmaceutically acceptable salts, and can be used for preparing and/or purifying the compounds of the present invention and/or for isolating intermediates of the enantiomers of the compounds of the present invention.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms.

Pharmaceutical Composition of the Compound of the Invention and Preparations and Administration The invention relates to a pharmaceutical composition comprising the compound of the present invention or the compound of the structure shown in the examples, or a stereoisomer, a geometric isomer, a tautomer, an N-oxide, a solvate, a metabolite, a pharmaceutically acceptable salt or a prodrug thereof. The pharmaceutical composition further comprises at least one pharmaceutically acceptable carrier, excipient, adjuvant, vehicle or a combination thereof, and optionally, other therapeutic and/or prophylactic ingredients. In some embodiments, the pharmaceutical composition comprises a therapeutically effective amount of the compound of the present invention and at least one pharmaceutically acceptable carrier, excipient, adjuvant or vehicle. The amount of the compound in the pharmaceutical composition of the present invention is effective to detectably activate thyroid hormone β receptors in biological specimens or patients.

Pharmaceutically acceptable carriers may contain inert ingredients that do not unduly inhibit the biological activity of the compound. The pharmaceutically acceptable carrier should be biocompatible, for example, non-toxic, non-inflammatory, non-immunogenic or without other adverse reactions or side effects once administered to the patient. Standard pharmaceutical technology can be used.

As described above, the pharmaceutical composition or pharmaceutically acceptable composition of the present invention further comprises a pharmaceutically acceptable carrier, excipient, adjuvant or vehicle, which, as used herein, includes any solvents, diluents, liquid excipients, dispersants, suspending agents, surfactants, isotonic agents, thickeners, emulsifiers, preservatives, solid binders, lubricants and the like, as suited to the particular dosage form desired. Remington: The Science and Practice of Pharmacy, 21st ed., 2005, Lippincott Williams & Wilkins, Philadelphia, and Swarbrick et al., Encyclopedia of Pharmaceutical Technology, eds. 1988-1999, Marcel Dekker, New York, both of which are herein incorporated by reference in their entireties, discloses various carriers used in formulating pharmaceutically acceptable compositions and known techniques for the preparation thereof. Except insofar as any conventional carrier medium incompatible with the compounds disclosed herein, such as by producing any undesirable biological effect or otherwise interacting in a deleterious manner with any other components of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as Tween 80, phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, methyl cellulose, hydroxypropyl methyl cellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical composition of the present invention can be administered directly or in a pharmaceutical composition or pharmaceutical form along with a suitable carrier or excipient, which is well known in the art. The treatment method of the present invention may comprise administering an effective compound of the present invention to an individual in need. In some embodiments, the individual is a mammalian individual, and in other embodiments, the individual is a human individual.

The effective amount of the compound, pharmaceutical composition or drug of the present invention can be easily determined by routine test, and the most effective and convenient route of administration and the most suitable formulation can also be determined by routine test.

The compound or composition of the present invention may be administered by any suitable means, and the above-mentioned compounds and pharmaceutically acceptable compositions can be administered to humans or other animals orally, rectally, parenterally, intracisternally, intravaginally, intraperitoneally, topically (as by powder, ointment or drops) or by nasal sprays, etc., according to the severity of the disease.

Liquid dosage forms for oral administration include, but are not limited to, pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, dimethylformamide, oils (in particular cottonseed, groundnut, corn, germ, olive, castor and sesame oils), glycerol, tetrahydrofuryl alcohol, polyethylene glycols and fatty acid esters of sorbitan, and mixtures thereof. In addition to the inert diluent, the oral compositions may also contain adjuvants such as wetting agents, emulsifying or suspending agents, sweetening agents, flavoring agents and fragrances.

Injectable formulations can be formulated according to known techniques using suitable dispersing or wetting agents and suspending agents, for example, sterile injectable water or oil suspensions. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound or a composition described herein, it is often desirable to slow the absorption of the compound from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolic acid. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are specifically suppositories which can be prepared by mixing the compounds described herein with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders and granules. In such solid dosage forms, the active compounds are mixed with at least one pharmaceutically acceptable inert excipients or carriers, such as sodium citrate or dicalcium phosphate and/or (a) fillers or swelling agents such as starch, lactose, sucrose, glucose, mannitol and silicic acid; (b) adhesives such as carboxymethylcellulose, alginates, gelatin, polyethylene pyrrole ketone, sucrose and gum arabic; (c) moisturizing agents such as glycerol; (d) disintegrating agents such as agar, calcium carbonate, potato starch or tapioca starch, alginic acid, certain silicates and sodium carbonate; (e) blocker solution, such as paraffin; (f) absorption promoter such as quaternary ammonium compounds; (g) wetting agents such as cetyl alcohol and glycerol monostearate; (h) absorbents such as kaolin and bentonite, (i) lubricants such as talc, calcium stearate, magnesium stearate, solid polyethylene glycol, laurylsodium sulfate, and mixtures thereof. In the case of capsules, tablets and pills, the pharmaceutical compositions may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

The active compound may also take the form of a microseal with one or more of the above-mentioned excipients. In such solid dosage forms, the active compound may be mixed with at least one inert diluent, such as sucrose, lactose or starch. Generally, this dosage form may also contain additional substances in addition to inert diluents, such as tableting lubricants and other tableting aids, such as magnesium stearate and microcrystalline cellulose. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of the compounds of the present invention include ointments, ointments, creams, lotions, gels, powders, solutions, sprays, inhalants, or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compositions described herein may be administered orally, parenterally, by inhalation spray, topically, rectally, nasally, buccally, vaginally or via an implanted reservoir. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Specifically, the compositions are administered orally, intraperitoneally or intravenously.

Sterile injectable forms of the compositions described herein may be aqueous or oleaginous suspension. These suspensions may be formulated according to techniques known in the art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil can be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions described herein may be orally administered in any orally acceptable dosage form including, but not limited to, capsules, tablets, aqueous suspensions or solutions. In the case of tablets for oral use, carriers commonly used include, but are not limited to, lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions described herein may be administered in the form of suppositories for rectal administration. These can be prepared by mixing the agent with a suitable non-irritating excipient. Such materials include, but are not limited to, cocoa butter, beeswax and polyethylene glycols.

The pharmaceutical compositions described herein may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carrier compounds for topical administration of the present invention include, but are not limited to, mineral oil, petrolatum oil, white petrolatum, propylene glycol, polyoxyethylene, polyoxypropylene compounds, emulsified waxes and water. Alternatively, the pharmaceutical composition may be formulated as a suitable lotion or cream containing the active components suspended or dissolved in one or more pharmaceutically acceptable carriers. Suitable carriers include, but are not limited to, mineral oil, sorbitan monostearate, polysorbate 60, cetyl ester wax, cetearyl alcohol, 2-octyldodecanol, benzyl alcohol and water.

For ophthalmic use, the pharmaceutical compositions may be formulated as micronized suspensions in isotonic, pH adjusted sterile saline, or, specifically, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Use of the Compounds and Pharmaceutical Compositions

The compound or the pharmaceutical composition provided by the present invention can be used in the manufacture of a medicament for agonizing thyroid hormone receptors, or preventing, treating or alleviating diseases regulated by thyroid hormone receptors.

The compound or the pharmaceutical composition provided by the present invention can be used for agonizing thyroid hormone receptors, or preventing, treating or alleviating diseases regulated by thyroid hormone receptors.

The present invention provides a method of agonizing thyroid hormone receptors, or preventing, treating or alleviating diseases regulated by thyroid hormone receptors comprising administering to the subject in need a therapeutically effective amount of the compound or the the pharmaceutical composition disclosed herein. Moreover, the compound provided by the present invention or the pharmaceutical composition thereof can be co-administered with other therapies or therapeutic agents. The mode of administration can be simultaneous, sequential or at certain time intervals.

The disease regulated by the thyroid hormone receptors in the present invention is a disease mediated by agonistic thyroid hormone receptors.

The thyroid hormone receptor of the present invention is a thyroid hormone β receptor.

The disease of the present invention is non-alcoholic fatty liver disease, atherosclerosis, coronary heart disease, hypertension, hypercholesterolemia, hyperlipidemia, hypertriglyceridemia, dyslipidemia, obesity, diabetes, metabolic disorders, type 1A glycogen storage disease, hypothyroidism or thyroid cancer, wherein the non-alcoholic fatty liver disease is non-alcoholic simple fatty liver, non-alcoholic steatohepatitis, cryptogenic cirrhosis or primary liver cancer, wherein the metabolic disorders comprise lipid metabolism disorders or glucose metabolism disorders.

Besides being useful for human treatment, these compounds are also useful for veterinary treatment of animals such as companion animals, exotic animals and farm animals, including mammals, rodents, and the like. In other embodiments, the animals disclosed herein include horses, dogs, and cats. As used herein, the compounds disclosed herein include the pharmaceutically acceptable derivatives thereof.

An “effective amount” or “effective dose” of the compound or pharmaceutically acceptable composition is an amount that is effective in treating or lessening the severity of one or more of the aforementioned disorders. The compounds and pharmaceutically acceptable compositions are effective administered in a fairly wide dose range. For example, the daily dose is from about 0.1 mg to 1000 mg per person, the compounds or pharmaceutically acceptable compositions can be administered in a single dose or in several divided doses a day. The compounds and compositions, according to the method disclosed herein, may be administered using any amount and any route of administration which is effective for treating or lessening the severity of the disorder or disease. The exact amount required will vary from subject to subject, depending on the species, age, and general condition of the subject, the severity of the infection, the particular agent, its mode of administration, and the like. A compound or composition can also be administered with one or more other therapeutic agents as discussed above.

General Synthesis and Determination Methods

To describe the invention, the following examples are listed. However, it should be understood that the present invention is not limited to these embodiments, but merely provides a method for practicing the present invention.

In the present invention, if the chemical name of the compound doesn’t match the corresponding structure, the compound is characterized by the corresponding structure.

Generally, the compounds disclosed herein may be prepared by methods described herein, wherein the substituents are as defined in the present invention, except where further noted. The following non-limiting schemes and examples are presented to further exemplify the invention.

Persons skilled in the art will recognize that the chemical reactions described may be readily adapted to prepare a number of other compounds disclosed herein, and alternative methods for preparing the compounds disclosed herein are deemed to be within the scope disclosed herein. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds disclosed herein.

The structures of the compounds were identified by nuclear magnetic resonance (e.g., $^{1}$H-NMR, $^{13}$C-NMR and/or $^{19}$F-NMR). $^{1}$H-NMR, $^{13}$C-NMR and 19F-NMR chemical shifts (δ) were recorded as ppm ($10^{-6}$). Measure of $^{1}$H-NMR, $^{13}$C-NMR, $^{9}$F-NMR are performed, respectively, on Bruker Ultrashield-400 nuclear magnetic resonance spectrometer and Bruker Avance III HD 600 nuclear magnetic resonance spectrometer using deuterated chloroform (CDCl3), deuterated methanol ($CD_3OD$ and MeOH-$d_4$) or deuterated DMSO (DMSO-$d_6$) as a solvent. TMS (0 ppm) or chloroform (7.25 ppm) is as the reference standard. When peak multiplicities were reported, the following abbreviations were used: s (singlet), d (doublet), t (triplet), m (multiplet), br (broadened), dd (doublet of doublets), dt (doublet of triplets), td (triplet of doublets), brs (broadened singlet). Coupling constants J, when given, were reported in Hertz (Hz).

Novasep pump 250 high performance liquid chromatography is generally used for preparation, purification or separation.

LC-MS spectra were determined on Agilen-6120 Quadrupole LC/MS mass spectrometer.

The silica gel used in column chromatography generally was Qingdao Ocean Chemical Factory 300 to 400 mesh silica gel.

The staring materials of the present invention were known or purchased from Shanghai Accela Company, Energy Company, J&K, Alfa Company and the like, or they could be prepared by the conventional synthesis methods in the prior art.

The term "nitrogen atmosphere" refers to such an atmosphere that a reaction flask is equipped with a balloon or a stainless steel autoclave filled with about 1 L nitrogen.

The term "hydrogen atmosphere" refers to such an atmosphere that a reaction flask is equipped with a balloon or a stainless steel autoclave filled with about 1 L hydrogen.

Unless otherwise stated, the solution used in the examples disclosed herein was an aqueous solution.

Unless otherwise stated, the reaction temperature was room temperature.

Unless otherwise stated, the room temperature was from 20° C. to 40° C.

The reaction process in the examples was monitored by thin layer chromatography (TLC). The solvent system for development of a TLC plate comprised dichloromethane and methanol, dichloromethane and ethyl acetate, petroleum ether and ethyl acetate. The volume ratio of the solvents in the solvent system was adjusted according to the polarity of the compounds.

The elution system of column chromatography comprised: A: petroleum ether and ethyl acetate, B: dichloromethane and ethyl acetate, C: dichloromethane and methanol. The volume ratio of the solvents in the elution system was adjusted according to the polarity of the compounds, and sometimes it was also adjusted by adding a basic agent such as aqueous ammonia or an acidic agent such as acetic acid.

IPLC refers to High Performance Liquid Chromatography;

HPLC was determined on Agilent 1260 high pressure liquid chromatography spectrometer (chromatographic column: Agilent ZORBAX Eclipse Plus C18 4.6 mm×150 mm, 3.5 μm);

The test condition of HPLC: the run time was 25 minutes (min); the column temperature was 35° C.; the detection was carried out at the wavelength of 210 nm and 245 nm using PDA detector;

Mobile phase: phase A: 0.05% phosphoric acid solution phase B: acetonitrile; flow rate: 1.0 ml/min;

the gradient of mobile phase was shown in the Table A.

TABLE A

| Time | Gradient of Mobile Phase A | Gradient of Mobile Phase B |
|---|---|---|
| 0 min | 90% | 10% |
| 15 min | 10% | 90% |
| 20 min | 10% | 90% |
| 25 min | 90% | 10% |

The LC/MS/MS system used in biological analysis test comprises Agilent 1200 series vacuum degassing furnace, binary pumps, well-plate autosampler, thermostatted column compartment, the Agilent G6430 Triple Quadru pole Mass Spectrometer with an electrosprayionization (ESI) source. Quantitative analysis was carried out using MRM mode. The parameters for MRM transitions are in the Table B.

TABLE B

| | |
|---|---|
| Full scan | 50~1400 |
| Fragmentor | 230 V |
| Capillary voltage | 55 V |
| Temperature of dryer | 350° C. |
| Nebulizer | 0.28 MPa |
| Drying gas flow rate | 10 L/min |

An Agilent XDB-C18, 2.1×30 mm, 3.5 m column was used for the analysis. 5 μL of the samples were injected. Analysis conditions: The mobile phase was 0.1% formic acid in water (A) and 0.1% formic acid in methanol (B). The flow rate was 0.4 mL/min. And the gradient of mobile phase was shown in the Table C.

TABLE C

| Time | Gradient of Mobile Phase B |
|---|---|
| 0.5 min | 5% |
| 1.0 min | 95 % |
| 2.2 min | 95 % |
| 2.3 min | 5% |
| 5.0 min | Stop |

Low-resolution mass spectral (MS) data were determined on an Agilent 6120 Quadrupole HPLC-MS spectrometer equipped with an Agilent Zorbax SB-C18 (2.1×30 mm, 3.5 μm). The flow rate was 0.6 mL/min; the mobile phases consisted of a combination of A (0.1% formic acid in $CH_3CN$) and B (0.1% formic acid in $H_2O$) in gradient mode (5% to 95%), and an ESI mode was used, the peak of HPLC was recorded with UV-Vis detection at 210 nm/254 nm.

The following abbreviations are used throughout the specification:

| | |
|---|---|
| DMSO-$d_6$: | dimethylsulfoxide-$d_6$; |
| DCC: | dicyclohexylcarbodiimide |
| $CDCl_3$: | chloroform-d; |
| $CD_3OD$: | methanol-d; |
| μL, μl: | microliter; |
| mol: | mole; |
| μmol/L, μmol/l, μM: | micromole/liter; |
| g: | gram; |
| mg: | milligram; |
| ng: | nanogram; |
| μm: | micrometer; |
| $H_2$ | hydrogen; |
| min: | minute; |
| TBSO: | tert-butyldimethylsiloxy; |
| Me: | methyl; |
| TFA: | trifluoroacetic acid; |
| Boc: | tert-butoxycarbonyl; |
| DMSO: | dimethylsulfoxide; |
| % wt, mass %: | weight percent; |
| mL, ml: | milliliter |
| mol/L, mol/l: | mole per liter; |
| mmol/L, mmol/l, mM: | millimole/liter; |
| nmol/L, nmol/l, nM: | nanomole/liter; |
| h: | hour; |
| μg | microgram; |
| nm: | nanometer; |
| mm: | millimeter; |
| $N_2$: | nitrogen; |
| MPa: | megapascal; |
| Et: | ethyl; |
| ACN: | acetonitrile; |
| $H_2O$ | water. |

General Synthetic Procedures

Typical synthetic steps for preparing the disclosed compounds of the present invention are shown in the following synthetic schemes. Unless otherwise stated, X is F, Cl, Br or I; each L, $E_1$, $E_2$, $E_3$, $R^{3a}$, $R^{3d}$ and $R^1$ has the definition as described in the present invention.

Synthetic scheme 1

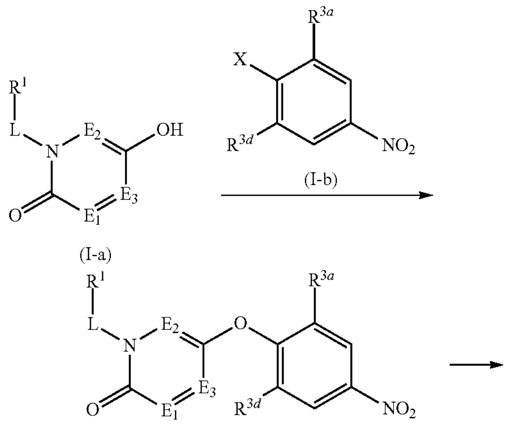

(I-a) (I-b) (I-c)

-continued

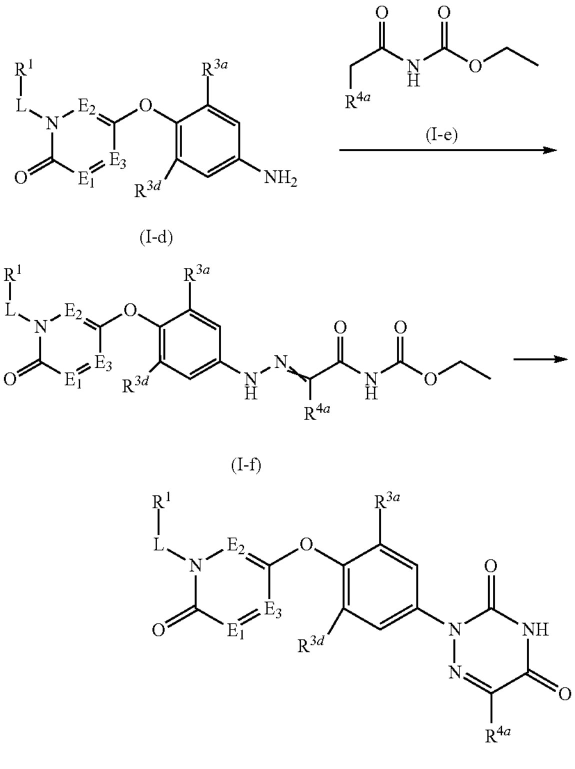

(I-d) (I-e) (I-f) (I-A)

Compound having formula (I-A) can be prepared by the general synthesis method described in synthesis scheme 1, wherein $R^{4a}$ is —CN or —$CF_3$. First, compound (I-a) can be reacted with compound (I-b) under alkaline conditions (such as potassium carbonate) to give compound (I-c); compound (I-c) can be subjected to a nitro reduction reaction to give compound (I-d); compound (I-d) can be subjected to an amino diazotization reaction, and then can be reacted with compound (I-e) to give compound (I-f); compound (I-f) can be ring closed under alkaline conditions (such as potassium acetate) to give the target compound (I-A).

Synthetic scheme 2

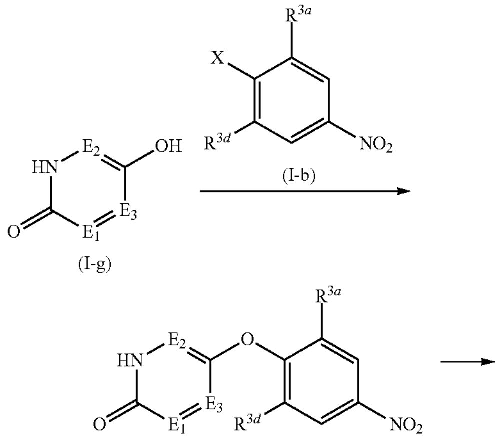

(I-g) (I-b) (I-h)

-continued

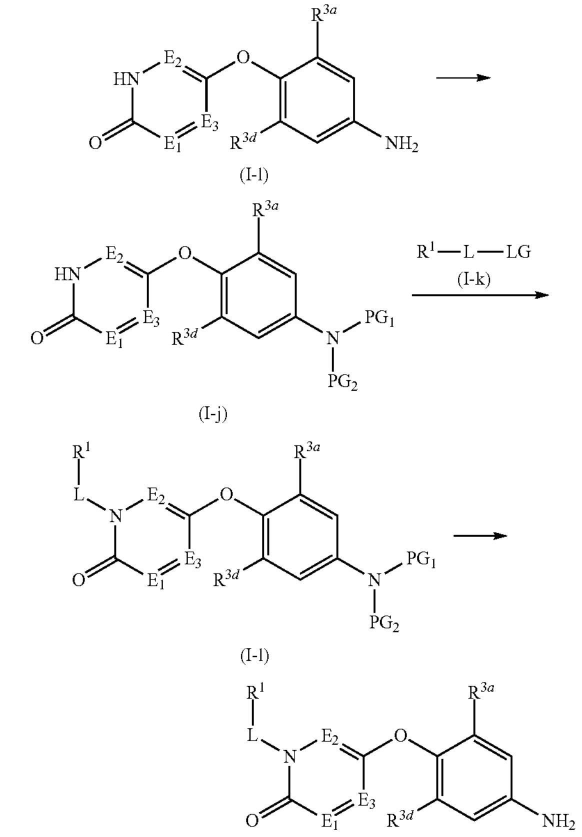

(I-l)

(I-j)

(I-l)

(I-d)

Intermediate having formula (I-d) can also be prepared by the general synthesis method described in synthetic scheme 2, wherein each of $PG_1$ and $PG_2$ is independently amino protecting group, or PG1 and PG2, together with the N atom to which they are attached, form 5-10 membered heterocyclyl or 5-10 membered heteroaryl, the 5-10 membered heterocyclyl or 5-10 membered heteroaryl can protect the amino group; LG is a leaving group. First, compound (I-g) can be reacted with compound (I-b) under alkaline conditions (such as potassium carbonate) to give compound (I-h); compound (I-h) can be subjected to a nitro reduction reaction to give compound (I-i); compound (I-i) can be protected by amino group to give compound (I-j); compound (I-j) can be reacted with compound (I-k) to give compound (I-i); compound (I-i) can be deprotected from the amino group to give an intermediate having formula (I-d).

Synthetic scheme 3

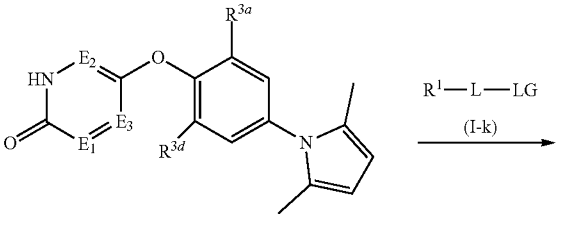

(I-m)

-continued

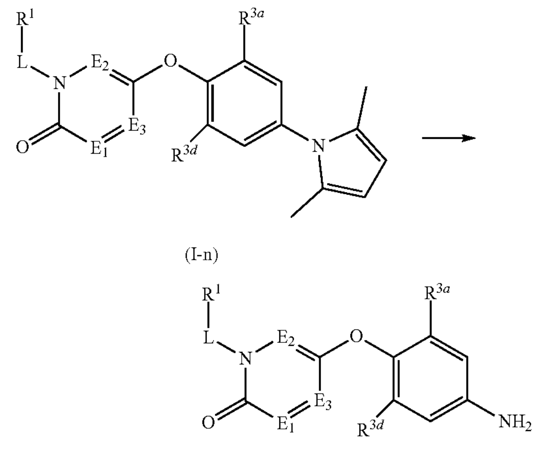

(I-n)

(I-d)

Intermediate having formula (I-d) can also be prepared by the general synthesis method described in synthesis scheme 3, wherein LG is a leaving group. First, the compound (I-m) can be reacted with compound (I-k) to give compound (I-n); then compound (I-n) can be deprotected from the amino group to give an intermediate having formula (I-d).

Synthetic scheme 4

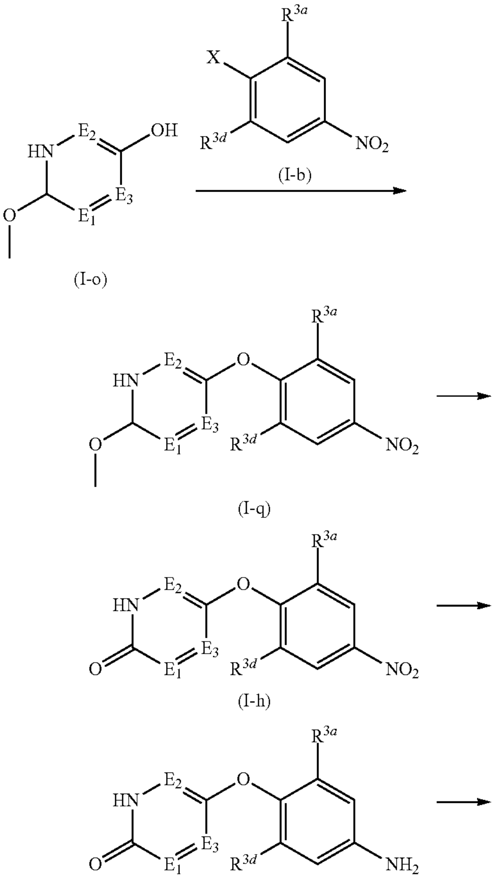

(I-b)

(I-o)

(I-q)

(I-h)

(I-i)

-continued

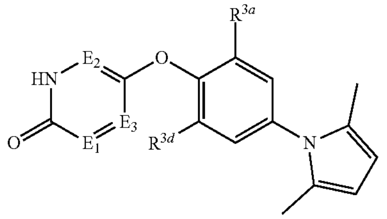

(I-m)

Intermediate having formula (I-m) can also be prepared by the general synthesis method described in synthesis scheme 4, wherein X is halogen. First, compound (I-o) can be reacted with compound (I-b) under alkaline conditions (such as potassium carbonate) to give compound (I-q); compound (I-q) can be demethylated to give compound (I-h); compound (I-h) can be subjected to a nitro reduction reaction to give compound (I-i); compound (I-i) can be protected by amino group to give compound (I-m).

Synthetic scheme 5

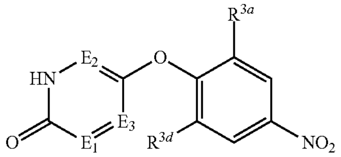

(I-h)

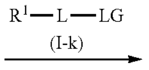

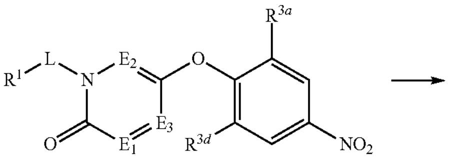

(I-r)

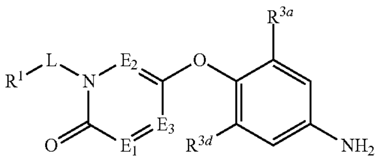

(I-d)

Intermediate having formula (I-d) can also be prepared by the general synthesis method described in synthesis scheme 5, wherein LG is a leaving group. First, the compound (I-h) can be reacted with compound (I-k) to give compound (I-r); then compound (I-r) can be deprotected from the amino group to give an intermediate having formula (I-d).

Synthetic scheme 6

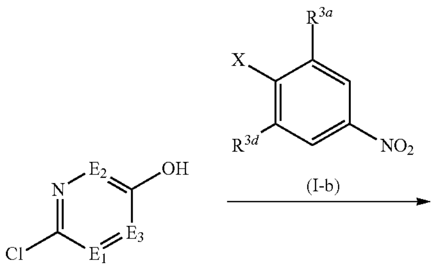

(I-s)

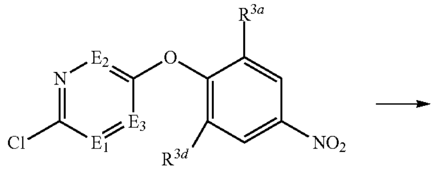

(I-t)

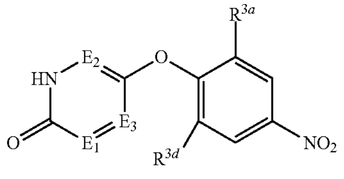

(I-h)

Intermediate having formula (I-h) can also be prepared by the general synthesis method described in synthesis scheme 6. First, compound (I-s) can be reacted with compound (I-b) under alkaline conditions (such as potassium carbonate) to give compound (I-t); then compound (I-t) can be hydrolyzed to give compound (I-h).

Synthetic scheme 7

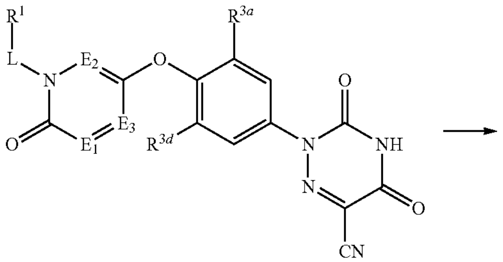

(I-u)

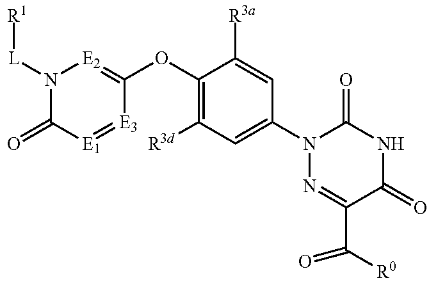

(I-B)

Compound having formula (I-B) can be prepared by the general synthesis method described in synthesis scheme 4, wherein $R^0$ is alkoxy, —OH or —$NH_2$. Compound (I-u) can be reacted under acidic conditions (such as concentrated hydrochloric acid) to give compound (I-B).

EXAMPLES

Example 1 2-[4-[(1-benzyl-6-oxo-1,6-dihydropyridin-3-yl)oxy]-3,5-dichlorophenyl]-3,5-dioxo-1,2,4-triazine-6-carbonitrile (Compound 1)

(1)

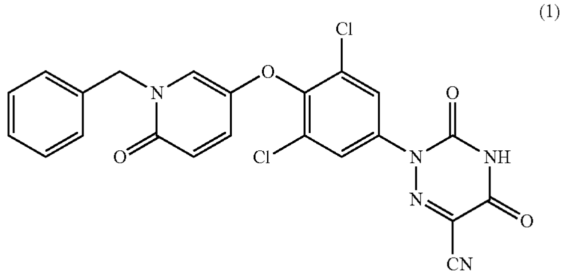 [SMILES: N#Cc1nn(-c2cc(Cl)c(Oc3ccc(=O)n(Cc4ccccc4)n3)c(Cl)c2)c(=O)[nH]c1=O]

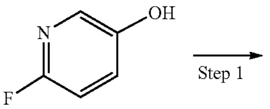

1a

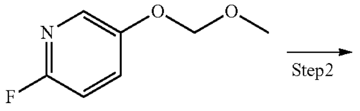

1b

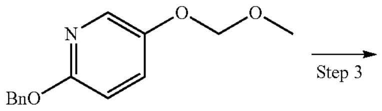

1c

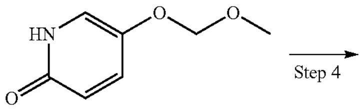

1d

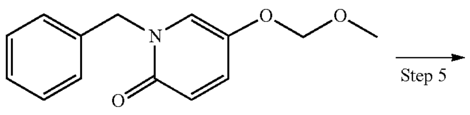

1e

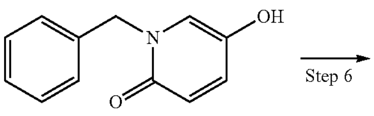

If

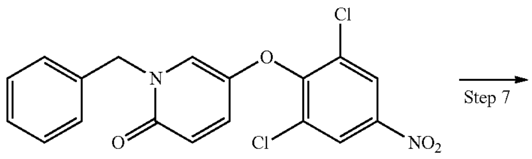

1g

-continued

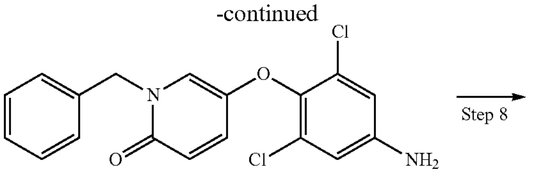

1h

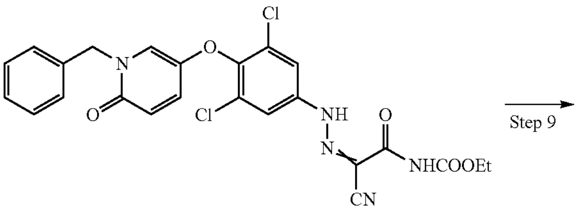

1i

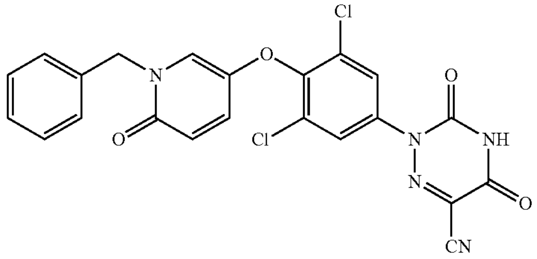

1

Step 1) 2-fluoro-5-(methoxymethoxy)pyridine 1b

At 0° C., sodium hydride (1.1 g, 28 mmol, 60 mass %) was added to anhydrous tetrahydrofuran (10 mL), then 6-fluoropyridin-3-ol 1a (2.0 g, 18 mmol) was added, and then chloromethyl methyl ether (1.6 mL, 21 mmol) was added dropwise to the mixture, and the mixture was reacted at 0° C. for 8 hours. The resulting mixture was quenched with water (50 mL), extracted with ethyl acetate (100 mL), the organic phase was washed with saturated sodium chloride solution (50 mL×3), then dried over anhydrous sodium sulfate, concentrated by suction filtration to obtain the title compound 1b (2.3 g, yield 83%) as a colorless oil.

Step 2) 2-benzyloxy-5-(methoxymethoxy)pyridine 1c

Benzyl alcohol (0.40 mL) and 2-fluoro-5-(methoxymethoxy)pyridine 1b (0.50 g, 3.2 mmol) were added to a solution of sodium hydride (0.19 g, 4.8 mmol, 60 mass %) in N,N-dimethylformamide (8 mL), the mixture was reacted at room temperature for 2 hours. The resulting mixture was quenched with water (10 mL), extracted with ethyl acetate (20 mL×3), the combined organic phase was washed with saturated sodium chloride solution (20 mL), then dried over anhydrous sodium sulfate, and concentrated by suction filtration. The obtained residue was purified by silica gel column chromatography [petroleum ether/ethyl acetate (v/v)=9/1] to obtain the title compound 1c (0.55 g, yield 70%) as colorless liquid.

$^1$H NMR (400 MHz, $CDCl_3$) δ (ppm) 8.01 (d, J=2.9 Hz, 1H), 7.49 (d, J=7.3 Hz, 2H), 7.38 (ddt, J=18.8, 14.5, 7.2 Hz, 4H), 6.79 (d, J=8.9 Hz, 1H), 5.37 (s, 2H), 5.13 (s, 2H), 3.52 (s, 3H).

Step 3) 5-(methoxymethoxy)pyridine-2(1H)-one 1d

2-Benzyloxy-5-(methoxymethoxy)pyridine 1c (0.50 g, 2.0 mmol) was dissolved in methanol (10 mL), then 10% palladium on carbon (50 mg) was added. The mixture was replaced with $H_2$ and hydrogenated for 40 minutes. The resulting mixture was filtered and the filtrate was concentrated to obtain the title compound 1d (0.31 g, yield 98%) as an off-white solid.

$^1$H NMR (400 MHz, $CDCl_3$) δ (ppm) 7.36 (dd, J=9.7, 3.1 Hz, 1H), 7.27 (t, J=5.2 Hz, 1H), 6.55 (d, J=9.7 Hz, 1H), 4.99 (s, 2H), 3.47 (s, 3H).

Step 4) 1-benzyl-5-(methoxymethoxy)pyridine-2(1H)-one 1e 5-(Methoxymethoxy)pyridine-2(1H)-one 1d (0.10 g, 0.64 mmol) was added to a solution of sodium hydride (52 mg, 1.3 mmol, 60 mass %) in N,N-dimethylformamide (5 mL), then benzyl bromide (0.10 mL, 0.84 mmol) was added dropwise, the mixture was reacted at room temperature for 3 hours. The resulting mixture was quenched with water (10 mL), extracted with ethyl acetate (20 mL×3), the combined organic phase was washed with saturated sodium chloride solution (20 mL), then dried over anhydrous sodium sulfate, and concentrated by suction filtration. The obtained residue was purified by silica gel column chromatography [petroleum ether/ethyl acetate (v/v)=1/2] to obtain the title compound 1e (0.11 g, yield 70%) as a colorless oil.

$^1$H NMR (400 MHz, $CDCl_3$) δ (ppm) 7.29 (dt, J=12.3, 6.9 Hz, 5H), 7.20 (dd, J=9.8, 1.4 Hz, 1H), 7.08 (d, J=2.5 Hz, 1H), 6.54 (d, J=9.8 Hz, 1H), 5.07 (s, 2H), 4.89 (d, J=1.1 Hz, 2H), 3.39 (dd, J=2.6, 1.3 Hz, 3H).

Step 5) 1-benzyl-5-hydroxy-pyridine-2(1H)-one 1f

Bromotrimethylsilane (0.82 mL, 6.1 mmol) was added to a solution of 1-benzyl-5-(methoxymethoxy)pyridine-2(1H)-one 1e (0.10 g, 0.41 mmol) in dichloromethane (5 mL), and the mixture was reacted at room temperature for 30 minutes. The reaction solution was concentrated to obtain the title compound 1f (82 mg, yield 100%) as a yellow solid.

$^1$H NMR (400 MHz, $CDCl_3$) δ (ppm) 7.93-7.67 (m, 2H), 7.33 (d, J=14.4 Hz, 5H), 7.28 (t, J=5.0 Hz, 1H), 5.39 (d, J=2.8 Hz, 2H).

Step 6) 1-benzyl-5-(2,6-dichloro-4-nitro-phenoxy)-pyridine-2(1H)-one 1g

1-Benzyl-5-hydroxy-pyridine-2(1H)-one 1f (1.2 g, 6.0 mmol), potassium carbonate (2.5 g, 18 mmol) and 1,3-dichloro-2-iodo-5-nitrobenzene (1.9 g, 6.0 mmol) were dissolved in N,N-dimethylformamide (15 mL) and the mixture was reacted at 120° C. for 2 hours. The reaction solution was cooled to room temperature, and quenched with water (20 ml), extracted with ethyl acetate (30 mL×3). The combined organic phase was washed with saturated sodium chloride solution (20 mL), then dried with anhydrous sodium sulfate, concentrated by suction filtration. The obtained residue was purified by silica gel column chromatography [petroleum ether/ethyl acetate (v/v)=4/1] to obtain the title compound 1g (1.2 g, yield 51%) as a yellow solid.

Step 7) 5-(4-nitro-2,6-dichloro-phenoxy)-1-benzyl-pyridine-2(1H)-one 1h

1-Benzyl-5-(2,6-dichloro-4-nitro-phenoxy)-pyridine-2(1H)-one 1g (64 mg, 0.16 mmol) was dissolved in acetic acid (3 mL), then iron powder (6 mg) was added and the mixture was reacted at 70° C. for 5 hours. The reaction solution was cooled to room temperature and concentrated, and to the residue were added water (10 mL) and ethyl acetate (10 mL), then sodium carbonate solid was added to adjust pH=8, then the resulting mixture was extracted with ethyl acetate (20 mL×3). The combined organic phase was washed with saturated sodium chloride solution (20 mL), dried with anhydrous sodium sulfate, concentrated by suction filtration. The obtained residue was purified by silica gel column chromatography [petroleum ether/ethyl acetate (v/v)=1/1] to obtain the title compound 1h (30 mg, yield 51%) as a yellow solid.

MS (ESI, pos. ion) m z: 361.1 $[M+H]^+$.

Step 8) Ethyl (2-(2-(4-((1-benzyl-6-oxo-1,6-dihydropyridin-3-yl)oxy)-3,5-dichlorophenyl)hydrazono)-2-cyanoacetyl)carbamate 1i 5-(4-Nitro-2,6-dichloro-phenoxy)-1-benzyl-pyridine-2(1H)-one 1h (0.20 g, 0.6 mmol), N-cyanoacetylurethane (0.097 g, 0.6 mmol) and concentrated hydrochloric acid (0.14 mL) were added to acetic acid (3 mL), and to the mixture was added dropwise an aqueous solution (2 mL) of sodium nitrite (0.043 g, 0.6 mmol) at 3° C., then the mixture was reacted for 6 hours. To the reaction solution was added water (20 mL), and the mixture was extracted with ethyl acetate (50 mL×2), the combined organic phase was dried over anhydrous sodium sulfate, concentrated by suction filtration to obtain a dark red solid, which was directly used for the next reaction.

MS (ESI, pos. ion) m z: 529.2 $[M+H]^+$.

Step 9) 2-[4-[(1-Benzyl-6-oxo-1,6-dihydropyridin-3-yl)oxy]-3,5-dichlorophenyl]-3,5-dioxo-1,2,4-triazine-6-carbonitrile 1

The dark red solid obtained from the previous step was dissolved in N,N-dimethylacetamide (2 mL), then potassium acetate (0.22 g, 2.2 mmol) was added, and the mixture was reacted at 120° C. for 24 hours. The reaction solution was cooled to room temperature, filtered, and the filtrate was purified by preparative chromatography column [49% ACN/51% $H_2O$ (0.1% TFA), Phenomenex ACE specifications: C18 10 μm×50 mm×250 mm, flow rate: 100 mL/min] to obtain the title compound 1 (11 mg, yield 4%, HPLC purity: 92.89%) as a white solid.

MS (ESI, neg. ion) m z: 481.8 $[M-H]^-$;

$^1$H NMR (400 MHz, DMSO-$d_6$) δ (ppm) 7.77 (s, 2H), 7.58 (d, J=3.3 Hz, 1H), 7.46 (dd, J=9.9, 3.3 Hz, 1H), 7.31 (d, J=7.5 Hz, 2H), 7.27 (d, J=7.2 Hz, 1H), 7.22-7.19 (m, 2H), 6.48 (d, J=9.9 Hz, 1H), 5.32 (s, 1H), 5.04 (s, 2H).

Example 2 2-[4-(1-benzyl-6-oxo-1,6-dihydro-pyridazin-3-yl)oxy-3,5-dichlorophenyl]-3,5-dioxo-1,2,4-triazine-6-carbonitrile (Compound 2)

(2)

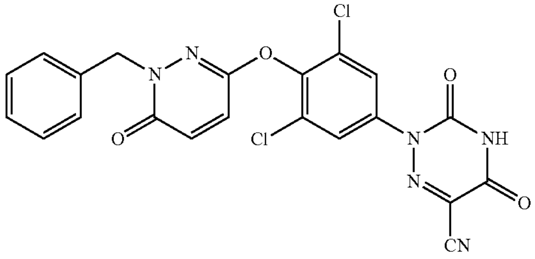

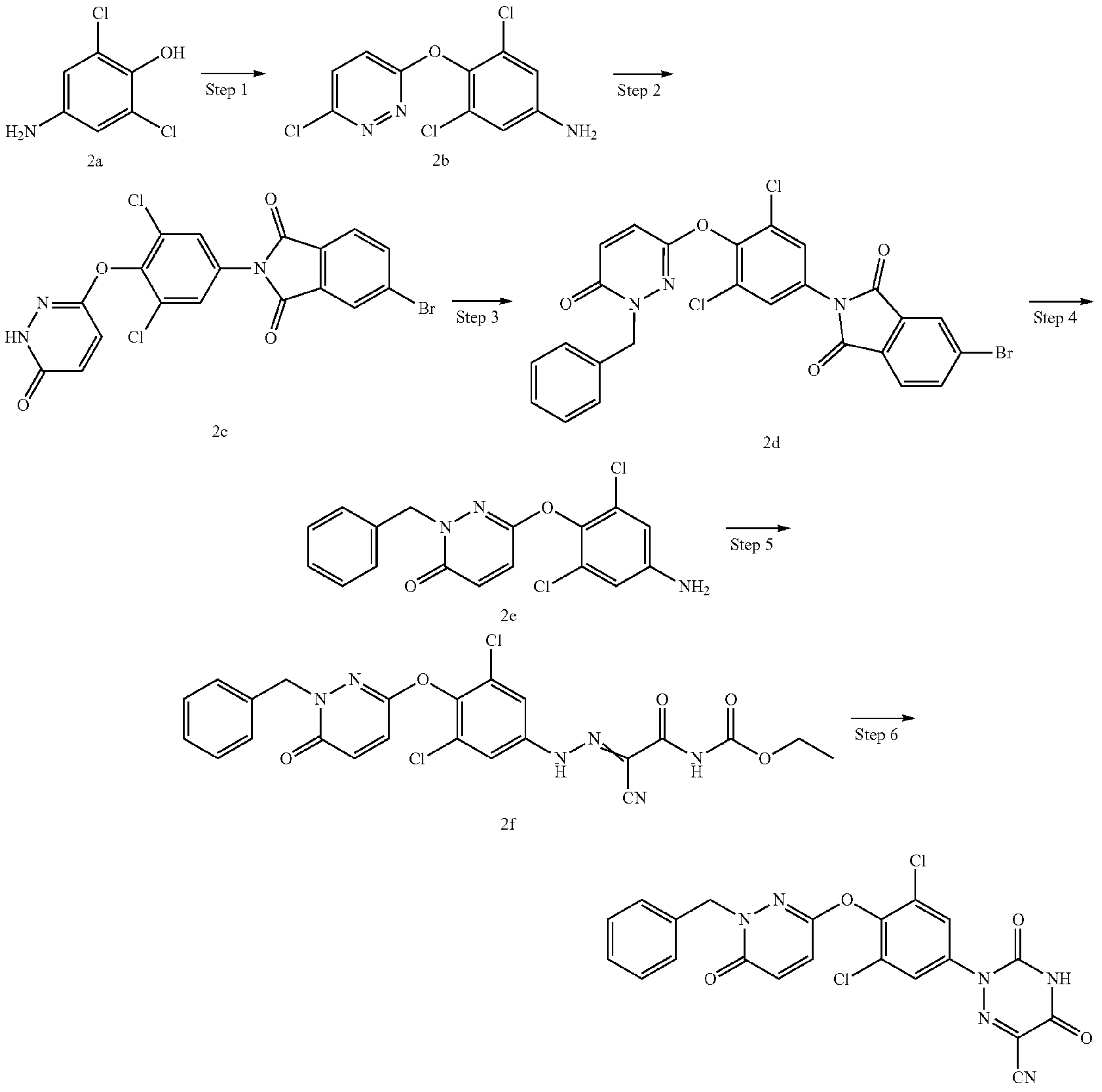

2

Step 1)

3,5-dichloro-4-(6-chloropyridazin-3-yl)oxy-aniline

2b

Cesium carbonate (3.75 g, 11.5 mmol) and 3,6-dichloropyridazine (1.49 g, 10.0 mmol) were added to a solution of 4-amino-2,6-dichloro-phenol 2a (1.82 g, 10.2 mmol) in N,N-dimethylacetamide (10 mL), the mixture was reacted at 110° C. for 6 hours. The reaction solution was cooled to room temperature, then ethyl acetate (20 mL) was added, the resulting mixture was filtered with diatomite, rinsed with ethyl acetate (20 mL). The filtrate was washed with saturated sodium chloride solution (10 mL×3), dried with anhydrous sodium sulfate, concentrated by suction filtration. The residue was purified by silica gel column chromatography [ethyl acetate/petroleum ether (v/v)=1/2] to obtain the title compound 2b (1.47 g, yield 51%) as a brown solid.

MS (ESI, pos. ion) m z: 291.9 $[M+H]^+$.

Step 2) 5-bromo-2-(3,5-dichloro-4-((6-oxo-1,6-dihydropyridazin-3-yl)oxy)phenyl)isoindoline-1,3-dione 2c 3,5-Dichloro-4-(6-chloropyridazin-3-yl)oxy-aniline 2b (0.2 g, 0.69 mmol) and 4-bromophthalic anhydride (0.20 g, 0.69 mmol) were dissolved in acetic acid (2 mL), the mixture was reacted at 120° C. for 3 hours, then sodium acetate (0.23 g, 2.8 mmol) was added. The mixture was reacted at 120° C. for 16 hours. The reaction solution was cooled to room temperature, then saturated sodium carbonate solution (50 mL) was added. The mixture was stirred for 15 minutes and filtered, and the filter cake was collected and dried to obtain the title compound 2c (0.20 g, yield 60%) as a white solid.

MS (ESI, pos. ion) m z: 481.8 $[M+H]^+$;

$^1$H NMR (400 MHz, DMSO-$d_6$) δ (ppm) 12.35 (s, 1H), 8.21 (d, J=1.3 Hz, 1H), 8.13 (dd, J=7.9, 1.5 Hz, 1H), 7.94 (d, J=8.0 Hz, 1H), 7.77 (s, 2H), 7.67 (d, J=9.9 Hz, 1H), 7.11 (d, J=9.9 Hz, 1H).

Step 3) 2-(4-((1-benzyl-6-oxo-1,6-dihydropyridazin-3-yl)oxy)-3,5-dichlorophenyl)-5-bromoisoindoline-1,3-dione 2d 5-Bromo-2-(3,5-dichloro-4-((6-oxo-1,6-dihydropyridazin-3-yl)oxy)phenyl)isoindoline-1,3-dione 2c (0.10 g, 0.21 mmol), potassium carbonate (0.058 g, 0.42 mmol), potassium iodide (0.003 g, 0.02 mmol) and benzyl bromide (0.036 g, 0.21 mmol) were dissolved in N,N-dimethylacetamide (1 mL). The mixture was reacted at room temperature for 13 hours. The resulting mixture was quenched with water (10 mL) and extracted with ethyl acetate (5 mL×2). The combined organic phase was dried over anhydrous sodium sulfate, concentrated by suction filtration. The residue was purified by silica gel column chromatography [petroleum ether/ethyl acetate (v/v)=1/1] to obtain the title compound 2d (50 mg, yield 42%) as a yellow solid.

$^1$H NMR (600 MHz, $CDCl_3$) δ (ppm) 8.15 (s, 1H), 7.99 (dd, J=7.9, 1.5 Hz, 1H), 7.87 (d, J=7.9 Hz, 1H), 7.61 (s, 2H), 7.31-7.27 (m, 3H), 7.24 (d, J=6.4 Hz, 3H), 7.06 (d, J=9.7 Hz, 1H), 5.04 (s, 2H).

Step 4) 6-(4-amino-2,6-dichlorophenoxy)-2-benzylpyridazin-3(2H)-one 2e 2-(4-((1-benzyl-6-oxo-1,6-dihydropyridazin-3-yl)oxy)-3,5-dichlorophenyl)-5-bromoisoindoline-1,3-dione 2d (50 mg, 0.09 mmol) was dissolved in ethanol (2 mL), then 35% hydrazine hydrate aqueous solution (0.08 mL) was added. The mixture was reacted at room temperature for 2 hours. The reaction solution was concentrated, and the residue was purified by silica gel column chromatography [petroleum ether/ethyl acetate (v/v)=3/1] to obtain the title compound 2e (10 mg, yield 32%) as a white solid.

MS (ESI, pos. ion) m z: 362.1 [M+H]+.

Step 5) Ethyl (2-(2-(4-((1-benzyl-6-oxo-1,6-dihydropyridazin-3-yl)oxy)-3,5-dichlorophenyl)hydrazono)-2-cyanoacetyl)carbamate 2f 6-(4-Amino-2,6-dichlorophenoxy)-2-benzylpyridazin-3(2H)-one 2e (0.10 g, 0.28 mmol), N-cyanoacetylurethane (0.048 g, 0.30 mmol) and concentrated hydrochloric acid (0.07 mL) were added to acetic acid (3 mL), and an aqueous solution (2 mL) of sodium nitrite (0.021 g, 0.30 mmol) was added dropwise at 3° C., then the mixture was reacted for 4 hours. To the reaction solution was added water (20 mL), then the mixture was extracted with ethyl acetate (20 mL×2), the combined organic phase was dried over anhydrous sodium sulfate, then concentrated by suction filtration to obtain the title compound 2f (0.15 g, yield 100%), which was directly used for the next reaction.

MS (ESI, neg. ion) m z: 529.1 $[M-H]^-$.

Step 6) 2-[4-(1-benzyl-6-oxo-1,6-dihydropyridazin-3-yl)oxy-3,5-dichlorophenyl]-3,5-dioxo-1,2,4-triazine-6-carbonitrile 2

Potassium acetate (0.11 g, 1.06 mmol) was added to a solution of ethyl (2-(2-(4-((1-benzyl-6-oxo-1,6-dihydropyridazin-3-yl)oxy)-3,5-dichlorophenyl)hydrazono)-2-cyanoacetyl)carbamate 2f in N,N-dimethylacetamide (2 mL), and the mixture was reacted at 120° C. for 3 hours. The reaction solution was cooled to room temperature, filtered, and the filtrate was concentrated, the residue was purified by preparative chromatography column [50% ACN/50% $H_2O$ (0.1% TFA), Phenomenex ACE specifications: C18 10 μm×50 mm×250 mm, flow rate: 100 mL/min] to obtain the title compound 2 (10 mg, yield 7.8%, HPLC purity: 98.92%) as a white solid.

MS (ESI, neg. ion) m z: 482.9 $[M-H]^-$.

$^1$H NMR (400 MHz, DMSO-$d_6$), δ (ppm) 7.79 (s, 2H), 7.68 (d, J=9.8 Hz, 1H), 7.27-7.23 (m, 3H), 7.19 (d, J=9.8 Hz, 1H), 7.06 (dd, J=7.0, 1.9 Hz, 2H), 4.92 (s, 2H).

Example 3 2-[3,5-dichloro-4-[(1-isopropyl-6-oxo-1,6-dihydropyridazin-3-yl)oxy]phenyl]-3,5-dioxo-1,2,4-triazine-6-carbonitrile (Compound 3)

(3)

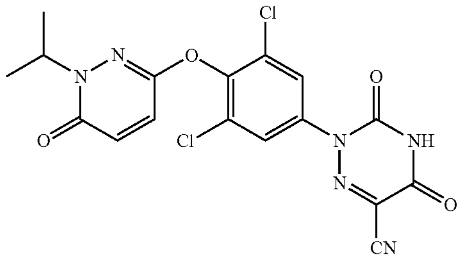

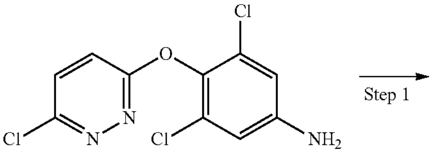

3a

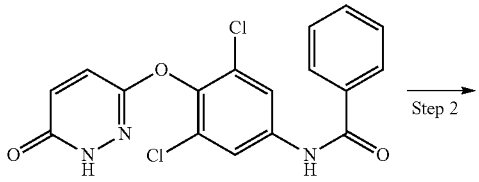

3b

-continued

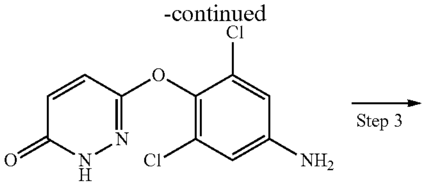

3c

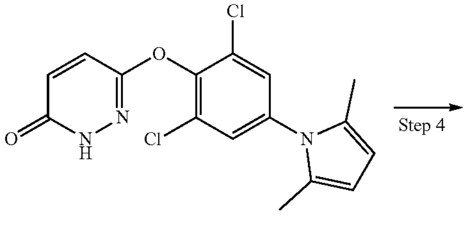

3d

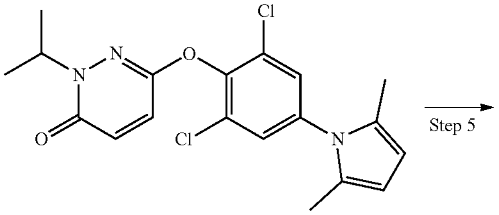

3d

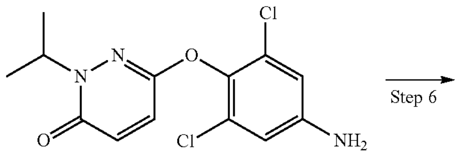

3f

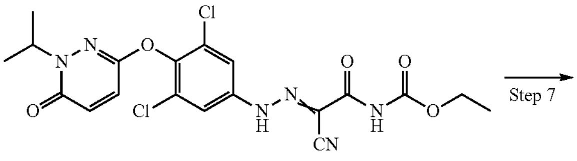

3g

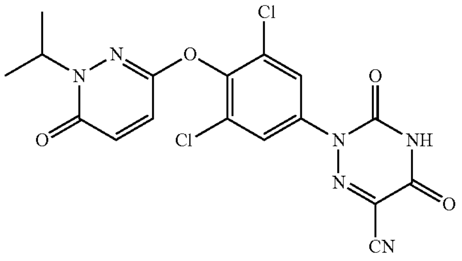

3

Step 1) N-(3,5-dichloro-4-((6-oxo-1,6-dihydro-pyridazin-3-yl)oxy)phenyl)benzamide 3b 3,5-Dichloro-4-((6-chloropyridazin-3-yl)oxy)aniline 3a (2.29 g, 7.88 mmol) and benzoic anhydride (2.06 g, 7.88 mmol) were dissolved in acetic acid (3 mL), the mixture was reacted at 110° C. for 3 hours. To the mixture was added sodium acetate (2.63 g, 31.5 mmol) and the mixture was reacted for 24 hours. The reaction solution was poured into saturated sodium carbonate solution (50 mL), the resulting mixture was stirred for 15 minutes, filtered, and the filter cake was collected and dried under vacuum to obtain the title compound 3b (2.50 g, yield 84%) as a light white solid.

Step 2) 6-(4-amino-2,6-dichlorophenoxy)pyridazin-3(2H)-one 3c

N-(3,5-dichloro-4-((6-oxo-1,6-dihydropyridazin-3-yl) oxy)phenyl)benzamide 3b (2.50 g, 6.65 mmol) and potassium hydroxide (4.39 g, 66.5 mmol) were dissolved in 50% ethanol aqueous solution (18 mL), and the mixture was reacted at 95° C. for 7 hours. The reaction solution was cooled to room temperature, extracted with dichloromethane (10 mL×2), the combined organic phase was dried with anhydrous sodium sulfate, concentrated by suction filtration to obtain the title compound 3c (1.17 g, yield 65%) as a gray solid.

MS (ESI, pos. ion) m z: 272.0 $[M+H]^+$.

Step 3) 6-(2,6-dichloro-4-(2,5-dimethyl-1H-pyrrol-1-yl)phenoxy)pyridazin-3(2H)-one 3d 6-(4-Amino-2,6-dichlorophenoxy)pyridazin-3(2H)-one 3c (0.67 g, 2.5 mmol), p-toluenesulfonic acid (0.045 g, 0.25 mmol) and 2,5-hexanedione (0.29 g, 2.5 mmol) were dissolved in toluene (3 mL), and the mixture was reacted at 110° C. for 1.5 hours. The reaction solution was cooled to room temperature, then saturated sodium carbonate solution (50 mL) was added, the resulting mixture was stirred for 10 minutes, and extracted with ethyl acetate (10 mL×2). The combined organic phase was dried over anhydrous sodium sulfate, concentrated by suction filtration to obtain the title compound 3d (0.85 g, yield 99%) as a dark solid.

MS (ESI, pos. ion) m z: 409.6 [M+H]+.

Step 4) 6-(2,6-dichloro-4-(2,5-dimethyl-1H-pyrrol-1-yl)phenoxy)-2-isopropylpyridazin-3(2H)-one 3e 6-(2,6-Dichloro-4-(2,5-dimethyl-1H-pyrrol-1-yl)phenoxy)pyridazin-3(2H)-one 3d (0.85 g, 2.4 mmol), cuprous iodide (49 mg, 0.24 mmol), potassium carbonate (0.68 g, 4.9 mmol) and isopropyl iodide (0.41 g, 2.4 mmol) were dissolved in N,N-dimethylformamide (10 mL), the mixture was reacted at 85° C. for 18 hours. The reaction solution was cooled to room temperature, then water (20 mL) was added, the resulting mixture was stirred for 10 minutes, then filtered with suction, and the filter cake was collected and dried under vacuum to obtain the title compound 3e (0.70 g, yield 74%) as a gray solid.

MS (ESI, pos. ion) m z: 392.0 [M+H]+.

Step 5) 6-(4-amino-2,6-dichlorophenoxy)-2-isopropylpyridazin-3(2H)-one 3f 6-(2,6-Dichloro-4-(2,5-dimethyl-1H-pyrrol-1-yl)phenoxy)-2-isopropylpyridazin-3(2H)-one 3e (0.20 g, 0.51 mmol), hydroxylamine hydrochloride (0.37 g, 5.1 mmol) and triethylamine (0.14 mL) were dissolved in ethanol (10 mL), and the mixture was reacted at 80° C. for 7 hours. The reaction solution was cooled to room temperature, then water (30 mL) was added, the resulting mixture was stirred for 10 minutes, filtered with suction, and the filter cake was collected and purified by silica gel column chromatography [petroleum ether/ethyl acetate (v/v)=1/1] to obtain the title compound 3f (30 mg, yield 19%) as a light-colored solid.

MS (ESI, pos. ion) m z: 314.0 $[M+H]^+$;

$^1H$ NMR (400 MHz, $CDCl_3$), δ (ppm) 7.15 (d, J=9.7 Hz, 1H), 6.98 (d, J=9.7 Hz, 1H), 6.67 (s, 2H), 5.10 (dt, J=13.2, 6.6 Hz, 1H), 3.76 (s, 2H), 1.10 (d, J=6.6 Hz, 6H).

Step 6) Ethyl (2-cyano-2-(2-(3,5-dichloro-4-((1-isopropyl-6-oxo-1,6-dihydropyridazin-3-yl)oxy)phenyl)hydrazono)acetyl)carbamate 32

6-(4-Amino-2,6-dichlorophenoxy)-2-isopropylpyridazin-3(2H)-one 3f (30 mg, 0.095 mmol), N-cyanoacetylurethane (16 mg, 0.105 mmol) and concentrated hydrochloric acid (0.4 mL) were dissolved in acetic acid (1 mL), and an aqueous solution (1 mL) of sodium nitrite (7 mg, 0.286 mmol) was added dropwise at 3° C., then the mixture was reacted for 10 minutes. To the reaction solution was added water (20 mL), and the mixture was stirred for 10 minutes and filtered with suction. The filter cake was collected and dried under vacuum to obtain the title compound 3g (45 mg, yield 98%) as a pale yellow solid.

MS (ESI, pos. ion) m z: 481.0 [M+H]+.

Step 7) 2-[3,5-dichloro-4-[(1-isopropyl-6-oxo-1,6-dihydropyridazin-3-yl)oxy]phenyl]-3,5-dioxo-1,2,4-triazine-6-carbonitrile 3

Potassium acetate (27 mg, 0.28 mmol) was added to a solution of ethyl (2-cyano-2-(2-(3,5-dichloro-4-((1-isopropyl-6-oxo-1,6-dihydropyridazin-3-yl)oxy)phenyl)hydrazono)acetyl)carbamate 3g (45 mg, 0.093 mmol) in N,N-dimethylacetamide (3 mL), the mixture was reacted at 120° C. for 1 hour. The reaction solution was cooled to room temperature, filtered, and the filtrate was purified by preparative chromatography column [43% ACN/57% $H_2O$ (0.1% TFA), Kromasil specifications: C18 10 μm×50 mm×250 mm, flow rate: 100 mL/min] to obtain the title compound 3 (30 mg, yield 74%, HPLC purity: 98.16%) as a white solid.

MS (ESI, neg. ion) m z: 432.9 $[M-H]^-$;

$^1H$ NMR (400 MHz, $CDCl_3$) δ (ppm) 7.69 (s, 2H), 7.34 (d, J=9.7 Hz, 1H), 7.28 (d, J=9.7 Hz, 1H), 5.13 (dt, J=13.1, 6.6 Hz, 1H), 1.10 (d, J=6.6 Hz, 6H).

Example 4 2-[3,5-dichloro-4-[(1-isopropyl-6-oxo-1,6-dihydropyridin-3-yl)oxy]phenyl]-3,5-dioxo-1,2,4-triazine-6-carbonitrile (compound 4)

(4)

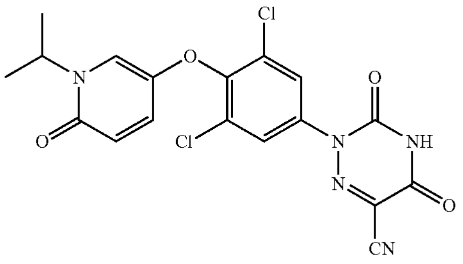

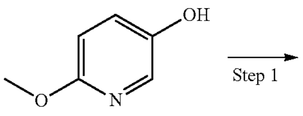

4a

-continued

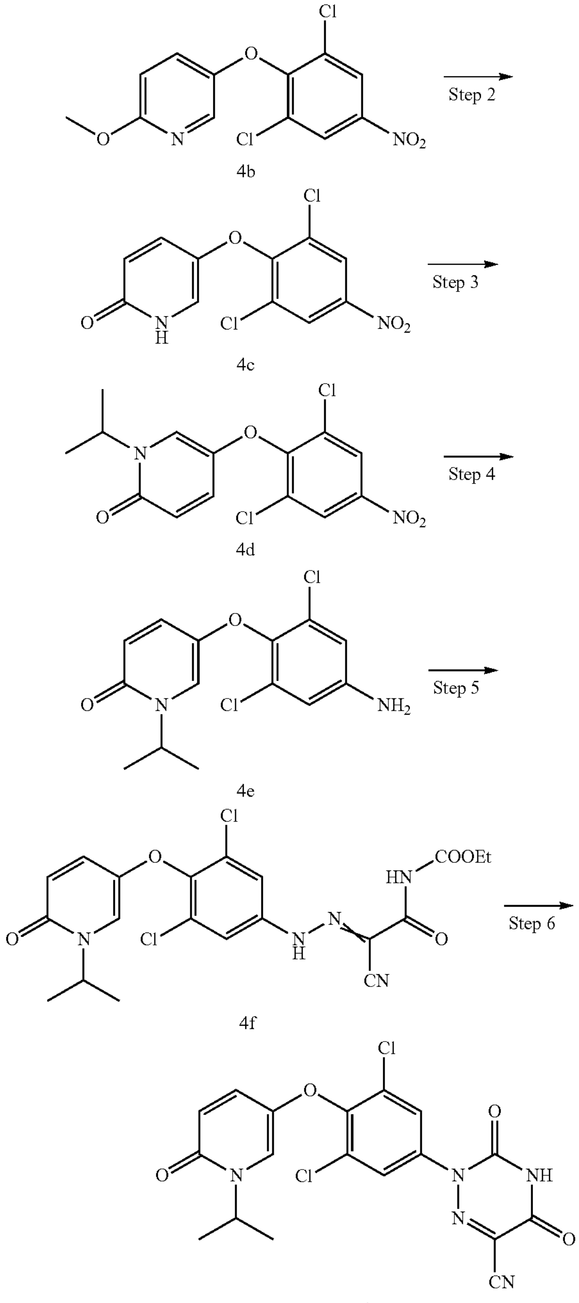

4b
4c
4d
4e
4f
4

Step 1) 5-(2,6-dichloro-4-nitrophenoxy)-2-methoxypyridine 4b

Potassium carbonate (0.56 g, 4.0 mmol) was added to a solution of 6-methoxypyridin-3-ol 4a (0.20 g, 1.6 mmol) and 1,3-dichloro-2-iodo-5-nitrobenzene (0.51 g, 1.6 mmol) in N,N-dimethylacetamide (2 mL), and the mixture was reacted at 120° C. for 1 hour. The reaction solution was cooled to room temperature, water (20 mL) was added, the resulting mixture was stirred for 5 minutes, then filtered, and the filter cake was collected and dried under vacuum to obtain the title compound 4b (0.30 g, yield 60%) as a yellow solid.

MS (ESI, pos. ion) m z: 315.0 $[M+H]^+$.

Step 2) 5-(2,6-dichloro-4-nitrophenoxy)pyridin-2(1H)-one 4c

P-toluenesulfonic acid (0.86 g, 4.7 mmol) and lithium chloride (0.20 g, 4.7 mmol) were added to a solution of 5-(2,6-dichloro-4-nitrophenoxy)-2-methoxypyridine 4b (0.35 g, 1.1 mmol) in N,N-dimethylformamide (2 mL), and the mixture was reacted at 120° C. for 30 minutes. The reaction solution was cooled to room temperature, saturated sodium carbonate solution (50 mL) was added, the mixture was extracted with ethyl acetate (20 mL×2), the combined organic phase was washed with saturated sodium chloride solution (20 mL) and dried with anhydrous sodium sulfate, then concentrated by suction filtration to obtain the title compound 4c (0.30 g, yield 90%) as a pale yellow solid.

MS (ESI, pos. ion) m z: 301.1 $[M+H]^+$;

$^1$H NMR (400 MHz, DMSO-$d_6$) δ (ppm) 11.25 (s, 1H), 8.50 (s, 2H), 7.40 (dd, J=9.6, 3.3 Hz, 1H), 7.24 (d, J=2.6 Hz, 1H), 6.46 (d, J=9.6 Hz, 1H).

Step 3) 5-(2,6-dichloro-4-nitrophenoxy)-1-isopropylpyridin-2(1H)-one 4d

Potassium carbonate (0.28 g, 2.0 mmol) and isopropyl iodide (0.19 g, 1.1 mmol) were added to a solution of 5-(2,6-dichloro-4-nitrophenoxy)pyridin-2(1H)-one 4c (0.30 g, 1.0 mmol) in N,N-dimethylformamide (2 mL), and the mixture was reacted at 85° C. for 16 hours. The reaction solution was cooled to room temperature, then water (30 mL) was added, the mixture was stirred for 10 minutes, then filtered, the filter cake was collected and dried under vacuum to obtain the title compound 4d (0.34 g, yield 99%) as a gray solid.

MS (ESI, pos. ion) m z: 343.0 [M+H]+.

Step 4) 5-(4-amino-2,6-dichlorophenoxy)-1-isopropylpyridin-2(1H)-one 4e 5-(2,6-Dichloro-4-nitrophenoxy)-1-isopropylpyridin-2(1H)-one 4d (0.34 g, 0.99 mmol) and sodium sulfide (0.39 g, 5.00 mmol) were dissolved in ethanol (3 mL), and the mixture was reacted at 80° C. for 40 minutes. The reaction solution was cooled to room temperature, then water (30 mL) was added, the mixture was stirred for 15 minutes, then filtered, and the filter cake was collected and dried under vacuum to obtain the title compound 4e (0.17 g, yield 55%) as a brown solid.

MS (ESI, pos. ion) m z: 313.3 [M+H]+.

Step 5) Ethyl (2-cyano-2-(2-(3,5-dichloro-4-((1-isopropyl-6-oxo-1,6-dihydropyridin-3-yl)oxy)phenyl)hydrazono)acetyl)carbamate 4f 5-(4-Amino-2,6-dichlorophenoxy)-1-isopropylpyridin-2(1H)-one 4e (0.17 g, 0.54 mmol), N-cyanoacetylurethane (0.095 g, 0.59 mmol) and concentrated hydrochloric acid (0.18 mL) were added to acetic acid (3 mL), and a solution of sodium nitrite (0.041 g, 0.59 mmol) in water (2 mL) was added dropwise at 3° C., the mixture was reacted for 4 hours. To the reaction solution was added water (20 mL) and the mixture was extracted with ethyl acetate (5 mL×2), the combined organic phase was dried over anhydrous sodium sulfate, then concentrated by suction filtration to obtain the title compound 4f (0.26 g, yield 100%) as a deep red solid.

MS (ESI, pos. ion) m z: 480.0 [M+H]+.

Step 6) 2-[3,5-dichloro-4-[(1-isopropyl-6-oxo-1,6-dihydropyridin-3-yl)oxy]phenyl]-3,5-dioxo-1,2,4-triazine-6-carbonitrile 4

Potassium acetate (0.21 g, 2.2 mmol) was added to a solution of ethyl (2-cyano-2-(2-(3,5-dichloro-4-((1-isopropyl-6-oxo-1,6-dihydropyridin-3-yl)oxy)phenyl)hydrazono)acetyl)carbamate 4f (0.26 g, 0.54 mmol) was dissolved in N,N-dimethylacetamide (2 mL), and the mixture was reacted at 120° C. for 2 hours. The reaction solution was cooled to room temperature, filtered, and the filtrate was purified by preparative chromatography column [60% ACN/40% $H_2O$ (0.1% TFA), Phenomenex ACE specifications: C18 10 μm×50 mm×250 mm, flow rate: 100 mL/min] to obtain the title compound 4 (7 mg, yield 2.8%, HPLC purity: 92.99%) as a white solid.

MS (ESI, pos. ion) m z: 434.5 $[M+H]^+$;

$^1$H NMR (400 MHz, DMSO-$d_6$) δ (ppm) 8.30 (s, 1H), 7.90 (s, 1H), 7.76 (s, 2H), 7.54 (d, J=8.8 Hz, 1H), 7.27 (d, J=8.6 Hz, 1H), 5.35-5.29 (m, 1H), 1.46 (d, J=10.2 Hz, 6H).

Example 5 2-[3,5-dichloro-4-(1-ethyl-6-oxo-1,6-dihydropyridazin-3-yl)oxy-phenyl]-3,5-dioxo-1,2,4-triazine-6-carbonitrile (Compound 5)

(3)

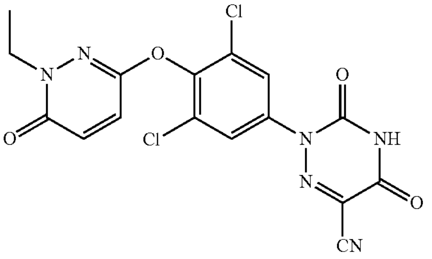

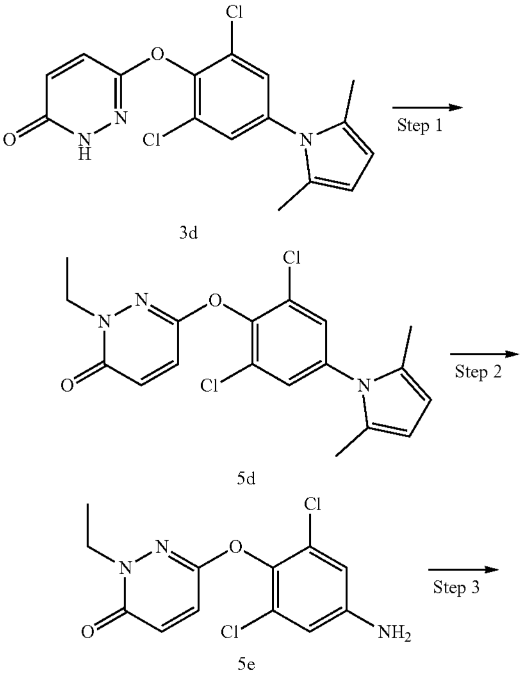

-continued

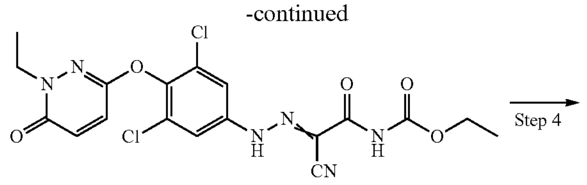

5f

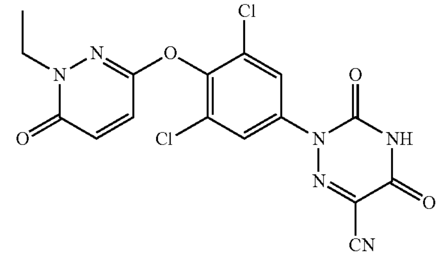

5

Step 1 6-(2,6-dichloro-4-(2,5-dimethyl-1H-pyrrol-1-yl)phenoxy)-2-ethylpyridazin-3(2H)-one 5d 6-(2,6-Dichloro-4-(2,5-dimethyl-1H-pyrrol-1-yl)phenoxy)pyridazin-3(2H)-one 3d (1.20 g, 3.43 mmol), cuprous iodide (68 mg, 0.34 mmol), potassium carbonate (0.95 g, 6.85 mmol) and ethyl iodide (0.53 g, 3.43 mmol) were dissolved in N,N-dimethylformamide (2 mL), the mixture was reacted at 70° C. for 1 hour. The reaction solution was cooled to room temperature, then water (20 mL) was added, the mixture was stirred for 10 minutes, then filtered, the filter cake was collected and dried under vacuum to obtain the title compound 5d (1.20 g, yield 92.6%) as a gray solid.

MS (ESI, pos. ion) m z: 378.0 [M+H]+.

Step 2 6-(4-amino-2,6-dichlorophenoxy)-2-ethylpyridazin-3(2H)-one 5e 6-(2,6-Dichloro-4-(2,5-dimethyl-1H-pyrrol-1-yl)phenoxy)-2-ethylpyridazin-3(2H)-one 5d (1.20 g, 3.17 mmol), hydroxylamine hydrochloride (2.32 g, 31.7 mmol) and triethylamine (0.89 mL) were dissolved in ethanol (10 mL), and the mixture was reacted at 80° C. for 24 hours. The reaction solution was cooled to room temperature, then water (30 mL) was added, the mixture was stirred for 10 minutes, then filtered, the filter cake was collected and dried under vacuum to obtain the title compound 5e (0.40 g, yield 42%) as a black solid.

MS (ESI, pos. ion) m z: 300.0 [M+H]+.

Step 3 Ethyl (2-cyano-2-(2-(3,5-dichloro-4-((1-ethyl-6-oxo-1,6-dihydropyridazin-3-yl)oxy)phenyl)hydrazono)acetyl)carbamate 5f 6-(4-Amino-2,6-dichlorophenoxy)-2-ethylpyridazin-3(2H)-one 5e (0.40 g, 1.00 mmol), N-cyanoacetylurethane (0.20 g, 1.00 mmol) and concentrated hydrochloric acid (0.30 mL) were dissolved in acetic acid (2 mL), and an aqueous solution (0.5 mL) of sodium nitrite (0.10 g, 1.00 mmol) was added dropwise at 3° C., then the mixture was reacted for 10 minutes. To the reaction solution was added water (20 mL), the mixture was stirred for 10 minutes, then filtered, the filter cake was collected and dried under vacuum to obtain the title compound 5f (0.60 g, yield 100%) as a pale yellow solid.

MS (ESI, pos. ion) m z: 467.6 [M+H]+.

Step 4 2-[3,5-dichloro-4-(1-ethyl-6-oxo-1,6-dihydropyridazin-3-yl)oxy-phenyl]-3,5-dioxo-1,2,4-triazine-6-carbonitrile 5

Potassium acetate (0.38 g, 3.90 mmol) was added to a solution of ethyl (2-cyano-2-(2-(3,5-dichloro-4-((1-ethyl-6-oxo-1,6-dihydropyridazin-3-yl)oxy)phenyl)hydrazono)acetyl)carbamate 5f (0.60 g, 1.30 mmol) in N,N-dimethylacetamide (3 mL), and the mixture was reacted at 120° C. for 4.5 hours. The reaction solution was cooled to room temperature, filtered, and the filtrate was purified by preparative chromatography column [40% ACN/60% $H_2O$ (0.1% TFA), Kromasil specifications: C18 10 μm×50 mm×250 mm, flow rate: 100 mL/min] to obtain the title compound 5 (50 mg, yield 9%, HPLC purity: 97.78%) as a white solid.

MS (ESI, neg. ion) m z: 419.5 $[M-H]^-$;

$^1H$ NMR (400 MHz, DMSO-$d_6$) δ (ppm) 8.31 (s, 1H), 7.82 (s, 2H), 7.67 (d, J=9.8 Hz, 1H), 7.18 (d, J=9.8 Hz, 1H), 2.04-1.95 (m, 2H), 1.05 (t, J=7.1 Hz, 3H).

Example 6 2-[3,5-dichloro-4-(1-cyclopropyl-6-oxo-1,6-dihydropyridazin-3-yl)oxy-phenyl]-3,5-dioxo-1,2,4-triazine-6-carbonitrile (Compound 6)

(6)

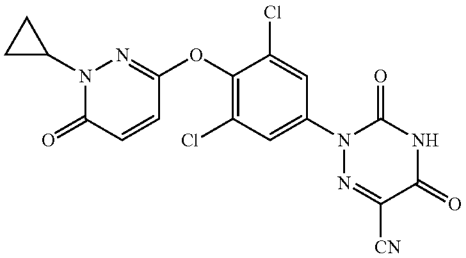

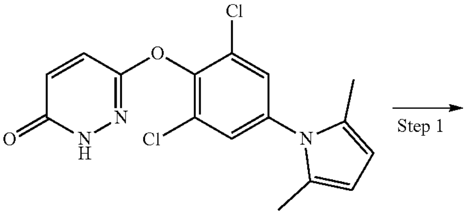

3d

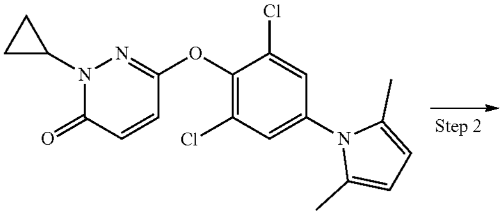

6a

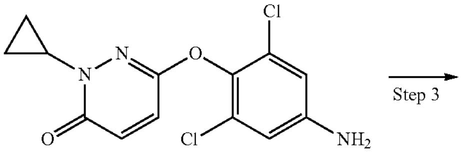

6b

-continued

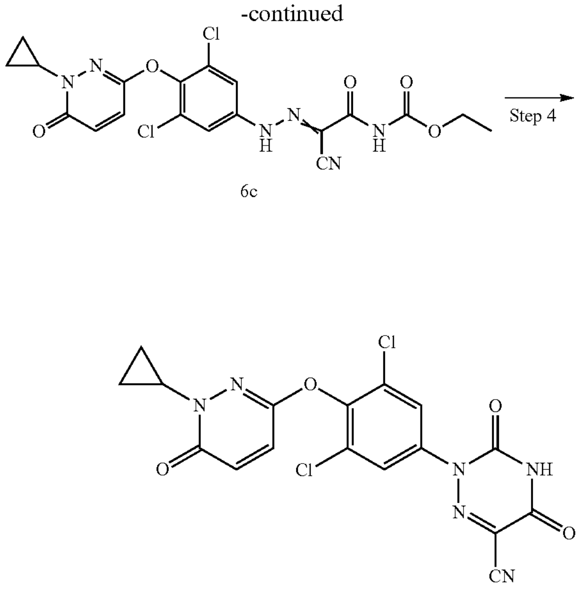

6c

6

Step 1 2-cyclopropyl-6-(2,6-dichloro-4-(2,5-dimethyl-1H-pyrrol-1-yl)phenoxy)pyridazin-3(2H)-one 6a 6-(2,6-Dichloro-4-(2,5-dimethyl-1H-pyrrol-1-yl)phenoxy)pyridazin-3(2H)-one 3d (0.85 g, 2.4 mmol), cuprous iodide (29 mg, 0.24 mmol) and potassium carbonate (0.68 g, 4.9 mmol) were dissolved in N,N-dimethylformamide (4 mL), and the mixture was reacted at 130° C. for 40 hours. The reaction solution was cooled to room temperature, then water (30 mL) was added, the mixture was stirred for 10 minutes, then filtered, the filter cake was collected and dried under vacuum. The crude product was purified by silica gel column chromatography [petroleum ether/ethyl acetate (v/v) =2/1] to obtain the title compound 6a (0.10 g, yield 11%) as a pale yellow solid.

MS (ESI, pos. ion) m z: 390.1 [M+H]+.

Step 2 6-(4-amino-2,6-dichlorophenoxy)-2-cyclopropylpyridazin-3(2H)-one 6b

2-Cyclopropyl-6-(2,6-dichloro-4-(2,5-dimethyl-1H-pyrrol-1-yl)phenoxy)pyridazin-3(2H)-one 6a (0.10 g, 0.26 mmol), hydroxylamine hydrochloride (0.19 g, 2.60 mmol) and triethylamine (0.07 mL) were dissolved in ethanol (3 mL), and the mixture was reacted at 80° C. for 15 hours. The reaction solution was cooled to room temperature, then water (30 mL) was added, the mixture was stirred for 10 minutes, then filtered, the filter cake was collected and dried under vacuum to obtain the title compound 6b (50 mg, yield 60%) as a black solid.

MS (ESI, pos. ion) m z: 314.1 [M+H]+.

Step 3 Ethyl (2-cyano-2-(2-(3,5-dichloro-4-((1-cyclopropyl-6-oxo-1,6-dihydropyridazin-3-yl)oxy)phenyl)hydrazono)acetyl)carbamate 6c 6-(4-Amino-2,6-dichlorophenoxy)-2-cyclopropylpyridazin-3(2H)-one 6b (0.05 g, 0.20 mmol), N-cyanoacetylurethane (0.03 g, 0.20 mmol) and concentrated hydrochloric acid (0.04 mL) were dissolved in acetic acid (2 mL), and a solution of sodium nitrite (0.010 g, 0.20 mmol) in water (0.5 mL) was added dropwise at 3° C., then the mixture was reacted for 10 minutes. To the reaction solution was added water (20 mL), the mixture was stirred for 10 minutes, then filtered, the filter cake was collected and dried under vacuum to obtain the title compound 6c (80 mg, yield 99%) as a black solid.

MS (ESI, pos. ion) m z: 479.0 $[M+H]^+$.

Step 4 2-[3,5-dichloro-4-(1-cyclopropyl-6-oxo-1,6-dihydropyridazin-3-yl)oxy-phenyl]-3,5-di oxo-1,2,4-triazine-6-carbonitrile 6

Potassium acetate (0.046 g, 0.50 mmol) was added to a solution of ethyl (2-cyano-2-(2-(3,5-dichloro-4-((1-cyclopropyl-6-oxo-1,6-dihydropyridazin-3-yl)oxy)phenyl)hydrazono)acetyl)carbamate 6c (0.08 g, 0.17 mmol) in N,N-dimethylacetamide (2 mL), the mixture was reacted at 120° C. for 4 hours. The reaction solution was cooled to room temperature, filtered, and the filtrate was purified by preparative chromatography column [45% ACN/55% $H_2O$ (0.1% TFA), Kromasil specifications: C18 10 μm×50 mm×250 mm, flow rate: 100 mL/min] to obtain the title compound 6 (8 mg, yield 10%, HPLC purity: 95.4%) as a light-colored solid.

MS (ESI, pos. ion) m z: 433.1 $[M+H]^+$;

$^1$H NMR (400 MHz, CDCl3) δ (ppm) 7.65 (s, 2H), 7.30 (d, J=9.8 Hz, 1H), 7.16 (d, J=9.8 Hz, 1H), 5.88-5.74 (m, 1H), 5.13 (dd, J=21.6, 13.3 Hz, 2H), 4.50 (d, J=5.8 Hz, 2H).

Example 7 2-[3,5-dichloro-4-(6-oxo-1-phenyl-1,6-dihydropyridazin-3-yl)oxy-phenyl]-3,5-dioxo-1,2,4-triazine-6-carbonitrile (Compound 21)

(21)

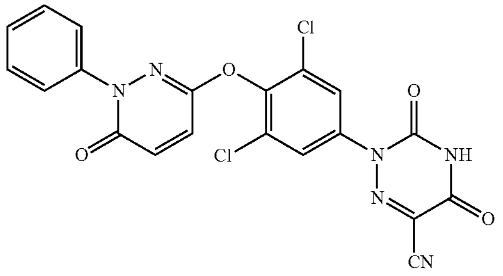

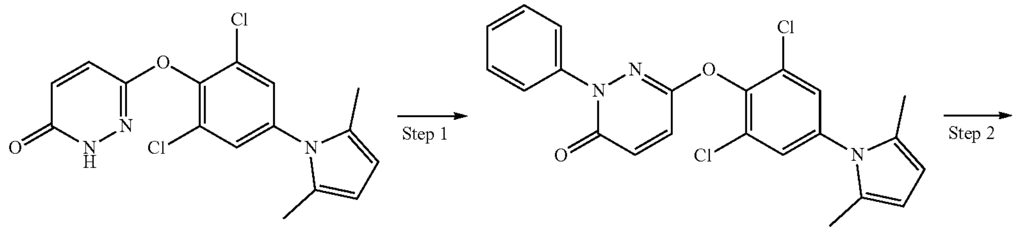

3d

21a

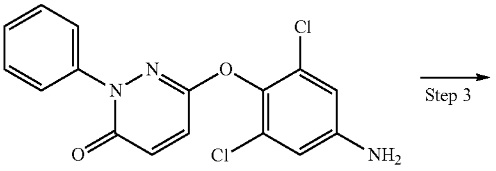

21b

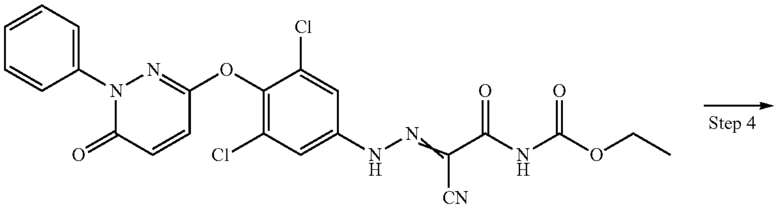

21c

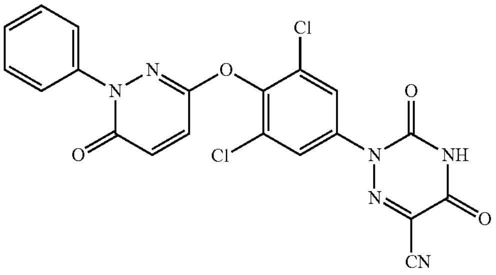

21

Step 1 6-(2,6-dichloro-4-(2,5-dimethyl-1H-pyrrol-1-yl)phenoxy)-2-phenylpyridazin-3(2H)-one 21a 6-(2,6-Dichloro-4-(2,5-dimethyl-1H-pyrrol-1-yl)phenoxy)pyridazin-3(2H)-one 3d (0.50 g, 1.4 mmol), cuprous iodide (29 mg, 0.14 mmol) and potassium carbonate (0.40 g, 2.9 mmol) were dissolved in iodobenzene (3 mL), and the mixture was reacted at 160° C. for 2 hours. The reaction solution was cooled to room temperature, then water (20 mL) was added, the mixture was stirred for 10 minutes, then filtered, the filter cake was collected and dried under vacuum to obtain the title compound 21a (0.50 g, yield 82%) as a gray solid.

MS (ESI, pos. ion) m z: 426.1 $[M+H]^+$.

Step 2 6-(4-amino-2,6-dichlorophenoxy)-2-phenylpyridazin-3(2H)-one 21b 6-(2,6-Dichloro-4-(2,5-dimethyl-1H-pyrrol-1-yl)phenoxy)-2-phenylpyridazin-3(2H)-one 21a (0.50 g, 1.2 mmol), hydroxylamine hydrochloride (0.86 g, 12 mmol) and triethylamine (0.33 mL) were dissolved in ethanol (10 mL), and the mixture was reacted at 80° C. for 22 hours. The reaction solution was cooled to room temperature, then water (30 mL) was added, and solid was precipitated out, filtered with suction, the filter cake was dried under vacuum and purified by silica gel column chromatography [petroleum ether/ethyl acetate (v/v)=1/1] to obtain the title compound 21b (212 mg, yield 52%) as a black solid.

MS (ESI, pos. ion) m z: 348.0 $[M+H]^+$.

Step 3 Ethyl (2-cyano-2-(2-(3,5-dichloro-4-((6-oxo-1-phenyl-1,6-dihydropyridazin-3-yl)oxy) phenyl) hydrazono)acetyl)carbamate 21c 6-(4-Amino-2,6-dichlorophenoxy)-2-phenylpyridazin-3(2H)-one 21b (0.21 g, 0.61 mmol), N-cyanoacetylurethane (0.11 g, 0.67 mmol) and concentrated hydrochloric acid (0.15 mL) were dissolved in acetic acid (2 mL), and a solution of sodium nitrite (0.05 g, 0.67 mmol) in water (2 mL) was added dropwise at 3° C., then the mixture was reacted for 10 minutes. To the reaction solution was added water (20 mL), the mixture was stirred for 10 minutes, then filtered, the filter cake was collected and dried under vacuum to obtain the title compound 21c (0.30 g, yield 96%) as a black solid.

MS (ESI, neg. ion) m z: 515.0 $[M-H]^-$.

Step 4 2-[3,5-dichloro-4-(6-oxo-1-phenyl-1,6-dihydropyridazin-3-yl)oxy-phenyl]-3,5-dioxo-1,2,4-triazine-6-carbonitrile 21

Potassium acetate (0.17 g, 0.17 mmol) was added to a solution of ethyl (2-cyano-2-(2-(3,5-dichloro-4-((6-oxo-1- phenyl-1,6-dihydropyridazin-3-yl)oxy)phenyl)hydrazono)acetyl)carbamate 21c (0.30 g, 0.58 mmol) in N,N-dimethylacetamide (3 mL), and the mixture was reacted at 120° C. for 1 hour. The reaction solution was cooled to room temperature, filtered, and the filtrate was purified by preparative chromatography column [48% ACN/52% $H_2O$ (0.1% TFA), Kromasil specifications: C18 10 μm×50 mm×250 mm, flow rate: 100 mL/min] to obtain the title compound 21 (4 mg, yield 1.2%, HPLC purity: 81.9%) as a dark solid.

MS (ESI, pos. ion) m z: 468.9 $[M+H]^+$;

$^1H$ NMR (600 MHz, CDCl3) δ (ppm) 7.65 (d, J=5.3 Hz, 2H), 7.46 (d, J=8.0 Hz, 2H), 7.37 (t, J=8.6 Hz, 3H), 7.31-7.28 (m, 1H), 7.20 (d, J=9.8 Hz, 1H).

Example 8 2-[3,5-dichloro-4-[1-(4-fluorophenyl)-6-oxo-1,6-dihydropyridazin-3-yl]oxy-phenyl]-3,5-dioxo-1,2,4-triazine-6-carbonitrile 27

(27)

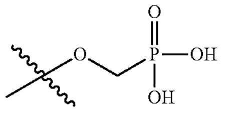

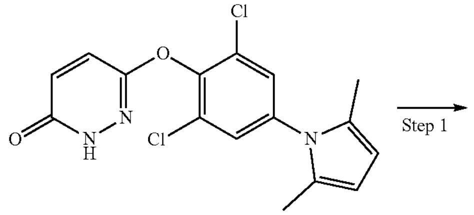

3d

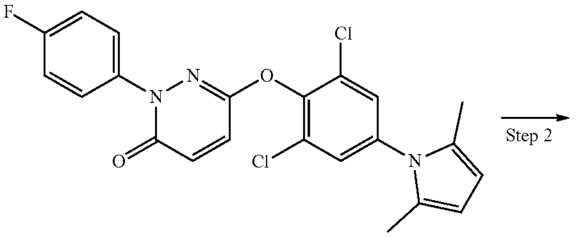

27a

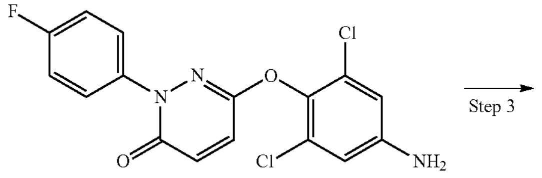

27b

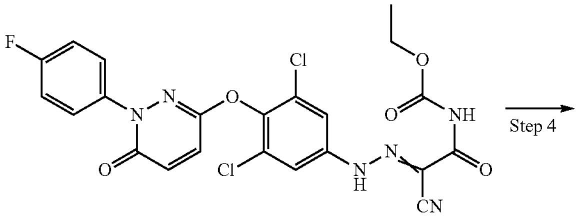

37c

-continued

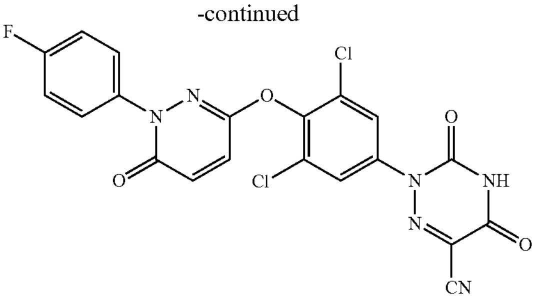

27

Step 1 6-(2,6-dichloro-4-(2,5-dimethyl-1H-pyrrol-1-yl)phenoxy)-2-(4-fluorophenyl)pyridazin-3(2H)-one 27a 6-(2,6-Dichloro-4-(2,5-dimethyl-1H-pyrrol-1-yl)phenoxy)pyridazin-3(2H)-one 3d (0.50 g, 1.4 mmol), cuprous iodide (29 mg, 0.14 mmol), potassium carbonate (0.40 g, 2.9 mmol) and p-fluoroiodobenzene (0.33 g, 1.4 mmol) were dissolved in N,N-dimethylformamide (2 mL), and the mixture was reacted at 160° C. for 22 hours. The reaction solution was cooled to room temperature, then water (10 mL) was added, the mixture was stirred for 10 minutes, then filtered, the filter cake was collected and dried under vacuum to obtain the title compound 27a (0.60 g, yield 95%) as a gray solid.

MS (ESI, pos. ion) m z: 444.6 $[M+H]^+$.

Step 2 6-(4-amino-2,6-dichlorophenoxy)-2-(4-fluorophenyl)pyridazin-3(2H)-one 27b 6-(2,6-Dichloro-4-(2,5-dimethyl-1H-pyrrol-1-yl)phenoxy)-2-(4-fluorophenyl)pyridazin-3(2H)-one 27a (0.60 g, 1.4 mmol), hydroxylamine hydrochloride (0.99 g, 14 mmol) and triethylamine (0.38 mL) were dissolved in ethanol (10 mL), and the mixture was reacted at 80° C. for 18 hours. The reaction solution was cooled to room temperature, then water (30 mL) was added, the mixture was stirred for 10 minutes, then filtered, the filter cake was collected and purified by silica gel column chromatography [petroleum ether/ethyl acetate (v/v)=1/1] to obtain the title compound 27b (380 mg, 77% yield) as a black solid.

MS (ESI, pos. ion) m z: 365.9.0 $[M+H]^+$.

Step 3 Ethyl (2-cyano-2-(2-(3,5-dichloro-4-((1-(4-fluorophenyl)-6-oxo-1,6-dihydropyridazin-3-yl)oxy)phenyl)hydrazono)acetyl)carbamate 27c 6-(4-Amino-2,6-dichlorophenoxy)-2-(4-fluorophenyl)pyridazin-3(2H)-one 27b (0.38 g, 1.0 mmol), N-cyanoacetylurethane (0.18 g, 1.1 mmol) and concentrated hydrochloric acid (0.3 mL) were dissolved in acetic acid (2 mL), and a solution of sodium nitrite (0.26 g, 3.1 mmol) in water (1 mL) was added dropwise at 3° C., then the mixture was reacted for 10 minutes. To the reaction solution was added water (20 mL), the mixture was stirred for 10 minutes, then filtered, the filter cake was collected and dried under vacuum to obtain the title compound 27c (0.55 g, yield 99%) as a black solid.

MS (ESI, neg. ion) m z: 531.0 $[M-H]^-$.

Step 4 2-[3,5-dichloro-4-[1-(4-fluorophenyl)-6-oxo-1,6-dihydropyridazin-3-yl]oxy-phenyl]-3,5-dioxo-1,2,4-triazine-6-carbonitrile 27

Potassium acetate (0.31 g, 3.1 mmol) was added to a solution of ethyl (2-cyano-2-(2-(3,5-dichloro-4-((1-(4-fluorophenyl)-6-oxo-1,6-dihydropyridazin-3-yl)oxy)phenyl)hydrazono)acetyl)carbamate 27c (0.55 g, 1.0 mmol) in N,N-dimethylacetamide (3 mL), and the mixture was reacted at 120° C. for 16 hours. The reaction solution was cooled to room temperature, filtered, and the filtrate was purified by preparative chromatography column [50% ACN/50% $H_2O$ (0.1% TFA), Kromasil specifications: C18 10 μm×50 mm×250 mm, flow rate: 100 mL/min] to obtain the title compound 27 (48 mg, yield 74%, HPLC purity: 86.92%) as a yellow solid.

MS (ESI, pos. ion) m z: 487.0 $[M+H]^+$;

$^1H$ NMR (400 MHz, DMSO-$d_6$) δ (ppm) 7.81 (s, 1H), 7.79 (s, 2H), 7.41 (dd, J=9.1, 5.0 Hz, 2H), 7.32 (d, J=9.8 Hz, 1H), 7.26 (t, J=8.7 Hz, 2H).

Example 9 2-[3,5-dichloro-4-[[6-oxo-1-(1-phenethyl)-1,6-dihydropyridazin-3-yl]oxyl]phenyl]-3,5-dioxo-1,2,4-triazine-6-carbonitrile (Compound 37)

(37)

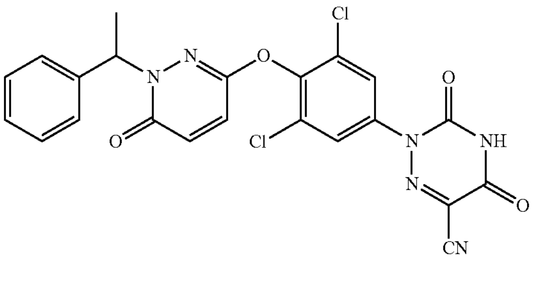

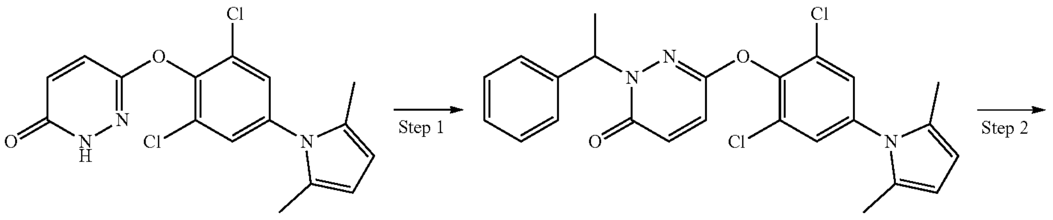

3d 37a

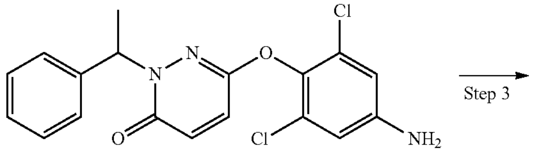

37b

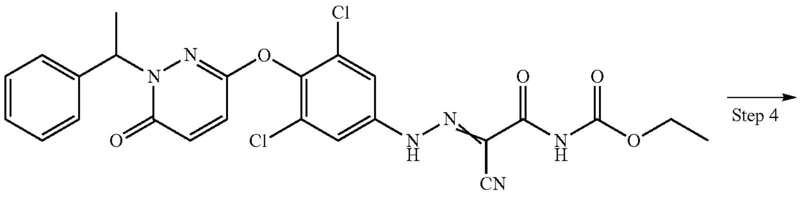

37c

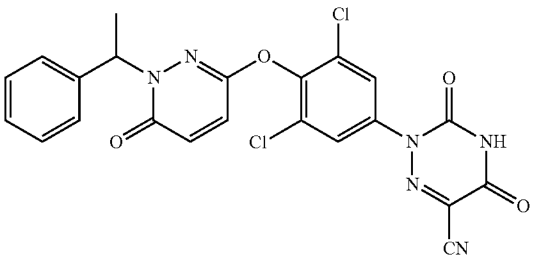

37

Step 1 6-(2,6-dichloro-4-(2,5-dimethyl-1H-pyrrol-1-yl)phenoxy)-2-(1-phenylethyl)pyridazin-3(2H)-one 37a 6-(2,6-Dichloro-4-(2,5-dimethyl-1H-pyrrol-1-yl)phenoxy)pyridazin-3(2H)-one 3d (1.20 g, 3.43 mmol), cuprous iodide (68 mg, 0.34 mmol), potassium carbonate (0.95 g, 6.85 mmol) and 1-bromoethylbenzene (0.53 g, 3.43 mmol) were dissolved in N,N-dimethylformamide (2 mL), and the mixture was reacted at 70° C. for 1 hour. The reaction solution was cooled to room temperature, then water (20 mL) was added, the mixture was stirred for 10 minutes, then filtered, the filter cake was collected and dried under vacuum to obtain the title compound 37a (1.40 g, yield 89.9%) as a gray solid.

MS (ESI, pos. ion) m z: 454.0 $[M+H]^+$.

Step 2 6-(4-amino-2,6-dichlorophenoxy)-2-(1-phenylethyl)pyridazin-3(2H)-one 37b 6-(2,6-Dichloro-4-(2,5-dimethyl-1H-pyrrol-1-yl)phenoxy)-2-(1-phenylethyl)pyridazin-3(2H)-one 37a (1.40 g, 3.08 mmol), hydroxylamine hydrochloride (2.25 g, 30.8 mmol) and triethylamine (0.86 mL) were dissolved in ethanol (10 mL), and the mixture was reacted at 80° C. for 24 hours. The reaction solution was cooled to room temperature, then water (30 mL) was added, the mixture was stirred for 10 minutes, then filtered, the filter cake was collected and dried under vacuum to obtain the title compound 37b (0.50 g, yield 43%) as a black solid.

MS (ESI, pos. ion) m z: 376.0 $[M+H]^+$.

Step 3 Ethyl (2-cyano-2-(2-(3,5-dichloro-4-((6-oxo-1-(1-phenylethyl)-1,6-dihydropyridazin-3-yl)oxy)phenyl)hydrazono)acetyl)carbamate 37c 6-(4-Amino-2,6-dichlorophenoxy)-2-(1-phenylethyl)pyridazin-3(2H)-one 37b (0.50 g, 1.30 mmol), N-cyanoacetylurethane (0.23 g, 1.50 mmol) and concentrated hydrochloric acid (0.34 mL) were dissolved in acetic acid (3 mL), and an aqueous solution (0.5 mL) of sodium nitrite (0.10 g, 1.50 mmol) was added dropwise at 3° C., then the mixture was reacted for 30 minutes. To the reaction solution was added water (20 mL), then the mixture was stirred for 10 minutes, filtered, the filter cake was collected and dried under vacuum to obtain the title compound 37c (0.70 g, yield 100%) as a pale yellow solid.

MS (ESI, pos. ion) m z: 543.6 $[M+H]^+$.

Step 4 2-[3,5-dichloro-4-[[6-oxo-1-(1-phenethyl)-1,6-dihydropyridazin-3-yl]oxyl]phenyl]-3,5-dioxo-1,2,4-triazine-6-carbonitrile 37

Potassium acetate (0.39 g, 4.00 mmol) was added to a solution of ethyl (2-cyano-2-(2-(3,5-dichloro-4-((6-oxo-1-(1-phenylethyl)-1,6-dihydropyridazin-3-yl)oxy)phenyl)hydrazono)acetyl)carbamate 37c (0.72 g, 1.30 mmol) in N,N-dimethylacetamide (3 mL), and the mixture was reacted at 120° C. for 5 hours. The reaction solution was cooled to room temperature, filtered, and the filtrate was purified by preparative chromatography column [40% ACN/60% $H_2O$ (0.1% TFA), Kromasil specifications: C18 10 μm×50 mm×250 mm, flow rate: 100 mL/min] to obtain the title compound 36 (100 mg, yield 15%, HPLC purity: 97.91%) as a red solid.

MS (ESI, neg. ion) m z: 495.0 $[M-H]^-$;

$^1H$ NMR (400 MHz, $CDCl_3$) δ (ppm) 7.61 (s, 2H), 7.20 (s, 5H), 7.11 (s, 2H), 4.13 (dd, J=14.2, 7.1 Hz, 1H), 1.47 (d, J=6.1 Hz, 3H).

Example 10 2-[4-(1-benzyl-2-oxo-1,2-dihydropyrimidin-5-yl)oxy-3,5-dichlorophenyl]-3,5-dioxo-1,2,4-triazine-6-carbonitrile (Compound 38)

(38)

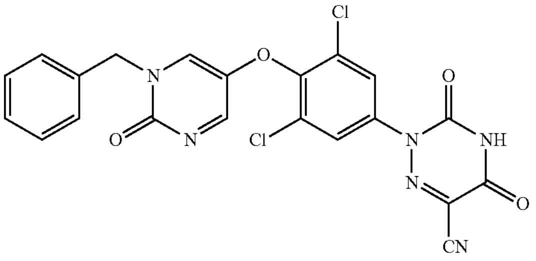

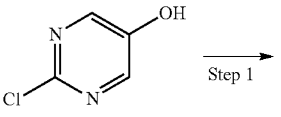

38a

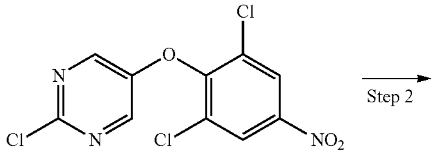

38b

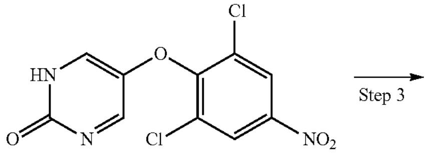

38c

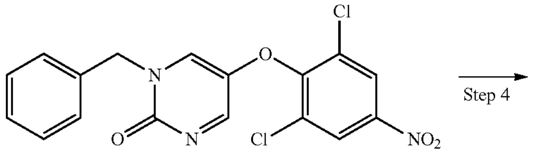

38d

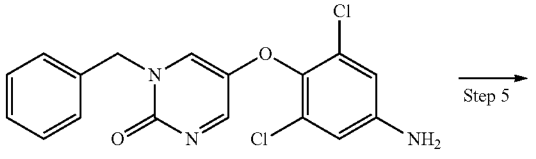

38e

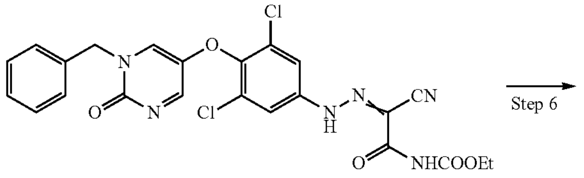

38f

-continued

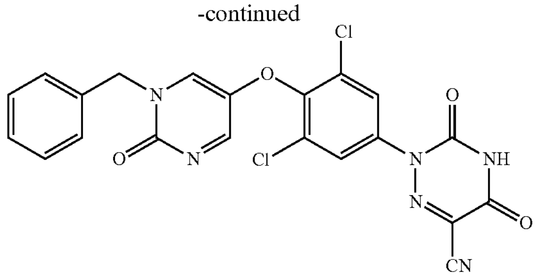

38

Step 1 2-chloro-5-(2,6-dichloro-4-nitrophenoxy)pyrimidine 38b 1,2,3-Trichloro-5-nitrobenzene (5.72 g, 25.3 mmol) and potassium carbonate (6.42 g, 46.0 mmol) were added to a solution of 2-chloropyrimidin-5-ol 38a (3.00 g, 23.0 mmol) in N,N-dimethylformamide (25 mL), and the mixture was reacted at 120° C. for 7 hours. The reaction solution was cooled to room temperature, then water (75 mL) was added dropwise, the mixture was stirred for 15 minutes, then filtered, and the filter cake was collected and dried under vacuum to obtain the title compound 38b (6.50 g, yield 88.2%) as an orange solid.

$^1$H NMR (400 MHz, $CDCl_3$) δ (ppm) 8.38 (s, 2H), 8.28 (s, 2H).

Step 2 5-(2,6-dichloro-4-nitrophenoxy)pyrimidin-2(1H)-one 38c

2-Chloro-5-(2,6-dichloro-4-nitrophenoxy)pyrimidine 38b (1.43 g, 4.46 mmol), potassium carbonate (1.25 g, 8.95 mmol) and triethylenediamine (0.255 g, 2.23 mmol) were dissolved in 1,4-dioxane (20 mL) and water (20 mL), and the mixture was reacted at 70° C. for 6 hours. The reaction solution was cooled to room temperature and concentrated in vacuo. The resulting residue was filtered, the filter cake was washed with water (10 mL×3) and collected and recrystallized (petroleum ether/ethyl acetate (v/v)=5/1, 50 mL) to obtain the title compound 38c (1.12 g, yield 83.1%) as a yellow solid.

MS (ESI, pos. ion) m z: 302.1 $[M+H]^+$.

$^1$H NMR (400 MHz, DMSO-$d_6$) δ (ppm) 11.75 (s, 1H), 8.71 (s, 1H), 8.60 (s, 1H), 8.52 (s, 1H), 8.26 (s, 1H).

Step 3 1-benzyl-5-(2,6-dichloro-4-nitrophenoxy) pyrimidin-2(1H)-one 38d 5-(2,6-Dichloro-4-nitrophenoxy)pyrimidin-2(1H)-one 38c (0.60 g, 1.99 mmol) and benzyl bromide (0.37 mL, 2.98 mmol) were dissolved in dichloromethane (10 mL), then triethylamine (0.57 mL, 4.0 mmol) was added, and the mixture was reacted at room temperature for 7 hours. The reaction solution was quenched with water (10 mL) and extracted with ethyl acetate (10 mL×3), the combined organic phase was washed with saturated sodium chloride solution (15 mL×3), dried with anhydrous sodium sulfate, then concentrated by suction filtration. The obtained residue was purified by silica gel column chromatography [petroleum ether/ethyl acetate (v/v)=1/2] to obtain the title compound 38d (0.68 g, yield 87%) as a yellow solid.

MS (ESI, pos. ion) m z: 392.5 $[M+H]^+$.

Step 4 5-(4-amino-2,6-dichlorophenoxy)-1-benzylpyrimidin-2(1H)-one 38e

1-Benzyl-5-(2,6-dichloro-4-nitrophenoxy)pyrimidin-2 (1H)-one 38d (0.68 g, 1.7 mmol) was dissolved in acetic acid (15 mL), then iron powder (0.40 g, 7.0 mmol) was added, the mixture was reacted at 90° C. for 2.5 hours. After the reaction solution was cooled to room temperature, the iron powder was removed by suction filtration, and the filtrate was concentrated to obtain the title compound 38e (0.55 g, 88%) as a yellow solid.

MS (ESI, pos. ion) m z: 362.0 $[M+H]^+$.

Step 5 ethyl (2-(2-(4-((1-benzyl-2-oxo-1,2-dihydropyrimidin-5-yl)oxy)-3,5-dichlorophenyl)hydrazono)-2-cyanoacetyl)carbamate 38f 5-(4-Amino-2,6-dichlorophenoxy)-1-benzylpyrimidin-2 (1H)-one 38e (0.30 g, 0.83 mmol) and N-(2-cyanoacetyl) ethyl carbamate (0.155 g, 0.99 mmol) were dissolved in acetic acid (4 mL), then an aqueous solution (1 mL) of sodium nitrite (0.087 g, 1.2 mmol) was added dropwise at 0° C., and the mixture was reacted for 2 hours. The reaction solution was directly added to the next reaction.

Step 6 2-[4-(1-benzyl-2-oxo-1,2-dihydropyrimidin-5-yl)oxy-3,5-dichlorophenyl]-3,5-dioxo-1,2,4-triazine-6-carbonitrile 38

Sodium acetate (0.343 g, 4.14 mmol) was added to the reaction solution obtained from the previous step, and reacted at 120° C. for 4 hours. The resulting solution was cooled to room temperature, concentrated under vacuum to remove acetic acid, then water (15 mL) was added. The mixture was extracted with ethyl acetate (15 mL×3), the combined organic phase was dried with anhydrous sodium sulfate, then concentrated by suction filtration. The obtained crude product was purified by preparative chromatography column [37% ACN/63% $H_2O$ (0.1% TFA), Philomon ACE specifications: C18 10 μm×50 mm×250 mm, flow rate: 100 mL/min] to obtain the title compound 38 (0.18 g, yield 45.0%, HPLC purity: 98.37%) as a yellow solid.

MS (ESI, neg. ion) m z: 481.1 $[M-H]^-$, $^1$H NMR (400 MHz, DMSO-$d_6$) δ (ppm) 13.27 (s, 1H), 8.80 (d, J=3.8 Hz, 1H), 8.29 (d, J=3.8 Hz, 1H), 7.80 (s, 2H), 7.36 (t, J=7.1 Hz, 2H), 7.30 (d, J=7.0 Hz, 1H), 7.26 (d, J=7.9 Hz, 2H), 5.02 (s, 2H).

Example 11 2-[3,5-dichloro-4-[[1-(3,4-difluorobenzyl)-6-oxo-1,6-dihydropyridin-3-yl]oxy]phenyl]-3,5-dioxo-1,2,4-triazine-6-carbonitrile (Compound 39)

(39)

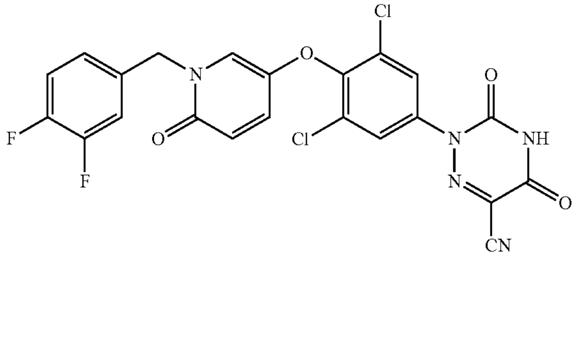

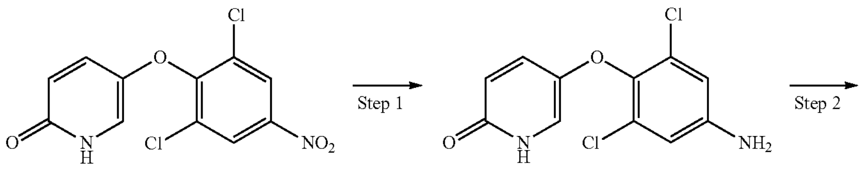

4c 39a

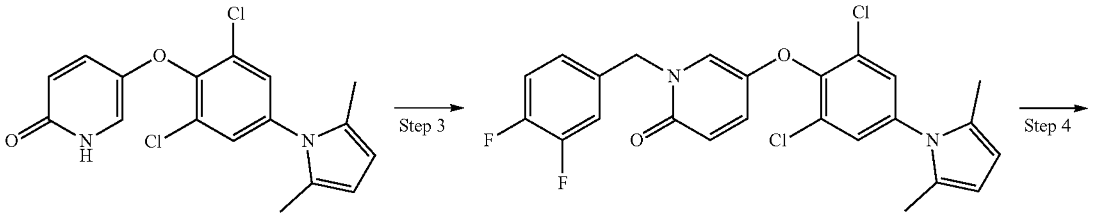

39b 39c

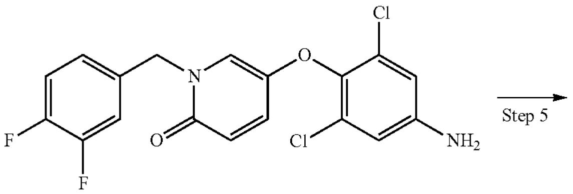

39d

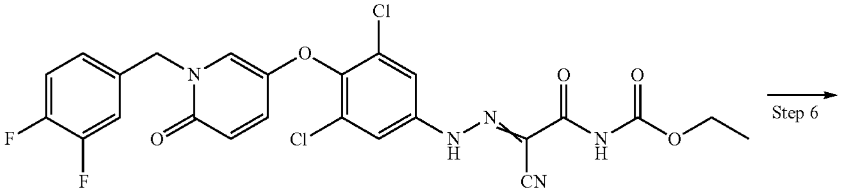

39e

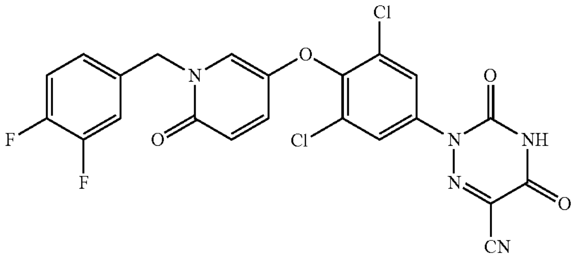

39

Step 1
5-(4-amino-2,6-dichlorophenoxy)pyridin-2(1H)-one
39a 5-(2,6-Dichloro-4-nitrophenoxy)pyridine-2(1H)-one 4c (5.00 g, 1.6 mmol) was dissolved in acetic acid (10 mL), then iron powder (2.79 g, 49.8 mmol) was added, the mixture was reacted at 75° C. for 3 hours. The reaction solution was cooled to room temperature, then water (100 mL) was added, the mixture was stirred for 15 minutes, then filtered, the filter cake was collected and dried under vacuum to obtain the title compound 39a (2.00 g, yield 44.4%) as a pale yellow solid.

MS (ESI, pos. ion) m z: 271.0 $[M+H]^+$.

Step 2 5-(2,6-dichloro-4-(2,5-dimethyl-1H-pyrrol-1-yl)phenoxy)pyridin-2(1H)-one 39b 5-(4-Amino-2,6-dichlorophenoxy)pyridin-2(1H)-one 39a (1.60 g, 5.9 mmol), p-toluenesulfonic acid (0.11 g, 0.59 mmol) and 2,5-hexanedione (0.69 g, 5.9 mmol) were dissolved in toluene (5 mL), and the mixture was reacted at 110° C. for 2 hours. The reaction solution was cooled to room temperature, then quenched with saturated sodium carbonate solution (50 mL), and extracted with ethyl acetate (10 mL×2). The combined organic phase was dried over anhydrous sodium sulfate, then concentrated by suction filtration to obtain the title compound 39b (1.90 g, yield 92%) as a gray solid.

MS (ESI, pos. ion) m z: 349.0 $[M+H]^+$.

Step 3 5-(2,6-dichloro-4-(2,5-dimethyl-1H-pyrrol-1-yl)phenoxy)-1-(3,4-difluorobenzyl)pyridin-2(1H)-one 39c 5-(2,6-Dichloro-4-(2,5-dimethyl-1H-pyrrol-1-yl)phenoxy)pyridin-2(1H)-one 39b (0.30 g, 0.85 mmol) and 3,4-difluorobenzyl bromide (0.18 g, 0.86 mmol) were dissolved in N,N-dimethylacetamide (8 mL), then potassium carbonate (0.30 g, 2.1 mmol) was added, and the mixture was reacted at room temperature for 24 hours. To the reaction solution was added water (30 mL), then the mixture was stirred for 10 minutes, filtered, and the filter cake was collected and dried under vacuum to obtain the title compound 39c (0.30 g, yield 73%) as a red solid.

MS (ESI, pos. ion) m z: 475.1 $[M+H]^+$.

Step 4 5-(4-amino-2,6-dichlorophenoxy)-1-(3,4-difluorobenzyl)pyridin-2(1H)-one 39d 5-(2,6-Dichloro-4-(2,5-dimethyl-1H-pyrrol-1-yl)phenoxy)-1-(3,4-difluorobenzyl)pyrid in-2(1H)-one 39c (0.30 g, 0.63 mmol), hydroxylamine hydrochloride (0.58 g, 6.3 mmol) and triethylamine (0.89 mL) were dissolved in ethanol (10 mL), and the mixture was reacted at 80° C. for 16 hours. The reaction solution was cooled to room temperature, then water (30 mL) was added, the mixture was stirred for 15 minutes, filtered, and the filter cake was collected and dried under vacuum to obtain the title compound 39d (0.20 g, yield 80%) as a black solid.

MS (ESI, pos. ion) m z: 399.0 $[M+H]^+$.

Step 5 Ethyl (2-cyano-2-(2-(3,5-dichloro-4-((1-(3,4-difluorobenzyl)-6-oxo-1,6-dihydropyridin-3-yl)oxy)phenyl)hydrazono)acetyl)carbamate 39e 5-(4-Amino-2,6-dichlorophenoxy)-1-(3,4-difluorobenzyl)pyridin-2(1H)-one 39d (0.20 g, 0.50 mmol), N-cyanoacetylurethane (0.088 g, 0.55 mmol) and concentrated hydrochloric acid (0.13 mL) were added to acetic acid (3 mL), and a solution of sodium nitrite (38 mg, 0.55 mmol) in water (2 mL) was added dropwise at 3° C., then the mixture was reacted for 15 minutes. To the reaction solution was added water (20 mL), and the mixture was extracted with ethyl acetate (10 mL×2). The combined organic phase was dried over anhydrous sodium sulfate, then concentrated by suction filtration to obtain the title compound 39e (0.28 g, yield 99%) as a deep red solid.

MS (ESI, pos. ion) m z: 564.0 $[M+H]^+$.

Step 6 2-[3,5-dichloro-4-[[1-(3,4-difluorobenzyl)-6-oxo-1,6-dihydropyridin-3-yl]oxy]phenyl]-3,5-dioxo-1,2,4-triazine-6-carbonitrile 39

Ethyl (2-cyano-2-(2-(3,5-dichloro-4-((1-(3,4-difluorobenzyl)-6-oxo-1,6-dihydropyridin-3-yl)oxy)phenyl)hydrazono)acetyl)carbamate 39e (0.28 g, 0.50 mmol) was dissolved in N,N-dimethylacetamide (3 mL), then potassium acetate (0.20 g, 2.00 mmol) was added, the mixture was reacted at 120° C. for 18 hours. The reaction solution was cooled to room temperature, filtered, and the filtrate was purified by preparative chromatography column [48% ACN/52% $H_2O$ (0.1% TFA), Phenomenex ACE specifications: C18 10 μm×50 mm×250 mm, flow rate: 100 mL/min] to obtain the title compound 39 (25 mg, yield 8.6%, HPLC purity: 88.95%) as a red solid.

MS (ESI, neg. ion) m z: 516.5 $[M-H]^-$;

$^1H$ NMR (400 MHz, $CDCl_3$) δ (ppm) 7.64 (s, 2H), 7.39 (dd, J=9.8, 3.1 Hz, 1H), 7.35 (s, 1H), 7.18-7.13 (m, 1H), 7.12-7.08 (m, 1H), 6.99 (d, J=3.1 Hz, 1H), 6.94 (d, J=9.8 Hz, 1H), 5.12 (s, 2H).

Example 12 2-[3,5-dichloro-4[[6-oxo-1-[4-(trifluoromethoxy)benzyl]-1,6-dihydropyridin-3-yl]oxy]phenyl]-3,5-dioxo-1,2,4-triazine-6-carbonitrile (Compound 40)

(40)

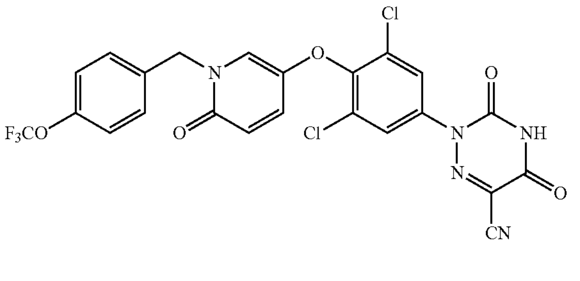

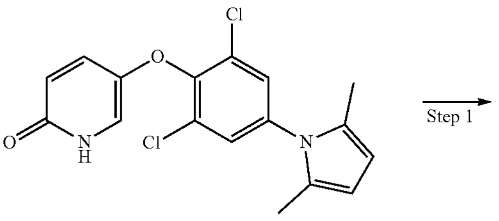

39b

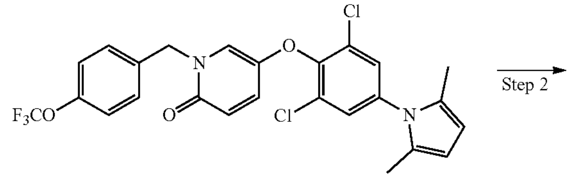

40a

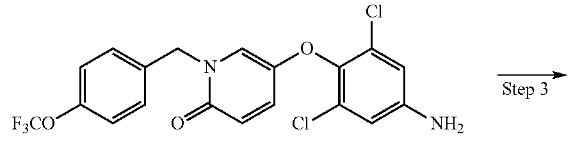

40b

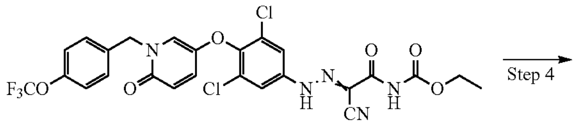

40c

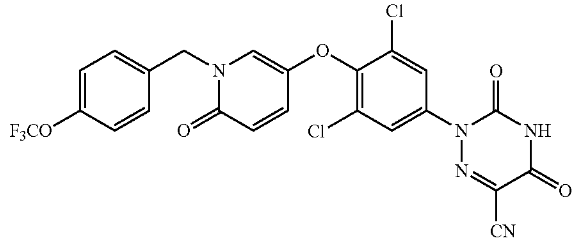

40

Step 1 5-(2,6-dichloro-4-(2,5-dimethyl-1H-pyrrol-1-yl)phenoxy)-1-(4-(trifluoromethoxy)benz yl)pyridin-2(1H)-one 40a 5-(2,6-Dichloro-4-(2,5-dimethyl-1H-pyrrol-1-yl)phenoxy)pyridin-2(1H)-one 39b (0.23 g, 0.66 mmol), potassium carbonate (0.23 g, 1.65 mmol) and 4-trifluoromethoxybenzyl bromide (0.17 g, 0.86 mmol) were dissolved in N,N-dimethylacetamide (4 mL), and the mixture was reacted at room temperature for 24 hours. To the reaction solution was added water (30 mL), then the mixture was stirred for 10 minutes, and filtered with suction to obtain the title compound 40a (0.30 g, yield 87%) as a red solid.

MS (ESI, pos. ion) m z: 523.0 $[M+H]^+$.

Step 2 5-(4-amino-2,6-dichlorophenoxy)-1-(4-(trifluoromethoxy)benzyl)pyridin-2(1H)-one 40b 5-(2,6-Dichloro-4-(2,5-dimethyl-1H-pyrrol-1-yl)phenoxy)-1-(4-(trifluoromethoxy)benzyl)pyridin-2(1H)-one 40a (0.30 g, 0.63 mmol) and hydroxylamine hydrochloride (0.58 g, 6.3 mmol) were dissolved in ethanol (10 mL), then triethylamine (0.89 mL) was added, and the mixture was reacted at 80° C. for 16 hours. The reaction solution was cooled to room temperature, then water (30 mL) was added, the mixture was stirred for 15 minutes, filtered, and the filter cake was collected and dried under vacuum to obtain the title compound 40b (0.24 g, yield 94%) as a black solid.

MS (ESI, pos. ion) m z: 445.0 $[M+H]^+$.

Step 3 Ethyl (2-cyano-2-(2-(3,5-dichloro-4-((6-oxo-1-(4-(trifluoromethoxy)benzyl)-1,6-dihydropyridin-3-yl)oxy)phenyl)hydrazono)acetyl)carbamate 40c 5-(4-Amino-2,6-dichlorophenoxy)-1-(4-(trifluoromethoxy)benzyl)pyridin-2(1H)-one 40b (0.24 g, 0.54 mmol), N-cyanoacetylurethane (0.11 g, 0.59 mmol) were dissolved in acetic acid (3 mL) and concentrated hydrochloric acid (0.18 mL), and then an aqueous solution (2 mL) of sodium nitrite (0.05 g, 0.59 mmol) was added dropwise at 3° C., and the mixture was reacted for 30 minutes. The reaction was quenched with water (20 mL), extracted with ethyl acetate (5 mL×2), the combined organic phase was dried over anhydrous sodium sulfate, filtered with suction and concentrated to obtain the title compound 40c (0.33 g, yield 100%)) as a deep red solid.

MS (ESI, neg. ion) m z: 610.0 $[M-H]^-$.

Step 4 2-[3,5-dichloro-4[[6-oxo-1-[4-(trifluoromethoxy)benzyl]-1,6-dihydropyridin-3-yl]oxy]phenyl]-3,5-dioxo-1,2,4-triazine-6-carbonitrile 40

Ethyl (2-cyano-2-(2-(3,5-dichloro-4-((6-oxo-1-(4-(trifluoromethoxy)benzyl)-1,6-dihydropyridin-3-yl)oxy) phenyl)hydrazono)acetyl)carbamate 40c (0.33 g, 0.54 mmol) was dissolved in N,N-dimethylformamide (3 mL), then potassium acetate (0.21 g, 2.20 mmol) was added, and the mixture was reacted at 120° C. for 2 hours. The reaction solution was cooled to room temperature, filtered, and the filtrate was purified by preparative chromatography column [52% ACN/48% $H_2O$ (0.1% TFA), Phenomenex ACE specifications: C18 10 μm×50 mm×250 mm, flow rate: 100 mL/min] to obtain the title compound 40 (7.0 mg, yield 2.0%, purity: 82.25%) as a yellow solid.

MS (ESI, neg. ion) m z: 564.0 $[M-H]^-$;

$^1H$ NMR (600 MHz, $CDCl_3$) δ (ppm) 10.02 (s, 1H), 7.64 (s, 2H), 7.39 (d, J=8.5 Hz, 1H), 7.31 (d, J=8.0 Hz, 2H), 7.24 (d, J=8.3 Hz, 1H), 7.21 (d, J=7.6 Hz, 2H), 6.61 (s, 1H), 4.33 (s, 2H).

Example 13 2-[3,5-dichloro-4-[[1-(4-fluorobenzyl)-6-oxo-1,6-dihydropyridin-3-yl]oxy]phenyl]-3,5-dioxo-1,2,4-triazine-6-carbonitrile (Compound 41)

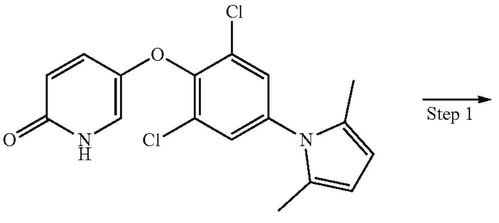

39b

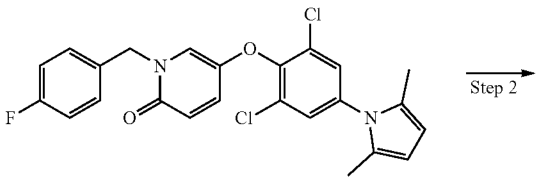

41a

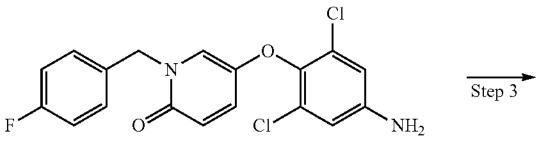

41b

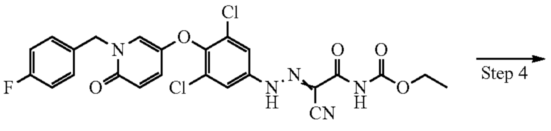

41c

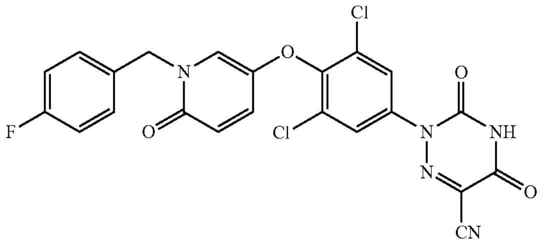

41

(41)

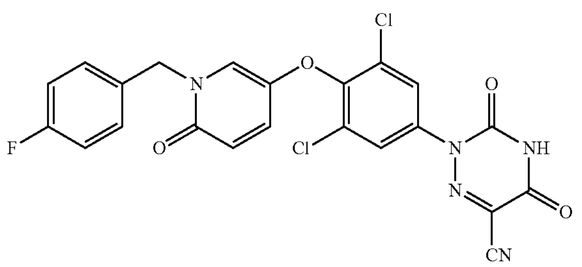

Step 1 5-(2,6-dichloro-4-(2,5-dimethyl-1H-pyrrol-1-yl)phenoxy)-1-(4-fluorobenzyl)pyridin-2 (1H)-one 41a 5-(2,6-Dichloro-4-(2,5-dimethyl-1H-pyrrol-1-yl)phenoxy)pyridin-2(1H)-one 39b (0.30 g, 1.0 mmol) and p-fluorobenzyl bromide (0.17 g, 0.86 mmol) was dissolved in N,N-dimethylformamide (8 mL), then potassium carbonate (0.30 g, 2.7 mmol) was added, and the mixture was reacted at room temperature for 16 hours. To the reaction solution was added water (30 mL), then the mixture was stirred for 10 minutes, filtered, and the filter cake was collected and dried under vacuum to obtain the title compound 41a (0.37 g, yield 94%) as a pink solid.

MS (ESI, pos. ion) m z: 457.5 $[M+H]^+$.

Step 2 5-(4-amino-2,6-dichlorophenoxy)-1-(4-fluorobenzyl)pyridin-2(1H)-one 41b 5-(2,6-Dichloro-4-(2,5-dimethyl-1H-pyrrol-1-yl)phenoxy)-1-(4-fluorobenzyl)pyridin-2 (1H)-one 41a (0.37 g, 0.81 mmol), hydroxylamine hydrochloride (0.59 g, 8.1 mmol) and triethylamine (0.24 mL) were dissolved in ethanol (10 mL), and the mixture was reacted at 80° C. for 24 hours. The reaction solution was cooled to room temperature, then water (30 mL) was added, the mixture was stirred for 15 minutes, then filtered, and the filter cake was collected and dried under vacuum to obtain the title compound 41b (0.28 g, yield 91%) as a black solid.

MS (ESI, pos. ion) m z: 381.4 $[M+H]^+$.

Step 5 Ethyl (2-cyano-2-(2-(3,5-dichloro-4-((1-(4-fluorobenzyl)-6-oxo-1,6-dihydropyridin-3-yl)oxy) phenyl)hydrazono)acetyl)carbamate 41c 5-(4-Amino-2,6-dichlorophenoxy)-1-(4-fluorobenzyl) pyridin-2(1H)-one 41b (0.28 g, 0.73 mmol), N-cyanoacetylurethane (0.13 g, 0.81 mmol) and concentrated hydrochloric acid (0.13 mL) were added to acetic acid (3 mL), and a solution of sodium nitrite (0.056 g, 0.81 mmol) in water (2 mL) was added dropwise at 3° C., then the mixture was reacted for 1 hour. To the reaction solution was added water (20 mL), the mixture was extracted with ethyl acetate (5 mL×2), the combined organic phase was dried with anhydrous sodium sulfate, then concentrated by suction filtration to obtain the title compound 41c (0.40 g, yield 99%) as a deep red solid.

MS (ESI, pos. ion) m z: 546.0 $[M+H]^+$.

Step 6 2-[3,5-dichloro-4-[[1-(4-fluorobenzyl)-6-oxo-1,6-dihydropyridin-3-yl]oxy]phenyl]-3,5-dioxo-1,2,4-triazine-6-carbonitrile 41

Ethyl (2-cyano-2-(2-(3,5-dichloro-4-((1-(4-fluorobenzyl)-6-oxo-1,6-dihydropyridin-3-yl)oxy)phenyl)hydrazono)acetyl)carbamate 41c (0.40 g, 0.73 mmol) was dissolved in N,N-dimethylacetamide (3 mL), then potassium acetate (0.29 g, 2.9 mmol) was added, the mixture was reacted at 120° C. for 4 hours. The reaction solution was cooled to room temperature, filtered, and the filtrate was purified by preparative chromatography column [48% ACN/52% $H_2O$ (0.1% TFA), Phenomenex ACE specifications: C18 10 μm×50 mm×250 mm, flow rate: 100 mL/min] to obtain the title compound 41 (94 mg, yield 24%, HPLC purity: 98.27%) as a red solid.

MS (ESI, pos. ion) m z: 500.0 $[M+H]^+$;

$^1H$ NMR (600 MHz, DMSO-$d_6$) δ (ppm) 13.28 (s, 1H), 7.77 (s, 2H), 7.62 (d, J=3.3 Hz, 1H), 7.45 (dd, J=9.9, 3.3 Hz, 1H), 7.30 (dd, J=8.4, 5.6 Hz, 2H), 7.16 (t, J=8.8 Hz, 2H), 6.47 (d, J=9.9 Hz, 1H), 5.02 (s, 2H).

Example 14 2-[3,5-dichloro-4-[[6-oxo-1-[3-(trifluoromethyl)benzyl]-1,6-dihydropyridin-3-yl]oxy]phenyl]-3,5-dioxo-1,2,4-triazine-6-carbonitrile (Compound 42)

(42)

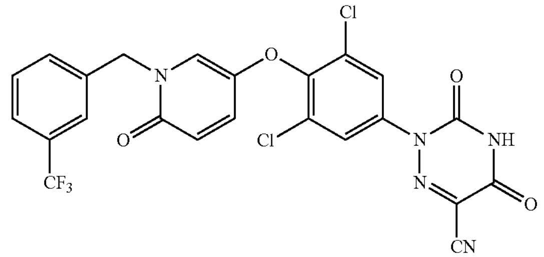

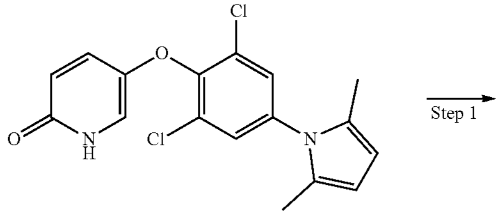

39b

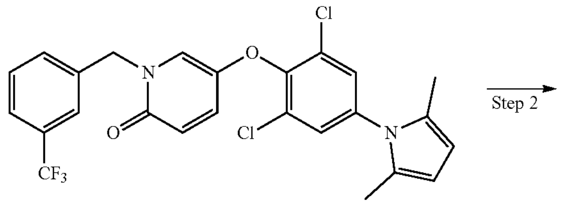

42a

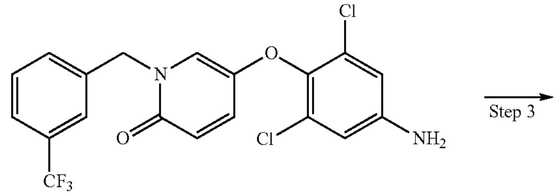

42b

-continued

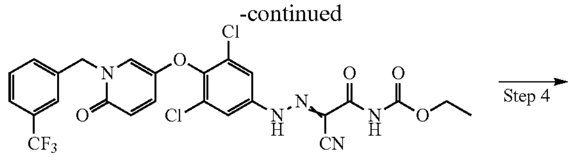

42c

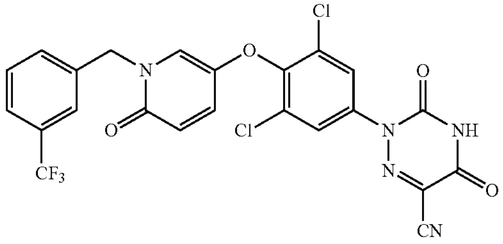

42

Step 1 5-(2,6-dichloro-4-(2,5-dimethyl-1H-pyrrol-1-yl)phenoxy)-1-(3-(trifluoromethyl)benzyl)pyridin-2(1H)-one 42a 5-(2,6-Dichloro-4-(2,5-dimethyl-1H-pyrrol-1-yl)phenoxy)pyridin-2(1H)-one 39b (0.30 g, 1.0 mmol) and m-trifluoromethylbenzyl bromide (0.21 g, 0.86 mmol) were dissolved in N,N-dimethylformamide (8 mL), then potassium carbonate (0.30 g, 2.7 mmol) was added, and the mixture was reacted at room temperature for 24 hours. To the reaction solution was added water (30 mL), the mixture was stirred for 10 minutes, then filtered, and the filter cake was collected and dried under vacuum to obtain the title compound 42a (0.40 g, yield 94%) as a gray solid.

MS (ESI, pos. ion) m z: 507.0 $[M+H]^+$.

Step 2 5-(4-amino-2,6-dichlorophenoxy)-1-(3-(trifluoromethyl)benzyl)pyridin-2(1H)-one 42b 5-(2,6-Dichloro-4-(2,5-dimethyl-1H-pyrrol-1-yl)phenoxy)-1-(3-(trifluoromethyl)benzyl)pyridin-2(1H)-one 42a (0.40 g, 0.79 mmol), hydroxylamine hydrochloride (0.58 g, 8.1 mmol) and triethylamine (0.89 mL) were dissolved in ethanol (10 mL), and the mixture was reacted at 80° C. for 16 hours. The reaction solution was cooled to room temperature, then water (30 mL) was added, the mixture was stirred for 15 minutes, then filtered, and the filter cake was collected and dried under vacuum to obtain the title compound 42b (0.34 g, yield 91%) as a black solid.

MS (ESI, pos. ion) m z: 429.0 $[M+H]^+$.

Step 3 Ethyl (2-cyano-2-(2-(3,5-dichloro-4-((6-oxo-1-(3-(trifluoromethyl)benzyl)-1,6-dihydropyridin-3-yl)oxy)phenyl)hydrazono)acetyl)carbamate 42c 5-(4-Amino-2,6-dichlorophenoxy)-1-(3-(trifluoromethyl)benzyl)pyridin-2(1H)-one 42b (0.34 g, 0.79 mmol), N-cyanoacetylurethane (0.14 g, 0.87 mmol) and concentrated hydrochloric acid (0.18 mL) were added to acetic acid (3 mL), and a solution of sodium nitrite (56 mg, 0.81 mmol) in water (2 mL) was added dropwise at 3° C., then the mixture was reacted for 6 hours. To the reaction solution was added water (20 mL), the mixture was extracted with ethyl acetate (5 mL×2), the combined organic phase was dried with anhydrous sodium sulfate, then concentrated by suction filtration to obtain the title compound 42c (0.47 g, yield 99%) as a deep red solid.

MS (ESI, pos. ion) m z: 596.0 $[M+H]^+$.

Step 4 2-[3,5-dichloro-4-[[6-oxo-1-[3-(trifluoromethyl)benzyl]-1,6-dihydropyridin-3-yl]oxy]phenyl]-3,5-dioxo-1,2,4-triazine-6-carbonitrile 42

Ethyl (2-cyano-2-(2-(3,5-dichloro-4-((6-oxo-1-(3-(trifluoromethyl)benzyl)-1,6-dihydropyridin-3-yl)oxy)phenyl)hydrazono)acetyl)carbamate 42c (0.47 g, 0.79 mmol) was dissolved in N,N-dimethylacetamide (3 mL), then potassium acetate (0.31 g, 3.2 mmol) was added, the mixture was reacted at 120° C. for 3 hours. The reaction solution was cooled to room temperature, filtered, and the filtrate was purified by preparative chromatography column [50% ACN/50% $H_2O$ (0.1% TFA), Phenomenex ACE specifications: C18 10 μm×50 mm×250 mm, flow rate: 100 mL/min] to obtain the title compound 42 (38 mg, yield 8.7%, HPLC purity: 98.74%) as a red solid.

MS (ESI, neg. ion) m z: 548.0 $[M-H]^-$;

$^1$H NMR (400 MHz, $CDCl_3$) δ (ppm) 7.63 (s, 2H), 7.57 (d, J=7.9 Hz, 1H), 7.46 (t, J=6.9 Hz, 3H), 7.32-7.28 (m, 1H), 6.88 (d, J=3.0 Hz, 1H), 6.71 (d, J=9.8 Hz, 1H), 5.15 (s, 2H).

Example 15 2-(3,5-dichloro-4-((6-isopropoxypyridin-3-yl)oxy)phenyl)-3,5-dioxo-1,2,4-triazine-6-carbonitrile (Compound 43)

(43)

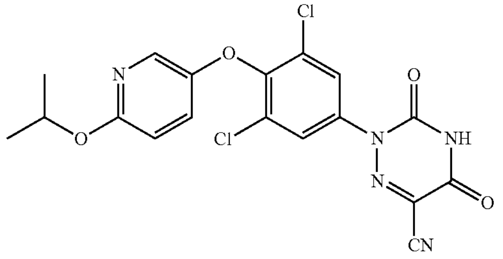

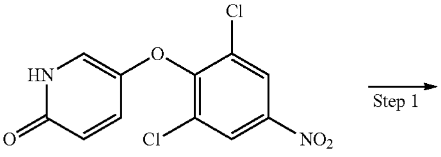

4c

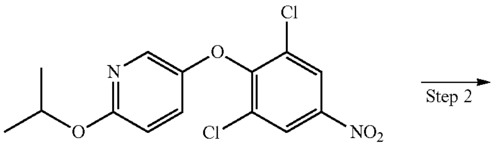

43a

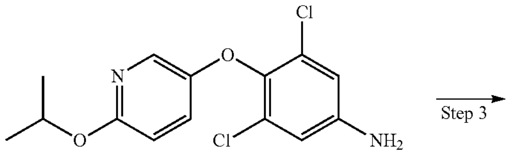

43b

-continued

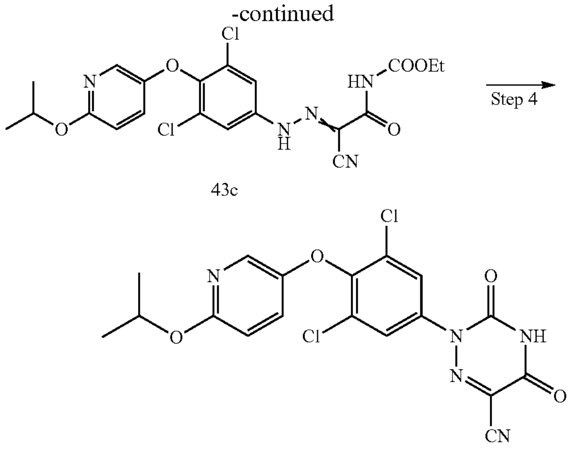

43c

43

Step 1 5-2,6-dichloro-4-nitrophenoxy)-2-isopropoxypyridine 43a 5-(2,6-Dichloro-4-nitro-phenoxy)-pyridine-2(1H)-one 4c (0.30 g, 1.0 mmol) was dissolved in N,N-dimethylformamide (2 mL), then potassium carbonate (0.28 g, 2.0 mmol) and isopropyl iodide (0.19 g, 1.1 mmol) were added, and the mixture was reacted at 85° C. for 16 hours. To the reaction solution was added water (30 mL), the mixture was stirred for 10 minutes, then filtered, and the filter cake was collected and dried under vacuum to obtain the title compound 43a (0.34 g, yield 94%) as a gray solid.

MS (ESI, pos. ion) m z: 343.0 $[M+H]^+$.

Step 2 3,5-dichloro-4-((6-isopropoxypyridin-3-yl)oxy)aniline 43b 5-(2,6-Dichloro-4-nitrophenoxy)-2-isopropoxypyridine 43a (0.34 g, 0.99 mmol) and sodium sulfide (0.39 g, 5.00 mmol) were dissolved in ethanol (3 mL), the mixture was reacted at 80° C. for 40 minutes. The reaction solution was cooled to room temperature, then water (30 mL) was added, the mixture was stirred for 15 minutes, then filtered, and the filter cake was collected and dried under vacuum to obtain the title compound 43b (0.28 g, yield 91%) as a brown solid.

MS (ESI, pos. ion) m z: 313.3 $[M+H]^+$.

Step 3 Ethyl (2-cyano-2-(2-(3,5-dichloro-4-((6-isopropoxypyridin-3-yl)oxy)phenyl)hydrazono)acetyl)carbamate 43c 3,5-Dichloro-4-((6-isopropoxypyridin-3-yl)oxy)aniline 43b (0.17 g, 0.54 mmol), N-cyanoacetylurethane (0.095 g, 0.59 mmol) and concentrated hydrochloric acid (0.18 mL) were added to acetic acid (3 mL), and a solution of sodium nitrite (0.041 g, 0.59 mmol) in water (2 mL) was added dropwise at 3° C., then the mixture was reacted for 4 hours. To the reaction solution was added water (20 mL), the mixture was extracted with ethyl acetate (5 mL×2), the combined organic phase was dried with anhydrous sodium sulfate, then concentrated by suction filtration to obtain the title compound 43c (0.26 g, yield 100%) as a deep red solid.

MS (ESI, pos. ion) m z: 480.0 $[M+H]^+$.

Step 4 2-(3,5-dichloro-4-((6-isopropoxypyridin-3-yl)oxy)phenyl)-3,5-dioxo-1,2,4-triazine-6-carbonitrile 43

Ethyl (2-cyano-2-(2-(3,5-dichloro-4-((6-isopropoxypyridin-3-yl)oxy)phenyl)hydrazono)acetyl)carbamate 43c (0.26 g, 0.54 mmol) was dissolved in N,N-dimethylacetamide (2 mL), then potassium acetate (0.21 g, 2.2 mmol) was added, the mixture was reacted at 120° C. for 2 hours. The reaction solution was cooled to room temperature, filtered, and the filtrate was purified by preparative chromatography column [60% ACN/40% $H_2O$ (0.1% TFA), Phenomenex ACE specifications: C18 10 μm×50 mm×250 mm, flow rate: 100 mL/min] to obtain the title compound 43 (15 mg, yield 6.3%, HPLC purity: 99.15%) as a yellow solid.

MS (ESI, pos. ion) m z: 434.5 $[M+H]^+$;

$^1H$ NMR (400 MHz, DMSO-$d_6$), δ (ppm) 7.79 (d, J=2.8 Hz, 1H), 7.66 (s, 2H), 7.30 (d, J=2.5 Hz, 1H), 6.73 (d, J=9.0 Hz, 1H), 5.14 (dt, J=11.8, 5.9 Hz, 1H), 1.35 (d, J=6.1 Hz, 6H).

Example 16 Methyl 2-(4-((1-benzyl-6-oxo-1,6-dihydropyridin-3-yl)oxy)-3,5-dichlorophenyl)-3,5-dioxo-2,3,4,5-tetrahydro-1,2,4-triazine-6-carboxylate (Compound 45)

(45)

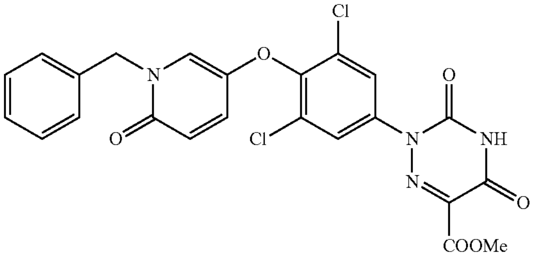

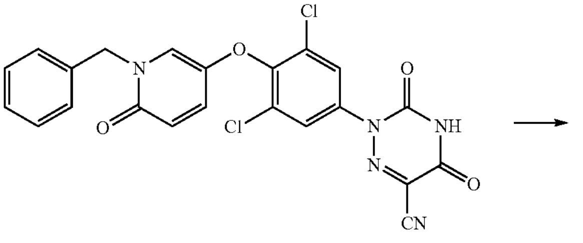

1

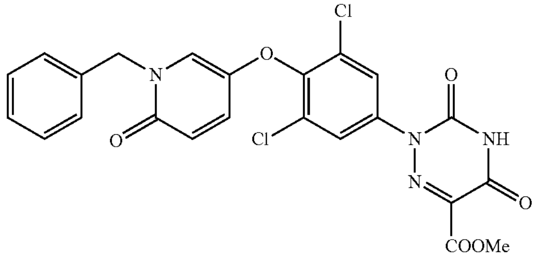

45

2-[4-[(1-Benzyl-6-oxo-1,6-dihydropyridin-3-yl)oxy]-3,5-dichlorophenyl]-3,5-dioxo-1,2,4-triazine-6-carbonitrile 1

(0.30 g, 0.60 mmol) was dissolved in a solution of hydrogen chloride in methanol (2 mL, 4.5 mol/L), and the mixture was reacted at 70° C. for 16 hours. The reaction solution was cooled to room temperature and concentrated, and the residue was purified by silica gel column chromatography [100% ethyl acetate] to obtain the title compound 45 (27 mg, yield 51%, HPLC purity: 96.10%) as a yellow solid.

MS (ESI, pos. ion) m z: 515.0 $[M+H]^+$;

$^1$H NMR (400 MHz, $CDCl_3$) δ (ppm) 10.10 (s, 1H), 7.67 (s, 2H), 7.44-7.27 (m, 6H), 6.91 (d, J=2.9 Hz, 1H), 6.71 (d, J=9.9 Hz, 1H), 5.14 (s, 2H), 4.01 (s, 3H).

Example 16 Ethyl 2-[5-[2,6-dichloro-4-(6-cyano-3,5-dioxo-1,2,4-triazin-2-yl)phenoxy]-2-oxy-pyridine-1(2H)-yl] acetate (Compound 48)

(48)

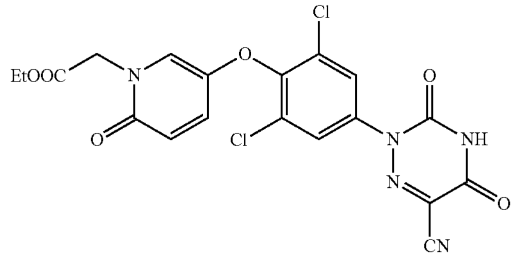

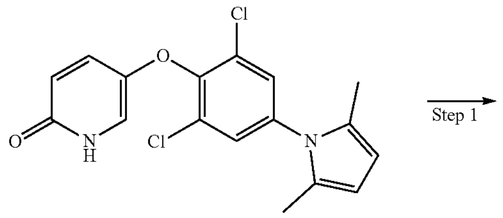

39b

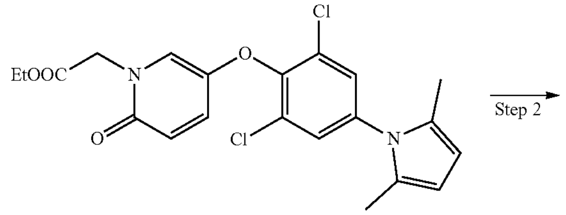

48a

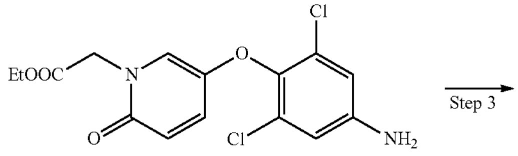

48b

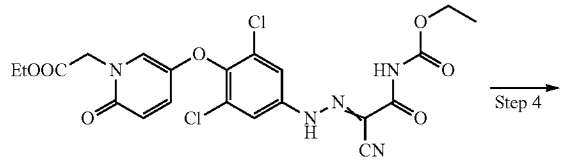

48c

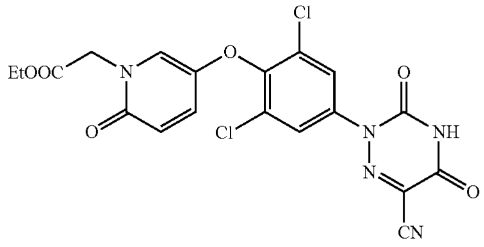

48

Step 1 Ethyl 2-(5-(2,6-dichloro-4-(2,5-dimethyl-1H-pyrrol-1-yl)phenoxy)-2-oxopyridin-1(2H)-yl)acetate 48a 5-[2,6-Dichloro-4-(2,5-dimethyl-1H-pyrrol-1-yl)phenoxy]pyridine-2(1H)-one 39b (1.00 g, 2.86 mmol), potassium carbonate (1.00 g, 7.16 mmol) and ethyl bromoacetate (0.49 g, 2.86 mmol) were dissolved in N,N-dimethylacetamide (5 mL), and the mixture was reacted at room temperature for 16 hours. To the reaction solution was added water (50 mL), the mixture was stirred for 10 minutes, then filtered, and the filter cake was collected and dried under vacuum to obtain the title compound 48a (0.75 g, yield 60%) as a red solid.

MS (ESI, pos. ion) m z: 435.1 $[M+H]^+$.

Step 2 Ethyl 2-(5-(4-amino-2,6-dichlorophenoxy)-2-oxopyridin-1(2H)-yl)acetate 48b Ethyl 2-(5-(2,6-dichloro-4-(2,5-dimethyl-1H-pyrrol-1-yl)phenoxy)-2-oxopyridin-1(2H)-yl)acetate 48a (0.75 g, 1.70 mmol), hydroxylamine hydrochloride (1.40 g, 17.00 mmol) and triethylamine (0.39 mL) were dissolved in ethanol (10 mL), and the mixture was reacted at 80° C. for 5 hours. The reaction solution was cooled to room temperature, then water (30 mL) was added, the mixture was stirred for 15 minutes, then filtered, and the filter cake was collected and dried under vacuum to obtain the title compound 48b (0.46 g, yield 75%) as a black solid.

MS (ESI, pos. ion) m z: 357.0 $[M+H]^+$.

Step 3 Ethyl 2-(5-(2,6-dichloro-4-(2-(1-cyano-2-((ethoxycarbonyl)amino)-2-oxoethylidene)hydrazinyl)phenoxy)-2-oxopyridin-1(2H)-yl)acetate 48c Ethyl 2-(5-(4-amino-2,6-dichlorophenoxy)-2-oxopyridin-1(2H)-yl)acetate 48b (0.46 g, 1.29 mmol), N-cyanoacetylurethane (0.23 g, 1.42 mmol) and concentrated hydrochloric acid (0.18 mL) were added to acetic acid (3 mL), and an aqueous solution (2 mL) of sodium nitrite (0.10 g, 1.42 mmol) was added dropwise at 3° C., then the mixture was reacted for 1 hour. To the reaction solution was added water (50 mL), the mixture was stirred for 10 minutes, then filtered, and the filter cake was collected and dried under vacuum to obtain the title compound 48c (0.46 g, yield 68%) as a deep red solid.

MS (ESI, pos. ion) m z: 524.0 $[M+H]^+$.

Step 4 Ethyl 2-[5-[2,6-dichloro-4-(6-cyano-3,5-dioxo-1,2,4-triazin-2-yl)phenoxy]-2-oxy-pyridine-1(2H)-yl] Acetate 48

Ethyl 2-(5-(2,6-dichloro-4-(2-(1-cyano-2-((ethoxycarbonyl)amino)-2-oxoethylidene)hydrazinyl)phenoxy)-2- oxopyridin-1(2H)-yl)acetate 48c (0.46 g, 0.88 mmol) was dissolved in N,N-dimethylformamide (3 mL), then potassium acetate (0.13 g, 1.30 mmol) was added, and the mixture was reacted at 120° C. for 6 hours. The reaction solution was cooled to room temperature, filtered, and the filtrate was purified by preparative chromatography column [58% ACN/42% $H_2O$ (0.1% TFA), Phenomenex ACE specifications: C18 10 μm×50 mm×250 mm, flow rate: 100 mL/min] to obtain the title compound 48 (55 mg, yield 12%, HPLC purity: 93.99%) as a yellow solid.

MS (ESI, pos. ion) m z: 478.0 $[M+H]^+$;

$^1H$ NMR (400 MHz, $CDCl_3$) δ (ppm) 7.66 (s, 2H), 7.43 (d, J=9.8 Hz, 1H), 6.86 (d, J=9.6 Hz, 2H), 4.65 (s, 2H), 4.27-4.21 (m, 2H), 1.30 (s, 3H).

Example 18 2-[3,5-dichloro-4-[[1-(2-methoxyethyl)-6-oxo-1,6-dihydropyridin-3-yl]oxy]phenyl]-3,5-dioxo-1,2,4-triazine-6-carbonitrile (Compound 49)

(49)

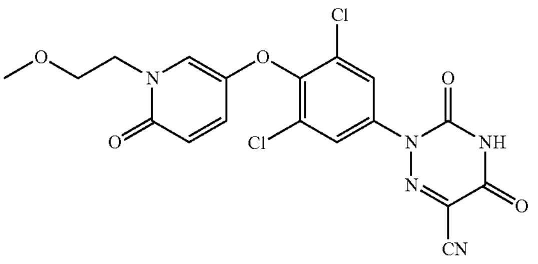

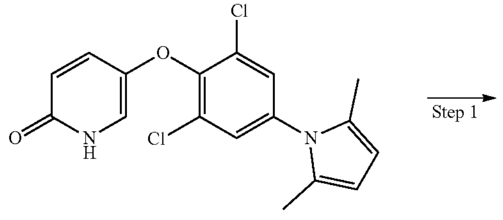

39b

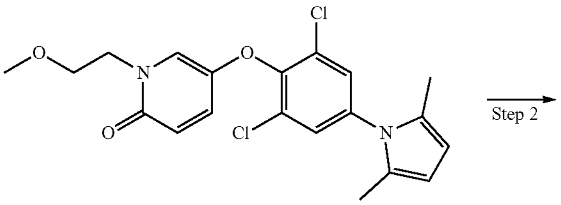

48a

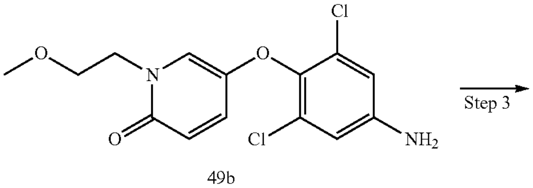

49b

-continued

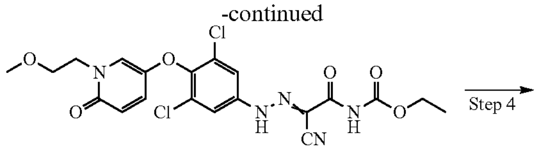

49c

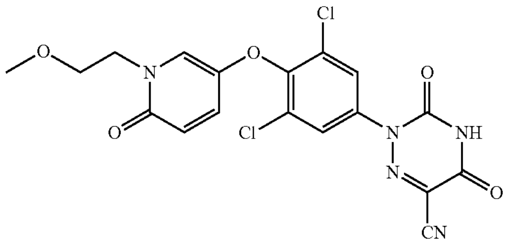

49

Step 1 5-(2,6-dichloro-4-(2,5-dimethyl-1H-pyrrol-1-yl)phenoxy)-1-(2-methoxyethyl)pyridin-2(1H)-one 49a 5-[2,6-Dichloro-4-(2,5-dimethyl-1H-pyrrol-1-yl)phenoxy]pyridine-2(1H)-one 39b (2.0 g, 5.7 mmol) was dissolved in N,N-dimethylformamide (20 mL), then potassium carbonate (1.6 g, 11 mmol) and 2-bromoethyl methyl ether (0.66 mL, 6.9 mmol) were added, and the mixture was reacted at 70° C. for 5 hours. The reaction solution was cooled to room temperature, then water (20 mL) was added, the mixture was extracted with ethyl acetate (80 mL×3). The combined organic phase was washed with saturated sodium chloride solution (40 mL), then dried over anhydrous sodium sulfate, and concentrated by suction filtration. The obtained residue was purified by silica gel column chromatography [petroleum ether/ethyl acetate (v/v)=1/1] to obtain the title compound 49a (1.2 g, yield 51%) as a reddish brown oil.

Step 2 5-(4-amino-2,6-dichlorophenoxy)-1-(2-methoxyethyl)pyridin-2(1H)-one 49b 5-(2,6-Dichloro-4-(2,5-dimethyl-1H-pyrrol-1-yl)phenoxy)-1-(2-methoxyethyl)pyridin-2(1H)-one 49a (0.50 g, 1.2 mmol) and hydroxylamine hydrochloride (1.3 g, 19 mmol) were dissolved in ethanol (4 mL), then triethylamine (0.51 mL, 3.7 mmol) was added, and the mixture was reacted at 85° C. for 16 hours. The reaction solution was cooled to room temperature, then ethyl acetate (20 mL) was added. The resulting mixture was stirred for 10 minutes, filtered, and the filtrate was concentrated. The resulting residue was purified by silica gel column chromatography [petroleum ether/ethyl acetate (v/v)=2/3] to obtain the title compound 49b (0.20 g, yield 49%) as a yellow solid.

Step 3 Ethyl (2-cyano-2-(2-(3,5-dichloro-4-((1-(2-methoxyethyl)-6-oxo-1,6-dihydropyridin-3-yl)oxy)phenyl)hydrazono)acetyl)carbamate 49c 5-(4-Amino-2,6-dichlorophenoxy)-1-(2-methoxyethyl)pyridin-2(1H)-one 49b (0.20 g, 0.61 mmol), N-cyanoacetylurethane (0.11 g, 0.69 mmol) were dissolved in acetic acid (4 mL), and an aqueous solution (2 mL) of sodium nitrite (85 mg, 1.2 mmol) was added dropwise at 0° C., then the mixture was reacted for 2 hours. To the reaction solution was added water (10 mL). The resulting mixture was stirred for 10 minutes, filtered, and the filter cake was washed with water (2 mL), collected and dried under vacuum to obtain the title compound 49c (0.30 g, yield 99%) as a red solid.

Step 4 2-[3,5-dichloro-4-[[1-(2-methoxyethyl)-6-oxo-1,6-dihydropyridin-3-yl]oxy]phenyl]-3,5-dioxo-1,2,4-triazine-6-carbonitrile 49

Ethyl (2-cyano-2-(2-(3,5-dichloro-4-((1-(2-methoxyethyl)-6-oxo-1,6-dihydropyridin-3-yl)oxy)phenyl)hydrazono)acetyl)carbamate 49c (0.30 g, 0.60 mmol) was dissolved in N,N-dimethylacetamide (3 mL), then sodium acetate (53 mg, 0.65 mmol) was added, the mixture was reacted at 120° C. for 5 hours. The reaction solution was cooled to room temperature, then water (20 mL) was added, the mixture was extracted with ethyl acetate (20 mL×3), the combined organic phase was washed with saturated sodium chloride solution (10 mL×3), dried with anhydrous sodium sulfate, then filtered and concentrated. The obtained residue was purified by silica gel column chromatography [petroleum ether/ethyl acetate (v/v)=1/3], and the obtained yellow solid was recrystallized with ethanol/ethyl acetate/petroleum ether (0.3/5/8, 13.3 mL) at 85° C. to obtain the title compound 49 (0.10 g, yield 37%, HPLC purity: 98.02%) as a white solid.

MS (ESI, neg. ion) m z: 448.0 $[M-H]^-$.

$^1H$ NMR (400 MHz, DMSO-$d_6$) δ (ppm) 13.27 (s, 1H), 7.78 (s, 2H), 7.44 (dd, J=9.9, 3.3 Hz, 1H), 7.32 (d, J=3.2 Hz, 1H), 6.43 (d, J=9.9 Hz, 1H), 4.01 (t, J=5.2 Hz, 2H), 3.51 (t, J=5.2 Hz, 2H), 3.20 (s, 3H).

Example 19 Ethyl 2-[3-[2,6-dichloro-4-(6-cyano-3,5-dioxo-1,2,4-triazin-2-yl)phenoxy]-6-oxy-pyridazine-1(6H)-yl] acetate (Compound 52)

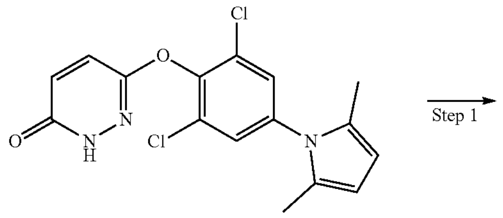

39b

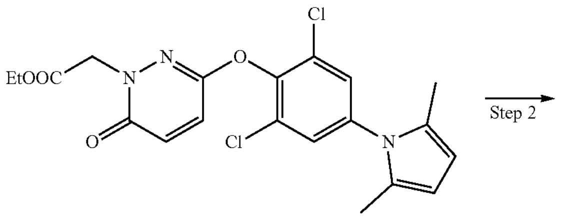

52a

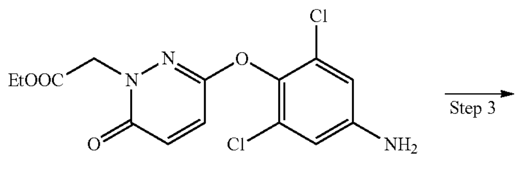

52b

-continued

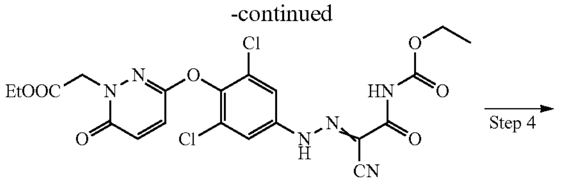

52c

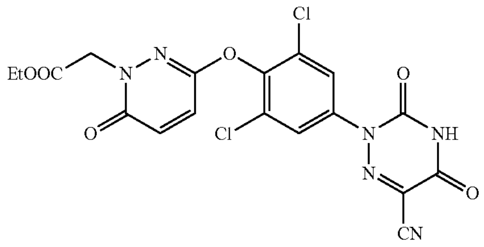

52

(52)

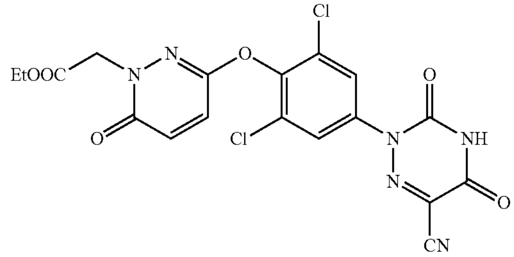

Step 1 Ethyl 2-(3-(2,6-dichloro-4-(2,5-dimethyl-1H-pyrrol-1-yl)phenoxy)-6-oxopyridazin-1(6H)-yl)acetate 52a 6-(2,6-Dichloro-4-(2,5-dimethyl-1H-pyrrol-1-yl)phenoxy)pyridazin-3(2H)-one 3d (1.00 g, 2.86 mmol), potassium carbonate (0.80 g, 5.70 mmol) and ethyl bromoacetate (0.49 g, 2.86 mmol) were dissolved in N,N-dimethylacetamide (2 mL), and the mixture was reacted at 70° C. for 24 hours. To the reaction solution was added water (20 mL), the resulting mixture was stirred for 10 minutes, then filtered, and the filter cake was collected and dried under vacuum to obtain the title compound 52a (1.05 g, yield 84%) as a gray solid.

Step 2 Ethyl 2-(3-(4-amino-2,6-dichlorophenoxy)-6-oxopyridazin-1(6H)-yl)acetate 52b Ethyl 2-(3-(2,6-dichloro-4-(2,5-dimethyl-1H-pyrrol-1-yl)phenoxy)-6-oxopyridazin-1(6H)-yl)acetate 52a (1.05 g, 2.41 mmol), hydroxylamine hydrochloride (1.76 g, 24.10 mmol) and triethylamine (0.67 mL) were dissolved in ethanol (10 mL), and the mixture was reacted at 80° C. for 15 hours. The reaction solution was cooled to room temperature, then water (30 mL) was added. The resulting mixture was stirred for 15 minutes, filtered, and the filtrate was concentrated. The resulting residue was purified by silica gel column chromatography [petroleum ether/ethyl acetate (v/v)=1/1] to obtain the title compound 52b (0.15 g, yield 17%) as a red solid.

MS (ESI, pos. ion) m z: 357.9 $[M+H]^+$.

Step 3 Ethyl 2-(3-(2,6-dichloro-4-(2-(1-cyano-2-((ethoxycarbonyl)amino)-2-oxoethylidene)hydrazinyl)phenoxy)-6-oxopyridazin-1(6H)-yl)acetate 52c Ethyl 2-(3-(4-amino-2,6-dichlorophenoxy)-6-oxopyridazin-1(6H)-yl)acetate 52b (0.15 g, 0.42 mmol), N-cyanoacetylurethane (0.07 g, 0.42 mmol) and concentrated hydrochloric acid (0.11 mL) were dissolved in acetic acid (3 mL), and an aqueous solution (2 mL) of sodium nitrite (0.03 g, 0.46 mmol) was added dropwise at 3° C., then the mixture was reacted for 50 minutes. To the reaction solution was added water (50 mL), the resulting mixture was stirred for 5 minutes, filtered, and the filter cake was collected and dried under vacuum to obtain the title compound 52c (156 mg, yield 71%) as a deep red solid.

MS (ESI, pos. ion) m z: 525.0 $[M+H]^+$.

Step 4 Ethyl 2-[3-[2,6-dichloro-4-(6-cyano-3,5-dioxo-1,2,4-triazin-2-yl)phenoxy]-6-oxy-pyridazine-1(6H)-yl] Acetate 52

Ethyl 2-(3-(2,6-dichloro-4-(2-(1-cyano-2-((ethoxycarbonyl)amino)-2-oxoethylidene)hydrazinyl)phenoxy)-6-oxopyridazin-1(6H)-yl)acetate 2c (0.156 g, 0.30 mmol) was dissolved in N,N-dimethylformamide (3 mL), then potassium acetate (0.05 g, 0.50 mmol) was added, the mixture was reacted at 120° C. for 6 hours. The reaction solution was cooled to room temperature, filtered, and the filtrate was purified by preparative chromatography column [40% ACN/60% $H_2O$ (0.1% TFA), Phenomenex ACE specifications: C18 10 μm×50 mm×250 mm, flow rate: 100 mL/min] to obtain the title compound 52 (70.0 mg, yield 48%, HPLC purity: 98.24%) as a white solid.

MS (ESI, pos. ion) m z: 476.8 $[M+H]^+$.

$^1H$ NMR (400 MHz, DMSO-$d_6$) δ (ppm) 7.79 (s, 2H), 7.74 (d, J=9.9 Hz, 1H), 7.25 (d, J=9.9 Hz, 1H), 4.56 (s, 2H), 4.07 (q, J=7.1 Hz, 2H), 1.14 (t, J=7.1 Hz, 3H).

Example 20 2-[3,5-dichloro-4-[1-(4-fluorobenzyl)-2-oxo-1,2-dihydropyrimidin-5-yl]oxy-phenyl]-3,5-dioxo-1,2,4-triazine-6-carbonitrile (Compound 50)

(50)

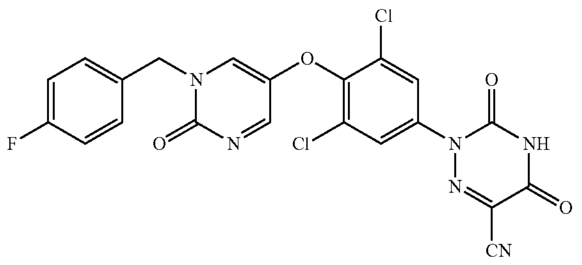

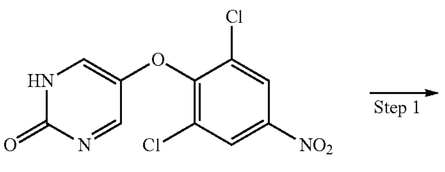

38c

-continued

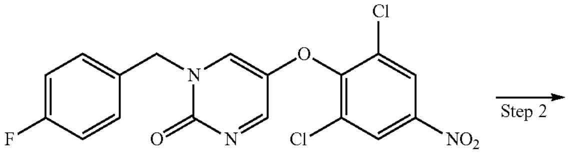

50a

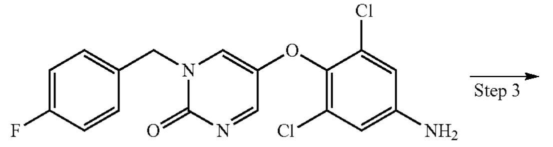

50b

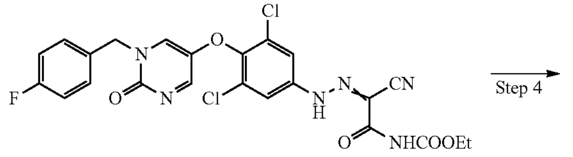

50c

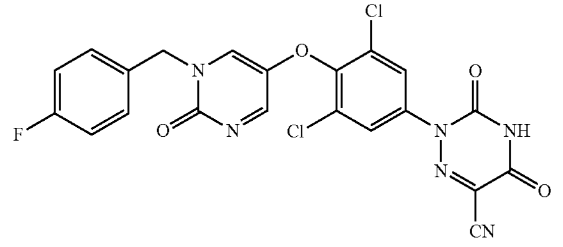

50

Step 1 5-(2,6-dichloro-4-nitrophenoxy)-1-(4-fluorobenzyl)pyrimidin-2(1H)-one 50a 5-(2,6-Dichloro-4-nitro-phenoxy)-pyrimidin-2(1H)-one 38c (1.15 g, 3.81 mmol) and 1-(bromomethyl)-4-fluorobenzene (0.54 mL, 4.20 mmol) were dissolved in dichloromethane (25 mL), then triethylamine (1.10 mL, 7.68 mmol) was added dropwise, and the mixture was reacted at room temperature for 4.5 hours. The mixture was quenched with water (30 mL) and extracted with ethyl acetate (30 mL×3). The combined organic phase was washed with saturated sodium chloride solution (30 mL), dried over anhydrous sodium sulfate, concentrated by suction filtration. The residue was purified by silica gel column chromatography [petroleum ether/ethyl acetate (v/v)=1/2] to obtain the title compound 50a (1.25 g, yield 80%) as a yellow solid.

MS (ESI, pos. ion) m z: 410.0 $[M+H]^+$.

Step 2 5-(4-amino-2,6-dichlorophenoxy)-1-(4-fluorobenzyl)pyrimidin-2(1H)-one 50b 5-(2,6-Dichloro-4-nitrophenoxy)-1-(4-fluorobenzyl)pyrimidin-2(1H)-one 50a (0.51 g, 1.24 mmol) was dissolved in acetic acid (20 mL), then iron powder (0.28 g, 4.97 mmol) was added, and the mixture was reacted at 90° C. for 2 hours. The reaction solution was cooled to room temperature, iron powder was removed, and concentrated under vacuum to obtain the title compound 50b (1.16 g, yield 94%) as a yellow solid.

MS (ESI, pos. ion) m z: 380.0 $[M+H]^+$.

Step 3 Ethyl (2-cyano-2-(2-(3,5-dichloro-4-((1-(4-fluorobenzyl)-2-oxo-1,2-dihydropyrimidin-5-yl)oxy) phenyl)hydrazono)acetyl)carbamate 50c 5-(4-Amino-2,6-dichlorophenoxy)-1-(4-fluorobenzyl)pyrimidin-2(1H)-one 50b (6, 0.53 g, 1.39 mmol) and N-cyanoacetylurethane (0.198 g, 1.34 mmol) were dissolved in acetic acid (5 mL), and an aqueous solution (1.5 mL) of sodium nitrite (0.119 g, 1.69 mmol) was added dropwise at 0° C., and the mixture was reacted for 2 hours. To the reaction solution was added water (20 mL). The resulting mixture was stirred for 30 minutes, filtered, and the filter cake was collected and dried under vacuum to obtain the title compound 50c (0.58 g, yield 76%) as a yellow solid.

Step 4 2-[3,5-dichloro-4-[1-(4-fluorobenzyl)-2-oxo-1,2-dihydropyrimidin-5-yl]oxy-phenyl]-3,5-dioxo-1,2,4-triazine-6-carbonitrile 50

Ethyl (2-cyano-2-(2-(3,5-dichloro-4-((1-(4-fluorobenzyl)-2-oxo-1,2-dihydropyrimidin-5-yl)oxy)phenyl)hydrazono)acetyl)carbamate 50c (0.31 g, 0.56 mmol) was dissolved in acetic acid (4 mL), then sodium acetate (0.23 g, 2.81 mmol) was added, and the mixture was reacted at 120° C. for 4 hours. The reaction solution was cooled to room temperature, filtered with suction and concentrated. The obtained residue was purified by preparative chromatography column [37% ACN/63% $H_2O$ (0.1% TFA), Phenomenex ACE specifications: C18 10 μm×50 mm×250 mm, flow rate: 100 mL/min] to obtain the title compound 50 (70 mg, yield 25%, HPLC purity: 96.63%) as a white solid.

MS (ESI, neg. ion) m z: 498.9 $[M-H]^-$.

$^1$H NMR (400 MHz, DMSO-$d_6$) δ (ppm) 13.31 (s, 1H), 8.79 (d, J=3.6 Hz, 1H), 8.30 (d, J=3.5 Hz, 1H), 7.80 (s, 2H), 7.37-7.33 (m, 1H), 7.19 (t, J=8.4 Hz, 1H), 7.13 (s, 1H), 7.00 (s, 1H), 4.99 (s, 2H).

Example 21 2-[3,5-dichloro-4-[[6-oxo-1-(4-pyridylmethyl)-1,6-dihydropyridin-3-yl]oxy]phenyl]-3,5-dioxo-1,2,4-triazine-6-carbonitrile (Compound 46)

(46)

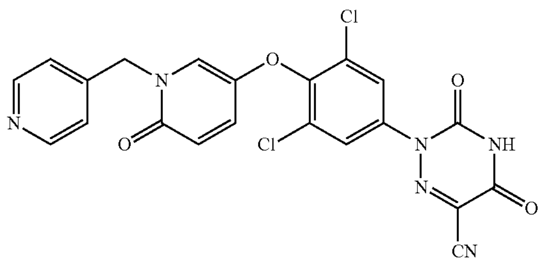

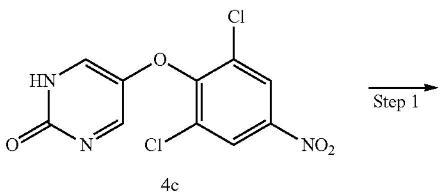

4c

-continued

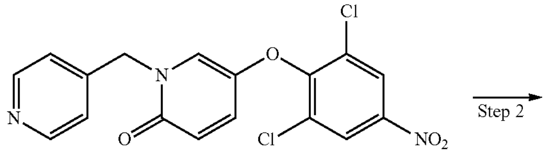

46a

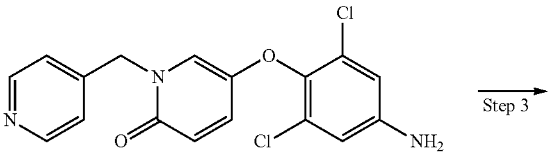

46b

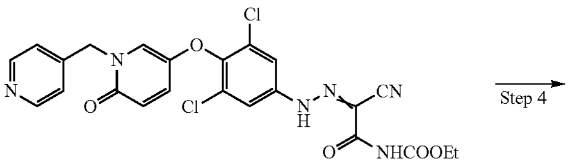

46c

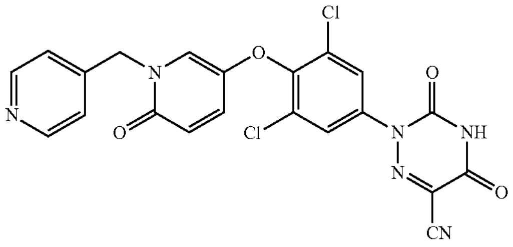

46

Step 1 5-(2,6-dichloro-4-nitrophenoxy)-1-(pyridin-4-ylmethyl)pyridin-2(1H)-one 46a 5-(2,6-Dichloro-4-nitro-phenoxy)-pyridine-2(1H)-one 4c (1.0 g, 3.3 mmol) and cesium carbonate (2.7 g, 8.2 mmol) was dissolved in acetonitrile (10 mL), then 4-(bromomethyl) pyridine hydrobromide (1.0 g, 4.0 mmol) was added, and the mixture was reacted at room temperature for 12 hours. The reaction solution was cooled to room temperature, then filtered and the filtrate was concentrated, the obtained residue was purified by silica gel column chromatography [petroleum ether/ethyl acetate (v/v)=1/4] to obtain the title compound 46a (0.83 g, yield 64%) as a yellow solid.

Step 2 5-(4-amino-2,6-dichlorophenoxy)-1-(pyridin-4-ylmethyl)pyridin-2(1Hf)-one 46b 5-(2,6-Dichloro-4-nitrophenoxy)-1-(pyridin-4-ylmethyl) pyridin-2(1H)-one 46a (0.63 g, 1.6 mmol) was dissolved in acetic acid (6 mL), then iron powder (0.22 g, 3.9 mmol) was added, and the mixture was reacted at 60° C. for 2.5 hours. The reaction solution was cooled to room temperature, then iron powder was removed, water (10 mL) was added. The resulting mixture was stirred for 10 minutes, extracted with ethyl acetate (50 mL×3), the combined organic phase was washed with saturated sodium chloride (10 mL×2), then dried over anhydrous sodium sulfate and concentrated by suction filtration to obtain the title compound 46b (0.58 g, yield 100%) as a brown solid.

Step 3 ethyl (2-cyano-2-(2-(3,5-dichloro-4-((6-oxo-1-(pyridin-4-ylmethyl)-1,6-dihydropyridin-3-yl)oxy)phenyl)hydrazono)acetyl)carbamate 46c 5-(4-Amino-2,6-dichlorophenoxy)-1-(pyridin-4-ylmethyl)pyridin-2(1H)-one 46b (0.58 g, 1.6 mmol) and N-cyanoacetylurethane (0.31 g, 1.9 mmol) was dissolved in acetic acid (12 mL), and a solution of sodium nitrite (0.22 g, 3.2 mmol) in water (5.8 mL) was added at 0° C., and the mixture was reacted at 0° C. for 3 hours. At 0° C., to the reaction solution was added water (25 mL). The resulting mixture was stirred for 15 minutes, filtered, and the filter cake was washed with water (10 mL×2), collected and dried under vacuum to obtain the title compound 46c (0.85 g, yield 99%) as a yellow solid.

Step 4 2-[3,5-dichloro-4-[[6-oxo-1-(4-pyridylmethyl)-1,6-dihydropyridin-3-yl]oxy]phenyl]-3,5-dioxo-1,2,4-triazine-6-carbonitrile 46

Ethyl (2-cyano-2-(2-(3,5-dichloro-4-((6-oxo-1-(pyridin-4-ylmethyl)-1,6-dihydropyridin-3-yl)oxy)phenyl) hydrazono)acetyl)carbamate 46c (0.85 g, 1.6 mmol) was dissolved in N,N-dimethylformamide (8.5 mL), then sodium acetate (0.14 g, 1.7 mmol) was added, the mixture was reacted at 120° C. for 6 hours. The reaction solution was cooled to room temperature and then concentrated. The residue obtained was purified by silica gel column chromatography (dichloromethane/methanol=4/1). The obtained solid was recrystallized at 85° C. (ethanol/ethyl acetate/petroleum ether=1/3/2, 30 mL) to obtain the title compound 46 (0.37 g, yield 48%, HPLC purity: 99.24%) as a yellow solid.

MS (ESI, neg. ion) m z: 480.0 $[M-H]^-$;

$^1$H NMR (400 MHz, DMSO-$d_6$) δ (ppm) 8.51 (d, J=4.7 Hz, 2H), 7.79 (s, 2H), 7.63-7.44 (m, 2H), 7.11 (d, J=5.2 Hz, 2H), 6.53 (d, J=9.8 Hz, 1H), 5.09 (s, 2H).

Example 22 2-[3,5-dichloro-4-[[1-[(3-methoxyphenyl)methyl]-6-oxopyridin-3-yl]oxy]phenyl]-3,5-dioxo-1,2,4-triazine-6-carbonitrile (Compound 55)

(55)

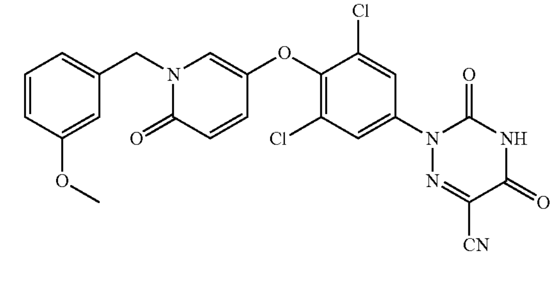

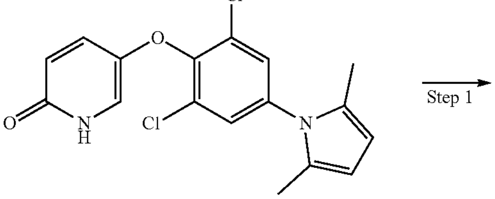

39b

-continued

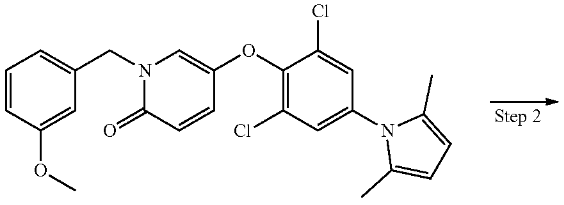

55a

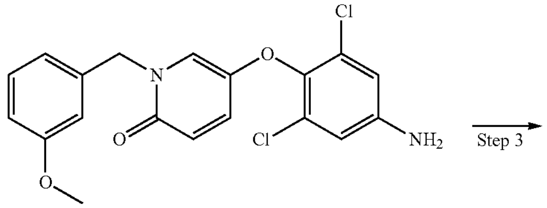

55b

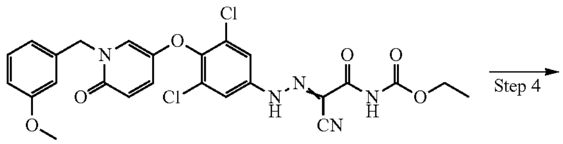

55c

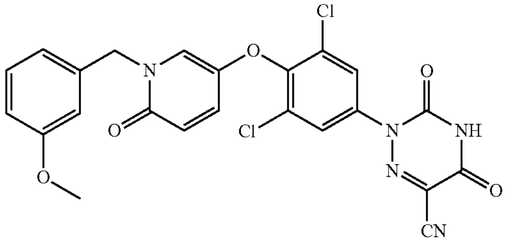

55

Step 1 5-(2,6-dichloro-4-(2,5-dimethyl-1H-pyrrol-1-yl)phenoxy)-1-(3-methoxybenzyl)pyridin-2(1H)-one 55a 5-(2,6-Dichloro-4-(2,5-dimethyl-1H-pyrrol-1-yl)phenoxy)pyridin-2(1H)-one 39b (1.00 g, 2.86 mmol), potassium carbonate (0.80 g, 5.73 mmol) and 3-methoxybenzyl chloride (0.46 g, 2.86 mmol) were dissolved in N,N-dimethylacetamide (4 mL), and the mixture was reacted at room temperature for 24 hours. To the reaction solution was added water (10 mL), the mixture was stirred for 10 minutes, filtered, and the solid was collected and dried to obtain the title compound 55a (1.00 g, yield 74%) as a gray solid.

MS (ESI, pos. ion) m z: 469.0 $[M+H]^+$.

Step 2 5-(4-amino-2,6-dichlorophenoxy)-1-(3-methoxybenzyl)pyridin-2(1H)-one 55b 5-(2,6-Dichloro-4-(2,5-dimethyl-1H-pyrrol-1-yl)phenoxy)-1-(3-methoxybenzyl)pyridin-2(1H)-one 55a (1.00 g, 2.13 mmol) was dissolved in ethanol (10 mL), then hydrochloric acid (4 mol/L, 4 mL) was added, and the mixture was reacted at 100° C. for 1.5 hours. The reaction solution was cooled to room temperature, then water (30 mL) was added. The resulting mixture was stirred for 15 minutes, filtered, and the filter cake was collected and dried under vacuum. The solid was purified by silica gel column chromatography

[petroleum ether/ethyl acetate=1/1] to obtain the title compound 55b (0.37 g, yield 44%) as a black solid.

MS (ESI, pos. ion) m z: 391.0 [M+H]$^+$.

Step 3 Ethyl (2-cyano-2-(2-(3,5-dichloro-4-((1-(3-methoxybenzyl)-6-oxo-1,6-dihydropyridin-3-yl)oxy)phenyl)hydrazono)acetyl)carbamate 55c 5-(4-Amino-2,6-dichlorophenoxy)-1-(3-methoxybenzyl)pyridin-2(1H)-one 55b (0.37 g, 0.95 mmol) and N-cyanoacetylurethane (0.16 g, 1.04 mmol) were dissolved in acetic acid (3 mL), and an aqueous solution (2 mL) of sodium nitrite (0.07 g, 1.04 mmol) was added dropwise at 3° C., and then the mixture was reacted for 4 hours. To the reaction solution was added water (20 mL). The resulting mixture was stirred for 5 minutes, filtered, and the filter cake was collected and dried under vacuum to obtain the title compound 55c (0.42 g, yield 80%) as an orange solid.

MS (ESI, pos. ion) m z: 558.1 [M+H]$^+$.

Step 4 2-[3,5-dichloro-4-[[1-[(3-methoxyphenyl)methyl]-6-oxopyridin-3-yl]oxy]phenyl]-3,5-dioxo-1,2,4-triazine-6-carbonitrile 55

Ethyl (2-cyano-2-(2-(3,5-dichloro-4-((1-(3-methoxybenzyl)-6-oxo-1,6-dihydropyridin-3-yl)oxy)phenyl)hydrazono)acetyl)carbamate 55c (0.42 g, 0.76 mmol) was dissolved in N,N-dimethylformamide (3 mL), then sodium acetate (0.09 g, 1.13 mmol) was added, the mixture was reacted at 120° C. for 7 hours. The reaction solution was cooled to room temperature, filtered, and the filtrate was purified by preparative chromatography column [45% ACN/55% $H_2O$ (0.1% TFA), Phenomenex ACE specifications: C18 10 μm×50 mm×250 mm, flow rate: 100 mL/min] to obtain the title compound 55 (15 mg, yield 3.6%, HPLC purity: 93.79%) as a white solid.

MS (ESI, pos. ion) m z: 514.0 [M+H]$^+$.

$^1$H NMR (400 MHz, $CDCl_3$) δ (ppm) 7.63 (s, 2H), 7.34-7.28 (m, 2H), 6.97 (s, 1H), 6.87-6.77 (m, 4H), 5.13 (s, 2H), 3.78 (s, 3H).

Example 23 2-[3,5-dichloro-4-[[I1-(4-methylbenzyl)-6-oxo-1,6-dihydropyridin-3-yl]oxy]phenyl]-3,5-dioxo-1,2,4-triazine-6-carbonitrile (Compound 56)

(56)

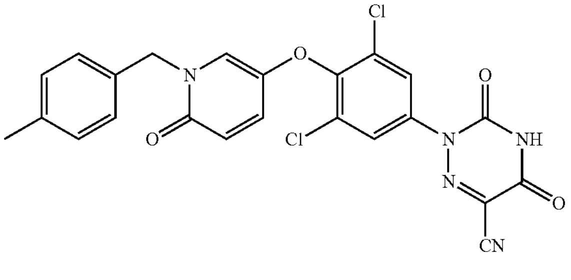

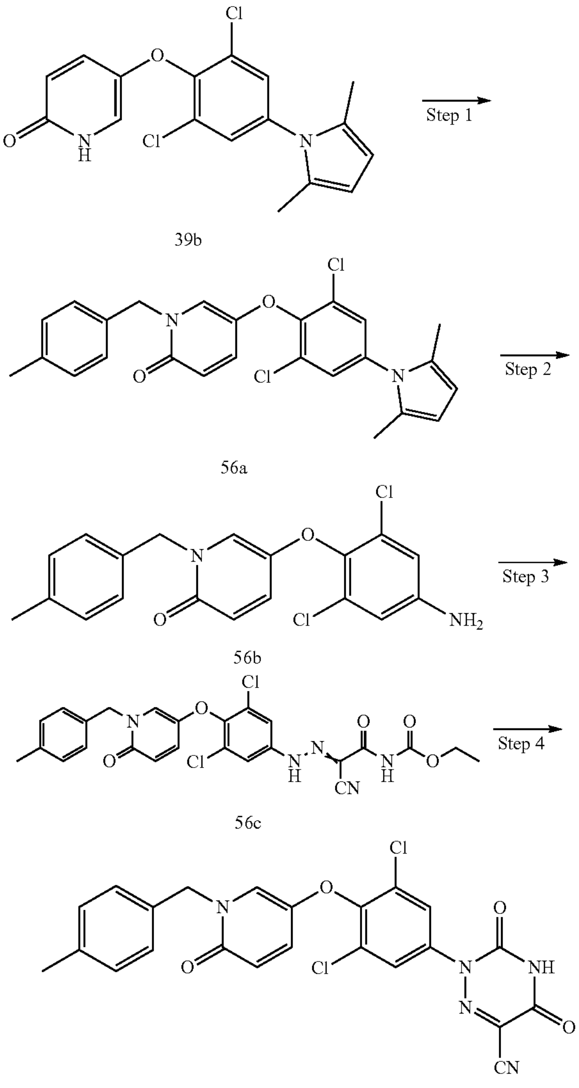

39b

56a

56b

56c

56

Step 1 5-(2,6-dichloro-4-(2,5-dimethyl-1H-pyrrol-1-yl)phenoxy)-1-(4-methylbenzyl)pyridin-2(1H)-one 56a 5-(2,6-Dichloro-4-(2,5-dimethyl-1H-pyrrol-1-yl)phenoxy)pyridin-2(1H)-one 39b (1.00 g, 2.86 mmol), potassium carbonate (0.80 g, 5.73 mmol) and 4-methylbenzyl chloride (0.41 g, 2.86 mmol) were dissolved in N,N-dimethylacetamide (4 mL), and the mixture was reacted at room temperature for 26 hours. To the reaction solution was added water (10 mL), the mixture was stirred for 10 minutes, then filtered, and the solid was collected and dried. The obtained solid was purified by silica gel column chromatography (petroleum ether/ethyl acetate=1/1) to obtain the title compound 56a (0.70 g, yield 54%) as a white solid.

Step 2 5-(4-amino-2,6-dichlorophenoxy)-1-(4-methylbenzyl)pyridin-2(1H)-one 56b 5-(2,6-Dichloro-4-(2,5-dimethyl-1H-pyrrol-1-yl)phenoxy)-1-(4-methylbenzyl)pyridin-2(1H)-one 56a (0.70 g, 1.50 mmol), hydroxylamine hydrochloride (1.70 g, 23.0 mmol) and triethylamine (1.10 mL) were dissolved in ethanol (10 mL), and the mixture was reacted at 90° C. for 18 hours. The reaction solution was cooled to room temperature, then ethyl acetate (20 mL) was added. The resulting mixture was stirred for 15 minutes, filtered, and the filtrate was concentrated to obtain the title compound 56b (0.53 g, yield 91%) as a white solid.

Step 3 Ethyl (2-cyano-2-(2-(3,5-dichloro-4-((1-(4-methylbenzyl)-6-oxo-1,6-dihydropyridin-3-yl)oxy) phenyl)hydrazono)acetyl)carbamate 56c 5-(4-Amino-2,6-dichlorophenoxy)-1-(4-methylbenzyl) pyridin-2(1H)-one 56b (0.53 g, 1.41 mmol) and N-cyanoacetylurethane (0.24 g, 1.55 mmol) were dissolved in acetic acid (3 mL), and an aqueous solution (2 mL) of sodium nitrite (0.11 g, 1.55 mmol) was added dropwise at 3° C., then the mixture was reacted for 2 hours. To the reaction solution was added water (20 mL), the mixture was stirred for 5 minutes, filtered, and the filter cake was dried to obtain the title compound 56c (0.70 g, yield 91%) as an orange solid.

MS (ESI, pos. ion) m z: 542.1 $[M+H]^+$.

Step 4 2-[3,5-dichloro-4-[[1-(4-methylbenzyl)-6-oxo-1,6-dihydropyridin-3-yl]oxy]phenyl]-3,5-dioxo-1,2,4-triazine-6-carbonitrile 56

Ethyl (2-cyano-2-(2-(3,5-dichloro-4-((1-(4-methylbenzyl)-6-oxo-1,6-dihydropyridin-3-yl)oxy)phenyl)hydrazono) acetyl)carbamate 56c (0.70 g, 1.30 mmol) was dissolved in N,N-dimethylformamide (3 mL), then sodium acetate (0.16 g, 1.90 mmol) was added, the mixture was reacted at 120° C. for 5 hours. The reaction solution was cooled to room temperature, then water (30 mL) was added. The resulting mixture was stirred for 10 minutes, filtered, and the filter cake was collected and dried. The obtained solid was purified by silica gel column chromatography [petroleum ether/ethyl acetate=1/1] to obtain the title compound 56 (77 mg, yield 11%, HPLC purity: 87.52%) as a white solid.

MS (ESI, pos. ion) m z: 496.0 $[M+H]^+$.

$^1H$ NMR (400 MHz, DMSO-$d_6$) δ (ppm) 8.30 (s, 1H), 7.77 (s, 2H), 7.56 (d, J=3.2 Hz, 1H), 7.43 (dd, J=9.9, 3.3 Hz, 1H), 7.12 (s, 4H), 6.46 (d, J=9.9 Hz, 1H), 4.99 (s, 2H), 2.25 (s, 3H).

Example 24 Ethyl 2-(5-(2,6-dichloro-4-(6-cyano-3,5-dioxo-1,2,4-triazin-2-yl)phenoxy)-2-oxypyridine-1 (2H)-yl)propionate (Compound 57)

(57)

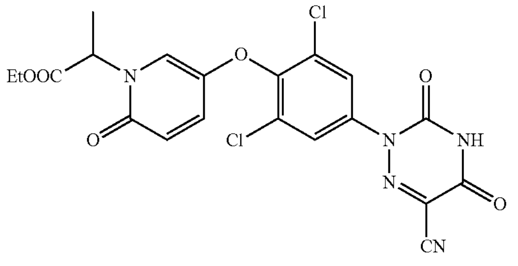

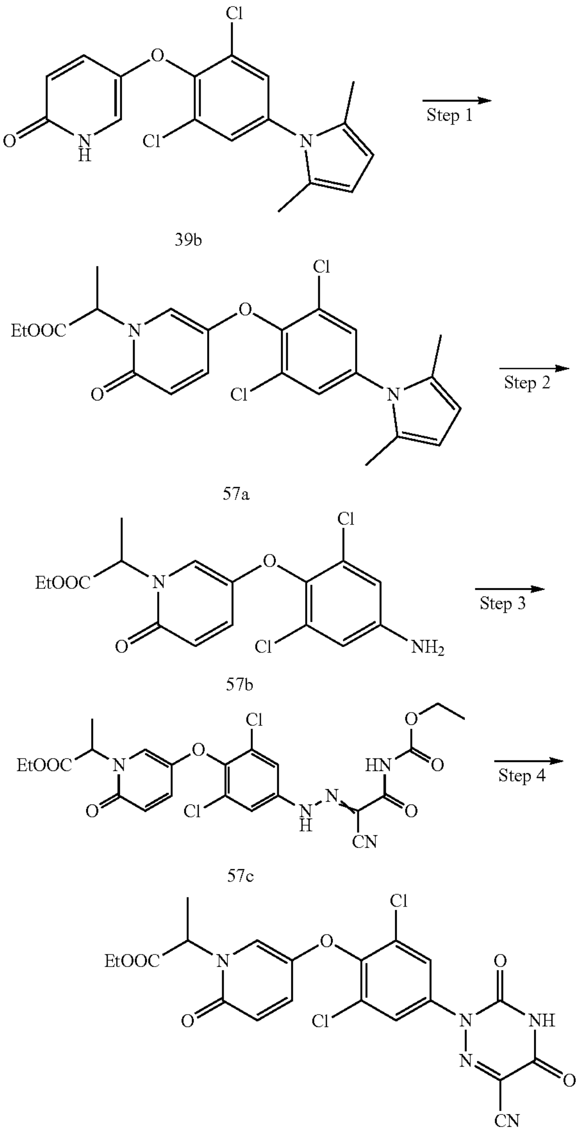

Step 1 Ethyl 2-(5-(2,6-dichloro-4-(2,5-dimethyl-1H-pyrrol-1-yl)phenoxy)-2-oxopyridin-1(2H)-yl)propanoate 57a 5-(2,6-Dichloro-4-(2,5-dimethyl-1H-pyrrol-1-yl)phenoxy)pyridin-2(1H)-one 39b (0.83 g, 2.40 mmol), potassium carbonate (0.66 g, 4.80 mmol) and ethyl 2-bromopropionate (0.44 g, 2.40 mmol) were dissolved in N,N-dimethylacetamide (4 mL), and the mixture was reacted at 60° C. for 21 hours. To the reaction solution was added water (50 mL), then the mixture was stirred for 10 minutes, filtered, and the filter cake was collected and purified by silica gel column chromatography [petroleum ether/ethyl acetate=3/1] to obtain the title compound 57a (0.34 g, yield 32%) as a yellow oil.

Step 2 Ethyl 2-(5-(4-amino-2,6-dichlorophenoxy)-2-oxopyridin-1(2H)-yl)propanoate 57b Ethyl 2-(5-(2,6-dichloro-4-(2,5-dimethyl-1H-pyrrol-1-yl) phenoxy)-2-oxopyridin-1(2H)-yl)propanoate 57a (0.34 g, 0.76 mmol), hydroxylamine hydrochloride (0.86 g, 11.00 mmol) and triethylamine (0.55 mL) were dissolved in ethanol (10 mL), and the mixture was reacted at 90° C. for 21 hours. The reaction solution was cooled to room temperature, then ethyl acetate (20 mL) was added. The resulting mixture was stirred at −10° C. for 15 minutes, filtered, and the filtrate was concentrated to obtain the title compound 57b (0.28 g, yield 100%) as a white solid.

Step 3 Ethyl 2-(5-(2,6-dichloro-4-(2-(1-cyano-2-((ethoxycarbonyl)amino)-2-oxoethylidene)hydrazinyl)phenoxy)-2-oxopyridin-1(2H)-yl)propanoate 57c Ethyl 2-(5-(4-amino-2,6-dichlorophenoxy)-2-oxopyridin-1(2H)-yl)propanoate 57b (0.28 g, 0.75 mmol) and N-cyanoacetylurethane (0.14 g, 0.83 mmol) were dissolved in acetic acid (3 mL), and an aqueous solution (2 mL) of sodium nitrite (0.06 g, 0.83 mmol) was added dropwise at 3° C., then the mixture was reacted for 1 hour. To the reaction solution was added water (20 mL), the mixture was stirred for 5 minutes, filtered, and the filter cake was dried to obtain the title compound 57c (0.23 g, yield 57%) as an orange solid.

MS (ESI, pos. ion) m z: 538.1 $[M+H]^+$.

Step 4 Ethyl 2-(5-(2,6-dichloro-4-(6-cyano-3,5-dioxo-1,2,4-triazin-2-yl)phenoxy)-2-oxypyridine-1(2H)-yl)propionate 57

Ethyl 2-(5-(2,6-dichloro-4-(2-(1-cyano-2-((ethoxycarbonyl)amino)-2-oxoethylidene)hydrazinyl)phenoxy)-2-oxopyridin-1(2H)-yl)propanoate 57c (0.23 g, 0.43 mmol) was dissolved in N,N-dimethylformamide (3 mL), then sodium acetate (0.06 g, 0.64 mmol) was added, the mixture was reacted at 120° C. for 6 hours. The reaction solution was cooled to room temperature, then water (30 mL) was added. The resulting mixture was stirred for 15 minutes, filtered, and the filter cake was collected and purified by silica gel column chromatography [petroleum ether/ethyl acetate=2/1] to obtain the title compound 57 (44.0 mg, yield 19%, HPLC purity: 91.31%) as a red solid.

MS (ESI, pos. ion) m z: 492.0 $[M+H]^+$.

$^1H$ NMR (400 MHz, $CDCl_3$) δ (ppm) 7.65 (s, 2H), 7.23 (d, J=2.6 Hz, 1H), 7.02 (d, J=2.8 Hz, 1H), 6.67 (d, J=9.7 Hz, 1H), 5.56 (d, J=7.4 Hz, 1H), 4.20 (dd, J=7.1, 2.4 Hz, 2H), 1.61 (d, J=7.2 Hz, 3H), 1.28-1.25 (m, 3H).

Example 25 2-[3,5-dichloro-4-[[6-oxo-1-((tetrahydropyran-4-yl)methyl)-1,6-dihydropyridin-3-yl]oxy]phenyl]-3,5-dioxo-1,2,4-triazine-6-carbonitrile (Compound 58)

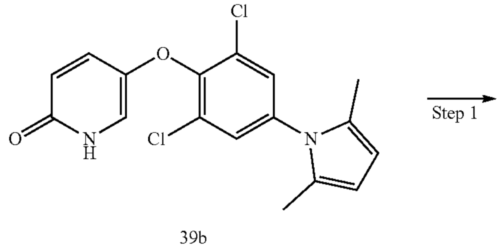

39b

-continued

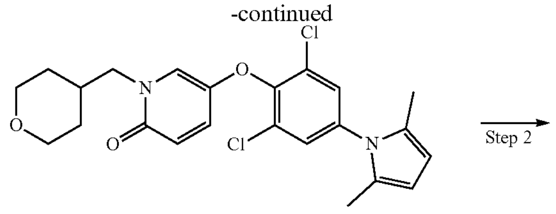

58a

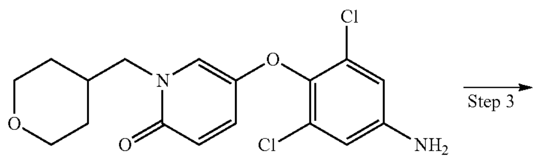

58b

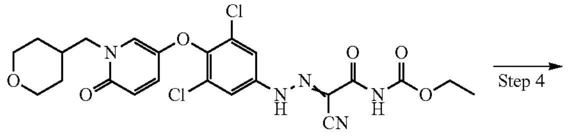

58c

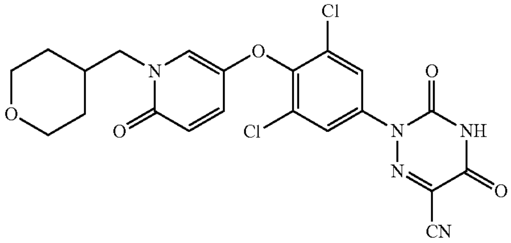

58

(58)

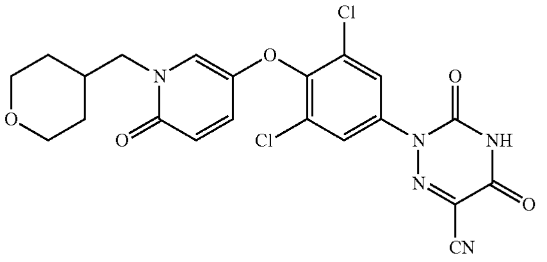

Step 1 5-(2,6-dichloro-4-(2,5-dimethyl-1H-pyrrol-1-yl)phenoxy)-1-((tetrahydro-2H-pyran-4-yl)methyl)pyridin-2(1H)-one 58a 5-(2,6-Dichloro-4-(2,5-dimethyl-1H-pyrrol-1-yl)phenoxy)pyridin-2(1H)-one 39b (2.0 g, 5.7 mmol) was dissolved in N,N-dimethylformamide (15 mL), then potassium carbonate (1.6 g, 11 mmol) and 4-(bromomethyl)tetrahydropyran (0.90 mL, 6.8 mmol) were added, the mixture was reacted at 70° C. for 6 hours. The reaction solution was cooled to room temperature, then water (50 mL) was added and the mixture was extracted with ethyl acetate (80 mL×2). The combined organic phase was washed with saturated sodium chloride solution (50 mL), dried over anhydrous sodium sulfate, concentrated by suction filtration, and the residue was purified by silica gel column chromatography

[petroleum ether/ethyl acetate=1/1] to obtain the title compound 58a (0.79 g, yield 31%) as a yellow solid.

Step 2 5-(4-amino-2,6-dichlorophenoxy)-1-((tetrahydro-2H-pyran-4-yl)methyl)pyridin-2(1H)-one 58b 5-(2,6-Dichloro-4-(2,5-dimethyl-1H-pyrrol-1-yl)phenoxy)-1-((tetrahydro-2H-pyran-4-yl)methyl)pyridin-2(1H)-one 58a (89 g, 2.0 mmol) and hydroxylamine hydrochloride (2.1 g, 30 mmol) were dissolved in ethanol (10 mL), then triethylamine (1.4 mL, 10 mmol) was added, and the mixture was reacted at 85° C. for 17 hours. The reaction solution was cooled to room temperature, then ethyl acetate (20 mL) was added. The resulting mixture was stirred for 10 minutes, filtered, and the filtrate was concentrated. The residue was purified by silica gel column chromatography [petroleum ether/ethyl acetate=2/3] to obtain the title compound 58b (0.54 g, yield 74%) as a yellow solid.

Step 3 Ethyl (2-cyano-2-(2-(3,5-dichloro-4-((6-oxo-1-((tetrahydro-2H-pyran-4-yl)methyl)-1,6-dihydropyridin-3-yl)oxy)phenyl)hydrazono)acetyl)carbamate 58c 5-(4-Amino-2,6-dichlorophenoxy)-1-((tetrahydro-2H-pyran-4-yl)methyl)pyridin-2(1H)-one 58b (0.54 g, 1.5 mmol), N-cyanoacetylurethane (0.26 g, 1.6 mmol) were dissolved in acetic acid (8 mL), then an aqueous solution (4 mL) of sodium nitrite (0.20 g, 2.9 mmol) was added dropwise at 0° C., and then the mixture was reacted for 2 hours. To the reaction solution was added water (20 mL), then the mixture was stirred for 10 minutes, filtered, and the filter cake was washed with water (4 mL), collected and dried to obtain the title compound 58c (0.78 g, yield 99%) as a red solid.

Step 4 2-[3,5-dichloro-4-[[6-oxo-1-((tetrahydropyran-4-yl)methyl)-1,6-dihydropyridin-3-yl]oxy]phenyl]-3,5-dioxo-1,2,4-triazine-6-carbonitrile 58

Ethyl (2-cyano-2-(2-(3,5-dichloro-4-((6-oxo-1-((tetrahydro-2H-pyran-4-yl)methyl)-1,6-dihydropyridin-3-yl)oxy)phenyl)hydrazono)acetyl)carbamate 58c (0.78 g, 1.5 mmol) was dissolved in N,N-dimethylacetamide (6 mL), then sodium acetate (0.13 g, 1.6 mmol) was added, the mixture was reacted at 120° C. for 5 hours. The reaction solution was cooled to room temperature, then water (20 mL) was added, and extracted with ethyl acetate (20 mL×3). The combined organic phase was washed with saturated sodium chloride solution (10 mL×3), dried over anhydrous sodium sulfate, filtered and concentrated. The residue obtained was purified by silica gel column chromatography (petroleum ether/ethyl acetate=2/1), and the brown solid obtained was recrystallized at 85° C. (petroleum ether/ethyl acetate=1/4, 5 mL) to obtain the title compound 58 (0.38 g, yield 53%, HPLC purity: 97.44%) as a yellow solid.

MS (ESI, pos. ion) m z: 490.0 $[M+H]^+$.

$^1$H NMR (400 MHz, DMSO-$d_6$) δ (ppm) 13.28 (s, 1H), 7.79 (s, 2H), 7.49-7.39 (m, 2H), 6.44 (d, J=9.4 Hz, 1H), 3.81 (d, J=9.1 Hz, 2H), 3.75 (d, J=7.3 Hz, 2H), 3.21 (t, J=10.9 Hz, 2H), 1.98 (dd, J=7.9, 4.1 Hz, 1H), 1.37 (d, J=11.5 Hz, 2H), 1.21 (dt, J=7.2, 5.9 Hz, 2H).

Example 26 Methyl 2-[3,5-dichloro-4-[[6-oxo-1-((tetrahydropyran-4-yl)methyl)-1,6-dihydropyridin-3-yl]oxy]phenyl]-3,5-dioxo-1,2,4-triazine-6-carboxylate (Compound 59)

(59)

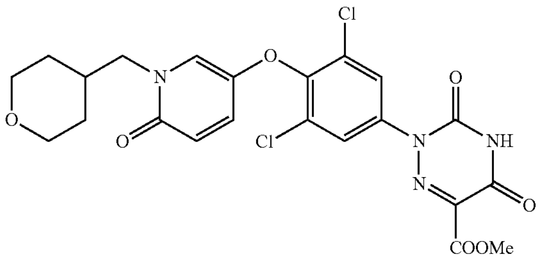

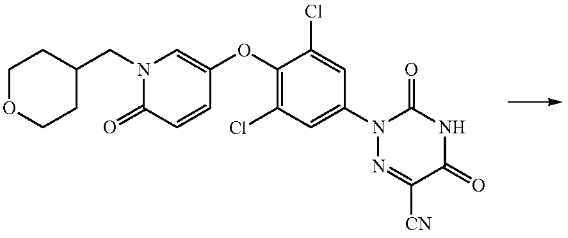

58

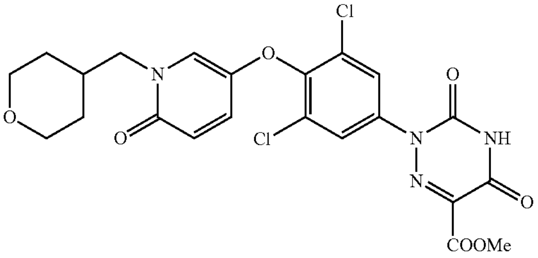

59

2-[3,5-Dichloro-4-[[6-oxo-1-((tetrahydropyran-4-yl)methyl)-1,6-dihydropyridin-3-yl]oxy]phenyl]-3,5-dioxo-1,2,4-triazine-6-carbonitrile 58 (0.10 g, 0.20 mmol) was dissolved in a solution of hydrogen chloride in methanol (3 mol/L, 3 mL), the mixture was reacted at 65° C. for 48 hours. The reaction solution was concentrated, slurried with ethyl acetate (5 mL), then filtered, and the filter cake was collected and dried to obtain the title compound 59 (17.0 mg, yield 14%, HPLC purity: 85.59%) as a white solid.

MS (ESI, pos. ion) m z: 525.0 $[M+H]^+$.

$^1$H NMR (400 MHz, DMSO-$d_6$) δ (ppm) 12.76 (s, 1H), 7.83-7.77 (m, 2H), 7.42 (d, J=8.3 Hz, 2H), 6.43 (d, J=10.4 Hz, 1H), 3.84 (s, 3H), 3.82-3.78 (m, 2H), 3.74 (d, J=7.4 Hz, 2H), 3.22 (d, J=10.9 Hz, 2H), 1.98 (dd, J=13.2, 6.8 Hz, 1H), 1.36 (d, J=12.3 Hz, 2H), 1.22 (dd, J=12.7, 8.8 Hz, 2H).

Example 27 Ethyl 2-(4-((1-benzyl-6-oxo-1,6-dihydropyridin-3-yl)oxy)-3,5-dichlorophenyl)-3,5-dioxo-1,2,4-triazine-6-carboxylate (Compound 60)

(60)

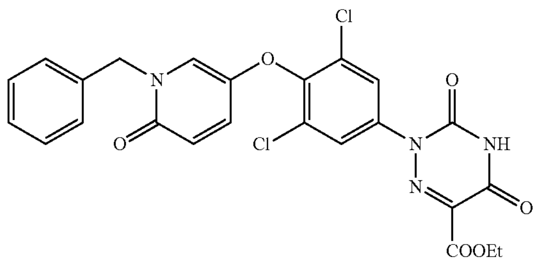

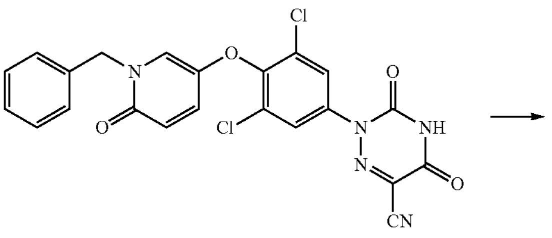

1

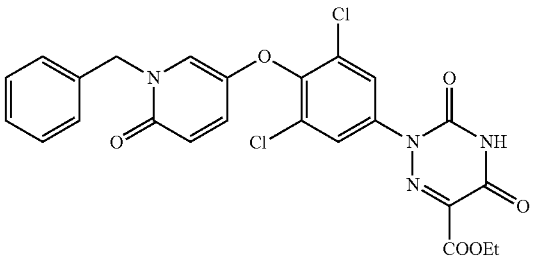

60

A solution of hydrogen chloride in ethyl acetate (3 mL, 4 mol/L) was added to a solution of 2-(4-((1-benzyl-6-oxo-1,6-dihydropyridin-3-yl)oxy)-3,5-dichlorophenyl)-3,5-dioxo-2,3,4,5-tetrahydro-1,2,4-triazine-6-carbonitrile 1 (0.15 g, 0.31 mmol) in ethanol (3 mL), the mixture was reacted at 70° C. for 19 hours. The reaction solution was cooled to room temperature, then concentrated, and recrystallized at 85° C. (petroleum ether/ethyl acetate=1/1, 20 mL) to obtain the title compound 60 (0.13 g, yield 81%, HPLC purity: 92.31%) as a yellow solid.

MS (ESI, pos. ion) m z: 531.0 $[M+H]^+$.

$^1$H NMR (400 MHz, $CDCl_3$) δ (ppm) 12.76 (s, 1H), 7.80 (s, 2H), 7.60 (d, J=3.3 Hz, 1H), 7.44-7.37 (m, 1H), 7.32 (d, J=7.5 Hz, 2H), 7.22 (d, J=7.1 Hz, 2H), 7.17-7.10 (m, 1H), 6.48 (d, J=9.9 Hz, 1H), 5.06 (s, 2H), 4.32 (q, J=7.1 Hz, 2H), 1.27 (t, J=7.1 Hz, 3H).

Example 28 2-hydroxyethyl 2-(4-((1-benzyl-6-oxo-1,6-dihydropyridin-3-yl)oxy)-3,5-dichlorophenyl)-3,5-dioxo-2,3,4,5-tetrahydro-1,2,4-triazine-6-carboxylate (Compound 61)

(61)

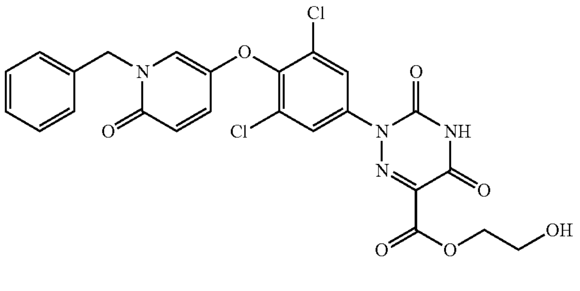

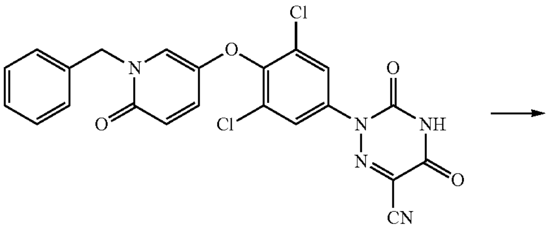

1

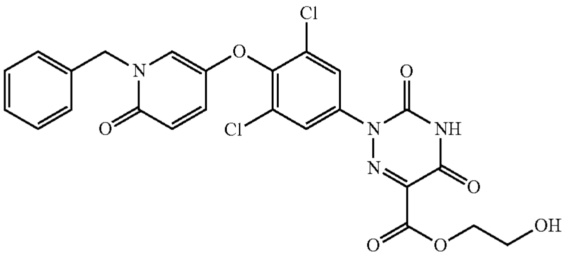

61

A solution of hydrogen chloride in 1,4-dioxane (4 mL, 16 mmol, 4 mol/L) was added to a solution of 2-(4-((1-benzyl-6-oxo-1,6-dihydropyridin-3-yl)oxy)-3,5-dichlorophenyl)-3,5-dioxo-2,3,4,5-tetrahydro-1,2,4-triazine-6-carbonitrile 1 (0.20 g, 0.41 mmol) in ethylene glycol (4 mL), the mixture was reacted at 70° C. for 16 hours. The reaction solution was cooled to room temperature and concentrated. The residue obtained was purified by silica gel column chromatography (100% ethyl acetate). The obtained yellow liquid was recrystallized at 85° C. (ethanol/ethyl acetate/petroleum ether=1/2/4, 17.5 mL) to obtain the title compound 61 (40 mg, yield 18%, HPLC: 95.88%) as a white solid.

MS (ESI, neg. ion) m z: 543.1 $[M-H]^-$;

$^1$H NMR (400 MHz, DMSO-$d_6$) δ (ppm) 12.77 (s, 1H), 7.81 (s, 2H), 7.60 (d, J=3.2 Hz, 1H), 7.46 (dd, J=9.9, 3.3 Hz, 1H), 7.33 (t, J=7.2 Hz, 2H), 7.27 (d, J=7.1 Hz, 1H), 7.22 (d, J=7.2 Hz, 2H), 6.48 (d, J=9.9 Hz, 1H), 5.06 (s, 2H), 4.91 (t, J=5.3 Hz, 1H), 4.34-4.25 (m, 2H), 3.65 (dd, J=10.0, 5.1 Hz, 2H).

Example 29 2-(4-((1-benzyl-6-oxo-1,6-dihydropyridin-3-yl)oxy)-3,5-dichlorophenyl)-1,2,4-triazine-3,5-dione (compound 62)

(62)

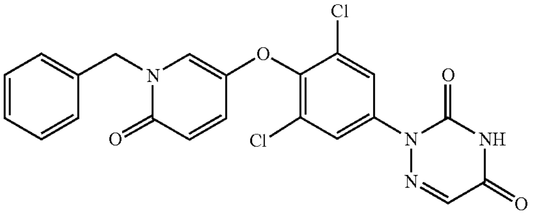

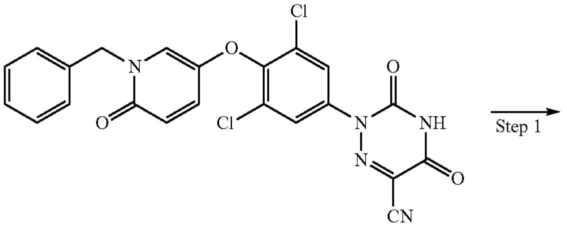

1

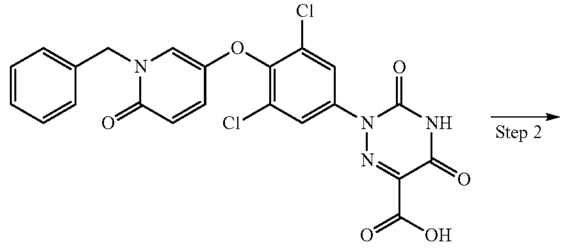

62a

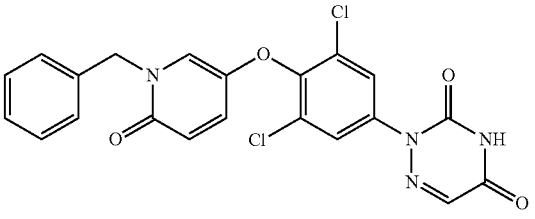

62

Step 1 2-(4-((1-benzyl-6-oxo-1,6-dihydropyridin-3-yl)oxy)-3,5-dichlorophenyl)-3,5-dioxo-1,2,4-triazine-6-carboxylic acid 62a Concentrated hydrochloric acid (1 mL) was added to a solution of 2-(4-((1-benzyl-6-oxo-1,6-dihydropyridin-3-yl)oxy)-3,5-dichlorophenyl)-3,5-dioxo-2,3,4,5-tetrahydro-1,2,4-triazine-6-carbonitrile 1 (0.10 g, 0.21 mmol) in acetic acid (2 mL), the mixture was reacted at 120° C. for 24 hours. The reaction solution was cooled to room temperature, then water (10 mL) was added. The resulting mixture was stirred for 10 minutes, filtered, and the filter cake was collected and dried under vacuum to obtain the title compound 62a (90 mg, yield 87%) as a yellow solid.

Step 2 2-(4-((1-benzyl-6-oxo-1,6-dihydropyridin-3-yl)oxy)-3,5-dichlorophenyl)-1,2,4-triazine-3,5-dione 62

2-(4-((1-Benzyl-6-oxo-1,6-dihydropyridin-3-yl)oxy)-3,5-dichlorophenyl)-3,5-dioxo-1,2,4-triazine-6-carboxylic acid 62a (90 mg, 0.18 mmol) was dissolved in thioglycolic acid (2 mL), and the mixture was reacted at 160° C. for 24 hours. The reaction solution was cooled to room temperature, water (10 mL) was added to quench the reaction, and extracted with ethyl acetate (20 mL×3). The combined organic phase was washed with saturated sodium chloride (20 mL), dried with anhydrous sodium sulfate, and concentrated by suction filtration. The residue obtained was purified by silica gel column chromatography (petroleum ether/ethyl acetate=1/3), and the obtained yellow solid was recrystallized at 85° C. (petroleum ether/ethyl acetate=1/2, 9 mL) to obtain the title compound 62 (82 mg, yield 100%, HPLC: 96.90%) as an off-white solid.

MS (ESI, neg. ion) m z: 457.9 $[M-H]^-$;

$^1H$ NMR (400 MHz, DMSO-$d_6$) δ (ppm) 12.49 (s, 1H), 7.80 (s, 2H), 7.70 (s, 1H), 7.56 (d, J=3.2 Hz, 1H), 7.43 (dd, J=9.9, 3.3 Hz, 1H), 7.32 (t, J=7.2 Hz, 2H), 7.27 (d, J=7.0 Hz, 1H), 7.22 (t, J=7.7 Hz, 2H), 6.48 (d, J=9.9 Hz, 1H), 5.05 (s, 2H).

Example 30 2-(4-((1-benzyl-6-oxo-1,6-dihydropyridin-3-yl)oxy)-3,5-dichlorophenyl)-3,5-dioxo-2,3,4,5-tetrahydro-1,2,4-triazine-6-carboxamide (compound 63)

(63)

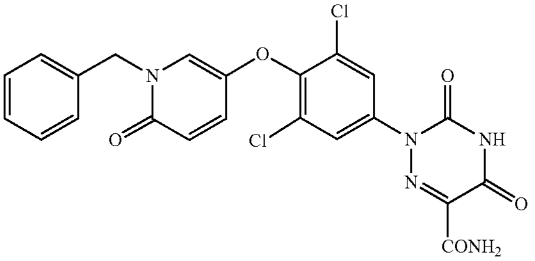

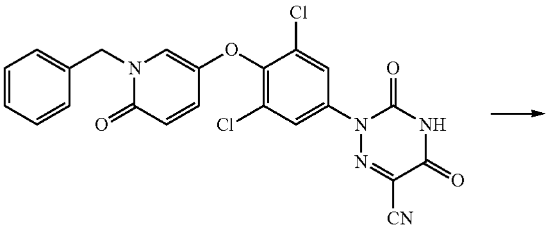

1

-continued

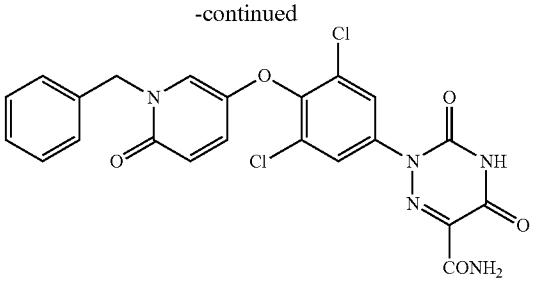

63

2-(4-((1-Benzyl-6-oxo-1,6-dihydropyridin-3-yl)oxy)-3,5-dichlorophenyl)-3,5-dioxo-2,3,4,5-tetrahydro-1,2,4-triazine-6-carbonitrile 1 (0.30 g, 0.62 mmol) was dissolved in a solution of hydrogen chloride in 1,4-dioxane (10 mL, 4.0 mol/L), the mixture was reacted at 60° C. for 7 hours. To the reaction solution was added ethyl acetate (10 mL), the mixture was slurried for 2 hours, then filtered, and the solid was collected and dried to obtain the title compound 63 (0.29 g, yield 93%, HPLC purity: 89.87%) as a white solid.

MS (ESI, pos. ion) m z: 500.0 $[M+H]^+$;

$^1$H NMR (400 MHz, DMSO-$d_6$) δ (ppm) 12.78 (s, 1H), 8.08 (s, 1H), 7.94 (s, 1H), 7.86 (s, 2H), 7.59 (d, J=3.2 Hz, 1H), 7.45 (dd, J=9.9, 3.2 Hz, 1H), 7.33 (t, J=7.2 Hz, 2H), 7.27 (d, J=7.0 Hz, 1H), 7.23 (t, J=6.3 Hz, 2H), 6.48 (d, J=9.9 Hz, 1H), 5.06 (s, 2H).

Example 31 2-(3,5-dichloro-4-((1-(4-methoxybenzyl)-6-oxo-1,6-dihydropyridin-3-yl)oxy) phenyl)-3,5-dioxo-2,3,4,5-tetrahydro-1,2,4-triazine-6-carbonitrile (Compound 64)

(64)

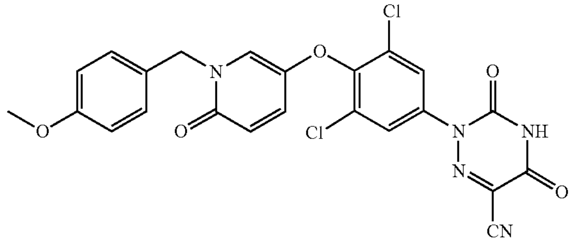

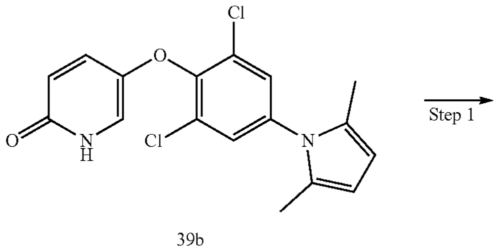

39b

-continued

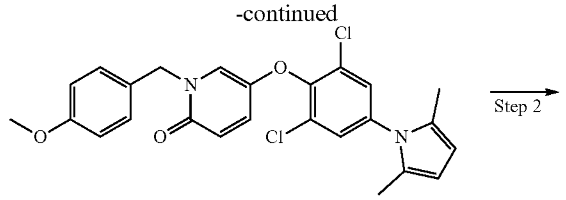

64a

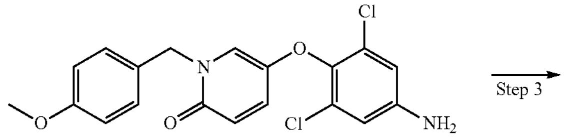

64b

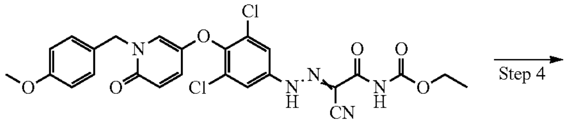

64c

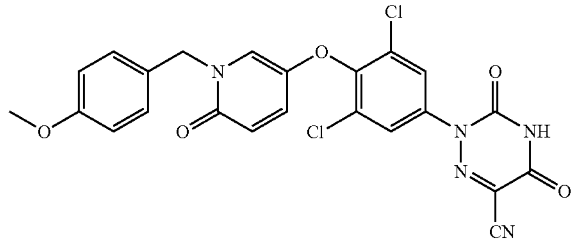

64

Step 1 5-(2,6-dichloro-4-(2,5-dimethyl-1H-pyrrol-1-yl)phenoxy)-1-(4-methoxybenzyl)pyridin-2(1H)-one 64a 5-(2,6-Dichloro-4-(2,5-dimethyl-1H-pyrrol-1-yl)phenoxy)pyridin-2(1H)-one 39b (2.00 g, 5.73 mmol), potassium carbonate (1.60 g, 11.50 mmol) and 4-methoxybenzyl chloride (0.92 g, 5.73 mmol) were dissolved in N,N-dimethylacetamide (4 mL), and the mixture was reacted at room temperature for 18 hours. To the reaction solution was added water (10 mL), the mixture was stirred for 10 minutes, filtered, and the filter cake was collected and dried under vacuum to obtain the title compound 64a (2.00 g, yield 74%) as a gray solid.

MS (ESI, pos. ion) m z: 469.1 $[M+H]^+$.

Step 2 5-(4-amino-2,6-dichlorophenoxy)-1-(4-methoxybenzyl)pyridin-2(1H)-one 64b 5-(2,6-Dichloro-4-(2,5-dimethyl-1H-pyrrol-1-yl)phenoxy)-1-(4-methoxybenzyl)pyridin-2(1H)-one 64a (2.00 g, 4.26 mmol), hydroxylamine hydrochloride (2.88 g, 42.6 mmol) and triethylamine (1.10 mL) were dissolved in ethanol (20 mL), and the mixture was reacted at 80° C. for 16 hours. The reaction solution was cooled to room temperature, then water (30 mL) was added. The resulting mixture was stirred for 15 minutes, filtered, and the filter cake was collected and dried. The solid was purified by silica gel column chromatography [petroleum ether/ethyl acetate=1/1] to obtain the title compound 64b (0.19 g, yield 11%) as a black solid.

MS (ESI, pos. ion) m z: 391.0 $[M+H]^+$.

Step 3 Ethyl (2-cyano-2-(2-(3,5-dichloro-4-((1-(4-methoxybenzyl)-6-oxo-1,6-dihydropyridin-3-yl)oxy)phenyl)hydrazono)acetyl)carbamate 64c 5-(4-Amino-2,6-dichlorophenoxy)-1-(4-methoxybenzyl)pyridin-2(1H)-one 64b (0.19 g, 0.48 mmol) and N-cyanoacetylurethane (0.09 g, 0.53 mmol) were dissolved in acetic acid (3 mL), and an aqueous solution (2 mL) of sodium nitrite (0.04 g, 0.53 mmol) was added dropwise at 3° C., then the mixture was reacted for 30 minutes. To the reaction solution was added water (20 mL). The resulting mixture was stirred for 5 minutes, filtered, and the filter cake was collected and dried under vacuum to obtain the title compound 64c (0.14 g, yield 52%) as a orange solid.

MS (ESI, neg. ion) m z: 560.1 $[M-H]^-$.

Step 4 2-(3,5-dichloro-4-((1-(4-methoxybenzyl)-6-oxo-1,6-dihydropyridin-3-yl)oxy)phenyl)-3,5-dioxo-2,3,4,5-tetrahydro-1,2,4-triazine-6-carbonitrile 64

Ethyl (2-cyano-2-(2-(3,5-dichloro-4-((1-(4-methoxybenzyl)-6-oxo-1,6-dihydropyridin-3-yl)oxy)phenyl)hydrazono)acetyl)carbamate 64c (0.14 g, 0.25 mmol) was dissolved in N,N-dimethylformamide (3 mL), then sodium acetate (0.03 g, 0.38 mmol) was added, the mixture was reacted at 120° C. for 4 hours. The reaction solution was cooled to room temperature, filtered, and the filtrate was purified by preparative chromatography column [45% CAN/55% $H_2O$ (0.1% formic acid), Phenomenex ACE specifications: C18 10 μm×50 mm×250 mm, flow rate: 100 mL/min] to obtain the title compound 64 (15 mg, yield 10%, HPLC purity: 90.73%) as a yellow solid.

MS (ESI, neg. ion) m z: 510.0 $[M-H]^-$.

$^1H$ NMR (400 MHz, $CDCl_3$) δ (ppm) 7.61 (s, 2H), 7.21 (d, J=4.6 Hz, 4H), 6.86 (d, J=8.5 Hz, 3H), 5.04 (s, 2H), 3.79 (s, 3H).

Example 32 2-(3,5-dichloro-4-((1-(2-hydroxyethyl)-6-oxo-1,6-dihydropyridin-3-yl)oxy)phenyl)-3,5-dioxo-2,3,4,5-tetrahydro-1,2,4-triazine-6-carbonitrile (Compound 65)

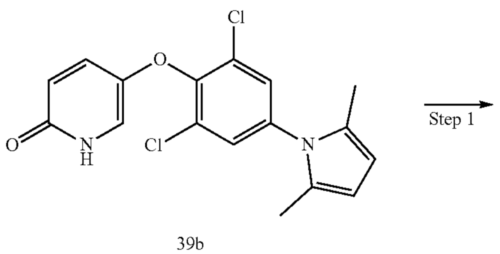

39b

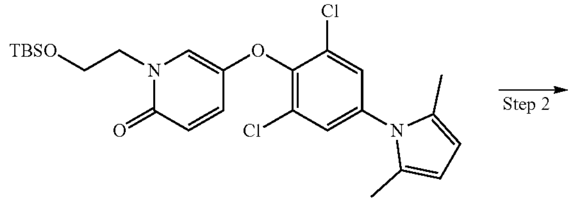

65a

-continued

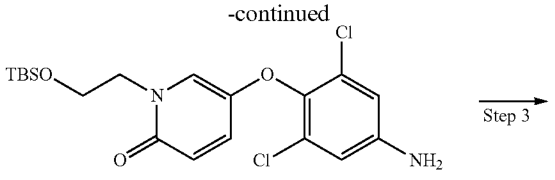

65b

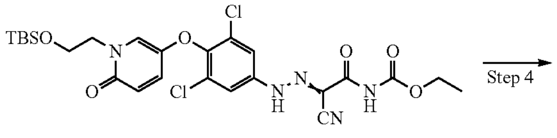

65c

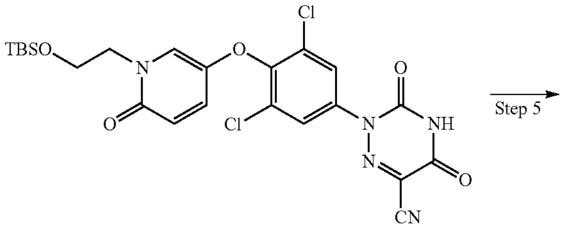

65d

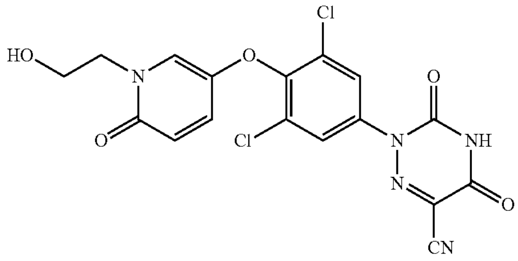

65

(65)

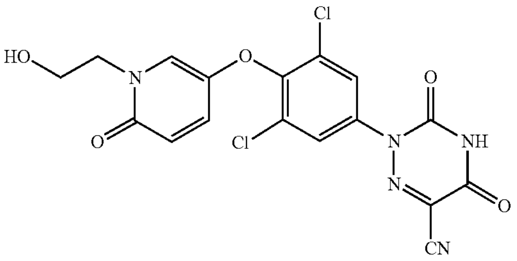

Step 1 1-(2-((tert-butyldimethylsilyl)oxy)ethyl)-5-(2,6-dichloro-4-(2,5-dimethyl-1H-pyrrol-1-yl)phenoxy)pyridin-2(1H)-one 65a 5-(2,6-Dichloro-4-(2,5-dimethyl-1H-pyrrol-1-yl)phenoxy)pyridin-2(1H)-one 39b (1.50 g, 4.30 mmol) was dissolved in N,N-dimethylformamide (15 mL), then potassium carbonate (1.2 g, 8.6 mmol) and 2-bromoethoxy-tert-butyl-dimethyl-silane (1.11 g, 4.64 mmol) were added, the mixture was reacted at 40° C. for 23 hours. The reaction solution was cooled to room temperature, then water (20 mL) was added, and extracted with ethyl acetate (30 mL×2). The combined organic phase was washed with saturated sodium chloride solution (20 mL), dried over anhydrous sodium sulfate, concentrated by suction filtration, and the residue was purified by silica gel column chromatography [petroleum ether/ethyl acetate=3/1] to obtain the title compound 65a (1.1 g, yield 50%) as a yellow oil.

Step 2 5-(4-amino-2,6-dichlorophenoxy)-1-(2-((tert-butyldimethylsilyl)oxy)ethyl)pyridin-2(1H)-one 65b 1-(2-((Tert-butyldimethylsilyl)oxy)ethyl)-5-(2,6-dichloro-4-(2,5-dimethyl-1H-pyrrol-1-yl)phenoxy)pyridin-2(1H)-one 65a (0.80 g, 1.6 mmol) and hydroxylamine hydrochloride (2.7 g, 39 mmol) were dissolved in ethanol (15 mL), then triethylamine (1.0 mL, 7.2 mmol) was added, the mixture was reacted at 85° C. for 16 hours. The reaction solution was cooled to room temperature, then ethyl acetate (20 mL) was added. The resulting mixture was stirred for 10 minutes, filtered, and the filtrate was concentrated. The residue was purified by silica gel column chromatography (petroleum ether/ethyl acetate=1/1) to obtain the title compound 65b (0.62 g, yield 92%) as a white solid.

Step 3 Ethyl (2-(2-(4-((1-(2-((tert-butyldimethylsilyl)oxy)ethyl)-6-oxo-1,6-dihydropyridin-3-yl)oxy)-3,5-dichlorophenyl)hydrazono)-2-cyanoacetyl)carbamate 65c 5-(4-Amino-2,6-dichlorophenoxy)-1-(2-((tert-butyldimethylsilyl)oxy)ethyl)pyridin-2(1H)-one 65b (0.51 g, 1.2 mmol) was dissolved in acetic acid (10 mL), then a solution of sodium nitrite (0.17 g, 2.4 mmol) in water (5 mL) was added at 0° C. After 20 minutes of reaction, to the mixture was added N-cyanoacetylurethane (0.23 g, 1.4 mmol) and reacted at 0° C. At 0° C., to the reaction solution was added water (10 mL), the mixture was stirred for 10 minutes, filtered, and the filter cake was washed with water (2 mL), collected and dried under vacuum to obtain the title compound 65c (0.45 g, yield 64%) as a red solid.

Step 4 2-(4-((1-(2-((tert-butyldimethylsilyl)oxy)ethyl)-6-oxo-1,6-dihydropyridin-3-yl)oxy)-3,5-dichlorophenyl)-3,5-dioxo-2,3,4,5-tetrahydro-1,2,4-triazine-6-carbonitrile 65d Ethyl (2-(2-(4-((1-(2-((tert-butyldimethylsilyl)oxy)ethyl)-6-oxo-1,6-dihydropyridin-3-yl)oxy)-3,5-dichlorophenyl)hydrazono)-2-cyanoacetyl)carbamate 65c (0.45 g, 0.75 mmol) was dissolved in N,N-dimethylformamide (8 mL), then sodium acetate (93 mg, 1.13 mmol) was added, and the mixture was reacted at 120° C. for 5.5 hours. The reaction solution was cooled to room temperature, then water (20 mL) was added, and extracted with ethyl acetate (20 mL×3). The combined organic phase was washed with saturated sodium chloride solution (10 mL×3), then dried over anhydrous sodium sulfate, filtered and concentrated. The residue was purified by silica gel column chromatography [petroleum ether/ethyl acetate=1/2] to obtain the title compound 65d (0.32 g, yield 77%) as a red oil.

Step 5 2-(3,5-dichloro-4-((1-(2-hydroxyethyl)-6-oxo-1,6-dihydropyridin-3-yl)oxy)phenyl)-3,5-dioxo-2,3,4,5-tetrahydro-1,2,4-triazine-6-carbonitrile 65

2-(4-((1-(2-((Tert-butyldimethylsilyl)oxy)ethyl)-6-oxo-1,6-dihydropyridin-3-yl)oxy)-3,5-dichlorophenyl)-3,5-dioxo-2,3,4,5-tetrahydro-1,2,4-triazine-6-carbonitrile 65d (0.31 g, 0.56 mmol) was dissolved in 1,4-dioxane (5 mL), then a solution of hydrogen chloride in 1,4-dioxane (0.60 mL, 2.4 mmol, 4 mol/L) was added at 0° C., and the mixture was reacted at room temperature for 45 minutes. The reaction solution was concentrated, the residue was dissolved in ethanol (20 mL), decolorized with activated carbon (0.20 g) at 85° C., then filtered, and the filtrate was concentrated. The resulting residue was slurried with ethanol/petroleum ether (1/2, 15 mL) and filtered, the filter cake was collected to obtain the title compound 65 (76 mg, yield 31%, HPLC purity: 87.26%) as a yellow solid.

MS (ESI, neg. ion) m z: 436.0 $[M-H]^-$.

$^1H$ NMR (400 MHz, DMSO-$d_6$) δ (ppm) 13.28 (s, 1H), 7.78 (s, 2H), 7.41 (dd, J=9.8, 3.2 Hz, 1H), 7.36 (d, J=3.0 Hz, 1H), 6.43 (d, J=9.8 Hz, 1H), 4.83 (s, 1H), 3.90 (t, J=5.1 Hz, 2H), 3.62-3.55 (m, 2H).

Example 33 2-(4-((1-benzyl-6-oxo-1,6-dihydropyridin-3-yl)oxy)-3,5-dichlorophenyl)-6-(hydroxymethyl)-1,2,4-triazine-3,5(2H,4H)-dione (compound 66)

(66)

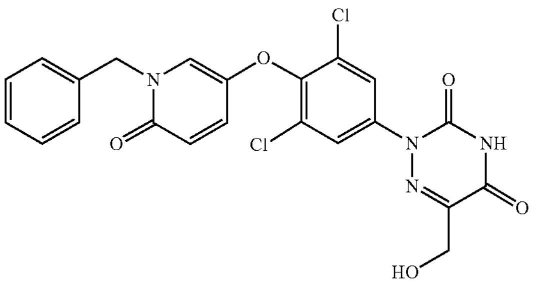

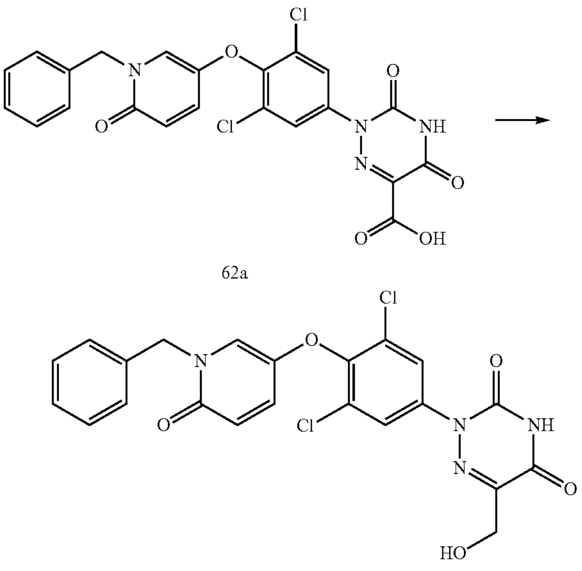

62a

66

At 0° C., isopropyl chloroformate (0.12 mL, 1.0 mmol) was added dropwise to a solution of 2-(4-((1-benzyl-6-oxo-1,6-dihydropyridin-3-yl)oxy)-3,5-dichlorophenyl)-3,5-dioxo-2,3,4,5-tetrahydro-1,2,4-triazine-6-carboxylic acid 62a (0.20 g, 0.40 mmol) and triethylamine (0.2 mL, 1.2 mmol) in tetrahydrofuran (6 mL), after reacting at 0° C. for 2 hours, methanol (4 mL) and calcium chloride (0.26 g, 2.4 mmol) were added. The mixture was stirred for 3 minutes, then sodium borohydride (90 mg, 0.24 mmol) was added and reacted at room temperature for 12 hours. The reaction solution was concentrated, and the residue obtained was purified by preparative chromatography column [38% ACN/ 62% $H_2O$ (0.1% TFA), Kromasil specifications: C18 10 μm×50 mm×250 mm, flow rate: 100 mL/min] to obtain the title compound 66 (21 mg, yield 11%, HPLC purity: 97.67%) as a light yellow solid.

MS (ESI, pos. ion) m z: 488.0 $[M+H]^+$;

$^1H$ NMR (400 MHz, DMSO-$d_6$) δ (ppm) 7.88 (s, 2H), 7.56 (d, J=3.0 Hz, 1H), 7.43 (dd, J=9.9, 3.1 Hz, 1H), 7.33 (t, J=7.1 Hz, 2H), 7.29-7.18 (m, 3H), 6.48 (d, J=9.9 Hz, 1H), 5.28 (s, 1H), 5.06 (s, 2H), 4.39 (s, 2H).

Example 34 2-(4-((1-benzyl-6-oxo-1,6-dihydropyridin-3-yl)oxy)-3,5-dimethylphenyl)-3,5-dioxo-2,3,4,5-tetrahydro-1,2,4-triazine-6-carbonitrile (Compound 67)

(67)

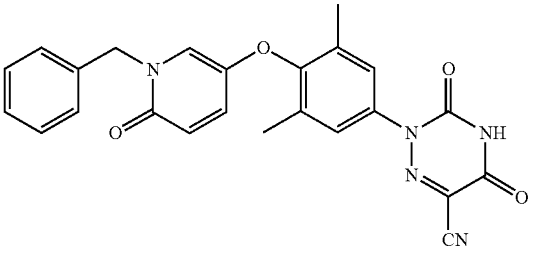

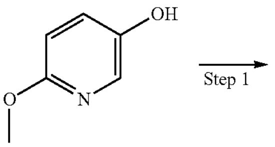

4a

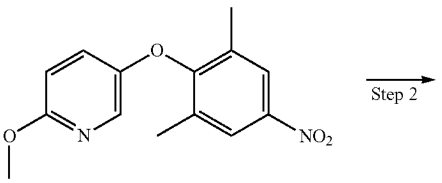

67a

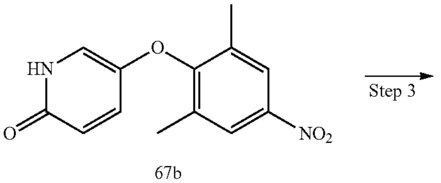

67b

-continued

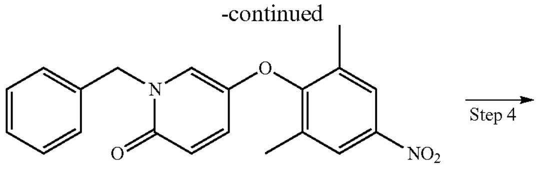

67c

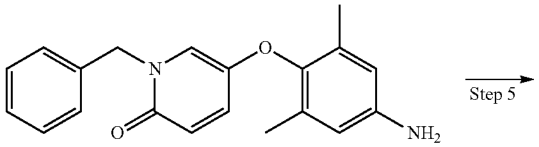

67d

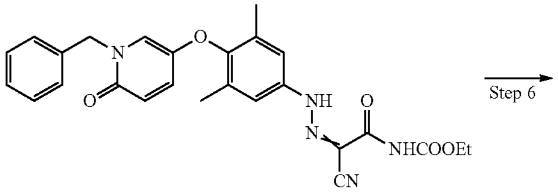

67e

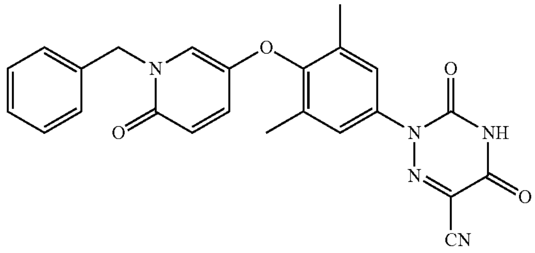

67

Step 1

5-(2,6-dimethyl-4-nitrophenoxy)-2-methoxypyridine 67a

6-Methoxypyridin-3-ol 4a (3.0 g, 24 mmol), 2-fluoro-1,3-dimethyl-5-nitro-benzene (4.50 g, 26.6 mmol) and potassium carbonate (2.60 g, 26.2 mmol) were dissolved in N,N-dimethylformamide (25 mL), and the mixture was reacted at 80° C. for 24 hours. The reaction solution was cooled to room temperature, and water (50 mL) was added. The resulting mixture was stirred for 10 minutes, filtered, and the filter cake was washed with water (10 mL×2), collected and dried to obtain the title compound 67a (6.10 g, yield 93%) as a light yellow solid.

Step 2

5-(2,6-dimethyl-4-nitrophenoxy)pyridin-2(1H)-one 67b 5-(2,6-Dimethyl-4-nitrophenoxy)-2-methoxypyridine 67a (2.00 g, 7.29 mmol), p-toluenesulfonic acid (6.30 g, 36.6 mmol) and lithium chloride (1.50 g, 35.4 mmol) were dissolved in N,N-dimethylformamide (8 mL), and the mixture was reacted at 120° C. for 4 hours. The reaction solution was poured into ice water (16 mL) while it was hot, then stirred for 10 minutes, filtered, the filter cake was washed with water (10 mL×2) and collected and dried to obtain the title compound 67b (1.70 g, yield 90%)) as an off-white solid.

Step 3 1-benzyl-5-(2,6-dimethyl-4-nitrophenoxy) pyridin-2(1H)-one 67c 5-(2,6-Dimethyl-4-nitrophenoxy)pyridin-2(1H)-one 67b (0.80 g, 3.1 mmol) and potassium carbonate (0.61 g, 6.2 mmol) were dissolved in acetonitrile (8 mL), then benzyl bromide (0.60 mL, 5.1 mmol) was added dropwise, and the mixture was reacted at 60° C. for 6 hours. The reaction solution was cooled to room temperature, then filtered, and the filtrate was concentrated. The resulting residue was recrystallized at 85° C. (petroleum ether/ethyl acetate=4/1, 12 mL), then filtered, and the filter cake was collected and dried to obtain the title compound 67c (0.70 g, yield 65%) as a yellow solid.

Step 4 5-(4-amino-2,6-dimethylphenoxy)-1-benzylpyridin-2(1H)-one 67d

1-Benzyl-5-(2,6-dimethyl-4-nitrophenoxy)pyridin-2(1H)-one 67c (0.70 g, 2.0 mmol) was dissolved in acetic acid (5 mL), then iron (0.33 g, 5.9 mmol) was added and the mixture was reacted at 60° C. for 2 hours. The reaction solution was quenched with water (15 mL) and extracted with ethyl acetate (20 mL×2). The combined organic phase was washed with saturated sodium chloride solution (10 mL×2), dried over anhydrous sodium sulfate. The residue was purified by silica gel column chromatography [petroleum ether/ethyl acetate=1/2] to obtain the title compound 67d (0.32 g, yield 50%) as a yellow solid.

Step 5 Ethyl (2-(2-(4-((1-benzyl-6-oxo-1,6-dihydropyridin-3-yl)oxy)-3,5-dimethylphenyl)hydrazono)-2-cyanoacetyl)carbamate 67e 5-(4-Amino-2,6-dimethylphenoxy)-1-benzylpyridin-2(1H)-one 67d (0.30 g, 0.94 mmol) and N-cyanoacetourethane (0.18 g, 1.2 mmol) were dissolved in acetic acid (6 mL), then a solution of sodium nitrite (0.13 g, 1.9 mmol) in water (3 mL) was added at 0° C., and the mixture was reacted for 4 hours. To the reaction solution was added water (30 mL), the mixture was stirred for 10 minutes, then filtered, and the filter cake was collected and dried to obtain the title compound 67d (0.20 g, yield 44%) as a red-brown solid.

Step 6 2-(4-((1-benzyl-6-oxo-1,6-dihydropyridin-3-yl)oxy)-3,5-dimethylphenyl)-3,5-dioxo-2,3,4,5-tetrahydro-1,2,4-triazine-6-carbonitrile 67

Ethyl (2-(2-(4-((1-benzyl-6-oxo-1,6-dihydropyridin-3-yl)oxy)-3,5-dimethylphenyl)hydrazono)-2-cyanoacetyl)carbamate 67e (1.5 g, 3.1 mmol) was dissolved in N,N-dimethylformamide (15 mL), then sodium acetate (0.28 g, 3.4 mmol) was added, and the mixture was reacted at 120° C. for 6 hours. The reaction solution was cooled to room temperature, then water (20 mL) was added, and extracted with ethyl acetate (10 mL×3). The combined organic phase was washed with saturated sodium chloride solution (20 mL×3), dried with anhydrous sodium sulfate, and concentrated by suction filtration. The residue obtained was recrystallized with ethanol/ethyl acetate/petroleum ether (1/5/10, 16 mL) at 85° C., then filtered, and the filter cake was collected and dried to obtain the title compound 67 (0.50 g, yield 40%, HPLC purity: 99.16%) as a light yellow solid.

MS (ESI, neg. ion) m z: 440.4 [M−H]$^-$;

$^1$H NMR (400 MHz, DMSO-$d_6$) δ (ppm) 13.04 (s, 1H), 7.41-7.14 (m, 9H), 6.48 (d, J=9.8 Hz, 1H), 5.05 (s, 2H), 2.15 (s, 6H).

Example 35 2-(4-((1-benzyl-6-oxo-1,6-dihydropyridin-3-yl)oxy)-3,5-dibromophenyl)-3,5-dioxo-2,3,4,5-tetrahydro-1,2,4-triazine-6-carbonitrile (Compound 68)

(68)

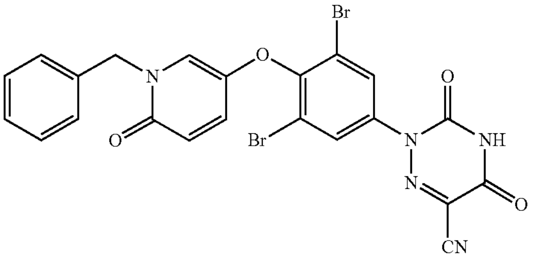

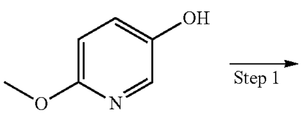

4a

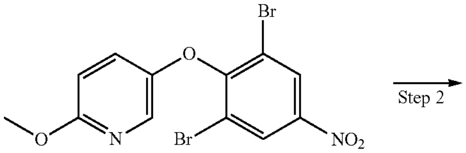

68a

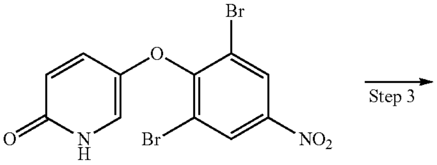

68b

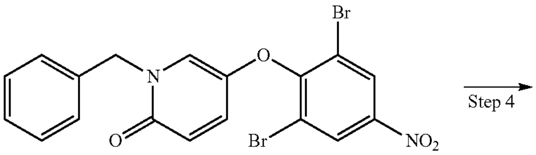

68c

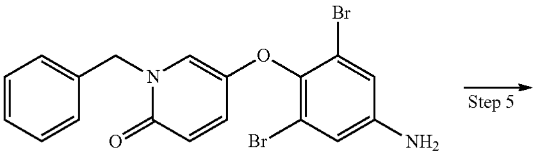

68d

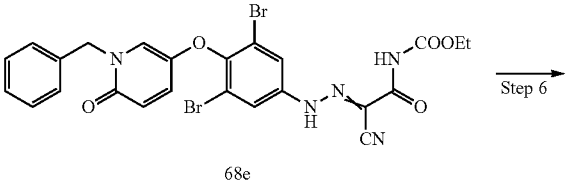

68e

-continued

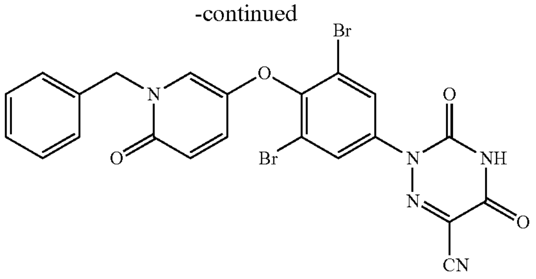

68

Step 1 5-(2,6-dibromo-4-nitrophenoxy)-2-methoxypyridine 68a

6-Methoxypyridin-3-ol 4a (0.50 g, 4.0 mmol), 1,3-dibromo-2-fluoro-5-nitrobenzene (1.20 g, 4.8 mmol) were dissolved in N,N-dimethylformamide (16 mL), then potassium carbonate (1.66 g, 12.0 mmol) was added, and the mixture was reacted at 60° C. for 13 hours. The reaction solution was cooled to room temperature, then water (15 mL) was added. The resulting mixture was stirred for 10 minutes, filtered, and the filter cake was collected and dried under vacuum to obtain the title compound 68a (1.60 g, yield 99%) as a light red solid.

Step 2 5-(2,6-dibromo-4-nitrophenoxy)pyridin-2(1H)-one 68b 5-(2,6-Dibromo-4-nitrophenoxy)-2-methoxypyridine 68a (1.60 g, 3.96 mmol), p-toluenesulfonic acid monohydrate (3.80 g, 20.0 mmol) and lithium chloride (0.85 g, 20 mmol) were dissolved in N,N-dimethylformamide (6 mL), and the mixture was reacted at 120° C. for 2 hours. The reaction solution was cooled to room temperature, then water (12 mL) was added. The resulting mixture was stirred for 10 minutes, filtered, and the filter cake was collected and dried under vacuum to obtain the title compound 68b (1.54 g, yield 99%) as an off-white solid.

Step 3 1-benzyl-5-(2,6-dibromo-4-nitrophenoxy) pyridin-2(1H)-one 68c 5-(2,6-Dibromo-4-nitrophenoxy)pyridin-2(1H)-one 68b (1.54 g, 3.95 mmol) was dissolved in acetonitrile (15 mL), then cesium carbonate (2.57 g, 7.90 mmol) and benzyl bromide (0.7 mL, 5.92 mmol) were added, the mixture was reacted 60° C. for 5 hours. The reaction solution was cooled to room temperature, then concentrated, to the obtained residue was added water (20 mL), and the mixture was extracted with ethyl acetate (40 mL×2). The combined organic phase was dried with anhydrous sodium sulfate, and concentrated by suction filtration. The residue was purified by silica gel column chromatography (100% ethyl acetate) to obtain the title compound 68c (1.45 g, yield 76%) as a white solid.

Step 4 5-(4-amino-2,6-dibromophenoxy)-1-benzylpyridin-2(1H)-one 68d

1-Benzyl-5-(2,6-dibromo-4-nitrophenoxy)pyridin-2(1H)-one 68c (1.45 g, 3.02 mmol) was dissolved in acetic acid (15 mL), then iron powder (0.50 g, 9.06 mmol) was added, the mixture was reacted at 60° C. for 6 hours. The reaction solution was cooled to room temperature, then water (15 mL) was added. The resulting mixture was stirred for 10 minutes, filtered, the filter cake was washed with water (15 mL), collected and dried under vacuum to obtain the title compound 68d (1.35 g, yield 99%) as a yellow solid.

Step 5 Ethyl (2-(2-(4-((1-benzyl-6-oxo-1,6-dihydropyridin-3-yl)oxy)-3,5-dibromophenyl)hydrazono)-2-cyanoacetyl)carbamate 68e 5-(4-Amino-2,6-dibromophenoxy)-1-benzylpyridin-2(1H)-one 68d (1.35 g, 3.0 mmol) was dissolved in acetic acid (12 mL), then N-cyanoacetylurethane (0.58 g, 3.6 mmol) was added at 0° C. The resulting mixture was stirred for 5 minutes, then a solution of sodium nitrite (0.41 g, 6.0 mmol) in water (10 mL) was added, and then the mixture was reacted at 0° C. for 1 hour. To the reaction solution was added water (5 mL) and the mixture was stirred for 10 minutes, then filtered, and the filter cake was collected and dried under vacuum to obtain the title compound 68e (1.80 g, yield 95%) as a red-brown solid.

Step 6 2-(4-((1-benzyl-6-oxo-1,6-dihydropyridin-3-yl)oxy)-3,5-dibromophenyl)-3,5-dioxo-2,3,4,5-tetrahydro-1,2,4-triazine-6-carbonitrile 68

Ethyl (2-(2-(4-((1-benzyl-6-oxo-1,6-dihydropyridin-3-yl)oxy)-3,5-dibromophenyl)hydrazono)-2-cyanoacetyl)carbamate 68e (1.80 g, 2.84 mmol) was dissolved in N,N-dimethylformamide (15 mL), then sodium acetate (0.29 g, 3.5 mmol) was added, and the mixture was reacted at 120° C. for 18 hours. The reaction solution was cooled to room temperature, then water (15 mL) was added. The resulting mixture was stirred for 10 minutes, then filtered, and the filter cake was collected and dried under vacuum. The crude product was purified by silica gel column chromatography [100% ethyl acetate] to obtain the title compound 68 (0.31 g, yield 19%, HPLC purity: 95.24%) as a white solid.

MS (ESI, pos. ion) m z: 570.0 $[M+H]^+$;

$^1H$ NMR (400 MHz, DMSO-$d_6$) δ (ppm) 13.27 (s, 1H), 7.93 (s, 2H), 7.53-7.41 (m, 2H), 7.37-7.19 (m, 5H), 6.50 (d, J=10.0 Hz, 1H), 5.06 (s, 2H).

Example 36 2-(3,5-dichloro-4-((1-(4-fluorobenzyl)-6-oxo-1,6-dihydropyridin-3-yl)oxy)phenyl)-1,2,4-triazine-3,5(2H,4H)-dione (Compound 69)

(69)

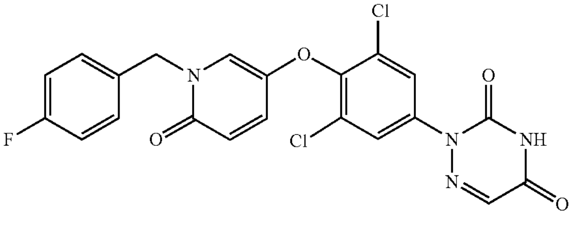

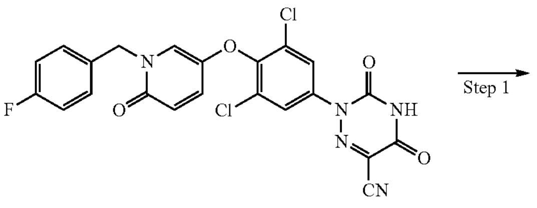

41

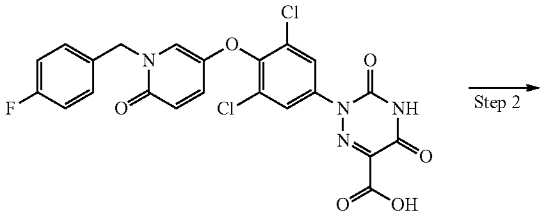

69a

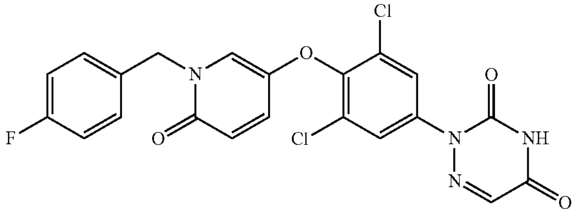

69

Step 1 2-(3,5-dichloro-4-((1-(4-fluorobenzyl)-6-oxo-1,6-dihydropyridin-3-yl)oxy)phenyl)-3,5-dioxo-2,3,4,5-tetrahydro-1,2,4-triazine-6-carboxylic acid 69a 2-(3,5-Dichloro-4-((1-(4-fluorobenzyl)-6-oxo-1,6-dihydropyridin-3-yl)oxy)phenyl)-3,5-dioxo-2,3,4,5-tetrahydro-1,2,4-triazine-6-carbonitrile 41 (0.50 g, 1.0 mmol) was dissolved in acetic acid (6 mL), then concentrated hydrochloric acid (3 mL) was added, and the mixture was reacted at 120° C. for 11 hours. The reaction solution was cooled to room temperature, then saturated brine (30 mL) was added. The resulting mixture was stirred for 10 minutes, filtered, and the filter cake was collected and dried under vacuum to obtain the title compound 69a (0.51 g, yield 99%) as a yellow solid.

Step 2 2-(3,5-dichloro-4-((1-(4-fluorobenzyl)-6-oxo-1,6-dihydropyridin-3-yl)oxy)phenyl)-1,2,4-triazine-3,5(2H,4H)-dione 69

2-(3,5-Dichloro-4-((1-(4-fluorobenzyl)-6-oxo-1,6-dihydropyridin-3-yl)oxy)phenyl)-3,5-dioxo-2,3,4,5-tetrahydro-1,2,4-triazine-6-carboxylic acid 69a (0.51 g, 0.99 mmol) was dissolved in thioglycolic acid (3 mL), and the mixture was reacted at 160° C. for 24 hours. The reaction solution was cooled to room temperature, then quenched with water (20 mL) and extracted with ethyl acetate (20 mL×3). The combined organic phase was washed with saturated sodium chloride solution (20 mL), dried over anhydrous sodium sulfate, concentrated by suction filtration, and the residue was purified by silica gel column chromatography [petroleum ether/ethyl acetate=1/2] to obtain the title compound 69 (0.15 g, yield 32%, HPLC purity: 99.10%) as a white solid.

MS (ESI, neg. ion) m z: 473.0 $[M-H]^-$;

$^1H$ NMR (400 MHz, DMSO-$d_6$) δ (ppm) 12.49 (s, 1H), 7.81 (s, 2H), 7.61 (d, J=16.6 Hz, 2H), 7.42 (s, 1H), 7.23 (d, J=56.0 Hz, 4H), 6.59-6.34 (m, 1H), 5.03 (s, 2H).

Example 37 2-(4-((1-benzyl-5-methyl-6-oxo-1,6-dihydropyridin-3-yl)oxy)-3,5-dichlorophenyl)-3,5-dioxo-2,3,4,5-tetrahydro-1,2,4-triazine-6-carbonitrile (Compound 70)

(70)

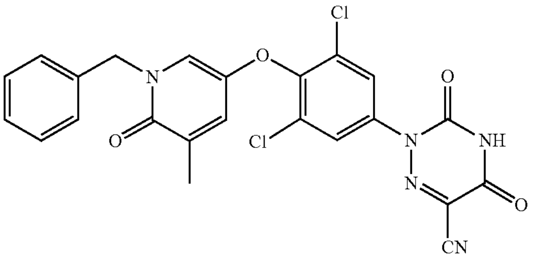

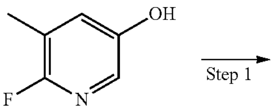

70a

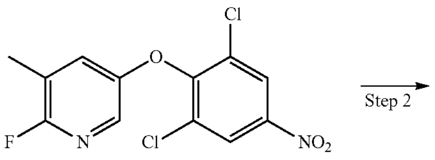

70b

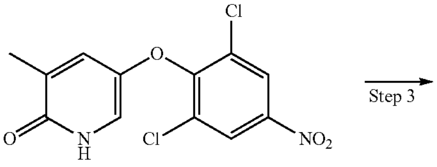

70c

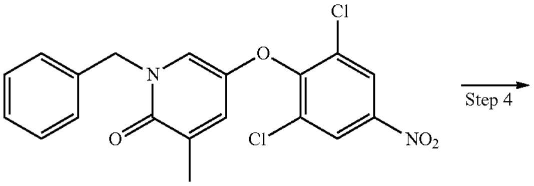

70d

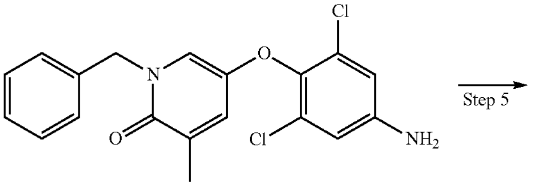

70e

-continued

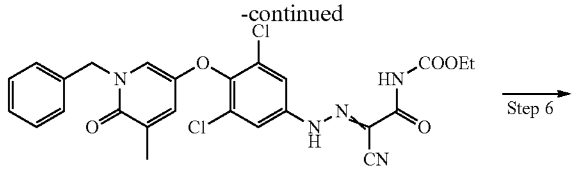

70f

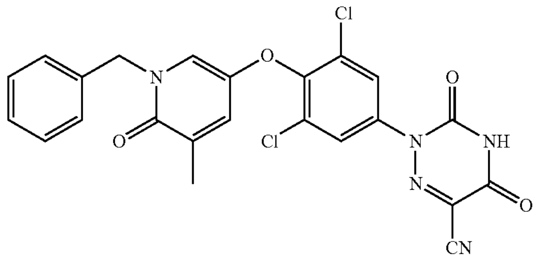

70

Step 1 5-(2,6-dichloro-4-nitrophenoxy)-2-fluoro-3-methylpyridine 70b

6-Fluoro-5-methylpyridin-3-ol 70a (0.70 g, 5.5 mmol) and 1,2,3-trichloro-5-nitrobenzene (1.50 g, 6.62 mmol) were dissolved in N,N-dimethylformamide (10 mL), then potassium carbonate (1.83 g, 13.2 mmol) was added, and the mixture was reacted at 60° C. for 5 hours. The reaction solution was cooled to room temperature, then water (10 mL) was added. The resulting mixture was stirred for 10 minutes, filtered, and the filter cake was collected and dried in vacuo to obtain the title compound 70b (1.74 g, yield 95%) as a gray solid.

Step 2 5-(2,6-dichloro-4-nitrophenoxv)-3-methylpyridin-2(1H)-one 70c 5-(2,6-Dichloro-4-nitrophenoxy)-2-fluoro-3-methylpyridine 70b (1.74 g, 5.23 mmol) was dissolved in acetic acid (16 mL) and water (8 mL), and the mixture was reacted at 120° C. for 24 hours. The reaction solution was cooled to room temperature, then water (20 mL) was added, saturated sodium carbonate solution was added to adjust pH=7, and then the mixture was extracted with ethyl acetate (50 mL×2). The combined organic phase was washed with saturated sodium chloride (20 mL), dried with anhydrous sodium sulfate, and concentrated by suction filtration. The residue obtained was purified by silica gel column chromatography (petroleum ether/ethyl acetate (v/v)=1/1) to obtain the title compound 70c (0.75 g, yield 45%) as a white solid.

Step 3 1-benzyl-5-(2,6-dichloro-4-nitrophenoxy)-3-methylpyridin-2(1H)-one 70d 5-(2,6-Dichloro-4-nitrophenoxy)-3-methylpyridin-2(1H)-one 70c (0.75 g, 2.4 mmol) was dissolved in acetonitrile (10 mL), then cesium carbonate (1.56 g, 4.8 mmol) and benzyl bromide (0.43 mL, 3.6 mmol) were added, and the mixture was reacted at 60° C. for 4.5 hours. The reaction solution was cooled to room temperature, then water (20 mL) was added, and the mixture was extracted with ethyl acetate (50 mL×2). The combined organic phase was washed with saturated sodium chloride solution (20 mL), dried over anhydrous sodium sulfate, then concentrated by suction filtration. The residue was purified by silica gel column chromatography [petroleum ether/ethyl acetate (v/v)= 1/1] to obtain the title compound 70d (0.80 g, yield 83%) as yellow liquid.

Step 4 5-(4-amino-2,6-dichlorophenoxy)-1-benzyl-3-methylpyridin-2(1H)-one 70e

1-Benzyl-5-(2,6-dichloro-4-nitrophenoxy)-3-methylpyridin-2(1H)-one 70d (0.80 g, 2.0 mmol) was dissolved in acetic acid (10 mL), then iron powder (0.34 g, 6.0 mmol) was added, and the mixture was reacted at 60° C. for 6 hours. The reaction solution was cooled to room temperature, then water (10 mL) was added. The resulting mixture was stirred for 10 minutes, filtered, and the filter cake was collected and dried under vacuum to obtain the title compound 70e (0.73 g, yield 99%) as a yellow solid.

Step 5 Ethyl (2-(2-(4-((1-benzyl-5-methyl-6-oxo-1,6-dihydropyridin-3-yl)oxy)-3,5-dichlorophenyl)hydrazono)-2-cyanoacetyl)carbamate 70f 5-(4-Amino-2,6-dichlorophenoxy)-1-benzyl-3-methylpyridin-2(1H)-one 70e (0.45 g, 1.20 mmol) was dissolved in acetic acid (12 mL), then N-cyanoacetylurethane (0.23 g, 1.44 mmol) was added, the mixture was reacted at 0° C. for 5 minutes. Then a solution of sodium nitrite (0.17 g, 2.40 mmol) in water (4 mL) was added to the mixture, and continued to react for 1 hour. To the reaction solution was added water (5 mL) and the mixture was stirred for 10 minutes, then filtered, and the filter cake was collected and dried under vacuum to obtain the title compound 70f (0.50 g, yield 77%) as a red-brown solid.

Step 6 2-(4-((1-benzyl-5-methyl-6-oxo-1,6-dihydropyridin-3-yl)oxy)-3,5-dichlorophenyl)-3,5-dioxo-2,3,4,5-tetrahydro-1,2,4-triazine-6-carbonitrile 70

Ethyl (2-(2-(4-((1-benzyl-5-methyl-6-oxo-1,6-dihydropyridin-3-yl)oxy)-3,5-dichlorophenyl)hydrazono)-2-cyanoacetyl)carbamate 70f (0.50 g, 0.92 mmol) was dissolved in N,N-dimethylformamide (8 mL), then sodium acetate (0.15 g, 1.8 mmol) was added, and the mixture was reacted at 120° C. for 5 hours. The reaction solution was cooled to room temperature, then water (5 mL) was added, the resulting mixture was stirred for 10 minutes, then filtered, and the filter cake was collected and dried under vacuum. The crude product was purified by preparative chromatography column [47% ACN/53% $H_2O$ (0.1% TFA), Kromasil specifications: C18 10 μm×50 mm×250 mm, flow rate: 100 mL/min] to obtain the title compound 70 (0.19 g, yield 42%, HPLC purity: 99.40%) as a white solid.

MS (ESI, pos. ion) m z: 496.0 $[M+H]^+$;

$^1H$ NMR (400 MHz, DMSO-$d_6$) δ (ppm) 13.29 (s, 1H), 7.77 (s, 2H), 7.43-7.37 (m, 2H), 7.32 (t, J=7.2 Hz, 1H), 7.28-7.23 (m, 1H), 7.21 (d, J=7.2 Hz, 1H), 5.06 (s, 2H), 2.03 (s, 3H).

Example 38 2-(4-((1-benzyl-5-chloro-6-oxo-1,6-dihydropyridin-3-yl)oxy)-3,5-dichlorophenyl)-3,5-dioxo-2,3,4,5-tetrahydro-1,2,4-triazine-6-carbonitrile (Compound 71)

(71)

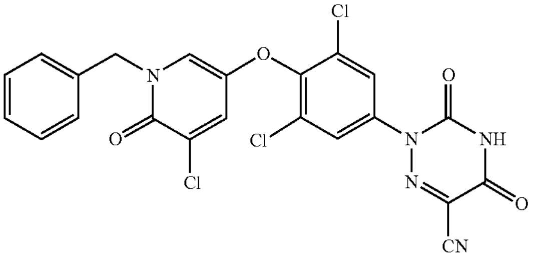

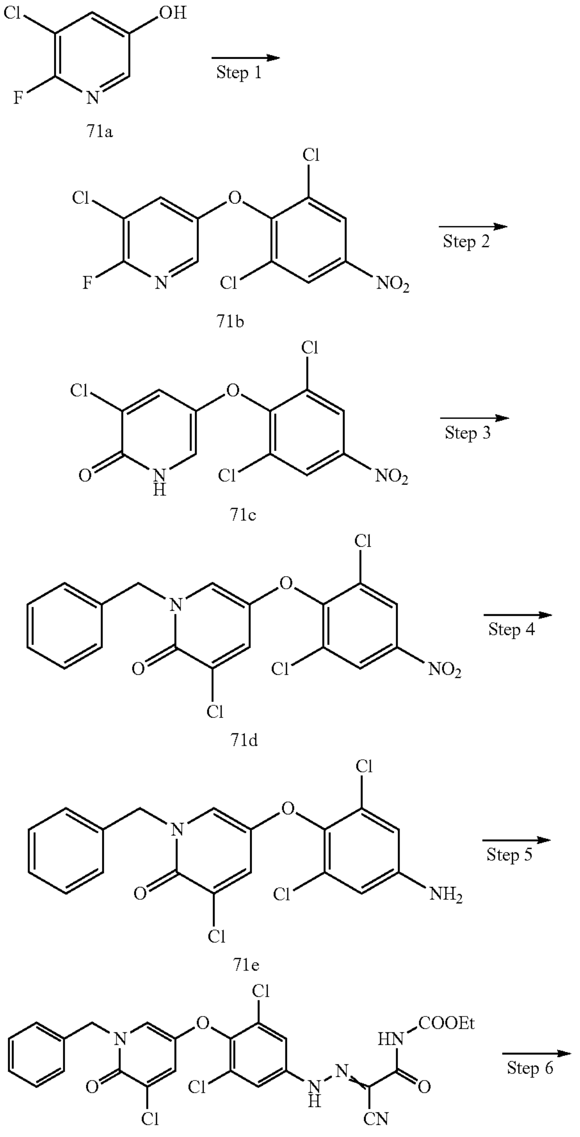

71a

71b

71c

71d

71e

71f

-continued

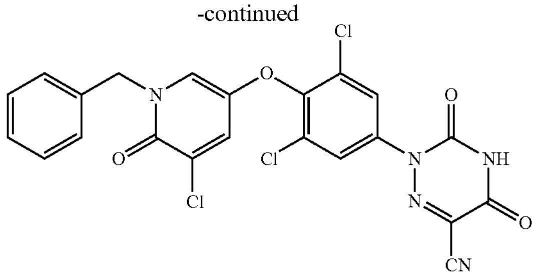

71

Step 1 3-chloro-5-(2,6-dichloro-4-nitrophenoxy)-2-fluoropyridine 71b

5-Chloro-6-fluoropyridin-3-ol 71a (2.71 g, 12.0 mmol) was dissolved in N,N-dimethylformamide (10 mL), then potassium carbonate (2.77 g, 20.0 mmol) was added, and the mixture was reacted at 60° C. for 6 hours. The reaction solution was cooled to room temperature, then water (10 mL) was added. The resulting mixture was stirred for 10 minutes, filtered, and the filter cake was collected and dried under vacuum to obtain the title compound 71b (3.30 g, yield 97%) as a gray solid.

Step 2 3-chloro-5-(2,6-dichloro-4-nitrophenoxy) pyridin-2(11H)-one 71c

3-Chloro-5-(2,6-dichloro-4-nitrophenoxy)-2-fluoropyridine 71b (1.10 g, 3.26 mmol) was dissolved in acetic acid (10 mL) and water (5 mL), and the mixture was reacted at 120° C. for 24 hours. The reaction solution was cooled to room temperature, then water (20 mL) was added, saturated sodium carbonate solution was added to adjust pH=7, and the mixture was extracted with ethyl acetate (50 mL×2). The combined organic phase was washed with saturated sodium chloride solution (20 mL), dried over anhydrous sodium sulfate, concentrated by suction filtration, and the residue was purified by silica gel column chromatography [petroleum ether/ethyl acetate (v/v)=1/1] to obtain the title compound 71c (0.40 g, yield 37%) as a white solid.

Step 3 1-benzyl-3-chloro-5-(2,6-dichloro-4-nitrophenoxy)pyridin-2(1H)-one 71d

3-Chloro-5-(2,6-dichloro-4-nitrophenoxy)pyridin-2(1H)-one 71c (0.40 g, 1.2 mmol) was dissolved in acetonitrile (8 mL), then cesium carbonate (0.78 g, 2.4 mmol) and benzyl bromide (0.22 mL, 1.8 mmol) were added, the mixture was reacted at 60° C. for 4.5 hours. The reaction solution was cooled to room temperature, then water (20 mL) was added, extracted with ethyl acetate (50 mL×2). The combined organic phase was washed with saturated sodium chloride solution (20 mL), dried over anhydrous sodium sulfate, concentrated by suction filtration. The residue was purified by silica gel column chromatography [petroleum ether/ethyl acetate (v/v)=1/1] to obtain the title compound 71d (0.50 g, yield 99%) as a yellow liquid.

Step 4 5-(4-amino-2,6-dichlorophenoxy)-1-benzyl-3-chloropyridin-2(1H)-one 71e

1-Benzyl-3-chloro-5-(2,6-dichloro-4-nitrophenoxy)pyridin-2(1H)-one 71d (0.50 g, 1.2 mmol) was dissolved in acetic acid (10 mL), then iron powder (0.20 g, 3.6 mmol) was added, and the mixture was reacted at 60° C. for 6 hours. The reaction solution was cooled to room temperature, then water (20 mL) was added, and extracted with ethyl acetate (50 mL×2). The combined organic phase was washed with saturated sodium chloride solution (20 mL), dried over anhydrous sodium sulfate, concentrated by suction filtration, and the residue was purified by silica gel column chromatography [petroleum ether/ethyl acetate (v/v)=1/1] to obtain the title compound 71e (0.32 g, yield 69%) as a white solid.

Step 5 Ethyl (2-(2-(4-((1-benzyl-5-chloro-6-oxo-1,6-dihydropyridin-3-yl)oxy)-3,5-dichlorophenyl)hydrazono)-2-cyanoacetyl)carbamate 71f 5-(4-Amino-2,6-dichlorophenoxy)-1-benzyl-3-chloropyridin-2(1H)-one 71e (0.32 g, 0.81 mmol) was dissolved in acetic acid (5 mL), then N-cyanoacetylurethane (0.15 g, 0.97 mmol) was added, the mixture was reacted at 0° C. for 5 minutes. A solution of sodium nitrite (0.11 g, 1.62 mmol) in water (3 mL) was added to the mixture, and the mixture was reacted for 1 hour. To the reaction solution was added water (5 mL) and the mixture was stirred for 10 minutes, then filtered, and the filter cake was collected and dried under vacuum to obtain the title compound 71f (0.42 g, yield 99%) as a red-brown solid.

Step 6 2-(4-((1-benzyl-5-chloro-6-oxo-1,6-dihydropyridin-3-yl)oxy)-3,5-dichlorophenyl)-3,5-dioxo-2,3,4,5-tetrahydro-1,2,4-triazine-6-carbonitrile 71

Ethyl (2-(2-(4-((1-benzyl-5-chloro-6-oxo-1,6-dihydropyridin-3-yl)oxy)-3,5-dichlorophenyl)hydrazono)-2-cyanoacetyl)carbamate 71f (0.42 g, 0.75 mmol) was dissolved in N,N-dimethylformamide (8 mL), then sodium acetate (73 g, 0.90 mmol) was added, and the mixture was reacted at 120° C. for 5 hours. The reaction solution was cooled to room temperature, then water (5 mL) was added, the resulting mixture was stirred for 10 minutes, then filtered, and the filter cake was collected and dried under vacuum. The crude product was purified by preparative chromatography column [47% ACN/53% $H_2O$ (0.1% TFA), Kromasil specifications: C18 10 μm×50 mm×250 mm, flow rate: 100 mL/min] to obtain the title compound 71 (0.13 g, yield 34%, HPLC purity: 99.16%) as a white solid.

MS (ESI, neg. ion) m/z: 516.0 $[M-H]^-$;

$^1$H NMR (400 MHz, DMSO-$d_6$) δ (ppm) 13.36 (s, 1H), 7.98 (d, J=3.2 Hz, 1H), 7.79 (s, 2H), 7.69 (d, J=3.2 Hz, 1H), 7.34 (t, J=7.2 Hz, 2H), 7.30-7.25 (m, 1H), 7.22 (d, J=7.6 Hz, 2H), 5.12 (s, 2H).

Example 39 2-(3,5-dichloro-4-((6-oxo-1-((tetrahydro-2H-pyran-4-yl)methyl)-1,6-dihydro pyridin-3-yl)oxy)phenyl)-1,2,4-triazine-3,5(2H,4H)-dione (Compound 72)

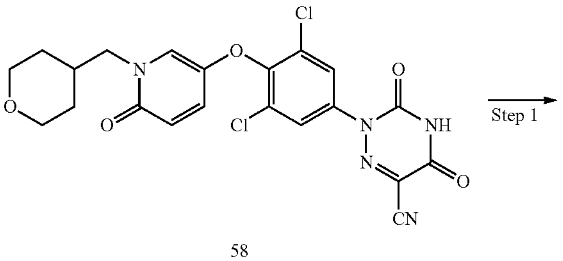

58

-continued

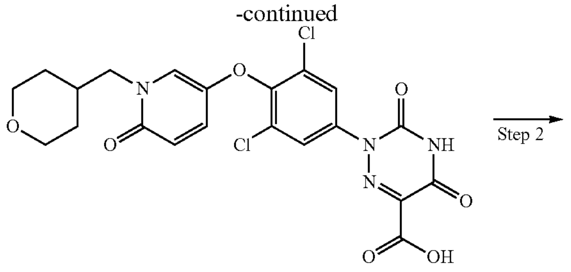

72a

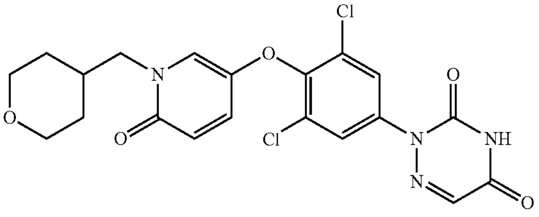

72

(72)

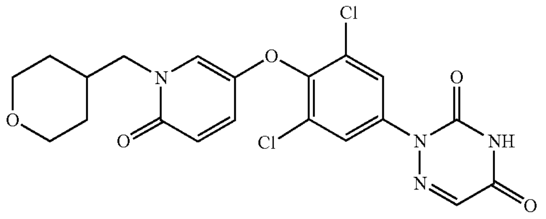

Step 1 2-(3,5-dichloro-4-((6-oxo-1-((tetrahydro-2H-pyran-4-yl)methyl)-1,6-dihydropyridin-3-yl)oxy)phenyl)-3,5-dioxo-2,3,4,5-tetrahydro-1,2,4-triazine-6-carboxylic Acid 72a 2-(3,5-Dichloro-4-((6-oxo-1-((tetrahydro-2H-pyran-4-yl)methyl)-1,6-dihydropyridin-3-yl)oxy)phenyl)-3,5-dioxo-2,3,4,5-tetrahydro-1,2,4-triazine-6-carbonitrile 58 (0.15 g, 0.31 mmol) was dissolved in acetic acid (4 mL), then concentrated hydrochloric acid (1.5 mL) was added, and the mixture was reacted at 120° C. for 24 hours. The reaction solution was cooled to room temperature, then water (20 mL) was added. The resulting mixture was stirred for 10 minutes, filtered, and the filter cake was collected and dried under vacuum to obtain the title compound 72a (0.136 g, yield 86.2%) as a yellow solid.

Step 2 2-(3,5-dichloro-4-((6-oxo-1-((tetrahydro-2H-pyran-4-yl)methyl)-1,6-dihydropyridin-3-yl)oxy)phenyl)-1,2,4-triazine-3,5(2H,4H)-dione 72

2-(3,5-Dichloro-4-((6-oxo-1-((tetrahydro-2H-pyran-4-yl)methyl)-1,6-dihydropyridin-3-yl)oxy)phenyl)-3,5-dioxo-2,3,4,5-tetrahydro-1,2,4-triazine-6-carboxylic acid 72a (0.11 g, 0.22 mmol) was dissolved in thioglycolic acid (3 mL), and the mixture was reacted at 160° C. for 24 hours. The reaction solution was cooled to room temperature, and quenched with water (15 mL) and extracted with ethyl acetate (20 mL×3). The combined organic phase was washed with saturated sodium chloride solution (20 mL), dried over anhydrous sodium sulfate, concentrated by suction filtration. The residue was purified by silica gel column chromatography [petroleum ether/ethyl acetate (v/v)=1/2] to obtain the title compound 72 (75 mg, yield 75%, HPLC purity: 92.35%) as a light yellow solid.

MS (ESI, pos. ion) m z: 465.0 $[M+H]^+$;

$^1H$ NMR (400 MHz, $CDCl_3$) δ (ppm) 10.54 (s, 1H), 7.71 (s, 2H), 7.60 (s, 1H), 7.33 (dd, J=9.8, 3.0 Hz, 1H), 6.79 (dd, J=18.2, 6.3 Hz, 2H), 3.79 (d, J=7.2 Hz, 2H), 3.73 (d, J=7.4 Hz, 2H), 3.52 (dd, J=10.3, 5.0 Hz, 2H), 3.35 (t, J=11.4 Hz, 2H), 2.21-2.09 (m, 1H), 1.53 (d, J=12.1 Hz, 2H).

Example 40 2-(3,5-dichloro-4-((1-isopropyl-6-oxo-1,6-dihydropyridin-3-yl)oxy)phenyl)-1,2,4-triazine-3,5(2H,4H)-dione (Compound 73)

(73)

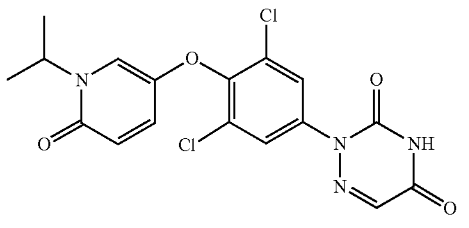

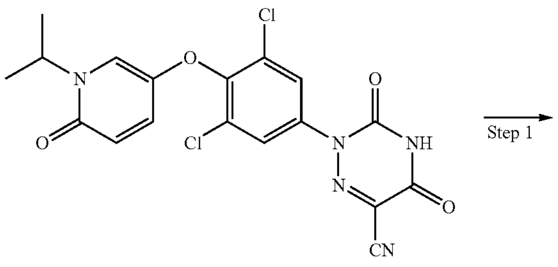

4

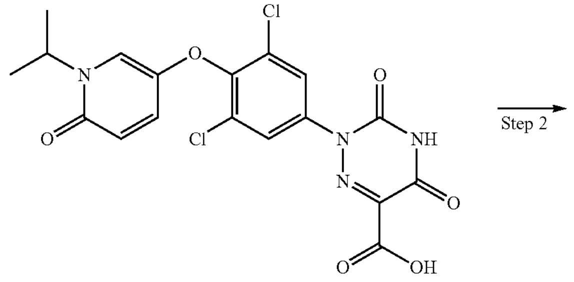

73a

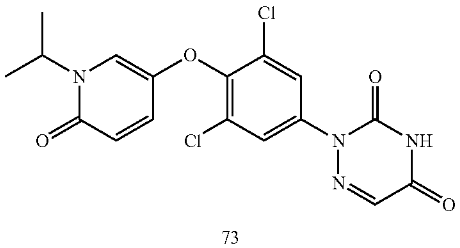

73

Step 1 2-(3,5-dichloro-4-((1-isopropyl-6-oxo-1,6-dihydropyridin-3-yl)oxy)phenyl)-3,5-dioxo-2,3,4,5-tetrahydro-1,2,4-triazine-6-carboxylic Acid 73a 2-(3,5-Dichloro-4-((1-isopropyl-6-oxo-1,6-dihydropyridin-3-yl)oxy)phenyl)-3,5-dioxo-2,3,4,5-tetrahydro-1,2,4-triazine-6-carbonitrile 4 (0.13 g, 0.29 mmol) was dissolved in acetic acid (4 mL), then concentrated hydrochloric acid (1.5 mL) was added, and the mixture was reacted at 120° C. for 24 hours. The reaction solution was cooled to room temperature, then water (20 mL) was added. The resulting mixture was stirred for 10 minutes, filtered, and the filter cake was collected and dried under vacuum to obtain the title compound 73a (0.12 g, yield 94%) as a yellow solid.

Step 2 2-(3,5-dichloro-4-((1-isopropyl-6-oxo-1,6-dihydropyridin-3-yl)oxy)phenyl)-1,2,4-triazine-3,5(2H,4H)-dione 73

2-(3,5-Dichloro-4-((1-isopropyl-6-oxo-1,6-dihydropyridin-3-yl)oxy)phenyl)-3,5-dioxo-2,3,4,5-tetrahydro-1,2,4-triazine-6-carboxylic acid 73a (85 mg, 0.19 mmol) was dissolved in thioglycolic acid (4 mL) and the mixture was reacted at 160° C. for 24 hours. The reaction solution was cooled to room temperature, and quenched with water (10 mL) and extracted with ethyl acetate (20 mL×3). The combined organic phase was washed with saturated sodium chloride solution (20 mL), dried over anhydrous sodium sulfate, concentrated by suction filtration. The residue was purified by silica gel column chromatography [petroleum ether/ethyl acetate (v/v)=1/2] to obtain the title compound 73 (58 mg, yield 76%, HPLC purity: 91.57%) as a yellow solid.

MS (ESI, pos. ion) m z: 409.0 $[M+H]^+$;

$^1H$ NMR (400 MHz, DMSO-$d_6$) δ (ppm) 12.49 (s, 1H), 7.81 (s, 2H), 7.71 (s, 1H), 7.53 (d, J=3.2 Hz, 1H), 7.19 (dd, J=9.9, 3.3 Hz, 1H), 6.38 (d, J=9.9 Hz, 1H), 5.07-4.95 (m, 1H), 1.26 (d, J=6.8 Hz, 6H).

Example 41 2-(3,5-dichloro-4-((1-isobutyl-6-oxo-1,6-dihydropyridin-3-yl)oxy)phenyl)-3,5-dioxo-2,3,4,5-tetrahydro-1,2,4-triazine-6-carbonitrile (Compound 74)

(74)

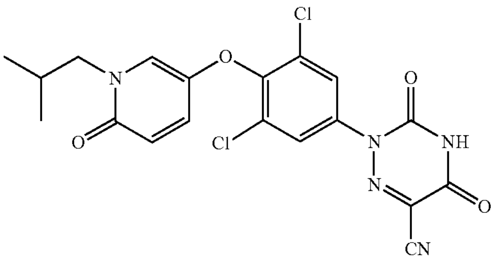

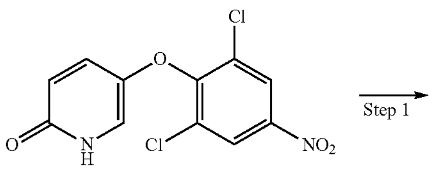

4c

-continued

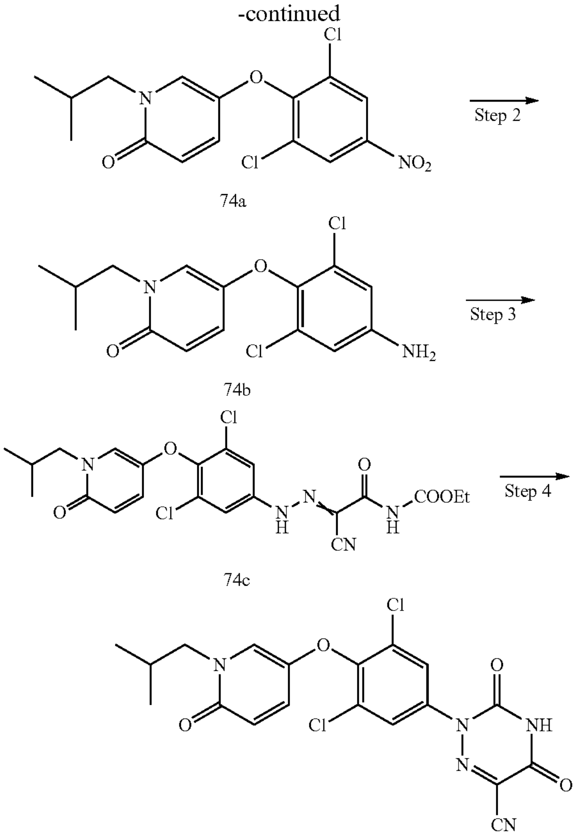

74a

74b

74c

74

Step 1 5-(2,6-dichloro-4-nitrophenoxy)-1-isobutylpyridin-2(1H)-one 74a 5-(2,6-Dichloro-4-nitrophenoxy)pyridin-2(1H)-one 4c (1.0 g, 3.3 mmol) and potassium carbonate (0.70 g, 4.98 mmol) were dissolved in acetonitrile (60 mL), then bromoisobutane (0.54 mL, 4.98 mmol) was added, and the mixture was reacted at room temperature for 18 hours. The reaction solution was cooled to room temperature, filtered, and the filtrate was concentrated. The resulting residue was purified by silica gel column chromatography (petroleum ether/ethyl acetate (v/v)=1/1) to obtain the title compound 74a (0.125 g, yield 11%) as a yellow solid.

MS (ESI, pos. ion) m z: 358.1 $[M+H]^+$;

$^1H$ NMR (400 MHz, DMSO-$d_6$) δ (ppm) 8.34-8.31 (m, 3H), 6.79 (d, J=3.3 Hz, 1H), 6.60 (d, J=9.9 Hz, 1H), 3.69 (d, J=7.5 Hz, 2H), 2.15 (tt, J=6.9 Hz, 1H), 0.94 (d, J=6.7 Hz, 6H).

Step 2 5-(4-amino-2,6-dichlorophenoxy)-1-isobutylpyridin-2(1H)-one 74b 5-(2,6-Dichloro-4-nitrophenoxy)-1-isobutylpyridin-2 (1H)-one 74a (0.23 g, 0.63 mmol) was dissolved in acetic acid (6 mL), then iron powder (0.072 g, 1.3 mmol) was added, the mixture was reacted at 50° C. for 2.5 hours. The reaction solution was cooled to room temperature, then iron powder was removed, and water (30 mL) was added. The resulting mixture was stirred for 10 minutes, and extracted with ethyl acetate (50 mL×2). The combined organic phase was washed with saturated sodium chloride (50 mL), dried over anhydrous sodium sulfate and concentrated by suction filtration to obtain the title compound 74b (0.11 g, yield 53%) as a yellow solid.

MS (ESI, pos. ion) m z: 328.1 $[M+H]^+$.

Step 3 Ethyl (2-cyano-2-(2-(3,5-dichloro-4-((1-isobutyl-6-oxo-1,6-dihydropyridin-3-yl)oxy)phenyl) hydrazono)acetyl)carbamate 74c 5-(4-Amino-2,6-dichlorophenoxy)-1-isobutylpyridin-2 (1H)-one 74b (0.11 g, 0.34 mmol) and N-cyanoacetylurethane (0.058 g, 0.37 mmol) were dissolved in acetic acid (4 mL), then a solution of sodium nitrite (0.050 g, 0.72 mmol) in water (2 mL) was added at 0° C., and the mixture was reacted for 3 hours. At 0° C., to the reaction solution was added water (10 mL). The resulting mixture was stirred for 20 minutes, filtered, and the filter cake was washed with water (5 mL), collected and dried under vacuum to obtain the title compound 74c (0.14 g, yield 85%) as a yellow solid.

Step 4 2-(3,5-dichloro-4-((1-isobutyl-6-oxo-1,6-dihydropyridin-3-yl)oxy)phenyl)-3,5-dioxo-2,3,4,5-tetrahydro-1,2,4-triazine-6-carbonitrile 74

Ethyl (2-cyano-2-(2-(3,5-dichloro-4-((1-isobutyl-6-oxo-1,6-dihydropyridin-3-yl)oxy)phenyl)hydrazono)acetyl)carbamate 74c (0.14 g, 0.29 mmol) was dissolved in N,N-dimethylformamide (4 mL), then sodium acetate (0.05 g, 0.37 mmol) was added, and the mixture was reacted at 120° C. for 16 hours. The reaction solution was cooled to room temperature, and the reaction solution was concentrated. The resulting residue was purified by silica gel column chromatography (petroleum ether/ethyl acetate (v/v)=1/8) to obtain the title compound 74 (62 mg, yield 48%, HPLC purity: 91.13%) as a light yellow solid.

MS (ESI, neg. ion) m z: 447.0 $[M-H]^-$;

$^1H$ NMR (400 MHz, DMSO-$d_6$) δ (ppm) 13.30 (s, 1H), 7.78 (s, 2H), 7.50-7.28 (m, 2H), 6.43 (d, J=8.5 Hz, 1H), 3.66 (s, 2H), 1.99 (s, 1H), 0.81 (s, 6H).

Examples of Activity Tests

1. Detection of TRα or TRβ Agonistic Activity of the Compounds of the Present Invention in the Dual Luciferase Reporter Gene Experiment Test Materials:

- HEK293 cells, purchased from ATCC, Cat No. CRL-1573;
- Fugene HD transfection reaagent, purchased from Promega, Cat No. E231A;
- DMEM, purchased from Gibco, Cat No. 11995;
- FBS, purchased from Biosera, Cat No. FB-1280/500;
- 0.25% Trypsin-EDTA, purchased from Gibco, Cat No. 25200-072;
- Dual-Luciferase Reporter Assay System, purchased from Promega, Cat No. E1960;
- 96-well plate (round bottom), purchased from Corning, Cat No. 3365.

Test Method:

HEK293 cells were cultured in 10% FBS+DMEM whole medium. pBind-TRα or pBind-TRβ (100 ng/μl), pGSLuc (100 ng/μl), FuGENE HD and Opti-MEM were mixed well and then incubated at room temperature for 15 min. At the same time, HEK293 cells were digested with 0.25% Trypsin-EDTA, then resuspended in the whole medium. The cell density was calculated, the cell density was adjusted to 500,000 cells/ml, then the transcription mixture was added and mixed well with the cell suspension. The mixture was plated in a 96-well plate (100 μL/well) and incubated at 37°

C. for 24 h. After 24 h, the test compound was dissolved in DMSO and diluted three-fold to obtain a total of 10 concentrations, and then the compounds were diluted into solutions containing 10% DMSO with DMEM. 5 μL of the compounds were taken to a 96-well plate. The final DMSO concentration of the compounds was 0.5%, and the compounds were co-cultured with cells for 18 h. After 18 h, the Dual-Luciferase Reporter Assay System was used to detect the firefly fluorescence signal and Renilla fluorescence signal. The firefly fluorescence signal (F) was divided by the Renilla fluorescence signal (R) to calculate the F/R ratio, and the graph was drawn using Graph Pad Prism software to calculate the $EC_{50}$ value. The test results show that the compounds of the present invention have very good TR β agonistic activity. At the same time, the compounds of the present invention have good selectivity to TRβ.

The test results show that the compounds of the present invention have obvious agonistic activity and selectivity for TRβ.

2. Detection of TRα or TRβ Binding Activity In Vitro of the Compound of the Present Invention Test Materials:

LanthaScreen TR-FRET Thyroid Receptor beta Coactivator Assay kit was purchased from Invitrogen, Cat. No. PV4686;

LanthaScreen TR-FRET Thyroid Receptor alfa Coactivator Assay kit was purchased from Invitrogen, Cat. No. PV4687.

Test Method:

This method was tested using LanthaScreen TR-FRET Thyroid Receptor beta/alfa Coactivator Assay kit. The test compound was dissolved in DMSO and diluted three-fold to obtain a total of 10 concentrations, then the compounds were diluted into solutions containing 2% DMSO with TR-FRET Coregulator Buffer C in the kit. 10 μL of the compounds containing 2% DMSO were taken to a 384-well plate. Then 5 μL of 4×TRα-LBD or TRP-LBD and 5 μL of a mixture containing 0.4 μM fluorescein-SRC2-2 and 8 nM Tb anti-GST antibody were added to each well. After mixing well, the compounds were incubated at room temperature in the dark for 1 h. After 1 h, the fluorescence value (RFU) was read at 520 nm and 495 nm using PHERAstar FSX microplate reader from BMG LABTECH. The emission signal at 520 nm was divided by the emission signal at 495 nm to calculate the TR-FRET ratio. The graph was drawn using Graph Pad Prism 5 software to calculate the $EC_{50}$ value, the results are shown in Table 1 below.

TABLE 1

In vitro binding activity data of the example compounds of the present invention

| Example No. | $EC_{50}$ (μM) TRα | $EC_{50}$ (μM) TRβ |
|---|---|---|
| 1 | 3.03 | 0.060 |
| 2 | >100 | >10 |
| 4 | >100 | 0.50 |
| 8 | >100 | >10 |
| 9 | >100 | >10 |
| 10 | >100 | >10 |
| 11 | 0.67 | 0.022 |

TABLE 1-continued

In vitro binding activity data of the example compounds of the present invention

| Example No. | $EC_{50}$ (μM) TRα | $EC_{50}$ (μM) TRβ |
|---|---|---|
| 12 | >100 | 1.34 |
| 13 | 0.60 | 0.020 |
| 14 | 5.74 | 0.35 |
| 16 | 16.34 | 0.36 |
| 17 | 15.39 | 0.35 |
| 18 | 1.35 | 0.086 |
| 19 | >100 | >10 |
| 20 | >100 | 7.37 |
| 22 | >100 | 0.69 |
| 23 | 3.00 | 0.060 |
| 24 | 0.57 | 0.020 |
| 25 | 6.66 | 0.14 |
| 27 | >100 | 1.49 |
| 29 | 0.37 | 0.011 |
| 30 | >100 | 3.76 |
| 31 | 4.40 | 0.094 |
| 32 | 22.65 | 1.52 |
| 33 | 3.232 | 0.231 |
| 34 | 7.312 | 0.367 |
| 35 | 0.473 | 0.017 |
| 36 | 0.092 | <0.0046 |
| 37 | >100 | 0.245 |
| 38 | >33.3 | 0.382 |

The test results show that the compounds of the present invention have strong binding affinity and selectivity for TRβ.

3. Pharmacokinetic Determination of the Compounds of the Present Invention

Test purpose: The following method is used to determine the pharmacokinetics of the compounds of the present invention.

Test Materials:

Experimental reagents and test compounds: Propranolol (internal standard), methanol, ammonium acetate, $K_2$EDTA (potassium ethylenediamine tetraacetate), formic acid, acetonitrile, MTBE (methyl tert-butyl ether), KolliphorHS15 (polyethylene glycol 12 hydroxystearate), DMSO (dimethyl sulfoxide) are commercially available;

SD rat: male, 180-220 g, 7-8 weeks old, purchased from Hunan Slake Experimental Animal Co., Ltd.

Test Method:

1. Preparation of Test Compounds

Each test compound prepared was completely dissolved in a mixture of 5% DMSO+5% KolliphorHS 15+90% Saline according solubility property thereof.

2. Design of Animal Experiment

| Test compound | Compounds of examples of the invention |
|---|---|
| Animal grouping | Intravenous injection/I.V: n = 3; blood collection time (hours/h): 0.083, 0.25, 0.5, 1, 2, 5, 7, 24<br>Oral gavage/I.G. : n = 3; blood collection time (hours/h): 0.083, 0.25, 0.5, 1, 2, 5, 7, 24 |
| drug-delivery way | Intravenous: intravenous administration of hind legs and feet; oral administration: intragastric administration. |
| Blood collection method | Tail vein blood collection |
| Blood collection | 200~400 μL/time point |
| Anticoagulant | $K_2$EDTA |
| Plasma preparation | All samples were centrifuged at 10,000 rpm, 4° C., for 2 minutes to separate plasma within 60 minutes. The samples were stored at −80° C. for testing. Back-up samples are stored for 1 month after the complete of the analysis. |
| Fasting situation | Fasting for 15 h before administration, drinking water freely.<br>Eating at 4 hours after administration. |
| Stock solution solvent | Test compound: 20% DMSO; internal standard: Propranolol aqueous solution (100 ng/mL) |
| data processing | Pharmacokinetic parameters were calculated using a noncompartmental method by Win NonLin 6.1 software |

3. Animal Administration Dose Table

| Group | Gender | Number | Administration dose | Administration concentration | Administration volume |
|---|---|---|---|---|---|
| Intravenous injection I.V. | male | 3 | 1 mg/kg | 1 mg/mL | 1 mL/kg |
| Oral gavage I.G. | male | 3 | 5 mg/kg | 1 mg/mL | 5 mL/kg |

4. Solution Preparation (1) Preparation of the test compound stock solution: an appropriate amount of test compound was precisely weighed, dissolved in DMSO, diluted to 1 mg/mL with acetonitrile, and shaken well to obtain the test compound stock solution, which was stored at −20° C. for use.

(2) Preparation of internal standard solution: a certain amount of 1 mg/mL Propranolol stock solution was precisely drawn and diluted to 100 ng/mL with water.

5. Sample Analysis

The liquid-liquid extraction method was used to process the samples for chromatographic separation. On a triple quadrupole tandem mass spectrometer, quantitative analysis was performed using multiple reactive ion monitoring (MRM), and the concentration were calculated using instrument quantitative software.

6. Pretreatment of Plasma Samples

30 μL of plasma sample was accurately drawn, and added with 250 μL of internal standard. The mixture was mixed well by vortexing. The mixture was extracted once with 1 mL of MTBE, centrifuged at 13,000 rpm, 4° C. for 2 min, then 800 μL of supernatant was sucked, and evaporated in a 96-well nitrogen blower. The residue was re-dissolved with 150 μL of methanol/water (v/v=50/50), mixed by vortexing, and injected. The injection volume was 8 μL.

7. Preparation of Standard Samples

An appropriate amount of compound stock solution was accurately drawn, and diluted with acetonitrile to obtain standard series solution. 20 μL of each of the above standard series solutions was accurately drawn, added with 180 μL of blank plasma, and mixed well by vortexing to prepare plasma samples equivalent to plasma concentrations of 3, 5, 10, 30, 100, 300, 1,000, 3,000, 5,000, and 10,000 ng/mL, which were all processed according to "pretreatment of plasma samples". Two samples were analyzed for each concentration to establish a standard curve.

8. Analysis Method

The content of the test compound in the plasma of rats after administration of different compounds was determined by LC/MS/MS method.

9. Data Processing

Pharmacokinetic parameters were calculated using a noncompartmental method by WinNonLin 6.1 software.

The pharmacokinetic test results of some of the example compounds of the present invention are shown in Table 2 below.

TABLE 2

Pharmacokinetic data of some example compounds of the present invention

| Example No. | Route | Dose (mg/kg) | Tmax (h) | Cmax (ng/ml) | AUClast (h * ng/ml) | $T_{1/2}$ (h) |
|---|---|---|---|---|---|---|
| MGL3196 | iv | 1 | 0.083 | 5990 | 8840 | 2.74 |
| | ig | 5 | 2 | 2610 | 20700 | 4.26 |
| 16 | iv | 1 | 0.083 | 17300 | 17400 | 4 |
| | ig | 5 | 0.5 | 12700 | 33600 | 3.05 |
| 29 | iv | 1 | 0.083 | 8920 | 16900 | 2.38 |
| | ig | 5 | 0.417 | 20000 | 115000 | 2.89 |

The test results show that when administered by intravenous injection or oral gavage, the example compounds of the present invention (Examples 16 and 29) have excellent pharmacokinetic properties. In particular, compared to the control compound MGL3196, the example compounds of the present invention have higher blood concentration and exposure, that is, have better pharmacokinetic properties.

4. Pharmacodynamic Evaluation of the Compounds of the Present Invention

Test Materials:

Western diet: purchased from Research diet, article number: D12079B;

MCD diet: purchased from Nantong Trophy Feed Technology Co., Ltd., article number: TP3006R;

ALT, AST, ALP, TQ CHO, HDL, LDL and GLU: purchased from Roche, article numbers are: 20764957322, 20764949322, 03333701190, 20767107322, 03039773190, 04399803190, 03038866322 and 0440483190;

8-week-old male OB/OB mice: purchased from Jiangsu Jicui Yaokang Biotechnology Co., Ltd.;

8-week-old male db/db mice: purchased from Jiangsu Jicui Yaokang Biotechnology Co., Ltd.

A. Pharmacodynamic Evaluation of the Compound in the Non-Alcoholic Steatohepatitis (NASH) Model of OB/OB Mice Induced by Western Diet OB/OB mice were leptin gene-deficient mice, and the OB/OB mouse NASH model induced by Western diet is a commonly used NASH in vivo drug efficacy evaluation model. The animals experiment began after 1 week of acclimation. OB/OB mice were fed with Western diet, and the feed was changed three times a week (Monday, Wednesday, and Friday). The mice began to be administered with the drug in the fifth week after feeding, and they were administered orally once a day for 6 weeks. The entire experiment period was 10 weeks. During the experiment, the basic conditions of the animals were monitored every day, and the weight of the mice was recorded once a week. After the experiment, the rats were fasted overnight. After anesthetizing the mice, whole blood was collected from the orbit. The serum was obtained by centrifugation at 4° C., 4,000 rpm for 10 min, and stored at −80° C. The serum was used for the detection of ALT, AST, ALP, TQ CHO, HDL, LDL and GLU. The mice were dissected to take the livers and weighed. The middle lobes of the livers were placed in EP tubes and stored at −80° C. for the determination of TG and CHO content in the livers. After the left lobes of livers were fixed in 10% formalin, HE staining was performed and NAS score was performed.

B. Pharmacodynamic Evaluation of the Compound in the Non-Alcoholic Steatohepatitis (NASH) Model of db/db Mice Induced by MCD Diet db/db Mice were leptin receptor gene-deficient mice, and the db/db mouse NASH model induced by MCD diet is a commonly used NASH in vivo drug efficacy evaluation model. The animals experiment began after 1 week of acclimation. db/db Mice were fed with MCD diet, and the feed was changed three times a week (Monday, Wednesday, and Friday). The mice were administered the drug while modeling, and they were administered orally once a day for 8 weeks. The entire experiment period was 8 weeks. During the experiment, the basic conditions of the animals were monitored every day, and the weight of the mice was recorded once a week. After the experiment, the rats were fasted overnight. After anesthetizing the mice, whole blood was collected from the orbit. The serum was obtained by centrifugation at 4° C., 4,000 rpm for 10 min, and stored at −80° C. The serum was used for the detection of ALT, AST, ALP, TQ CHO, HDL, LDL and GLU. The mice were dissected to take the livers and weighed. The middle lobes of the livers were placed in EP tubes and stored at −80° C. for the determination of TG and CHO content in the livers. After the left lobes of livers were fixed in 10% formalin, HE staining was performed and NAS score was performed.

The test results show that the compounds of the present invention can effectively reduce the accumulation of fat in the liver, reduce inflammation, and improve liver fibrosis.

Reference throughout this specification to "an embodiment," "some embodiments," "one embodiment", "another example," "an example," "a specific example," or "some examples," means that a particular feature, structure, material, or characteristic described in connection with the embodiment or example is included in at least one embodiment or example of the present disclosure. Thus, the appearances of the above terms throughout this specification are not necessarily referring to the same embodiment or example of the present disclosure. Furthermore, the particular features, structures, materials, or characteristics may be combined in any suitable manner in one or more embodiments or examples. In addition, those skilled in the art can integrate and combine different embodiments, examples or the features of them as long as they are not contradictory to one another.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A compound having Formula (I) or a stereoisomer, a tautomer, an N-oxide, a solvate, or a pharmaceutically acceptable salt thereof, (I)

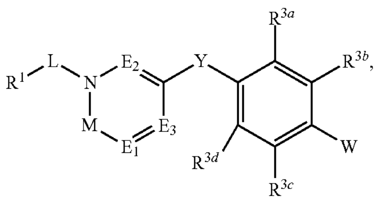

wherein,

Y is —O—, —S—, —$NR^c$—, —$CR^aR^b$—, —S(═O)$_2$—, —S(═O)— or —C(═O)—;

L is absent, —O—, —S—, —$NR^c$—, —$CR^dR^e$—, —S(═O)$_2$—, —S(═O)— or —C(═O)—;

each of $R^a$, $R^b$, $R^c$, $R^d$ and $R^e$ is independently H, deuterium, F, Cl, Br, I, —CN, —$NO_2$, —COOH, —OH, —$NH_2$, —SH, $C_{1-6}$ alkyl, $C_{1-6}$ alkoxy, $C_{1-6}$ haloalkyl or $C_{1-6}$ haloalkoxy;

each of $R^{3a}$, $R^{3b}$, $R^{3c}$, and $R^{3d}$ is independently H, deuterium, F, Cl, Br, I, —CN, —$NO_2$, —COOH, —OH, —$NH_2$, —SH, $C_{1-6}$ alkyl, $C_{1-6}$ alkoxy, $C_{1-6}$ alkylthio, $C_{1-6}$ alkylamino, $C_{1-6}$ haloalkyl, $C_{1-6}$ haloalkoxy, hydroxy $C_{1-6}$ alkyl, amino $C_{1-6}$ alkyl or cyano $C_{1-6}$ alkyl;

M is —C(═O)—, —C(═S)—, —S(═O)$_2$— or —S(═O)—;

$E_1$ is N or CH;

$E_2$ is $CR^2$;

$E_3$ is N or $CR^3$;

each of $R^2$ and $R^3$ is independently H or deuterium;

$R^1$ is $C_{1-6}$ alkyl, $C_{1-6}$ alkoxy, $C_{1-6}$ haloalkyl, $C_{1-6}$ haloalkoxy, —C(═O)—$C_{1-6}$ alkoxy, —C(═O)—$C_{1-6}$ alkylamino, —C(═O)—$C_{1-6}$ alkyl, —S(═O)$_2$—$C_{1-6}$ alkyl, —S(═O)$_2$—$C_{1-6}$ alkylamino, $C_{2-6}$ alkenyl, $C_{2-6}$ alkynyl, $C_{3-8}$ cycloalkyl, 5-8 membered heterocyclyl, $C_{6-10}$ aryl or 5-8 membered heteroaryl, wherein each of the $C_{1-6}$ alkyl, $C_{1-6}$ alkoxy, $C_{1-6}$ haloalkyl, $C_{1-6}$ haloalkoxy, —C(═O)—$C_{1-6}$ alkoxy, —C(═O)—$C_{1-6}$ alkylamino, —C(═O)—$C_{1-6}$ alkyl, —S(═O)$_2$—$C_{1-6}$ alkyl, —S(═O)$_2$—$C_{1-6}$ alkylamino, $C_{2-6}$ alkenyl, $C_{2-6}$ alkynyl, $C_{3-8}$ cycloalkyl, 5-8 membered heterocyclyl, $C_{6-10}$ aryl and 5-8 membered heteroaryl is independently unsubstituted or substituted with 1, 2 or 3 substituents selected from Deuterium, F, Cl, Br, I, —CN, —$NO_2$, —COOH, —C(═O)$NH_2$, —S(═O)$_2$ $NH_2$, —SH, —OH, —$NH_2$, ═O, —C(═O)—$C_{1-6}$ alkyl, —C(═O)—$C_{1-6}$ alkoxy, $C_{1-6}$ alkyl, $C_{1-6}$ alkoxy, $C_{1-6}$ haloalkyl or $C_{1-6}$ haloalkoxy;

W is

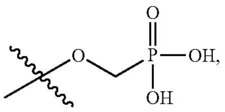

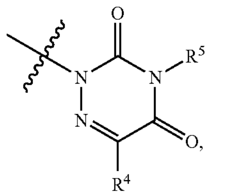

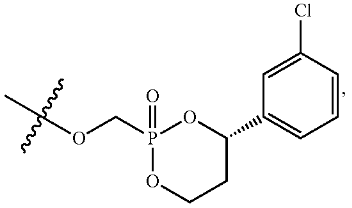

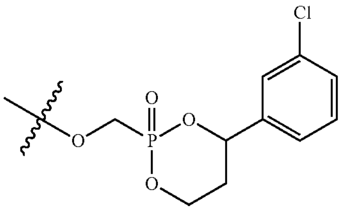

or

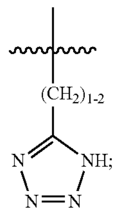

$R^4$ is H, deuterium, F, Cl, Br, I, —CN, —$NO_2$, —COOH, —OH, —$NH_2$, —SH, $C_{1-6}$ alkyl, $C_{2-6}$ alkenyl, $C_{2-6}$ alkynyl, —C(═O)—$C_{1-6}$ alkoxy, —C(═O)—$C_{1-6}$ alkyl, —C(═O)—$C_{1-6}$ alkylamino, —C(═O)$NH_2$, —S(═O)$_2$—$C_{1-6}$ alkyl, —S(═O)$_2$—$C_{1-6}$ alkylamino, $C_{1-6}$ alkylamino, $C_{1-6}$ alkoxy, $C_{1-6}$ haloalkyl, $C_{1-6}$ haloalkoxy, hydroxy $C_{1-6}$ alkyl, amino $C_{1-6}$ alkyl, carboxy $C_{1-6}$ alkyl or cyano $C_{1-6}$ alkyl, wherein each of the $C_{1-6}$ alkyl, $C_{2-6}$ alkenyl, $C_{2-6}$ alkynyl, —C(═O)—$C_{1-6}$ alkoxy, —C(═O)—$C_{1-6}$ alkyl, —C(═O)—$C_{1-6}$ alkylamino, —C(═O)$NH_2$, —S(═O)$_2$—$C_{1-6}$ alkyl, —S(═O)$_2$—$C_{1-6}$ alkylamino, $C_{1-6}$ alkylamino, $C_{1-6}$ alkoxy, $C_{1-6}$ haloalkyl, $C_{1-6}$ haloalkoxy, hydroxy $C_{1-6}$ alkyl, amino $C_{1-6}$ alkyl, carboxy $C_{1-6}$ alkyl and cyano $C_{1-6}$ alkyl is independently unsubstituted or substituted with 1, 2 or 3 substituents selected from deuterium, F, Cl, Br, I, —CN, —$NO_2$, —COOH, —OH, —$NH_2$, —SH, $C_{1-6}$ alkyl, $C_{2-6}$ alkenyl or $C_{2-6}$ alkynyl;

$R^5$ is H, deuterium, $C_{1-6}$ alkyl, $C_{2-6}$ alkenyl, $C_{2-6}$ alkynyl, $C_{3-6}$ cycloalkyl, 5-6 membered heterocyclyl, $C_{6-10}$ aryl or 5-6 membered heteroaryl.

2. The compound of claim 1, wherein each of $R^{3a}$, $R^{3b}$, $R^{3c}$ and $R^{3d}$ is independently H, deuterium, F, Cl, Br, I, —CN, —$NO_2$, —COOH, —OH, $NH_2$, —SH, methyl, ethyl, n-propyl, isopropyl, methoxy, ethoxy, methylthio, methylamino, —$CF_3$, —$CHF_2$, —$CH_2F$, —$CH_2CF_3$, trifluoromethoxy, difluoromethoxy, hydroxymethyl, aminomethyl or cyanomethyl.

3. The compound of claim 1, wherein each of $R^a$, $R^b$, $R^c$, $R^d$ and $R^e$ is independently H, deuterium, F, Cl, Br, I, —CN, —$NO_2$, —COOH, —OH, $NH_2$, —SH, methyl, ethyl, n-propyl, isopropyl, methoxy, ethoxy, —$CF_3$, —$CHF_2$, —$CH_2F$, —$CH_2CF_3$ or trifluoromethoxy.

4. The compound of claim 1, wherein $R^1$ is $C_{1-4}$ alkyl, $C_{1-4}$ alkoxy, $C_{1-4}$ haloalkyl, $C_{1-4}$ haloalkoxy, —C(═O)—$C_{1-4}$ alkoxy, —C(═O)—$C_{1-4}$ alkylamino, —C(═O)—$C_{1-4}$ alkyl, —S(═O)$_2$—$C_{1-4}$ alkyl, —S(═O)$_2$—$C_{1-4}$ alkylamino, $C_{2-4}$ alkenyl, $C_{2-4}$ alkynyl, $C_{3-6}$ cycloalkyl, 5-6 membered heterocyclyl, $C_{6-10}$ aryl or 5-6 membered heterocyclyl, wherein each of the $C_{1-4}$ alkyl, $C_{1-4}$ alkoxy, $C_{1-4}$ haloalkyl, $C_{1-4}$ haloalkoxy, —C(═O)—$C_{1-4}$ alkoxy, —C(═O)—$C_{1-4}$ alkylamino, —C(═O)—$C_{1-4}$ alkyl, —S(═O)$_2$—$C_{1-4}$ alkyl, —S(═O)$_2$—$C_{1-4}$ alkylamino, $C_{2-4}$ alkenyl, $C_{2-4}$ alkynyl, $C_{3-6}$ cycloalkyl, 5-6 membered heterocyclyl, $C_{6-10}$ aryl and 5-6 membered heterocyclyl is independently unsubstituted or substituted with 1, 2 or 3 substituents selected from Deuterium, F, Cl, Br, I, —CN, —$NO_2$, —COOH, —C(═O)$NH_2$, —S(═O)$_2NH_2$, —SH, —OH, —$NH_2$, ═O, —C(═O)—$C_{1-4}$ alkyl, —C(═O)—$C_{1-4}$ alkoxy, $C_{1-4}$ alkyl, $C_{1-4}$ alkoxy, $C_{1-4}$ haloalkyl or $C_{1-4}$ haloalkoxy.

5. The compound of claim 1, wherein $R^1$ is methyl, ethyl, n-propyl, isopropyl, n-butyl, isobutyl, sec-butyl, tert-butyl, methoxy, ethoxy, n-propoxy, isopropoxy, —$CF_3$, —$CHF_2$, —$CH_2F$, —$CH_2CF_3$, trifluoromethoxy, difluoromethoxy, —C(═O)—$OCH_3$, —C(═O)—$OCH_2CH_3$, —C(═O)—$OCH(CH_3)_2$, —C(═O)—$OCH_2CH_2CH_3$, —C(═O)—O$(CH_2)_3CH_3$, —C(═O)—$OCH_2CH(CH_3)_2$, —C(═O)—$NHCH_3$, —C(═O)—$N(CH_3)_2$, —C(═O)—$CH_3$, —C(═O)—$CH_2CH_3$, —S(═O)$_2$—$CH_3$, —S(═O)$_2$—$CH_2CH_3$, —S(═O)$_2$—$CH_2CH_2CH_3$, —S(═O)$_2$—$NHCH_3$, —S(═O)$_2$—$N(CH_3)_2$, —CH═$CH_2$, —$CH_2$CH═$CH_2$, —CH═C≡$CH_3$, —C≡CH, cyclopropyl, cyclobutyl, cyclopentyl, cyclohexyl, pyrrolidinyl, pyrazolidinyl, imidazolidinyl, piperidinyl, morpholinyl, thiomorpholinyl, piperazinyl, tetrahydropyrrolyl, tetrahydrofuranyl, tetrahydropyranyl, tetrahydrothienyl, tetrahydropyridinyl, tetrahydropyrimidinyl, tetrahydropyrazinyl, tetrahydropyridazinyl, dihydropyrrolyl, dihydrofuranyl, dihydropyranyl, dihydrothienyl, dihydropyridyl, dihydropyrimidinyl, dihydropyrazinyl, dihydropyridazinyl, phenyl, naphthyl, furyl, thienyl, imidazolyl, pyrazolyl, pyrimidinyl, pyridyl, pyrrolyl, pyrazinyl, pyridazinyl, thiazolyl, tetrazolyl, triazolyl, isoxazolyl, isothiazolyl, oxadiazolyl or oxazolyl, wherein each of the methyl, ethyl, n-propyl, isopropyl, n-butyl, isobutyl, sec-butyl, tert-butyl, methoxy, ethoxy, n-propoxy, isopropoxy, —$CHF_2$, —$CH_2F$, —$CH_2CF_3$, difluoromethoxy, —C(═O)—$OCH_3$, —C(═O)—$OCH_2CH_3$, —C(═O)—$OCH(CH_3)_2$, —C(═O)—$OCH_2CH_2CH_3$, —C(═O)—O$(CH_2)_3CH_3$, —C(═O)—$OCH_2CH(CH_3)_2$, —C(═O)—$NHCH_3$, —C(═O)—$N(CH_3)_2$, —C(═O)—$CH_3$, —C(═O)—$CH_2CH_3$, —S(═O)$_2$—$CH_3$, —S(═O)$_2$—$CH_2CH_3$, —S(═O)$_2$—$CH_2CH_2CH_3$, —S(═O)$_2$—$NHCH_3$, —S(═O)$_2$—$N(CH_3)_2$, —CH═$CH_2$, —$CH_2$CH═$CH_2$, —CH≡$CHCH_3$, —C≡CH, cyclopropyl, cyclobutyl, cyclopentyl, cyclohexyl, pyrrolidinyl, pyrazolidinyl, imidazolidinyl, piperidinyl, morpholinyl, thiomorpholinyl, piperazinyl, tetrahydropyrrolyl, tetrahydrofuranyl, tetrahydropyranyl, tetrahydrothienyl, tetrahydropyridinyl, tetrahydropyrimidinyl, tetrahydropyrazinyl, tetrahydropyridazinyl, dihydropyrrolyl, dihydrofuranyl, dihydropyranyl, dihydrothienyl, dihydropyridyl, dihydropyrimidinyl, dihydropyrazinyl, dihydropyridazinyl, phenyl, naphthyl, furyl, thienyl, imidazolyl, pyrazolyl, pyrimidinyl, pyridyl, pyrrolyl, pyrazinyl, pyridazinyl, thiazolyl, tetrazolyl, triazolyl, isoxazolyl, isothiazolyl, oxadiazolyl and oxazolyl is independently unsubstituted or substituted with 1, 2 or 3 substituents selected from deuterium, F, Cl, Br, I, —CN, $—NO_2$, —COOH, $—C(=O)NH_2$, $—S(=O)_2NH_2$, —SH, —OH, $—NH_2$, =O, $—C(=O)—CH_3$, $—C(=O)—CH_2CH_3$, $—C(=O)—OCH_3$, $—C(=O)—OCH_2CH_3$, $—C(=O)—OCH(CH_3)_2$, $—C(=O)—OCH_2CH_2CH_3$, $—C(=O)—O(CH_2)_3CH_3$, $—C(=O)—OCH_2CH(CH_3)_2$, $—C(=O)—CH_3$, $—C(=O)—CH_2CH_3$, methyl, ethyl, n-propyl, isopropyl, methoxy, ethoxy, n-propoxy, isopropoxy, $—CF_3$, $—CHF_2$, $—CH_2CF_3$, trifluoromethoxy or difluoromethoxy.

6. The compound of claim 1, wherein $R^4$ is H, deuterium, F, Cl, Br, I, —CN, $—NO_2$, —COOH, —OH, $—NH_2$, —SH, methyl, ethyl, n-propyl, isopropyl, $—CH=CH_2$, $—CH_2CH—CH_2$, $—CH—CHCH_3$, —C=CH, $—C(=O)—OCH_3$, $—C(=O)—OCH_2CH_3$, $—C(=O)—OCH(CH_3)_2$, $—C(=O)—OCH_2CH_2CH_3$, $—C(=O)—O(CH_2)_3CH_3$, $—C(=O)—OCH_2CH(CH_3)_2$, $—C(=O)—CH_3$, $—C(=O)—CH_2CH_3$, $—C(=O)—NHCH_3$, $—C(=O)—N(CH_3)_2$, $—C(=O)NH_2$, $—S(=O)_2—CH_3$, $—S(=O)_2—CH_2CH_3$, $—S(=O)_2—NHCH_3$, methylamino, ethylamino, methoxy, ethoxy, $—CF_3$, $—CHF_2$, $—CH_2F$, $—CH_2CF_3$, $—CH_2CHF_2$, trifluoromethoxy, difluoromethoxy, hydroxymethyl, aminomethyl, carboxymethyl or cyanomethyl, wherein each of the methyl, ethyl, n-propyl, isopropyl, $—CH=CH_2$, $—CH_2CH=CH_2$, $—CH=CHCH_3$, —C=CH, $—C(=O)—OCH_3$, $—C(=O)—OCH_2CH_3$, $—C(=O)—OCH(CH_3)_2$, $—C(=O)—OCH_2CH_2CH_3$, $—C(=O)—O(CH_2)_3CH_3$, $—C(=O)—OCH_2CH(CH_3)_2$, $—C(=O)—CH_3$, $—C(=O)—CH_2CH_3$, $—C(=O)—NHCH_3$, $—C(=O)—N(CH_3)_2$, $—C(=O)NH_2$, $—S(=O)_2—CH_3$, $—S(=O)_2—CH_2CH_3$, $—S(=O)_2—NHCH_3$, methylamino, ethylamino, methoxy, ethoxy, $—CF_3$, $—CHF_2$, $—CH_2F$, $—CH_2CF_3$, $—CH_2CHF_2$, difluoromethoxy, hydroxymethyl, aminomethyl, carboxymethyl and cyanomethyl is independently unsubstituted or substituted with 1, 2 or 3 substituents selected from deuterium, F, Cl, Br, I, —CN, $—NO_2$, —COOH, —OH, $—NH_2$, —SH, C1-6 alkyl, $C_{2-6}$ alkenyl or $C_{2-6}$ alkynyl.

7. The compound of claim 1, wherein $R^5$ is H, deuterium, methyl, ethyl, n-propyl, isopropyl, tert-butyl, $—CH=CH_2$, $—CH_2CH=CH_2$, $—CH=CHCH_3$, —C≡CH, cyclopropyl, cyclobutyl, cyclopentyl, cyclohexyl, 5-6 membered heterocyclyl, phenyl, naphthyl or 5-6 membered heteroaryl.

8. A compound having one of the following structures:

(1)

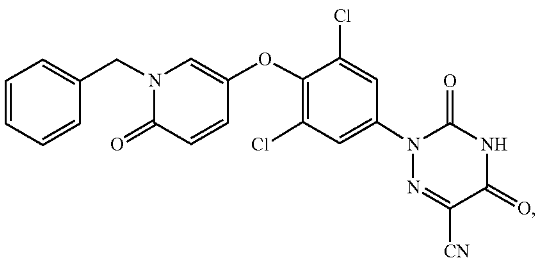

-continued (2)

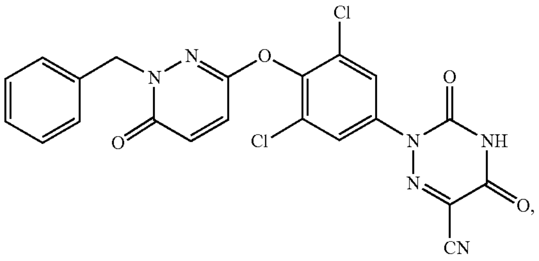

(4)

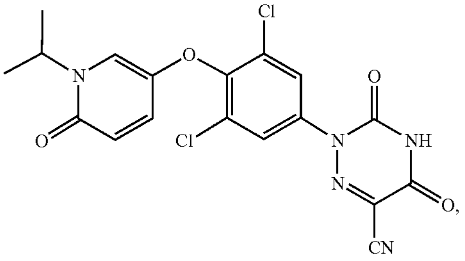

(5)

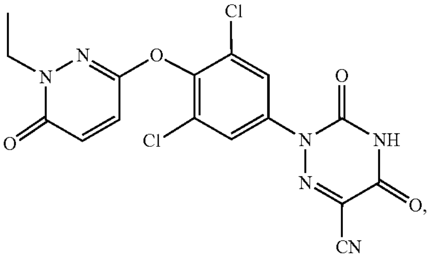

(6)

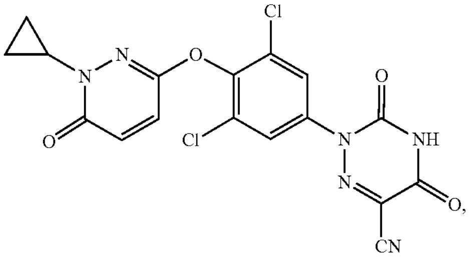

(7)

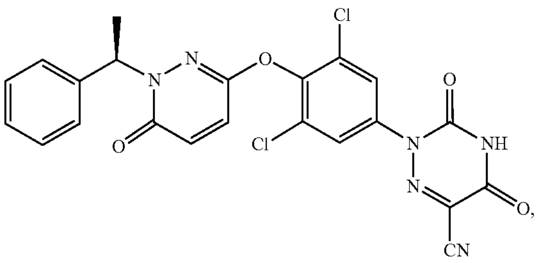

(8)

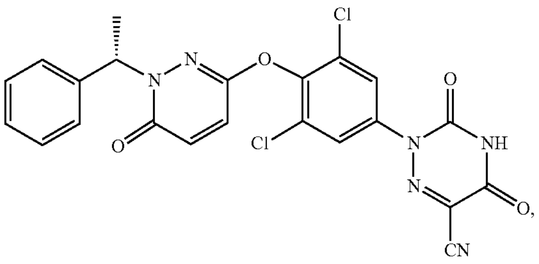

-continued
(9)
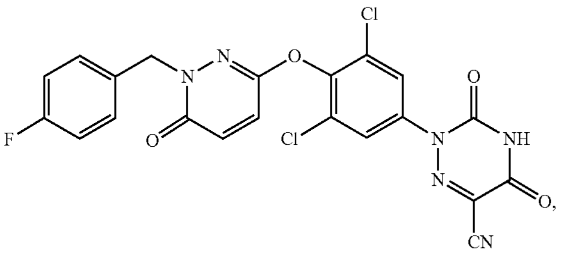
(10)
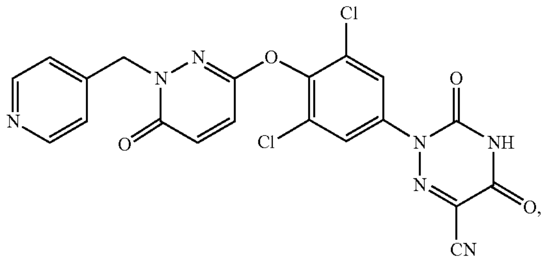
(11)
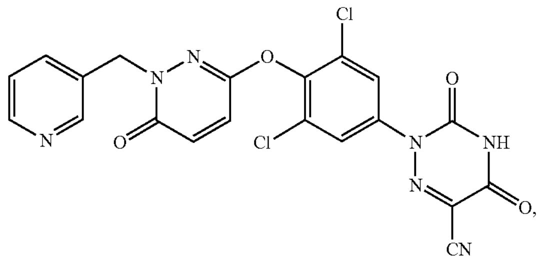
(12)
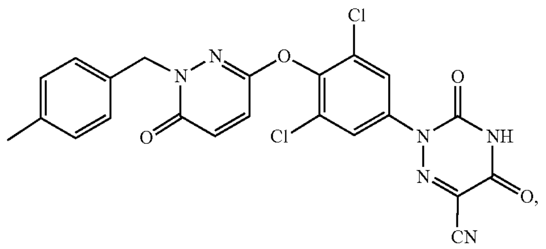
(13)
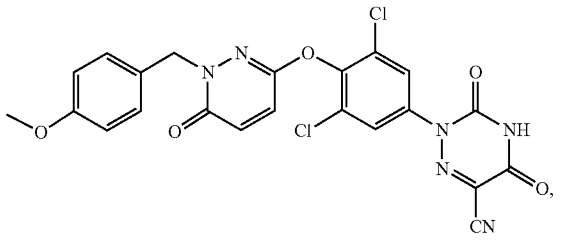
(14)
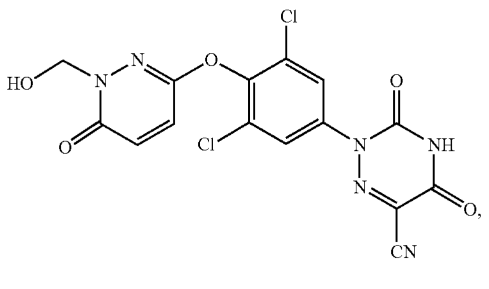
-continued
(15)
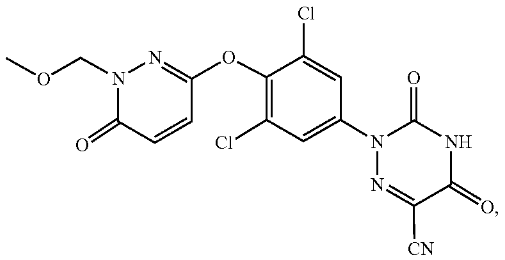
(16)
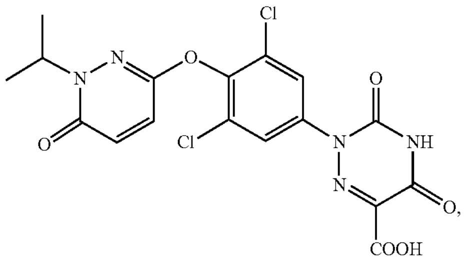
(17)
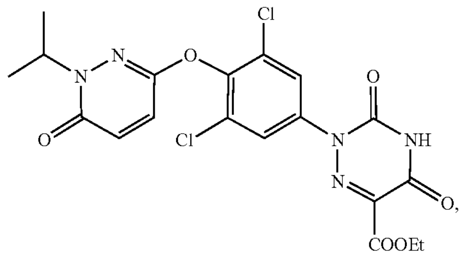
(18)
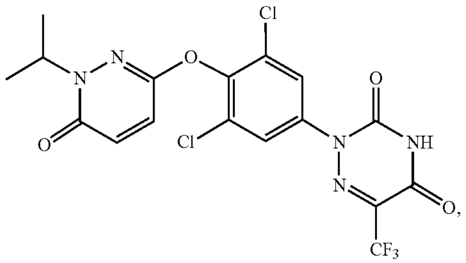
(19)
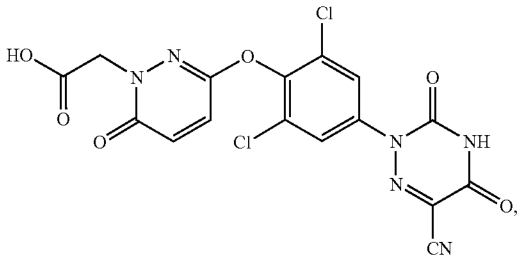
(20)
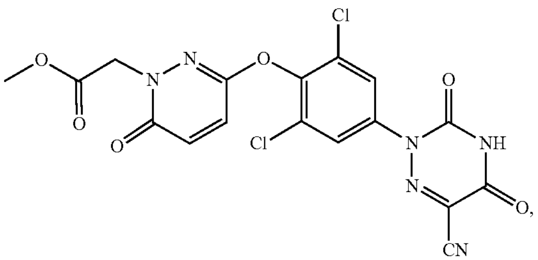

-continued
(21)
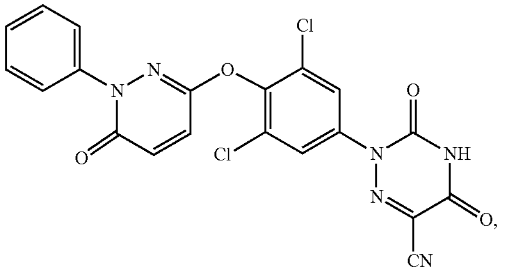
(22)
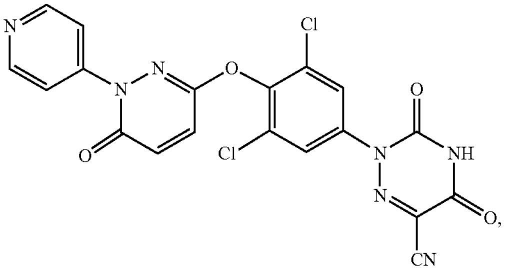
(23)
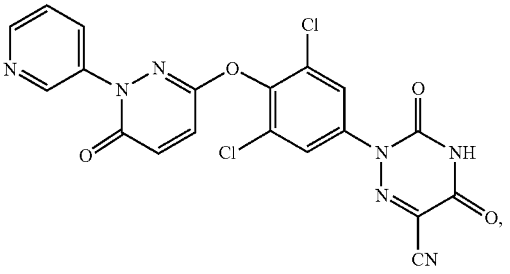
(24)
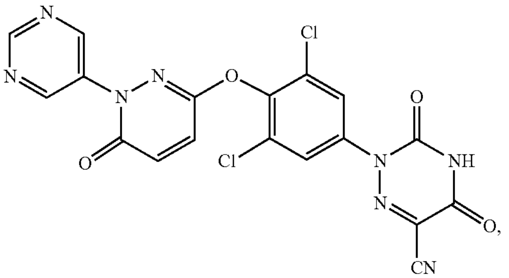
(25)
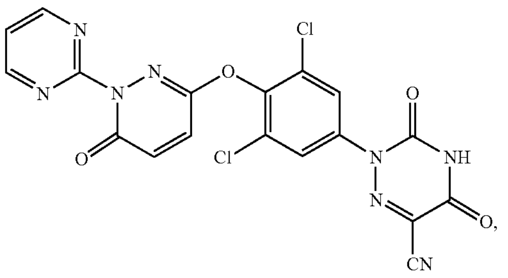
-continued
(26)
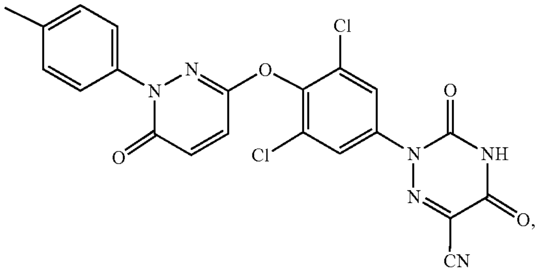
(27)
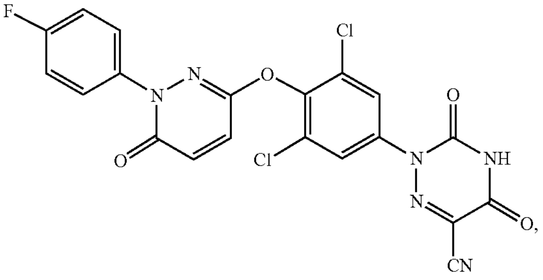
(28)
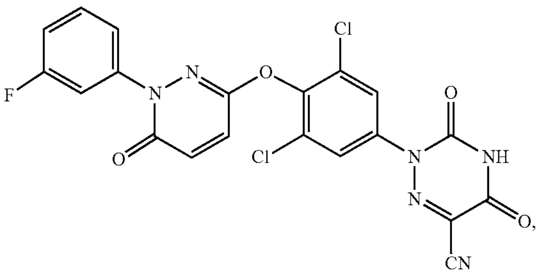
(29)
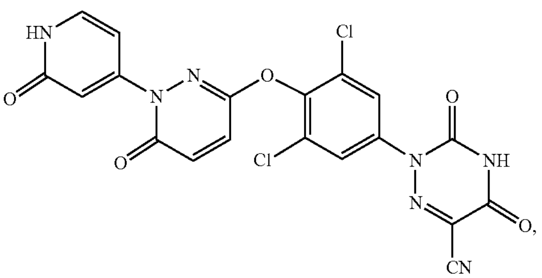
(30)
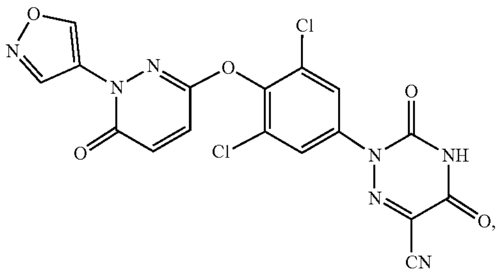

-continued
(31)
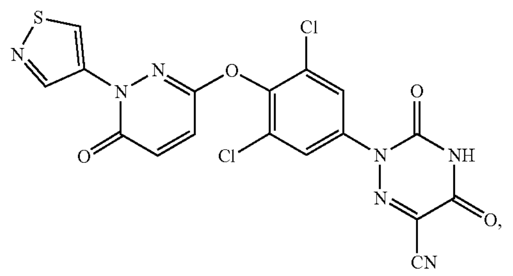
(32)
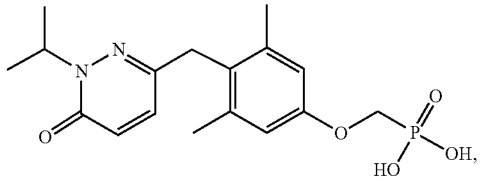
(33)
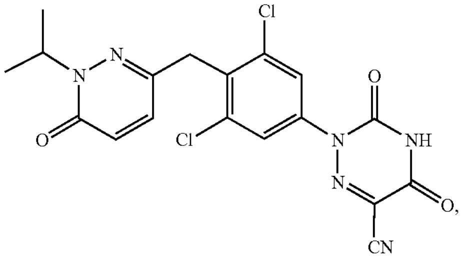
(34)
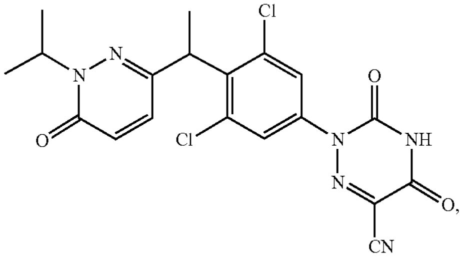
(35)
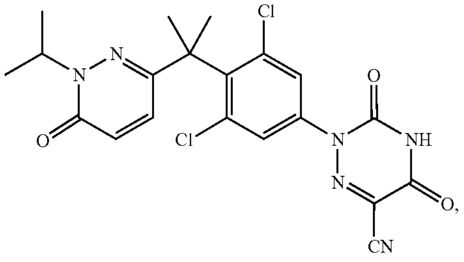
(36)
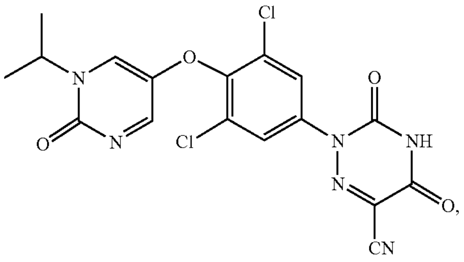
-continued
(37)
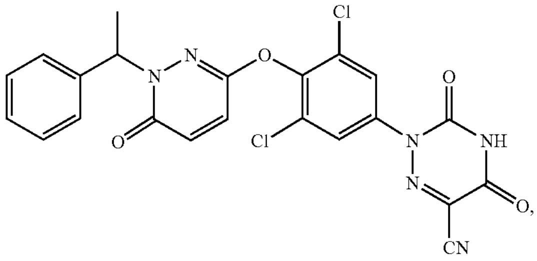
(38)
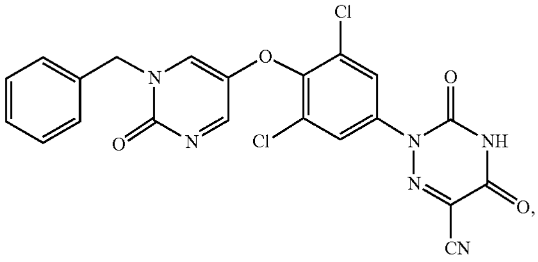
(39)
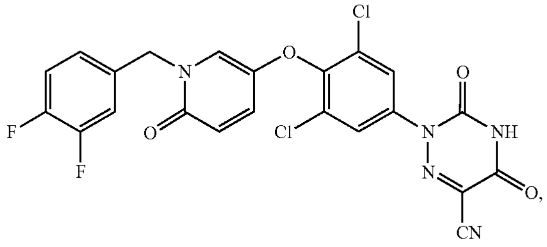
(40)
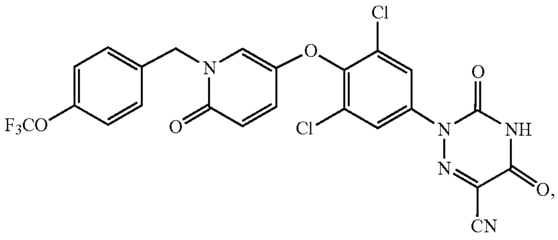
(41)
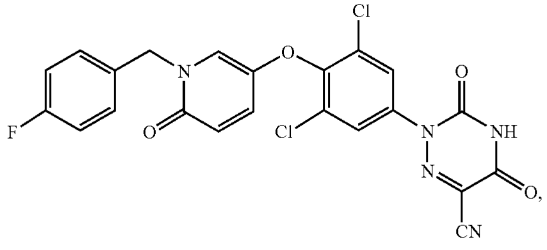
(42)
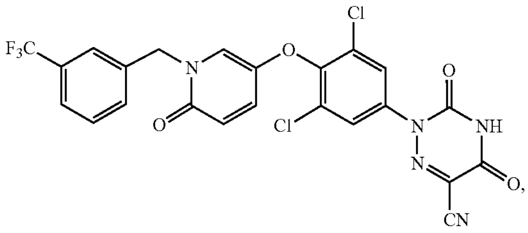

-continued
(44)
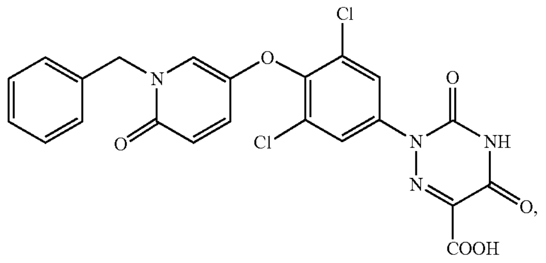
(45)
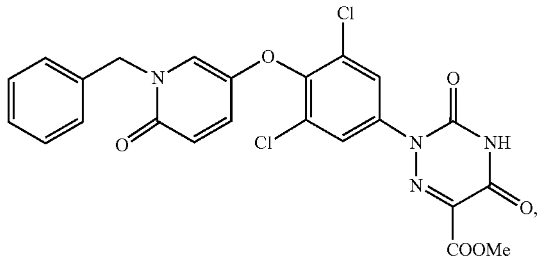
(46)
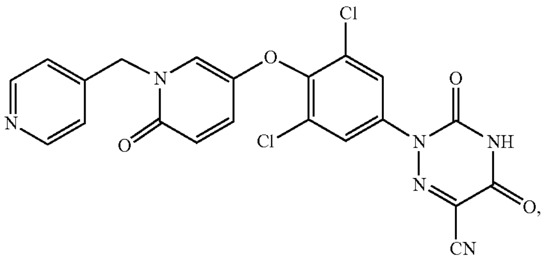
(47)
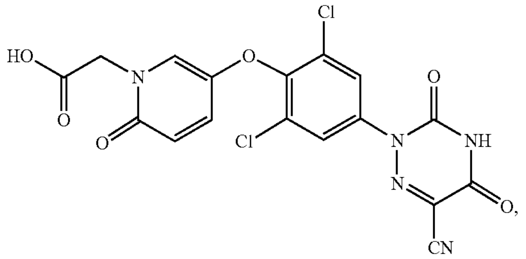
(48)
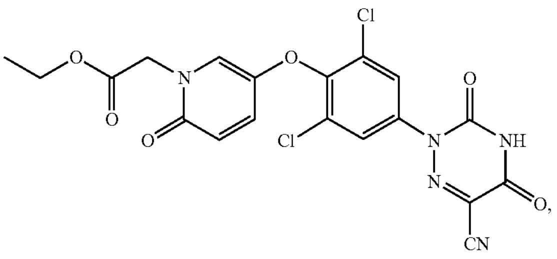
-continued
(49)
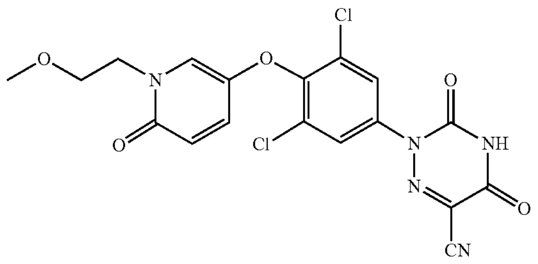
(50)
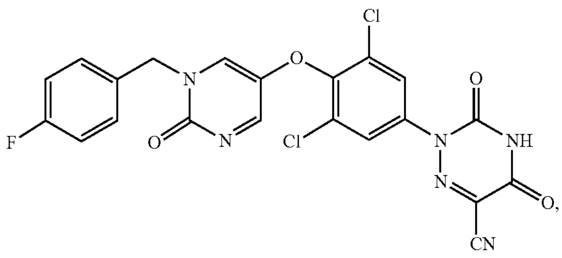
(51)
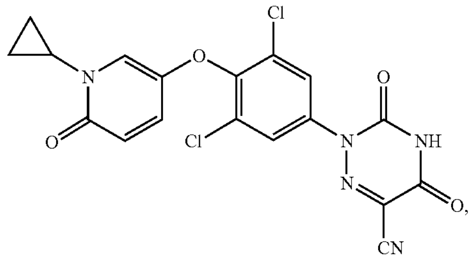
(52)
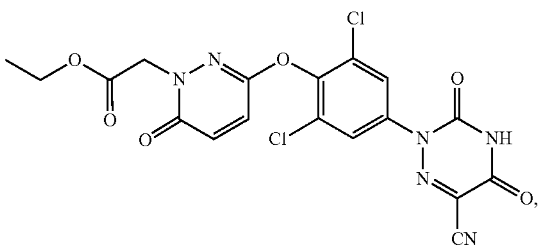
(53)
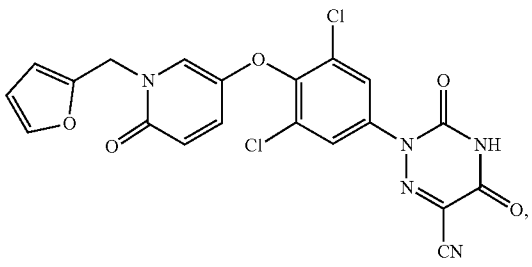

-continued
(54)
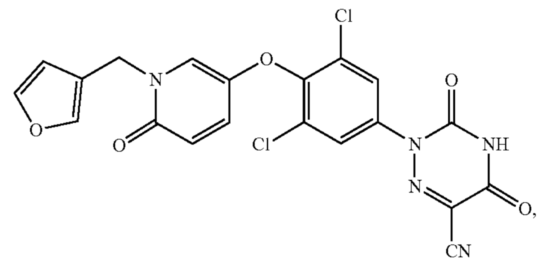
(55)
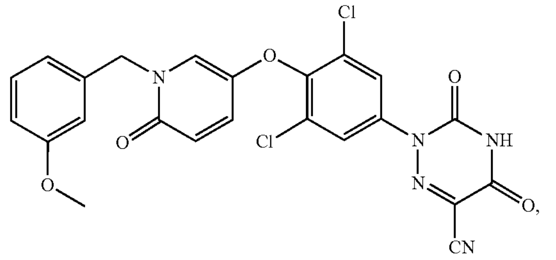
(56)
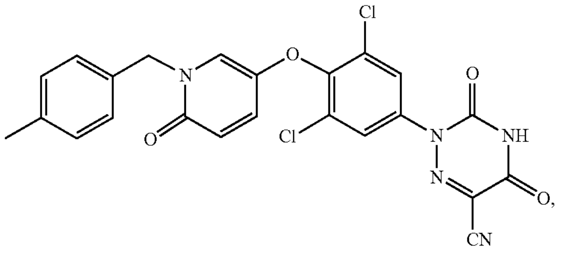
(57)
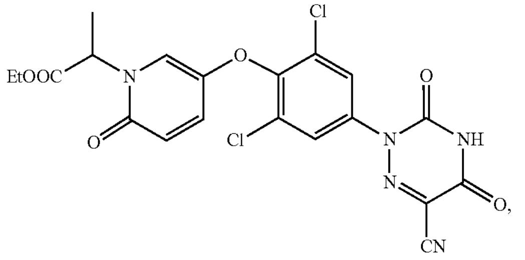
(58)
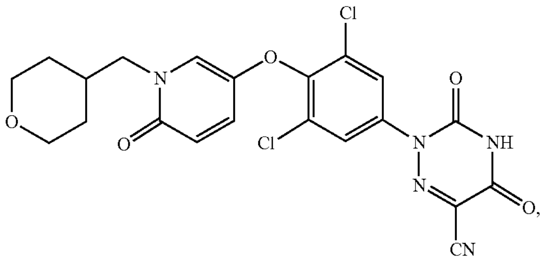
-continued
(59)
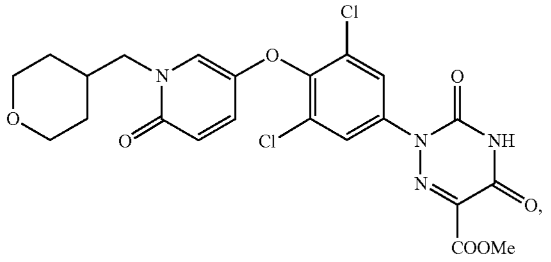
(60)
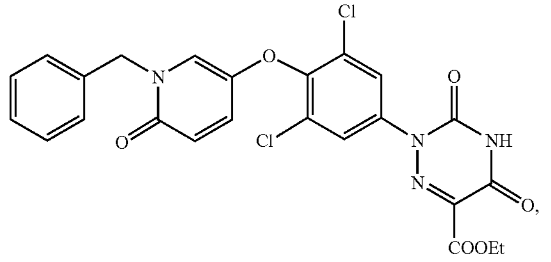
(61)
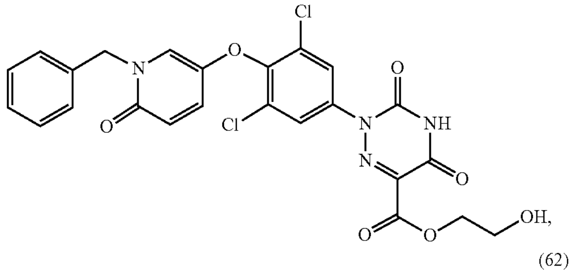
(62)
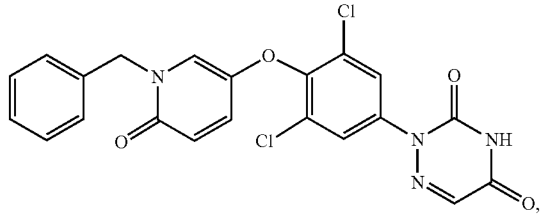
(63)
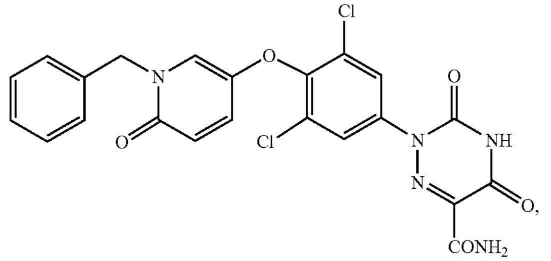
(64)
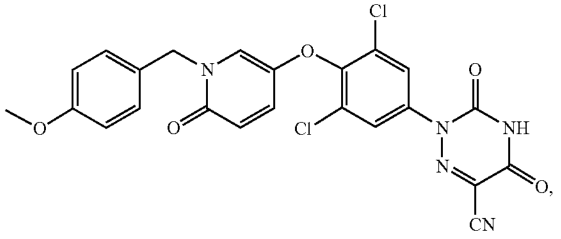

-continued
(65)
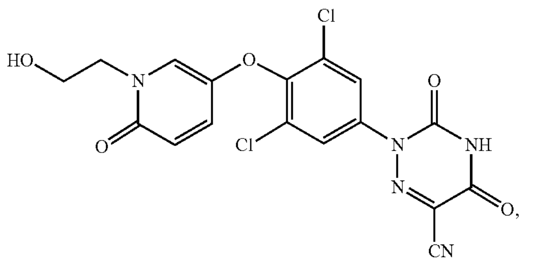
(66)
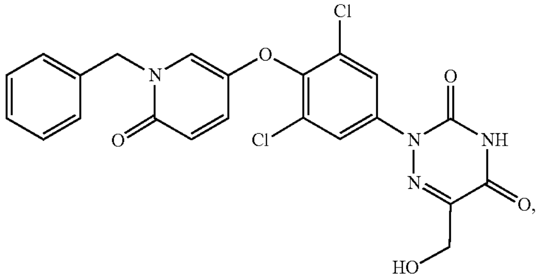
(67)
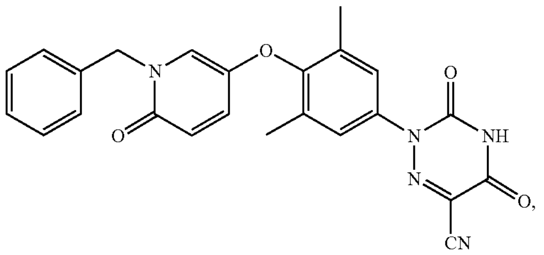
(68)
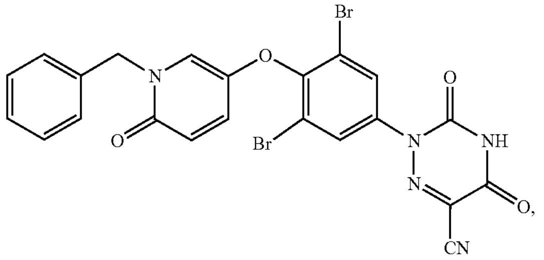
(69)
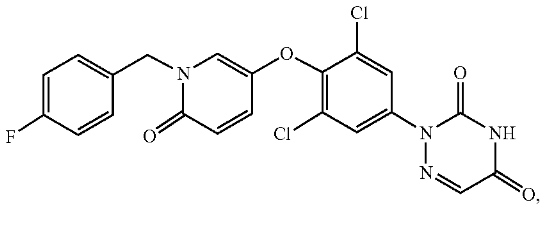
-continued
(70)
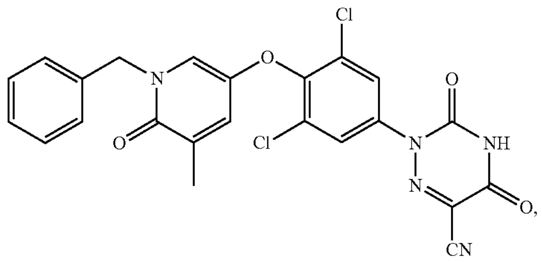
(71)
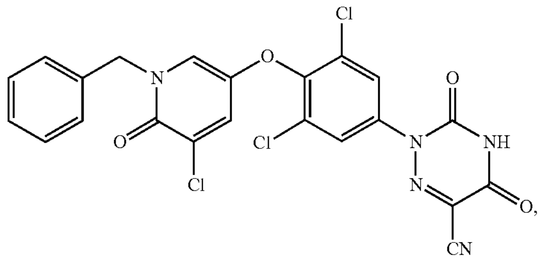
(72)
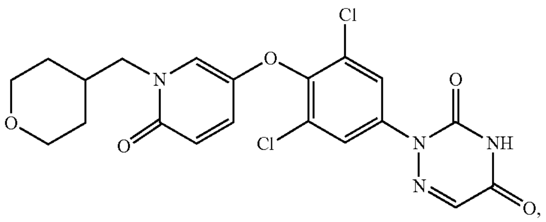
(73)
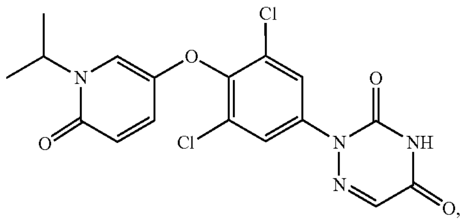
(74)
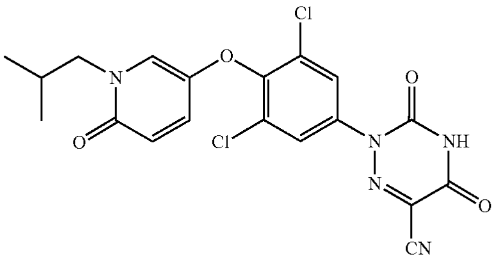
or
(75)
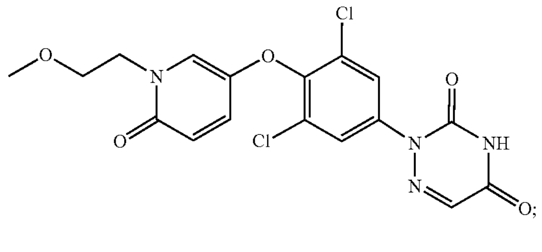
or a stereoisomer, a tautomer, an N-oxide, a solvate, or a pharmaceutically acceptable salt thereof.

9. A pharmaceutical composition comprising the compound of claim 1, optionally, further comprising any one of a pharmaceutically acceptable carrier, excipient, adjuvant, vehicle or a combination thereof.

* * * * *